(12) United States Patent
Recipon et al.

(10) Patent No.: US 6,846,650 B2
(45) Date of Patent: Jan. 25, 2005

(54) COMPOSITIONS AND METHODS RELATING TO LUNG SPECIFIC GENES AND PROTEINS

(75) Inventors: Herve E. Recipon, San Francisco, CA (US); Yongming Sun, San Jose, CA (US); Sei-Yu Chen, Foster City, CA (US); Chenghua Liu, San Jose, CA (US); Leah R. Turner, Sunnyvale, CA (US)

(73) Assignee: diaDexus, Inc., South San Francisco, CA (US)

( * ) Notice: Subject to any disclaimer, the term of this patent is extended or adjusted under 35 U.S.C. 154(b) by 234 days.

(21) Appl. No.: 10/002,344

(22) Filed: Oct. 25, 2001

(65) Prior Publication Data

US 2002/0172959 A1 Nov. 21, 2002

Related U.S. Application Data

(60) Provisional application No. 60/242,998, filed on Oct. 25, 2000.

(51) Int. Cl.[7] .......................... C12Q 1/68; C07H 21/04
(52) U.S. Cl. .................................... 435/69.1; 536/23.5
(58) Field of Search ............................ 435/69.1, 320.1, 435/252.3, 810; 536/23.5

(56) References Cited

U.S. PATENT DOCUMENTS

| | | | |
|---|---|---|---|
| 2002/0155438 A1 | 10/2002 | Simpson et al. | 435/6 |
| 2003/0022279 A1 | 1/2003 | Fraser et al. | 435/69.1 |

FOREIGN PATENT DOCUMENTS

| | | |
|---|---|---|
| EP | 1 074 617 A2 | 7/2001 |
| WO | WO 00/09552 | 2/2000 |
| WO | WO 01/55368 A1 | 2/2001 |
| WO | WO 02/062945 A2 | 8/2002 |
| WO | WO 02/079492 A2 | 10/2002 |

OTHER PUBLICATIONS

Hirano et al., J. Neuroscience 19(3), 995–1005 (Feb. 1999).*
Hirano et al., "Expression of a Novel Protocadherin, OL–Protocadherin, in a Subset of Functional Systems of the Developing Mouse Brain", J. Neurosci. 1999 19(3):995–1005 Reprint provided herewith as pp. 1–15.
Nagase et al., "Prediction of the Coding sequences of Unidentified Human Genes. XVI. The Complete Sequences of 150 New cDNA Clones from Brain Which Code for Large Proteins in vitro", DNA Research 2000 7:65–73.
Ning–Sheng L., "Renal involvement in Chinese patients with rheumatoid arthritis", Annals of the Rheumatic Diseases 1998 57(9):571.
Nollet et al., "Phylogenetic Analysis of the Cadherin Superfamily allows Identification of Six Major Subfamilies Besides Several Solitary Members", J. Mol. Biol. 2000 299(3):551–572.

Wolverton et al., "Identification and Characterization of Three Members of a Novel Subclass of Protocadherins", Genomics 2001 76(1–3):66–72.
Wu et al., "Comparative DNA Sequence Analysis of Mouse and Human Protocadherin Gene Clusters", Genome Research 2001 11(3):389–404 Reprint provided herewith as pp. 1–12.
Wu et al., "Large exons encoding multiple ectodomains are a characteristic feature of protocadherin genes", Proc. Natl. Acad. Sci. USA 2000 97(7):3124–3129 Reprint provided herewith as pp. 1–14.
Wu et al., "A Striking Organization of a Large Family of Human Neural Cadherin–like Cell Adhesion Genes", Cell 1999 97(6):779–790.
Yagi et al., "Cadherin superfamily genes:functions, genomic organization, and neurologic diversity", Genes & Development 2000 14(10):1169–1180 Reprint provided herewith as pp. 1–10.
NCBI Genbank Accession No. NM_032961 [gi:14589915] Jul. 3, 2001–Dec. 18, 2001 with Revision History.
NCBI Genbank Accession No. NM_020815 [gi:14589913] Jul. 3, 2001–Dec. 18, 2001 with Revision History.
NCBI Genbank Accession No. AK022094 [gi:10433415] Sep. 29, 2000 with Revision History.
NCBI Genbank Accession No. $NP_{13}$ 035173 [gi:7242169] Mar. 8, 2000–Nov. 1, 2000 with Revision History—the Revision History for 42476150 replaced by 7242169 is provided.
NCBI Genbank Accession No. T46909 [gi:648892] and [gi:1136026] Feb. 1, 1995–Mar. 17, 2000 with Revision History.
NCBI Genbank Accession No. AK026188 [gi:10438958] Sep. 29, 2000 with Revision History.

(List continued on next page.)

Primary Examiner—Kenneth R. Horlick
(74) Attorney, Agent, or Firm—Licata & Tyrrell P.C.; Nathan P. Letts

(57) ABSTRACT

The present invention relates to newly identified nucleic acids and polypeptides present in normal and neoplastic lung cells, including fragments, variants and derivatives of the nucleic acids and polypeptides. The present invention also relates to antibodies to the polypeptides of the invention, as well as agonists and antagonists of the polypeptides of the invention. The invention also relates to compositions comprising the nucleic acids, polypeptides, antibodies, variants, derivatives, agonists and antagonists of the invention and methods for the use of these compositions. These uses include identifying, diagnosing, monitoring, staging, imaging and treating lung cancer and non-cancerous disease states in lung, identifying lung tissue, monitoring and identifying and/or designing agonists and antagonists of polypeptides of the invention. The uses also include gene therapy, production of transgenic animals and cells, and production of engineered lung tissue for treatment and research.

8 Claims, No Drawings

OTHER PUBLICATIONS

NCBI Genbank Accession No. AAD00651 [gi:4099551] Jan. 5, 1999–Jun. 5, 1999 with Revision History.
NCBI Genbank Accession No. NP_065866 [gi:14589914] Jul. 3, 2001–Dec. 18, 2001 with Revision History.
NCBI Genbank Accession No. AAK57196 [gi:14210853] May 28, 2001 with Revision History.
NCBI Genbank Accession No. AAK57195 [gi:14210851] May 28, 2001 with Revision History.
NCBI Genbank Accession No. NP_116586 [gi:14589916] Jul. 3, 2001–Dec. 18, 2001 with Revision History.
NCBI Genbank Accession No. BAA92638 [gi:7243181] Mar. 14, 2000 with Revision History.

* cited by examiner

SEQUENCE LISTING

```
<160> NUMBER OF SEQ ID NOS: 277

<210> SEQ ID NO 1
<211> LENGTH: 898
<212> TYPE: DNA
<213> ORGANISM: Homo sapien
<220> FEATURE:
<221> NAME/KEY: misc_feature
<222> LOCATION: (124)..(185)
<223> OTHER INFORMATION: n= a, c, g or t
<220> FEATURE:
<221> NAME/KEY: misc_feature
<222> LOCATION: (773)..(773)
<223> OTHER INFORMATION: n= a, c, g or t

<400> SEQUENCE: 1
tttaaagaat agctcgtgta tatgattttt taaaaaaaaa tctaccaaat caaataaaga      60
agtcctggga gttcacccgg tgttttctac agaaccaagg tattcatatt gagatccttc     120
aatnnnnnnn nnnnnnnnnn nnnnnnnnnn nnnnnnnnnn nnnnnnnnnn nnnnnnnnnn     180
```

```
nnnnngtgaa atggagatat tcaacaaagc accctgtggg gattagatga gattgcacat    240
ctgactgcct agagtatagt aagggggtcac tgtttcctct tcactcctca ggaaaatttg    300
attgaacaag gatagaaact ttgattctag ggacagaagg tcttcagaag tctttgaggc    360
cagagggcct gtcatagaac tgcagtgtag gttcattaaa acgctgtcat cctaatgttt    420
atccacagta tctaatagat ttaaaaggaa gacaatatgg cacagactat ttcggaaacc    480
tatgcccatt ctgccaagag gatatcgcta ttggtggtca gactatttca cttataaggt    540
ttcttttttc cttaagtcat aaagattaac atttactaaa aatttgaggg tccattaatg    600
gactcccaca tggctttcct ctttcctttg agctggattc attttcactg agtcccgagt    660
cctgcacatc tgacaattgc ttcagacctt ggacatgctt gaattatttt atgcaaatca    720
tttgaaaagg caaagtacca ctgttctttc ttgagtttct tcgtaaactg gtntctaatt    780
tatctgctgc ttttttctcga tccaatttgt gcctatgtct tactatagat tctttggaaa    840
taaagaaata aagaatatat ctgtagctat tttgttaaac taagaatgtt ttaaaata      898

<210> SEQ ID NO 2
<211> LENGTH: 1047
<212> TYPE: DNA
<213> ORGANISM: Homo sapien
<220> FEATURE:
<221> NAME/KEY: misc_feature
<222> LOCATION: (125)..(186)
<223> OTHER INFORMATION: n= a, c, g or t

<400> SEQUENCE: 2
tttaaagaat agctcgtgta tatgattttt taaaacaaaa atctaccaaa tcaaataaag    60
aagtcctggg agttcacccg gtgttttcta cagaaccaag gtattcatat tgagatcctt    120
caatnnnnnn nnnnnnnnnn nnnnnnnnnn nnnnnnnnnn nnnnnnnnnn nnnnnnnnnn    180 nnnnngtga atggagata tcaacaaag caccctgtgg ggattagatg agattgcaca    240
tctgactgcc tagagtatag taagggggtca ctgtttcctc ttcactcctc aggaaaattt    300
gattgaacaa ggatagaaac tttgattcta gggacagaag gtcttcagaa gtctttgagg    360
ccagagggcc tgtcatagaa ctgcagtgta ggttcattaa aacgctgtca tcctaatgtt    420
tatccacagt atctaataga tttaaaagga agacaatatg gcacagacta tttcggaaac    480
ctatgcccat tctgccaaga ggatatcgct attggtggtc agactatttc acttataagg    540 tttcttttt cctaagtca taaagattaa catttactaa aaatttgagg gtccattaat    600
ggactcccac atggctttcc tctttccttt gagctggatt cattttcact gagtcccgag    660
tcctgcacat ctgacaattg cttcagacct tggacatgct tgaattattt tatgcaaatc    720
atttgaaaag gcaaagtacc actgttcttt cttgagtttc ttcgtaaact ggtttctaat    780
ttatctgctg cttttttctcg atccaatttg tgcctatgtc ttactataga ttctttggaa    840
ataaagaaat aaagaatata tctgtagcta ttttgttaaa ctaagaatgt tttaaaatat    900
tttattgtaa aataaaattc ctttgttctc tcagaaataa aaaattttt ttttattttt    960 gtattaattt ttttttatta tttttatttt attaaaatat gggggcctga agttttttcc   1020
ctttgtgggg ggtttatttt tctggaa                                       1047

<210> SEQ ID NO 3
<211> LENGTH: 538
<212> TYPE: DNA
<213> ORGANISM: Homo sapien
```

<400> SEQUENCE: 3

```
gctccatacc ttctttattc tgggaccaag ctggagagat gagtctctat ctgtggaaga      60
ccttggaaga ccccactcag ggttgttctg aaagggatct cacatggatt gagccataac     120
ctagagccaa gagaagccag atttgctagg agaaagtcct gtcagcatag tcaaacactt     180
aggaggagta aaaaggtgta tttttctgca tagatggtgt gatcacattt ttatcaatta     240
atctgcaccc tagggacaaa gagttaacat ttgaattttt ctcagtaaga atctactcct     300
cagggaaagt tagcgtttga aaaactctaa ctagaaatcc actttccaga ggctgtctca     360
gcaagtgctt aagtatctag actagaaatt cccttcataa gcatgaggag tgctggaagt     420
gatttttcat tggtgaaatg ggtggttttc aagttatgta gatggactgg agatattttt     480
cctctactct tgcatgaaga aatatgtctt aatgtagata gactggagat attttttcc     538
```

<210> SEQ ID NO 4
<211> LENGTH: 303
<212> TYPE: DNA
<213> ORGANISM: Homo sapien

<400> SEQUENCE: 4

```
ctccatctca aaaacaaag ggatcaaggt cagatgaggt caagagaaga ctgaggaact      60
gtgccagact gaggaagatg aaggagacat gacatttaat gtttctgaac tggatccttt     120
cctatgaaac tactggaaca actggcatac ttgaatggaa tttgttgatt agatggtagc     180
aatgtatcag tggtaatcac ccgactttga tgagcgtaat acggtgatgc agtaaaatgt     240
atttgtttct agaaaataca caccatcgtg gccgggcacg gtggctcata cctataatcc     300
cag                                                                   303
```

<210> SEQ ID NO 5
<211> LENGTH: 519
<212> TYPE: DNA
<213> ORGANISM: Homo sapien

<400> SEQUENCE: 5

```
gtacgacgtg gcgcagtctt ggctcactgc aacagccacc tcccgggttc aagcgattct      60
cctgcctcag tctcctgagt agctgggatt aataggcgcc tgacaccaca cctggttaat     120
ttttgtatt ttagtagaga cagggtttca tcatgttggc caggatggta ttgaactcct      180
gacctcgtga tctgcctgcc tcggcctccc aaagtgctgg gattataggt atgagccacc     240
gtgcccggcc acgatggtgt gtattttcta gaaacaaata catttactg catcaccgta      300
ttacgctcat caaagtcggg tgattaccac tgatacattg ctaccatcta atcaacaaat     360
tccattcaag tatgccagtt gttccagtag tttcatagga aaggatccag ttcagaaaca     420
ttaaatgtca tgtctccttc atcttcctca gtctggcaca gttcctcagt cttctcttga     480
cctcatctga ccttgatccc tttgtttttt gagatggag                           519
```

<210> SEQ ID NO 6
<211> LENGTH: 781
<212> TYPE: DNA
<213> ORGANISM: Homo sapien

<400> SEQUENCE: 6

```
tatgaaggta gatgccatat atgtttacct tgccactgta tttctactgt cttacattgc      60
tcctaacgta tatcatgagc tcttaaatat ttgttgaaga aatgaactag cgtatttga     120
taactataat gtgtgaagcc cctggttgcg tctgttgcac actggaatta aggggttaaa     180
```

```
aacctttcc cttgctgctt gagaatctga tctttggttt agccacctag ctctgttacc    240
ctggaaacca ggtaagagct taggcatcca caatattgct aagcaacact gcttacggta    300
aaaatgatcc ttggttggta aactgcatct gaaccaggaa gaaatatgaa tgagctgtaa    360
atgtctgata ggacacttg gccttcctg aatgcagttt cttcttggga accctacaaa    420
ctatatcaag aattgttaca agagatactg gctgcttaag caggaggct tcttctgagc    480 cagggcagct cccgtacctc cctgatgtgg agcttaggct ttgtacctgg aactacgtcg    540
tgtggggaga caacagtccc cagaaaggta tgtgagctgt catttgtgca acatgcaga    600 gccctgctg agaggaattc ttgatgctgc cctgctggca agctggcaag aaatgtggcc    660
tgtggtagcc ttgtgagtcc acatgtttag ttaacttaaa aagacccttg gtggccacta    720
aacacacctt atttcattta atgctcgcaa caactttgag agacaggaaa taccattttc    780
c                                                                     781
```

<210> SEQ ID NO 7
<211> LENGTH: 996
<212> TYPE: DNA
<213> ORGANISM: Homo sapien

<400> SEQUENCE: 7

```
tcatagaagc cagggaaagg aaggagctgg ccggtggagg gtgctcctga ccaggagtca     60
aacttctttc actgaccttc ttggacaaag cggccaaggt agaactggca gactgggagc    120
taaaaggggg aggaaaagga ctcaaatcgc atggtctcct cagtcctggt gagagatttg    180
tcctgcagaa cggcattggc tgcagctttc agttttagga tggctgaata ccggagacaa    240
gctgcaggtg gtggttgagt ttggcaacca cttaccttga ttccatataa aacgttact    300 tggagtgtat tggtcattct gttcctgctt ctcggccaac ttcctggcca gaacactgag    360
ctgctgggcg tggtgggaag gcggggaaaa ggagaggttt cgagccaacg tttacggggg    420
actccactct gccattagcc gtggctgcag catcgagttt gagggaacca gcctccagca    480
gccgcctcaa attgctgctc aggggcttgt tggagcctgg gtcatcgtca cacaaagaag    540
acactcccgg ggaaaggtga tcttgacact gcagtgagtc tcgcaggacc tcactgtcca    600
gtgccaccag ctccaacgtg tggctgctgg gagtcgtgct tcccaaggag gtgtccgggg    660
acgtggactg ctccctggat ccggtcctcc agagacaact tatagttctc ctggacttcc    720
ccataggatg cttctgacgg agtctctgaa gagtttccat accagtgttc tccttcactg    780
agctctccct ccgcctcttc ctgcctacta acatgtgagg gaaggcgctt gggctgctcc    840
tgcttcctcc tgggcatttt cccccttttc tcacattctc ctccttggtt aatgtgagat    900
caaataacac cccgtggg gcagagaggc agacactggc aggagcgggg aggtagttgg    960
ggggcgggcg gcgggcagg ggaaaccctt ctccgg                                996
```

<210> SEQ ID NO 8
<211> LENGTH: 1678
<212> TYPE: DNA
<213> ORGANISM: Homo sapien

<400> SEQUENCE: 8

```
atgctgctca gtgactgtca ctgttggcag cgggcagcgg agaggcaagt tccaggaggt     60
accggacaca ggatgaagcg ggctgcatct tcccagggag taaaacaatc catgaaatgc    120
actggacttt acgacgtgcc ccgaagcatg tttgtactgt cctccaactg gttacttcag    180
```

```
ccagttacca actgttccag aaaaggagcc aagacaaagg agacacgttt tatccgtgga    240
cccaaaactc tggcgccagt cacggactgg gaaggcagcc ttcccttggt gtttaatcat    300
tgcagggctg cctctctgat tattcaccca cgtttcaaag gtgtcagacc acgcagggac    360
gcctgcctta gtccttcacc cttagtggca agtcccgctt tcctgggggca ggggcaacac    420 gcttttaaaag gattagagcc tgttatcact cacctgctac agcatggcct tttaaagact    480
ataaactctc cttacaatac ccccatttta cctgtcctaa aaccagacaa gccttttacaa    540 gttagttcag gatctgcgcc ttatcaacca aattgttttg cctatccacc ccgtgatgtt    600
agtaggcagg aagaggcgga gggagagctc agtgaaggaa acactggta tggaaactct    660 tcagagactc cgtcagaagc atcctatggg gaagtccagg agaactataa gttgtctctg    720
gaggaccgga tccaggagca gtccacgtcc cggacacct ccttgggaag cacgactccc    780
agcagccaca cgttggagct ggtggcactg gacagtgagg tcctgcgaga ctcactgcag    840
tgtcaagatc cctttcccc gggagtgtct tctttgtgtg acgatgaccc aggctccaac    900 aagccctga gcagcaattt gaggcggctg ctggaggctg gttccctcaa actcgatgct    960
gcagccacgc taatggcag agtggagtcc ccgtaaacg ttggctcgaa cctctccttt   1020
tccccgcctt ccaccacgc ccagcagctc agtgttctgg ccaggaagtt ggccgagaag   1080
caggaacaga atgaccaata cactccaagt aaccgtttta tatggaatca aggtaagtgg   1140 ttgccaaaact caaccaccac ctgcagcttg tctccggatt cagccatcct aaaactgaaa   1200
gctgcagcca atgccgttct gcaggacaaa tctctcacca ggactgagga gaccatgcga   1260
tttgagtcct tttcctcccc ctttttagctc ccagtctgcc agttctacct tggccgcttt   1320
gtccaagaag gtcagtgaaa gaagtttgac tcctggtcag gagcaccctc caccggccag   1380
ctccttcctt tccctggctt ctatgacctc ctcagcggcc cttctgaagg aggtggccgc   1440
aagggctgcg ggcagtcttc tggctgagaa atcatcgctg ctgcctgagg accctctacc   1500
gcccccgcct tcagagaaga accagaaaaa agtcactccg ccacctccac cgccacctcc   1560
accacctcca ccaccaccac cacaatccct ggaattatta ttactcccag ttcctaaggg   1620
aagagtttct aaaccctcca attcaggtat ggcatctttt cttttcaatca tcgtgtaa    1678
```

<210> SEQ ID NO 9
<211> LENGTH: 659
<212> TYPE: DNA
<213> ORGANISM: Homo sapien

<400> SEQUENCE: 9

```
cccacgtgaa tgcccagatc ctgcccattc aaagcctgat atcattggca tccctgttgt     60
gaagacatcc tggaccgcct caactgaatc aggtttctag cccaactccg attgctctta    120
aaggcactat ccctttccgt cttctttacc agactctgtg ctcccagtag gcaggatgca    180
gtctaactta agaaaacacc cagggaggag cctccaggct actgacattc agaagaggtt    240 tcttttttctc tcttctctct gtccgtaact tctaattgag cactaaatgt acaggtgcta    300
agacaaaggc tttccacaaa tcctctcctt tctcaattgc cccaggggtt aagcaccctg    360
tactccaaag gtcccacctt tggtgaaaag cagagctcac tggaaggtgt tgttctagac    420
tcccatggaa acctgaaatg ctgttgactc tcagcctgta ccattggtac ccatttctg    480 agcagcagca gagaattcgt cactggatgt gtgactccca gcctccactc tcagggcagg    540
attcagggtg acccagaagt ttgttttaga aataaacctg ttaatattct taacacatta    600
agtttcaata aattagagaa aacaggctat aaaaatggca taatgtgaca aaaacccaa     659
```

<210> SEQ ID NO 10
<211> LENGTH: 947
<212> TYPE: DNA
<213> ORGANISM: Homo sapien

<400> SEQUENCE: 10

| | | | | | |
|---|---|---|---|---|---|
| acacggtcgt | tgtctgtgaa | caaaatcgca | tctgcagccc | tctacagttt | gcacggtttt | 60 |
| tccagctttg | atacctacat | catcttgtag | ggtagttact | actgcccccc | atttacaggt | 120 |
| gagaaaactg | gggctcagga | aggcagtgag | aaactggaag | tcagccacgt | gtcaggacag | 180 |
| gagcctggat | ttggcccaca | tctttggctt | tggttttgca | cacagctgct | gctgggagct | 240 |
| ggggccaggg | caggcaggtg | cctcctctct | ggcctcagcc | tcgtgggaaa | gcttgggcct | 300 |
| caggtggagt | gaggatgtct | tgggtgcatc | ttctcgtctc | ggctcttgga | cccagcaggg | 360 |
| gtcggagggg | gatttcttaa | gggaggggggc | tttttcagaa | atggacaggg | actttcggga | 420 |
| ccatggctgc | ccacctcagt | gaagtctgag | gggagttcct | ggaaggcatt | tccatctgtc | 480 |
| catgtgttct | aagtcagtgg | acaattaagt | ccagaaacct | cctggactta | aaaagcaagc | 540 |
| accgccagga | tccctggggc | tgcagacagc | ctcggggggtt | ttggagggct | ggctcctcag | 600 |
| gcacccatga | aggaaggtgt | cctggggtca | gtattcagac | ccaaatgccc | gcagggaccc | 660 |
| tcaggggtgcc | tttatctact | catgtctcca | cacacttgct | ggcagagctg | ggacaagtca | 720 |
| ctaaccctct | gtgtgacctc | tgattcgcca | tggaaaaaag | agtgaataga | ataaatcatt | 780 |
| tattcccagg | gtaggttctt | ggggtggcag | tgccgagctt | gggtgagtct | ccaccccttc | 840 |
| gatttaggag | ccgatgccct | ggtgcggatc | tctcctctga | gctgagcgtc | ctccactaag | 900 |
| tcaggcacag | agcacgtgca | gcatagggcc | ggtgtccagg | ccccacc | | 947 |

<210> SEQ ID NO 11
<211> LENGTH: 577
<212> TYPE: DNA
<213> ORGANISM: Homo sapien

<400> SEQUENCE: 11

| | | | | | |
|---|---|---|---|---|---|
| gtaactttac | agtgttttcg | ctcacgagcc | gaaacttcaa | gttccctttt | tgccagcaga | 60 |
| gtttgggttg | cggtcgctgg | aaaacttgat | gcgcactgaa | atctcttggt | ctgtgcatga | 120 |
| ggaagagtgg | atccagcttc | ttgtcttggc | tctctgttct | ctgaatgcct | tgtacttttt | 180 |
| gcttttctat | cttaccatttt | ttttttggtt | tgctttcact | gtgaataata | tattttcatc | 240 |
| tttccttgcc | cttgcttttt | tggctgacag | aaaatggtga | atgcacaccg | tgggtgcagt | 300 |
| gagggcttgg | tgcctgctac | gtgggcagct | tccacctgtg | gctggcttat | gggctactt | 360 |
| ggagccacag | aatcattgct | gagctccgat | gtgccagaga | gtcccaggcc | attggggtca | 420 |
| ctcttctagc | tggggaatct | taagtccagc | ttttgggatg | tcatcctccc | gtggaggggg | 480 |
| agctcatgaa | agtccaaggt | tcgagtcttc | ctccccagag | ggctaccctg | taatgccgtg | 540 |
| gggggggtgtg | tgtgggggggg | tggcaaggga | agctctg | | | 577 |

<210> SEQ ID NO 12
<211> LENGTH: 3725
<212> TYPE: DNA
<213> ORGANISM: Homo sapien

<400> SEQUENCE: 12

| | | | | | |
|---|---|---|---|---|---|
| gtcttgctct | ttaattgtaa | ctttacagtg | ttttcgctca | cgagccgaaa | cttcaagttc | 60 |

-continued

```
ccttttttgcc agcagagttt gggttgcggt cgctggaaaa cttgatgcgc actgaaatct    120
cttggtctgt gcatgaggaa gagtggatcc agcttcttgt cttggctctc tgttctctga    180
atgccttgta cttttttgctt ttctatctta ccattttttt ttggtttgct ttcactgtga   240
ataatatatt ttcatctttc cttgcccttg ctttttttggc tgacagaaaa tggtgaatgc   300
acaccgtggg tgcagtgagg gcttggtgcc tgctacgtgg gcagcttcca cctgtggctg    360
gcttattggg ctacttggag ccacagaatc attgctgagc tccgatgtgc cagagagtcc    420
caggccattg gggtcactct tctagctggg gaatcttaag tccagctttt gggatgtcat    480
cctcccgtgg agggggagct catgaaagtc caaggttcga gtcttcctcc ccagagggct    540
accctgtaat gccgtggggg ggtgtgtgtg gggggtggc aagggaagct ctgtcagcct     600
tggctatggc tgatgccagt cagggtcata gacacctgtt tgttctcccc tcccgcccac    660
aaacgttgag gactgtgaac attatgtcac tgtgacctgc ttacaatggt aactaagcgt    720
taggcagaag gggttgagga gggggagac ataggctctt ctgtaatagt atgagtgtcg     780
acatggtgtt cttcccctc ccttttagct attgaaacaa tccacccggt agagtgaaca     840
gcttgaggtt gatcctggcc tgtgataaga gccaggtcag tatacttgtt agggacatgt    900
gagagacctc cccgccacac tgcagcattc acagcacctt tcctggacct cctgtcacct    960
cgcaggtcag ggagttatgt cccctgggaa cccagggctt gtccagagct acccacagtt    1020
gtctgcactt ccaggtagcc cgattttggg gttctaggat gtttcatctc ctggggggggt   1080
aatcaaatcc ctggaagagg acaagaaaga ctgaggtagg aataaagttc ttttaaacct    1140
caagggtgcc cattgcaggt tatcaaaact cacttggtga accctgaaga gggagatggg    1200
tttggtggaa atggtttccc cacttgccta tttggcctct tttatgatgc ttccaaggaa    1260
tcttgaattc agcacagtca aaaccaaact caggatcttc tcttgccaaa agcagtccct    1320
tcccagggcc ccttctgggt gtctggcacc gatatttgaa cactcattgc cataagccag    1380
aaatatagaa ggcgatctgt gtaccccctc tctgttagca tccataccta gtccacctcc    1440
aagttctgaa aaatctctcc agctcttcac ttgaatctgc ctgccttctg ccactgccct    1500
ggtccaagtc accatctgct catgactgaa cttagagtag ccttcgtctg gcccaccttt    1560
atctgctctg actcacctct agtgctttct ccattcttct gccatcctgg tcttttcaga    1620
gccataacat ttgcttgtca cccttattat gaaaaaccaa ccacttggtg gccttctgtt    1680
gctcttggga cagatcttca tgtggcccac aaggctctgt gcagcccagc tttgtctccc    1740
tgccagcctt gtcttacaca ccgtgttgtc catcgtatct gtagcctggc catacccag    1800
cagttgcctt cctatcctca actacatcac atgctttctg gcctcaggac ctttgcacat   1860
gctgtttatg ctacttggag tgttttgttc cttttcttcac cctcagccac tccctctgga  1920
ctgcactcca cagggcagaa gctgaggatg ttcagaagcc caaacggagt tggctgccct   1980
gtgggaccca agcgagttgt aaacattctg gcttcagatg taaatcaaag gcagagccct  2040
gagttttagg gcagagaatt ccttctatca gctctgcagt gagccctcac aggcagactc   2100
gggcccaaat atagcctagg tgctgtttat gtatttgaaa gtatttaagg ctggtccttc   2160
tgtcatcggt cctccaaagt cttttattac attttgggac tgtggtatat agagttccaa   2220
atttcttttct cccctagagc aaatggtttc agtttactgt aatgcataat aaacatgtaa  2280
acataaatag gcacacttca gaccaggttt tccctgtagc ttagctttct ctgctaaggc   2340
cccccttccag gttttttgggt cggtgtggtc ccaggttatg ctcagactcg cccttcatca  2400
cctcctcctt ggcctgcgag gcggtcatgg cttcttcgtg actcatcttc gtggcactgg   2460
```

```
ggattgcagg gaggcatggt gatgtccttt tccagtcaca aggctggact gccaaacgaa    2520
ctgcacagat tcctttccag tgccccaagc tgaaggaaag cgtgatcagg aagcaggcag    2580
cagacgtatt tgaacccaga catgctcgag cccctccctg agcaggtgtg aaattatgta    2640
tgcagctcca tagctccact gaggattctg aagtgatcct ctgcacgaca cttcccggaa    2700
ataagtggaa aagcttactg catgactgaa agtacgtat cagtcctgca ccctaggat     2760 tgccctggac tcttgtctaa actgtttgtt gttgatacca gcctcagaag ctggatgcct   2820
ttaagccatg gctagtgtgt ttaaccgatc cctttatga agatcttgta agcgcgtggt    2880
aatagcccac tatgcttttt aactgaacca gcagagcaaa catagttaat ggagagacat   2940
ttttgtcatt ccttggcctc tgtttatttg caaaaacgag taaagtgtta cctgcaagtg   3000
gttcagtgcg tgccggggtg tcaggctgca ggtatgtgag cttgttcaag gcttgtcttg   3060
cccacgcagc agtttgagag ccccagaggg cgaacgctgg ggccctgttg gaagcggtgt   3120
gtggatgaag ccacccagga gtcccttctc tcctggtcac ctatagggct tgcatcactt   3180
tttaaaggag cactggcccg aggcctagaa aaacagccat gtgggtgggt aagaatcaca   3240
aagacattgc aagtcagtcc taactgtctc tccaagatgg tcttgaattt gacaaggtga   3300
tgaagagttg gtgctggcag gtttaagaaa acaaacacaa aaccaggttg gggtgctgat   3360
ttagtgcctt gctgccttt  cagatccctc ccctgaactg ctggcacctg atgtttgagc   3420
tatttttgta cctgtctctt ctcaaactag atgataagtg gcctcagggc agggactaca   3480
tactcctgag agctgcttga gctcgagtg tttatttcc tcagtaagca ttttttttca     3540
ggagcatgac ttggctcaaa aaaacaaaaa gaaaaagaa accctcccct caatttacct    3600
gtgtctaaac tttggtgaat tattctccca tctgccttct gggcagagga gaaatgtgga   3660
atgcatcaag ttcaaggtct tggtatttaa gagctggctt taaaggttgc catgttaaca   3720
attgt                                                               3725

<210> SEQ ID NO 13
<211> LENGTH: 1299
<212> TYPE: DNA
<213> ORGANISM: Homo sapien

<400> SEQUENCE: 13
tacacctaaa tattaatatc tagaaattat aaatatcacc agaggacatt aacatatatc      60
aatttctagt taagagtcac aaggcctttc ttttccacga gcaaattcat ttgcaccat     120 tacgataaac ataacaatct catcaggact tcttcatacg tcttcccttt ctcatccact    180
gttacggttc ataaagcaca aagacatttg aacaaagcag cctgtggctg gaactgcagt    240
ttttcctttt ggcaaagaaa gctactgacc ctggtcaccc cataccctaa agtgactgtc    300
agaatacaga tagctcccta accatgctct cctactctag gacaatgct gagggtctt     360 aggaaagttt ttataccctg acccaatgat tccccttcta gagtcaatcc ttcaagaact   420
agccagaatt aaaacaaaga tcaatcattc aagcttacta tagcttgatt ttttttcagc   480
tcagataaaa tcagaaacaa cagtaatgtc tacattgaga aaattgccaa gtaaattaga   540
atatctaatt attgaatata caggtaaagc tttccctggc tcactttcta agggctctga   600
attggtctct gacttactta gactatgtcc ttagattctc tagcctctaa aagctaatgg   660
tctacacatt ctcatgtttc ttttcaagct tcctggagtc tggggatact catcgaagaa   720
taaatggatc tggaaaggtc ccaggtctca tgcacgagga ggacctggta agactagaaa   780
```

-continued

| | |
|---|---|
| cctgtttggc aagccaggga agtgcagtat catatccatg tgcaaaataa gctaagactc | 840 |
| ccttccacag gggatgcagg tctgcaaaca atatgatgca tttagggaaa tgcttttctt | 900 |
| ccttaattgg aacctagact atattatttc tgagaacgga catctgaatg atacatatca | 960 |
| taaccagtaa ttacctgtac tctgcattgg tatatggcaa tcttgaggtg actaaactga | 1020 |
| agagagttac agcttacttt tgccttttg gttagatata aaatgtcata ttccaatcct | 1080 |
| gtggaagacc tccaggagta ctgatcttgg ctgagtaact cagaacttag agatatattgt | 1140 |
| gctggaaatg acgtactgta gggactgctt gactggggaa gagaatatgg aaagggttt | 1200 |
| ccgcaaaaca caggagtaaa gattcacccg tgcaggtttg aagggagata cttcttttc | 1260 |
| agagcaggga gatcaaagga aagtgggtca agccttacc | 1299 |

<210> SEQ ID NO 14
<211> LENGTH: 2005
<212> TYPE: DNA
<213> ORGANISM: Homo sapien

<400> SEQUENCE: 14

| | |
|---|---|
| gggtatggag ttctgccctg aaggcagaac tgggcagatt ctctggactc ccactgaagg | 60 |
| ggagggccca ggcttgggga agaagggttc caggggtcac atccttacat tcacattcat | 120 |
| tgccttcttc caatctcagg agacacagaa agtggctggg acgacactgc tgtggtcaat | 180 |
| gacctctcat ccacatcatc gggcactgaa tcaggtcctc agtctcctct gacaccagat | 240 |
| ggtaaacgga atcccaaggg cattaagaag tcctggggaa aaatccgaag aactcagtca | 300 |
| ggaaatttct acactgacac gctggggatg gcagagtttc gacgaggtgg gctccgggca | 360 |
| accgcagggc caggactctc taggaccagg gacttcaagg gacagaaaag gtaaggcttg | 420 |
| acccactttc ctttgatctc cctgctctga aaaagaagta tctcccttca aacctgcacg | 480 |
| ggtgaatctt tactcctgtg ttttgcggaa acccctttcc atattctctt ccccagtcaa | 540 |
| gcagtcccta cagtacgtca tttccagcac aatatctcct aagttctgag ttactcagcc | 600 |
| aagatcagta ctcctggagg tcttccacag gattggaata tgacatttta tatctaacca | 660 |
| aaaggcaaaa agtaagctgt aactctcttc agtttagtca cctcaagatt gccatatacc | 720 |
| aatgcagagt acaggtaatt actggttatg atatgtatca ttcagatgtc cgttctcaga | 780 |
| aataatatag tctaggttcc aattaaggaa gaaaagcatt tccctaaatg catcatattg | 840 |
| tttgcagacc tgcatcccct gtggaaggga gtcttagctt attttgcaca tggatatgat | 900 |
| actgcacttc cctggcttgc caaacaggtt tctagtctta ccaggtcctc ctcgtgcatg | 960 |
| agacctggga cctttccaga tccatttatt cttcgatgag tatccccaga ctccaggaag | 1020 |
| cttgaaaaga aacatgagaa tgtgtagacc attagctttt agaggctaga gaatctaagg | 1080 |
| acatagtcta agtaagtcag agaccaattc agagcccttta gaaagtgagc agggaaagc | 1140 |
| tttacctgta tattcaataa ttagatattc taatttactt ggcaattttc tcaatgtaga | 1200 |
| cattactgtt gtttctgatt tatctgagct gaaaaaaaat caagctatag taagcttgaa | 1260 |
| tgattgatct ttgttttaat tctggctagt tcttgaagga ttgactctag aaggggaatc | 1320 |
| attgggtcag ggtataaaaa ctttcctaag acccctcagc attgtcccta gagtaggaga | 1380 |
| gcatggttag ggagctatct gtattctgac agtcactta gggtatgggg tgaccagggt | 1440 |
| cagtagcttt cttttgccaaa ggaaaaaact gcagttccag ccacaggctg ctttgttcaa | 1500 |
| atgtctttgt gctttatgaa ccgtaacagt ggatgagaaa gggaagacgt atgaagaagt | 1560 |
| cctgatgaga ttgttatgtt tatcgtaatg gtgcaaaatg aatttgctcg tggaaaagaa | 1620 |

```
aggccttgtg actcttaact agaaattgat atatgttaat gtcctctggt gatatttata    1680
atttctagat attaatattt aggtgtagct ttaaaactgt tgttgctagt attctttagg    1740
aaaagtactt tgatactgaa agcctccagc cccaaccttt ttttgttcaa taaaacaatt    1800 gattttttt taaatatgat atttgataac attgtgtagg cactctctct cagattatgg    1860
atgaacacat tttattttct ttcttctccc agtaaagtt ttacagagtt acattccagt    1920
cagcactgct ggacagagtg cgcctattac acccacatcc ttgtcagcat tgagtagtta    1980 aattttctt tttcaaagtt ttcta                                           2005

<210> SEQ ID NO 15
<211> LENGTH: 667
<212> TYPE: DNA
<213> ORGANISM: Homo sapien

<400> SEQUENCE: 15
caaatattta tctctggatc gagaaggagg aagggctttg gaaccccagt ctggctcagc      60
cctgcctggt aggaggggga ggaggaaggg gcaggggag ggtgcagccc ctgagaggac      120
aggaacaggg ctgggagtca tgcaaacccg ggttcaaatc ccagctctgc caccacccag     180
ggcagggtcc tcatgcccct gtgcctctgt gtcctccctg gaaacatggt cctaagacca     240
ccctgacgtc tcagggcaaa tgaaggttca gtgcctggaa caggggtagga gtccagctat    300 ggccgcctct atgccaggca ctgggcaagc gtttgtgatc ctgcagggaa gaaggcaaca    360
ggtagcaggt atttctatta gagaaaaaaa aggcgtgcag ggagaaggtc tcacgggta    420 acctacagag ctctgaggag ctggcagcac cggggaatgg gacattcagc acacctcctg    480
cagagggtca aataaatcga tcaatatgcc cccgacgact agacgcacag cagcgctctc   540
ctggtttcac aggcccactc accctaaggg aaaaatggct gggccgccac atggggaaca   600
ggatgcaaaa ttcagaactc aaattcagag catctttttt tttcttttg agacgagtct    660 ctctctg                                                              667

<210> SEQ ID NO 16
<211> LENGTH: 615
<212> TYPE: DNA
<213> ORGANISM: Homo sapien

<400> SEQUENCE: 16
ggttttttag attaacataa gatatttcgt tgttttttct tctgagatga gaaccattag    60
taagaattga aacgttttaa atgttgatt tttttctttt gaggactaaa cagaatggta    120
gcaaggatca aatcagagaa accagggaac agtaaactac tagaaatctt ggtaattttg    180
accagaaggg tagaagtgaa agtgatgaaa tgtggaaagt tctggaagcc ttttgaaagt    240
aaagctgaaa gtatttgctg ttacatttaa cttgagtgag gtgaagacag tgttacagga    300
tatatccaca ttttctgacc tgaacaacta aaggtctgaa tttcctgagg tgaagaatac    360
tattaaataa aagttttagg tcatagggaa tcaagatact ttttttggaca ttttaattt    420 gagatgttga gtgaaaatca agtagaata ttgaatatgc agtttgatat acactttcaa    480
aatttgagaa ataaatttgg gagtaaacat ggatctttaa agcatgtgac aaaatgatac    540
tactcttgaa gtacaaaaat agattctagt tacataagtc tttagaattc aggagctaga    600
aaaaaaaaaa aaggg                                                      615

<210> SEQ ID NO 17
```

<211> LENGTH: 1108
<212> TYPE: DNA
<213> ORGANISM: Homo sapien
<220> FEATURE:
<221> NAME/KEY: misc_feature
<222> LOCATION: (300)..(300)
<223> OTHER INFORMATION: n= a, c, g or t

<400> SEQUENCE: 17

| | | |
|---|---|---|
| gaattttaac aatgttccag atttattaat ttaaaaagtg gccattcatg ctatgcatat | 60 |
| tttagggact gaagcatcaa cagtgaacaa aaaaaccagt ctgtgtcttc cagactttac | 120 |
| atatgaatga gagaaagcat aaagtatgta cacattaaaa aaattatatt tcaaaaagtc | 180 |
| atgaattcta cagagaaaaa cgaaaccaag taagtggtac agggcaggtg gatgagtgtg | 240 |
| gggcgcagca gtgggtgttt tctttcctag ccctctgtga taataatata tatataaacn | 300 |
| aagactagaa ggaagggagg aacaagtcac atgggtgtat aaggaaaggc actctagaag | 360 |
| aagataaata aatgtaacat tcaaaagtcc tgccatcttt gtgcattaaa ggagaggaaa | 420 |
| agtgctctgt gttgatgtat ttcagaaaaa gaggaggaaa atggtagaaa atgagatcaa | 480 |
| gtaggtcact gaaggttttt tagattaaca taagatattt cgttgttttt tcttctgaga | 540 |
| tgagaaccat tagtaagaat tgaaacgttt taaaatgttg atttttttc tttgaggact | 600 |
| aaacagaatg gtagcaagga tcaaatcaga gaaaccaggg aacagtaaac tactagaaat | 660 |
| cttggtaatt ttgaccagaa gggtagaagt gaaagtgatg aaatgtggaa agttctggaa | 720 |
| gcctttgaa agtaaagctg aaagtatttg ctgttacatt taacttgagt gaggtgaaga | 780 |
| cagtgttaca ggatatatcc acattttctg acctgaacaa ctaaaggtct gaatttcctg | 840 |
| aggtgaagaa tactattaaa taaaagtttt aggtcatagg gaatcaagat acttttttgg | 900 |
| acattttaat tttgagatgt tgagtgaaaa tcaaagtaga atattgaata tgcagtttga | 960 |
| tatacacttt caaaatttga gaaataaatt tgggagtaaa catggatctt taaagcatgt | 1020 |
| gacaaaatga tactactctt gaagtacaaa aatagattct agttacataa gtctttagaa | 1080 |
| ttcaggagct agaaaaaaaa aaaaaggg | 1108 |

<210> SEQ ID NO 18
<211> LENGTH: 552
<212> TYPE: DNA
<213> ORGANISM: Homo sapien
<220> FEATURE:
<221> NAME/KEY: misc_feature
<222> LOCATION: (454)..(480)
<223> OTHER INFORMATION: n= a, c, g or t

<400> SEQUENCE: 18

| | | |
|---|---|---|
| caggatatta agtgatatct aacaaaaatc atttcccaaa ttcatgttac agtggttcct | 60 |
| ggtttagctg gaattcaggg aacgacacta ggagtgtttt gtaatcagaa gaatccagca | 120 |
| tcagacagtc cgaccagaca ggaaattgat ttgtcagtct tacacttaaa aacttaatag | 180 |
| tggagaaaca gtattggatt gtctatgttc aatttcacag caatttcctg gcattagtgt | 240 |
| aaggaacaca aagctatgtg tacttttggc gttgatatta tttaagctgg tattctaagc | 300 |
| ttatgagcat aaaattcttta ttgtttttcg caagtatata catatttgta tgcccttgta | 360 |
| gatacatatg taggcatata cattcatgt acataaatat gtaggcatat acattacata | 420 |
| tgcatatata aatacatgaa tacatatata tacnnnnnnn nnnnnnnnn nnnnnnnnn | 480 |
| cttttttacaa ttgattaatg gccaagatgc cactgcaatg cagtgaggaa tatgatggtt | 540 |
| ctgcatccat tg | 552 |

<210> SEQ ID NO 19
<211> LENGTH: 307
<212> TYPE: DNA
<213> ORGANISM: Homo sapien

<400> SEQUENCE: 19

```
tatacaacca gaataataac taacatttct aaaactgaca ataataccaa gtacgcagct      60
gcagcaactg aactcagaaa catttctggt aggaatacaa attgtcacaa taactttgga     120
acactgtata gcagtatctt ccaaacctaa acattacagg gatccaatga tctagcactt     180
ccaccccaga tgcatacaca agtacatatg ttcactgaaa gtcaagtgca agaacgttca     240
aaagagccaa aactagaagc aacacatatg tttatcaaca gtagagatga taaaatatat     300
ttggata                                                               307
```

<210> SEQ ID NO 20
<211> LENGTH: 602
<212> TYPE: DNA
<213> ORGANISM: Homo sapien

<400> SEQUENCE: 20

```
gggacaagaa agactaagaa aatggctgtg tgctgttgtt tcagttttga atattgtctc      60
attgctttct aataatttag ctcttgttaa tatcaacaaa gtaaataaat cataatgttt     120
tggcttgaac ccaaagtagc tttcaaatgt attaatatac cctaaggaaa tatacaatgt     180
aagtggtaac caacaaatgg gtcttcatat tgttgttgct ttggaatcct tagaggtaaa     240
aagtatttta tccgtctttt aaatgatgaa ctaaatactt ttcaaatatt ggcttcatag     300
agtgtaataa ccatatgaaa atccaaatta acataatatg ttctctccag aaataaactg     360
tacaatgtgg acttaacgtg gcagggtggg ccacttgcaa acatgaccta agcaatgaga     420
aattgaattc aggaaattta gttttctttt cttttctct tttctctctg ccttttggg      480
acaactttcc attgagggag ataaaatatt caggaaaaaa tactctaagg agtcaaagaa     540
atttgtttaa atgagtaaca ttaatctttg tgttgagact gaattttgct gataaaaatc     600
tg                                                                    602
```

<210> SEQ ID NO 21
<211> LENGTH: 934
<212> TYPE: DNA
<213> ORGANISM: Homo sapien

<400> SEQUENCE: 21

```
gggacaagaa agactaagaa aatggctgtg tgctgttgtt tcagttttga atattgtctc      60
attgctttct aataatttag ctcttgttaa tatcaacaaa gtaaataaat cataatgttt     120
tggcttgaac ccaaagtagc tttcaaatgt attaatatac cctaaggaaa tatacaatgt     180
aagtggtaac caacaaatgg gtcttcatat tgttgttgct ttggaatcct tagaggtaaa     240
aagtatttta tccgtctttt aaatgatgaa ctaaatactt ttcaaatatt ggcttcatag     300
agtgtaataa ccatatgaaa atccaaatta acataatatg ttctctccag aaataaactg     360
tacaatgtgg acttaacgtg gcagggtggg ccacttgcaa acatgaccta agcaatgaga     420
aattgaattc aggaaattta gttttctttt cttttctct tttctctctg ccttttggg      480
acaactttcc attgagggag ataaaatatt caggaaaaaa tactctaagg agtcaaaaga     540
aatttgttta aatgagtaaa cattaaatct ttgtgttgag actgaatttt gcatgataaa     600
```

| | |
|---|---|
| aatctgcttt ttgggttgga ggaacggtgc gttgcactgc tctcatggga caattgtgta | 660 |
| atattttggc acgaaaatgg gttatcagac accaaagaat tgtgtacctc agaaaagcca | 720 |
| aagtaacaat tggtttgagg tgaaggaaa atctaagtga tgaaattcag agtctggaag | 780 |
| agaatatgtt ggtgtttgat tgggtgtagt gggaagaatt tctttgccta ggagtacttc | 840 |
| attatctaaa tggttgttgt atatgtttca tcctaaaata cttttaagtt ggaatgtgca | 900 |
| tgcaattcaa gtttatcttc ttgaaatctg gtaa | 934 |

<210> SEQ ID NO 22
<211> LENGTH: 568
<212> TYPE: DNA
<213> ORGANISM: Homo sapien

<400> SEQUENCE: 22

| | |
|---|---|
| tgatcttgtt actcttttag ctctaagagg tgaacattat agccttttgg gaataaggta | 60 |
| cactgcctac atttcagtgt gtaattttac aaacctctcc atatggcttg ccctaaaatt | 120 |
| ttaatatatg tcctaaaggg caaatgtagc ataaaccaga ttatggtact ttggcacaag | 180 |
| cttttcactc acgagctgaa tgctaactaa gttacaaact taattttgct ttttcatatt | 240 |
| ttttgaactt gttttggccc catgaaatgc tttgatatct ggaattttct tccactgttt | 300 |
| catttcgctg tgaatcagtc tgaatttaga tccattatgt ggatatatga aacgtcagc | 360 |
| aatggtctct tttagaaagg cctgaattcg tggaacaaag aattaggcta tgccctgatg | 420 |
| gtgatttctt tctatagaat ttctttatat tgggcctgag tgagctttag aagtgaagac | 480 |
| ctggagagta tttcagattg tctctagctt cagtgtatcc acagcactag tgaattgtta | 540 |
| ctctaatccc gaaccagcag gatcagca | 568 |

<210> SEQ ID NO 23
<211> LENGTH: 969
<212> TYPE: DNA
<213> ORGANISM: Homo sapien
<220> FEATURE:
<221> NAME/KEY: misc_feature
<222> LOCATION: (610)..(712)
<223> OTHER INFORMATION: n= a, c, g or t

<400> SEQUENCE: 23

| | |
|---|---|
| tgatcttgtt actcttttag ctctaagagg tgaacattat agccttttgg gaataaggta | 60 |
| cactgcctac atttcagtgt gtaattttac aaacctctcc atatggcttg ccctaaaatt | 120 |
| ttaatatatg tcctaaaggg caaatgtagc ataaaccaga ttatggtact ttggcacaag | 180 |
| cttttcactc acgagctgaa tgctaactaa gttacaaact taattttgct ttttcatatt | 240 |
| ttttgaactt gttttggccc catgaaatgc tttgatatct ggaattttct tccactgttt | 300 |
| catttcgctg tgaatcagtc tgaatttaga tccattatgt ggatatatga aacgtcagc | 360 |
| aatggtctct tttagaaagg cctgaattcg tggaacaaag aattaggcta tgccctgatg | 420 |
| gtgatttctt tctatagaat ttctttatat tgggcctgag tgagctttag aagtgaagac | 480 |
| ctggagagta tttcagattg tctctagctt cagtgtatcc acagcactag tgaattgtta | 540 |
| ctctaatccc gaaccagcag gatcagcatc cctgagagtt tgtcagaaat gcaaattctc | 600 |
| tggctattgn nnnnnnnnn nnnnnnnnnn nnnnnnnnnn nnnnnnnnnn nnnnnnnnnn | 660 |
| nnnnnnnnnn nnnnnnnnnn nnnnnnnnnn nnnnnnnnnn nnnnnnnnnn nnattctaac | 720 |
| ccacgattgt gttactggt ggccctcaaa ccatagctta ggaatctaag aacttcaaga | 780 |
| aaattttgag ccttaatctt taaagcagtt attgaatctg tgggtcaaac gagaaaagga | 840 |

```
gtacttgaaa cctagagttg cgttttcact tgagaagaca cactttggaa acacctatcc        900
aacagactac aaatataggc tattaaatta aaaatctggt ttcaaaataa tacccactta        960
ggttggtaa                                                               969
```

<210> SEQ ID NO 24
<211> LENGTH: 870
<212> TYPE: DNA
<213> ORGANISM: Homo sapien

<400> SEQUENCE: 24

```
cacgaagcta agttttcaac tcacaaactc ttggtgataa agaactaaa ggatgttctt         60 cagtaaagag aaaataaat gcagaaagaa gtggaatact aaagcaaaga gtgttaaaat        120
atgagctaaa gctaatatgc ttcaaaagct agaactaaat cttagcaata ataatatggt       180
attaaagatg taaatgtgtg ctaaagtcct tgttttgagt agaaaagata cagatgaatg       240
ttatagactt ttaaaaaata tatatttaaa taagtatgtt aaatataagg gtatccagta       300
tagtaataga aatatagaaa tagaaggtac aagtccttaa tcagtagggg aaagagaaaa       360
gataggtaat attttaaatg ctttcactcc attcaataga gggcaggaaa gaagataaaa       420
agaagcaaag gaaaaacatg gaaataggaa atacaaaata aaatatgtaa gtagtcataa       480
tataaattaa tctacaaagc cagagagata gtcagattat ccttccatat gctgttttca      540
aagtaacact gaaagataaa aaaatacaag tataagacag gaaaaatttt ctcttggtta       600
ccaccaagtg aaagctggca gcatgaacat catttgaaac atgaacatgt ttttgcttaa       660
aaacagcaaa tgacagaaat atatgtctca cttataaata aggaacaatc catgaagatg       720
atataaaatg actctagata ctgaaaatat actctcaaaa tatataaaac aaaaccgaca       780
gaattatcaa gaaatagcat atccacagtc agtgttgcag attttaacac acctctctta       840
gaaaccagta tatcaaaaaa aaaaaaaagg                                        870
```

<210> SEQ ID NO 25
<211> LENGTH: 3795
<212> TYPE: DNA
<213> ORGANISM: Homo sapien
<220> FEATURE:
<221> NAME/KEY: misc_feature
<222> LOCATION: (3362)..(3362)
<223> OTHER INFORMATION: n= a, c, g or t

<400> SEQUENCE: 25

```
cctttttttt tttttttgata tactggtttc taagagaggt gtgttaaaat ctgcaacact         60
gactgtggat atgctatttc ttgataattc tgtcggtttt gttttatata ttttgagagt       120
atattttcag tatctagagt catttttatat catcttcatg gattgttcct tatttataag       180
tgagacatat atttctgtca tttgctgttt ttaagcaaaa acatgttcat gtttcaaatg       240
atgttcatgc tgccagcttt cacttggtgg taaccaagag aaaattttc ctgtcttata        300 cttgtatttt tttatctttc agtgttactt tgaaaacagc atatggaagg ataatctgac       360
tatctctctg gctttgtaga ttaatttata ttatgactac ttacatattt tatttttgtat     420 ttcctatttc catgttttc ctttgcttct ttttatcttc tttcctgccc tctattgaat       480
ggagtgaaag catttaaaat attacctatc ttttctcttt cccctactga ttaaggactt      540
gtaccttcta tttctatatt tctattacta tactggatac ccttatattt aacatactta      600
tttaaatata tattttttaa aagtctataa cattcatctg tatcttttct actcaaaaca      660
```

```
aggactttag cacacattta catctttaat accatattat tattgctaag atttagttct      720
agcttttgaa gcatattagc tttagctcat attttaacac tctttgcttt agtattccac      780
ttctttctgc atttatttt ctctttactg aagaacatcc tttagttctt ttatcaccaa       840
gagtttgtga gttgaaaact tagcttcgtg tatctgaaga tgtgtttatt ttgctcccac      900
tctgtatata aaccactgta tgaaactgga agctcacagt tatttttcta cagcactttg      960
aagatactag tcagttttct ggtatctact gttgccaaag cctactgcca atttgactac     1020
cattccatta ttcagaattt tttcttatac ttgtattcag aatttcagat tttctcttta     1080
tcattaattt cctacgattt tattatcatg tatgtagttg tggatttatc tatcctgtgt     1140
tacatatggc agcattttct attttgaaga ctcagcttca tttctgaaaa aattcttagc     1200
tgcagttatt gttattatta ttgccacttt ttattcatt ctttttctc ctttgcaact       1260 cctagcagat gtatgttaga gcttctcagg tcatctttca tgtccatctt tctctttcat     1320
tttcttctaa ctctctctaa actgcattct gaaagatttt ctcagttcta tttcctaatt     1380
ctgtaatttt ctcttaagct atagaaagta tgtgcagtct aactgttctt ttacttcaat     1440
attgtattta taatatttt cacttcaaga tgtctaaacg cttcttttctc acagctttct    1500 cttcttgttt cattatctgt tcttcattct gtaaaatcta acttcttctg tacatatatt     1560
gagaatttta acttatttt aaactctcac cagattgttc ttcttttctc aggtataaat      1620
tctctcattt gttgggttct cttgactgct ttttcatgat cttaggtttt actgggttct     1680
ttgtaatgtt ttgggggctc aattttatg ataactaaaa aatgtaagta cctgtatcta      1740
tagggcagtt ttaagttgcc tcagcttaaa tctgataatg tgccaacctt gaaccagacc     1800
ttaagttggt agctctgggt cttctttcct cctaggtagc ccagttctga atttttagcc     1860
caaaagtatt ttgggtccaa gtcctatctt gagtggtttc ctgcgcttgc ttgtgactgc     1920
caattcttct ttacttctgg tcaggaacaa gcagcttatt cctggctgtg acactgctgg     1980
gataagttag attagcccag ctcctatttg tattgtgctc ttgggtcctg ggttcatgca     2040
cagacaggat cattgcaaaa aaacctggtc ccaattgccc atatccattc atagcacccc     2100
ccgatcccct gccatcatag tggcttttct attactggcc caaagagact tttctttctt     2160 attttaaga ataactatgt attttttaaa acctttaaaa atatttatgc ataatttctc       2220 tgttttgaa tgagaggaat aagattcagg agtattcact ctgccaccct gacctagaag      2280
tcccagagta gctttcactt ttgaaataac agcagttcaa ttttcctgat ctcaccagtc     2340
tgtaaacatt agcatatata ctcaaagttc aaacttgaat aagctgtagt agagacaaat     2400
ttccattatt tggaatttgt ttacattgaa ataaataata gatgtactag gaaatcagaa     2460
atggaaggaa gatgacttta aaagggttaa gaaacttggg acagcagcag actttactgt     2520
aaatcttatg tacaaactcc accactgctt cccataaatg gaatcagact gagcaaagaa     2580
gagggtactt tccacagcac cagaaagagc cactgcagcc agcagagtcc tgtaataagt     2640
accaacctgc actcctgcac ctggaagaca gccatcagct tagtggaaag aatgctggac     2700
tgggaattca gaaatgttct agttcatttt ctaccactaa gtcattgtac agcttaggct     2760
aagccaggcc ctcttttggg ccccaggttt tccatctgta aaataagaga gttgggctag     2820
aacaacttct aatgtacctt ccagaaataa ttttctgtga ccttaacagt ttggtacttt     2880
ataagtaggc tgagtcctcc attcttcagc ttgctcagaa ataatctgcc aggtaaaaga     2940
agaaaataat gtgtttctga aatcagtttt caaatcaaat gaaagaatca ccagatgcat     3000 attttttgttt gatcaccact ctacaaagga atagcctggt agctggatga agtttctgtg   3060
```

-continued

```
tgggtgtaca cacaatctaa gttttaaata gaaaaagcaa accaacccag accaaaacaa    3120
aaaccctcca cacaagtccc agacgcaaca aatggtaaga gttcttttct acaaacatgt    3180
ctgtttctaa tagctgagaa gaccaaaaaa gaaaaaaatg tatcaaactg ccaagatata    3240
tgtgtagata agaaaaaaac taaggagcat gcagcaaagt tacaggatat gagagatttg    3300
actctgcaca ctgcaaagtc tgtacaatta gaaatttcat gtgaacagaa atgtagggaa    3360
gncaatgaga aagaaagaa taaaattgga gttccactaa atggaagtta agagtggatt    3420 aataatttt aaattgaggc caggcacagt ggttcacgcc tgtaatccca gccccatgtc    3480
attactataa aacagatagg cattatattt gaattttac cttttcatt tcatcttcaa    3540 atgccttctc caaatactta tatctcctga tgagtttatt gaagacctaa aaaaaaaaca    3600
accattaaat attaggtcaa ccaaaaagac acagaagtag gtaatagaaa ctcactataa    3660
tgacaccata gatctataat aataaaagtg tatagttaaa caggctcaca ctgtaatata    3720
agaactataa gcatttcaaa gatgctatca tgacctaggg gaacaaatat gatcaaaatg    3780
tacacgtaag ataag                                                      3795
```

<210> SEQ ID NO 26
<211> LENGTH: 618
<212> TYPE: DNA
<213> ORGANISM: Homo sapien

<400> SEQUENCE: 26

```
aaaatattta agaggcattt aagagcaaat caatgagatt tggagattaa ttttgtaga    60 aggtgaggga aaaggaggca tcaaggttga tcccaagtgt gtgggttagg caaaaggatg    120
aataatagat ggatgctacc tcccttttcc ccacgcagaa ataaagggaa aggagagggc    180
ctgggtgggt ggatcagcag gcagacaggt gagtgtgagg ggacaatcag gagggaggtc    240 cacccctgaaa tcagatatgt cagtccactt aggtttccaa caattgactc tgaactcctg    300
gaatctgtgt ccagcatctc tgatgctgtt ggttcatcta aaagtggcaa atattcctgc    360
acatttgtcc ccgaatcctc aaattaaatg tcaccttctc agacagatct tcccacacca    420
cctaagctct tctcctaccc cacactgatt ccccaccatt gcactcttcc atcttccctc    480
acagcaagta ccatgtttgc taattttatat ttacctgttt gctttcttgt ttcttatctg    540
actccccact agtcattcag cactgtaagg tcaggggttg tatgttgttc ccactccaga    600
tctacacagt gacagtca                                                  618
```

<210> SEQ ID NO 27
<211> LENGTH: 451
<212> TYPE: DNA
<213> ORGANISM: Homo sapien

<400> SEQUENCE: 27

```
ggtaccatgt atccccacca tccaggacca gccagatgac atcagggtgc ggagaggcag    60
ttaggcctcc cctcattgta tagcagagtc ttgttttaat gaaaaagtcc cactttcttc    120
cccgactgaa actcccttaa gtccatataa gtcactgtgg atggagaggt actgttaccg    180
tagctgtgtg tgtactgaag gggcaccctct acaaccgaca gtggccagaa gtgagaaaat    240
aaaatggaga gtagtctaga aacatgtgcc tcatccaacc cactccgcct gaaaaaaact    300
tccttccttt ctcaagagac acctgggcgc ttttcattc tccctaccac gtggccaaat    360
gctcacaact aatgcttaag ttctgaagtt tacccaggta gagacggaat cattgatgac    420
```

-continued

| atttatgtgt tcactcaaaa caaacgaacg g | 451 |

<210> SEQ ID NO 28
<211> LENGTH: 573
<212> TYPE: DNA
<213> ORGANISM: Homo sapien
<400> SEQUENCE: 28

| ggaactgcct cttctctgct ggacagagtc taccaggctc cctctgccct gccctgccat | 60 |
| agggtggaca tgtgacccac ctagccagta agattgtcca ctcctctaat tcatgggcag | 120 |
| aaggacaagg acagtcagag tctcccggct gcctcctgcc acgcattcct gctccccacc | 180 |
| cccaatctat gcgcttgccc ttcccgcctt ttggccctca ggagctgtct tggttcctgc | 240 |
| ccttgcccag gcctgttttt ccagccttcc caccaatttt ctgagctcct gtgggtgtgc | 300 |
| ctatcttgtg tgggtttggt tttggctttt aaatgagcaa aggcagaatg agggtgccat | 360 |
| gagcacagat gaggcttttg ggaaacgccc cccttccatt gcactgttgg aagggagtgt | 420 |
| agaggctgct gtgtttcctg ggccggcca ccttgacacc gtgcctgcat gcacgcagcc | 480 |
| ccccagcacg cttcttcacc agccagcctg agtgcagggc cctggccagc cttgccggga | 540 |
| ggaaatgcca gcccccgttt ctttaagcct cag | 573 |

<210> SEQ ID NO 29
<211> LENGTH: 643
<212> TYPE: DNA
<213> ORGANISM: Homo sapien
<400> SEQUENCE: 29

| tagcacagcc ctttacccag ttccctggga agcctgggtg gagaggccgg agcaaaggtc | 60 |
| tggggctgaa catgccttaa ctggagcctg gcctgctcca gggcccccgt ggggaggtgc | 120 |
| agggccggga gggagggagt cctgaagagg cttgcaattt ccctggtgca cagccccact | 180 |
| gcaggcccctt caggaaacgt ccctggaggc tgtgagcttg gccacccca gcccatctca | 240 |
| gcccctcag ctgccggcca gcccagctcc actcccagtt cggtgccaag cctttccagc | 300 |
| ccgctccagc ccacgcagct ctctctcctc tgaactctca catacccata attacaactg | 360 |
| accatatttt ccaaagcaga aatcaagaaa ccactaaata aaggatttct ggctacttc | 420 |
| tgagtgtcag aggcagcctg ggaggtgaag tttggatgca gaggtattca aatctctgag | 480 |
| acacgttgat agtttttttgc gatgactact atatctatca tattttatta ataagtcaaa | 540 |
| gccatcctag gaaatgtgtg ttgggcacat gccacccata ccactgttaa ctgttgacgt | 600 |
| ggacacttta gcctggcagt tcctagctgt gtggcctggg caa | 643 |

<210> SEQ ID NO 30
<211> LENGTH: 761
<212> TYPE: DNA
<213> ORGANISM: Homo sapien
<400> SEQUENCE: 30

| ccctgccaca ctcagaggac ccaaaagagg cctcagtggg gatctgggta gaataaaaga | 60 |
| ggcagtagca caccaagtca ccaacatggc cccagacatt ccacaccctt accctgtaag | 120 |
| tcctcttttta agacttcctc taactcatga ttgctctccc agacagacac acggccacca | 180 |
| gctgcactcc tatttccagc cactcagctg gctttgcaag cctgccagga gcacagatat | 240 |
| ggtcctccct tattctgtca ctaagctgtc cttgtcacct tgggacacca gctgcctaga | 300 |
| aggcagacaa tgaatggagg ccaagcactg tctgtgctgg ggacactgtg ctgggggcag | 360 |

-continued

| | |
|---|---|
| gttccaccct gggacaagca aagacaggca gaatataagc tagagatagg cagagttttc | 420 |
| aatggagaca ccaggggaca gactgggtct gtaagggaca ggagggaagc aaggactgtt | 480 |
| gaagcaagga cggttggttc cctctctaac ctgcacagta ttccactcac tccctgtaac | 540 |
| tagaagagac agccgcgaaa ccagtatcct aggcaagggg tagctgctgt ccttagccac | 600 |
| acccggtaga acagcagcca gaaaaggggc ccagagcctc cagcaggcca aagccatgtt | 660 |
| tccatgggat ggcaaggtca gcaatatccc aggctcagcc agaaagtcct gtggcagcac | 720 |
| catgtctgga gagaccga gagaagaatg ttggacagag a | 761 |

<210> SEQ ID NO 31
<211> LENGTH: 1658
<212> TYPE: DNA
<213> ORGANISM: Homo sapien

<400> SEQUENCE: 31

| | |
|---|---|
| cacatctgag gtttcagaga gagggagaac ttttcatgtc agagccgagg aggttgcact | 60 |
| gacttgggaa tggcagttga tgacagggat tctggctttg aaatgcattc tcttagagat | 120 |
| gcaatggttc agtaacaagg gactctagga tgatcaaagg agatttgagt gaagggaaac | 180 |
| cattccattc agtggaatcc tccatctgac ctccattaca cagatggacg aaagtgagtc | 240 |
| tcacagagaa cctagcactt gcccaaagtt atagactgaa tcagaagcaa tgctgagact | 300 |
| aaaaccaagt ctcccaactc ctaaccatgg gatggatggg agaggcaccc cgagtctgat | 360 |
| gtttctgctg gggtgatcct ccaccccact gatttagagg ctgtgggagg gtctgggca | 420 |
| gggtgctggg gaagcctgcc aggctcagct gcagccctc cagccagagc tcttcctgtg | 480 |
| gccccactca cagaagggca ttacctgcta gttagcatag cctcccacct tctggggttg | 540 |
| ttatggaaac caaacctgga ggggaaggga ggaagggcag agaggagggt ggcaattcct | 600 |
| gcagtcacta acggcgtggg cttcaccatc tcaagataag ggaggggcag gaagaaggct | 660 |
| tccctgcagt ggggctggtg atgggatagg attctcaacc accaccctt gctctttctg | 720 |
| cccctgtctg ctgtccagct gtctgcctct ggccagcagc ttagccatca ctgaaggagc | 780 |
| agactggctt ggaggagggt tttgccagcc tgagagggc aaagctctga cccctcacgt | 840 |
| gacccccacac ttgccacctc tgcaactggc cctgtgtcat accaagcatt cctccagccc | 900 |
| tgccacactc agaggaccca aaagaggcct cagtggggat ctgggtagaa taaaagaggc | 960 |
| agtagcacac caagtcacca acatggcccc agacattcca cacccttacc ctgtaagtcc | 1020 |
| tcttttaaga cttcctctaa ctcatgattg ctctcccaga cagacacacg gccaccagct | 1080 |
| gcactcctat ttccagccac tcagctggct ttgcaagcct gccaggagca cagatatggt | 1140 |
| cctcccttat tctgtcacta agctgtcctt gtcaccttgg gacaccagct gcctagaagg | 1200 |
| cagacaatga atgagggcca agcactgtct gtgctggga cactgtgctg ggggcaggtt | 1260 |
| ccaccctggg acaagcaaag acaggcagaa tataagctag atagggcag agttttcaat | 1320 |
| ggagacacca ggggacagac tgggtctgta agggacagga gggaagcaag gactgttgaa | 1380 |
| gcaaggacgg ttggttccct ctctaacctg cacagtattc cactcactcc ctgtaactag | 1440 |
| aagagacagc cgcgaaacca gtatcctagg caagggtag ctgctgtcct tagccacacc | 1500 |
| cggtagaaca gcagccagaa aagggcccca gagcctccag caggccaaag ccatgtttcc | 1560 |
| atgggatggc aaggtcagca atatcccagg ctcagccaga aagtcctgtg gcagcaccat | 1620 |
| gtctggagag agaccgagag aagaatgttg gacagaga | 1658 |

```
<210> SEQ ID NO 32
<211> LENGTH: 627
<212> TYPE: DNA
<213> ORGANISM: Homo sapien

<400> SEQUENCE: 32
gtgaagggtc acatcattat ttccctcaag gtcttttgtg caaagtaatt ggcacagggc      60
agctaactat gtggcaggag acaaggctat acttcgctgt ctaaatgaga acaattccca     120
tctgactgat attaatttgt attttagtca aggcctctgc tgagaaacaa gaactaaggt     180
agcagcaaaa atctcttctt actttacttg ggtacctgtg aagtccactt gggatagtga     240
aggagaaatc cgcattcctc tccctggtga gtgtgagacc cagtgaccac cacaccatct     300
tgatgacaaa tcacgcatca tcagaggcct acctccttct ccgtaatgtc ttggagctaa     360
ctggtctcat cgtgtcccag atcttcagtt caaactcttc cccaagtctg gactgctttc     420
tatctctcta attcacacac ccagatattt ttcttttgac agccaacaca aaccccattg     480
cttgagaaat ctgctccaat taccctgaga ttcaaatctt gattcagctg tgatgctgga     540
cagctaaccc aaatttgctg agccccaata tcctaattta gaaaatgaaa tactaatatt     600
taagatatgt ggcttttgag gattatg                                         627

<210> SEQ ID NO 33
<211> LENGTH: 1212
<212> TYPE: DNA
<213> ORGANISM: Homo sapien

<400> SEQUENCE: 33
tttatgcttc caccaaaggt tttgggtaga aagaagatat ttttgatata taatatcata      60
gtactataat tttaaaacta gcttttcaga caaatgtgtc cactcaggca caggtaccgt     120
ggacccccaa agcaggagat gcttcacact acctcaatga agccaccgtc accactactc     180
actcactgaa cagatattta ctgggcatac actacatact aggtgacttt ctaacccagt     240
gctactccaa gtgtggtcca tggaacagaa ccagaccatg gactgtttgt tactggtctg     300
ctacaagata agtacaaaaa tgaagagtaa gcatctagaa acatagcata aatgacactg     360
ccatttaatc agtggtctca tttcgctgga cagagtatag acaagctcag gagttgtcac     420
actactgtgg tgagttactg tggctgttgt ccaggcacat gccatgctgt ctagcctttg     480
taagacatgg aagcaaggga gtgataaaat cacatgtacg ttttaggcag atgccttctg     540
cctaaagatg aggaaaggac aagaaggagg gtgctgaact acattgtgaa gggtcacatc     600
attatttccc tcaaggtctt ttgtgcaaag taattggcac agggcagcta actatgtggc     660
aggagacaag gctatacttc gctgtctaaa tgagaacaat tcccatctga ctgatattaa     720
tttgtatttt agtcaaggcc tctgctgaga acaagaact aaggtagcag caaaatctc      780
ttcttacttt acttgggtac ctgtgaagtc cacttggat agtgaaggag aaatccgcat     840
tcctctccct ggtgagtgtg agacccagtg accaccacac catcttgatg acaaatcacg     900
catcatcaga ggcctacctc cttctccgta atgtcttgga gctaactggt ctcatcgtgt     960
cccagatctt cagttcaaac tcttccccaa gtctggactg ctttctatct ctctaattca    1020
cacacccaga tatttttctt ttgacagcca acacaaaccc cattgcttga gaaatctgct    1080
ccaattaccc tgagattcaa atcttgattc agctgtgatg ctggacagct aacccaaatt    1140
tgctgagccc caatatccta atttagaaaa tgaaatacta atatttaaga tatgtggctt    1200
ttgaggatta tg                                                        1212
```

<210> SEQ ID NO 34
<211> LENGTH: 447
<212> TYPE: DNA
<213> ORGANISM: Homo sapien

<400> SEQUENCE: 34

```
ggctgtcccc cccaaaaaag tttatatatg taatgtataa acataaaata gtgattaccg      60
aattgctctc tagaaaagtc ttaagtgtca aaatcttaaa tgccattctc cttgtcccca     120
cagttctaca ttttgaaatc tattctaagg aaagaagata agtgtgtaga tatccagacg     180
tgtgtggagg tcgggctgc attatttata aaggagtac ttgttaaacc tgctggcatt      240
tctgcactgt ggcatcctcc atgtgtagac aggcagaagt gtgcagtgta agagggaaag    300
gcggggtctg gagcagtccc cgggccactc ctggttttaa gtacatgggt ctctaaggta    360
accatcagag gtgaggagac ggggtacact tttcttttat acatggtggt attgtagaga   420
ttcttttggt aagcgtgtat tactttt                                         447
```

<210> SEQ ID NO 35
<211> LENGTH: 1078
<212> TYPE: DNA
<213> ORGANISM: Homo sapien

<400> SEQUENCE: 35

```
ggctgtcccc cccaaaaaag tttatatatg taatgtataa acataaaata gtgattaccg      60
aattgctctc tagaaaagtc ttaagtgtca aaatcttaaa tgccattctc cttgtcccca     120
cagttctaca ttttgaaatc tattctaagg aaagaagata agtgtgtaga tatccagacg     180
tgtgtggagg tcgggctgc attatttata aaggagtac ttgttaaacc tgctggcatt      240
tctgcactgt ggcatcctcc atgtgtagac aggcagaagt gtgcagtgta agagggaaag    300
gtggggtctg gagcagtccc cgggccactc ctggttttaa gtacatgggt ctctaaggta    360
accatcagag gtgaggagac ggggtacact tttcttttat acatggtggt attgtagaga   420
ttcttttggt aagcgtgtat tacttttta cagtagtaat ttgaaaacat ttagatatct    480
tcattggaaa gaaagtact ctttaagtcc ttggcaagtt gataaatatg ctttgcaata     540
gaagaattta gggcatttg ttttctaac tcacatgtaa gctcttcaag gtggggactg       600
accctcgggg tctgagcggg gctctgctac agcccatcct acaaacagtc tcccaggttt     660
ccatccagaa gcaggtttgt acctctcatt cccttgcttg aaaccctggc atgactttcc    720
tgtattctta ggatcctaag gtctcagggt ccctggaagg cctgcctgat cctggcctct    780
gttttaccag cctcatctga tagcacttgc tgtgtttgtg gagtttcagc tgccacctgc    840
tttactttct agctctctct aagtcccctt tgacctcggg gcctttgcac acactgttcc    900
ccttccttgg aatggcctcc ctttaccttc ctcttctcca gccctcagt tcatgctcat      960
cctctcatcc tttgatcccc tgttaaactt agcctaatag cttttttcct cctttctaac   1020
agcatcccat tgtgcaattt caggaaggag ctcattgtga ccttagttgt ttaatgcc     1078
```

<210> SEQ ID NO 36
<211> LENGTH: 424
<212> TYPE: DNA
<213> ORGANISM: Homo sapien

<400> SEQUENCE: 36

```
aagatagtca catgggttac taagaatcag gtagacaaga aatgaaacaa gaatcttaaa    60
```

```
ttttgttttt gacatcaaaa ctcctcttca tctaatatttt tacccagaaa cccaatatgt    120
aacaaattga gaatgaaatg ctttctctaa agccagttga gaggcccaaa tccccaagaa    180
ttcatcctct acccaagtac ccaaagtacc tatgaataca tttcaaaaac cacttcaata    240
aaacaattaa atgaatatac aaactgacat acagaaaggt agtgatgtca tcagatataa    300
actgcttgca gaaaggcagt tccattaaat tcacactaca gttcaaagag ttccttggtc    360
agcttatgaa cagactcatc tgaaattcaa tgtttgaagg atcgactggg tgcagtggct    420
caca                                                                 424
```

```
<210> SEQ ID NO 37
<211> LENGTH: 860
<212> TYPE: DNA
<213> ORGANISM: Homo sapien

<400> SEQUENCE: 37
tgtgccttgg gccttggcca ctcatattgg gccctagaat atttatttct tcaaacattc     60
tacagagttt gactctttct tgttgacact agtcagcttg agacgtgcaa ttatttactg    120
gcaatcttaa agctcaaaat accaggatct aagacaaagg tagctaaaac tgaatcacaa    180
tcaaactgac ttcataatta atgctttaat caggaaagtc tcagcatatt ccttaagata    240
ctcaagcact cacgtcaaga aaatttctct aaataaaccc tgtaaagttt gccattgttc    300
ctagccacat ttttctggtg tttctaatag atcatttgtt ctagaaaaca cttagaatct    360
gaaacccaaa ggttgagcat gtagacttca tgaaagccca atcccctaaa acctgaaatg    420
cccaggaatt ttctcaattt gagtaaaaag atttactgtt caagttatgt aaaaccaaat    480
cctgtgaatt tgacttttga aagaattaca gtcacacagc aaaattcact ttaagatgca    540
atgcaaccca caccatgaat ctgttaattc tgtctttgtc aaactaccca aaaaatcaat    600
ttgtctttct tgttattgca ggaaatagag gtttatgcct cattaatcag aagggagca    660 gtttaggagc agttatttac taagccctt aagttatact agacagacca ttttaaaatc    720
acagtatcat tttagaaaaa tacagtccaa atagcaagtt tagggtacca atcatttaaa    780
atgtaataga gatgagtaca catagacaca ctcacaacct taacactgag cttgaggaaa    840
gtataaagct tgctcatttt                                                860
```

```
<210> SEQ ID NO 38
<211> LENGTH: 272
<212> TYPE: DNA
<213> ORGANISM: Homo sapien

<400> SEQUENCE: 38
cattttgact gtctttacag aaaaagttta ttgacccgtg gtgtagataa gaaatcattg     60
tgacctgagt gagaatatta gtcaatgtaa ctcttcaagg taatgaaaag agtactgagc    120
tatgatttaa acttaactgc agagaagtct agcatattcc agttatcagc agtgtagcat    180
gataactaaa ttacttgacc tttcagaatc ttagtttct caattgttaa atgaacatac    240
tgatactatt ctactcactt cacagtctta aa                                  272
```

```
<210> SEQ ID NO 39
<211> LENGTH: 207
<212> TYPE: DNA
<213> ORGANISM: Homo sapien

<400> SEQUENCE: 39
ctgagcctgt cggtgcatca ggagcagtgc actgcacagc gagatccggg ccagctggaa     60
```

-continued

```
gggaggggt    tgcagaggt    gccggagcca   gatggaaccc   tgtggtgcct   ggggaggaac    120
ttggattttg   gattgagggg   cagccggcac   gtgcagtggc   agcagtttgg   gcaaggaggt    180
gatgaactga   gttgcttttt   gttgaga                                              207

<210> SEQ ID NO 40
<211> LENGTH: 134
<212> TYPE: DNA
<213> ORGANISM: Homo sapien

<400> SEQUENCE: 40
gtgtgagcta   ccaccactgg   cagttaagaa   ttttaacaat   ttgtcaatga   aacaagaatc    60
tcaattagag   tctttatata   caatctgtac   tgttggaatt   ttcaaataaa   tattgtaaag   120
aaaattaaca   aaac                                                             134

<210> SEQ ID NO 41
<211> LENGTH: 546
<212> TYPE: DNA
<213> ORGANISM: Homo sapien

<400> SEQUENCE: 41
ccaatgaata   caaagcagag   atttaagaag   ttgaaagaca   gattttacag   ggtgaacaaa    60
gttacagttc   tgcactagaa   ggaatgaaga   tggaaatctc   ccatctaact   caggagttac   120
atcagcgaga   tatcactatt   gcttccacca   aaggttcttc   ctcagacatg   gaaaagcgac   180
tcagagcaga   gatgcaaaag   gcagaagaca   agcagtagaa   gcataaggag   attttggatc   240
agctggagtc   actcaaatta   gaaaatcgtc   atctttctga   aatggtgatg   aaattggaat   300
tgggtttaca   tgagagatgg   ggttttacca   tgttgtccag   tctggttttg   aacttcggga   360
ttcaagcaat   ccgccagcct   cagcgtccca   aagtgctgga   attacaagtg   tgagctacca   420
ccactggcag   ttaagaattt   taacaatttg   tcaatgaaac   aagaatctca   attagagtct   480
ttatatacaa   tctgtactgt   tggaattttc   aaataaatat   tgtaaagaaa   attaaaaaaa   540
aaaaaa                                                                       546

<210> SEQ ID NO 42
<211> LENGTH: 1134
<212> TYPE: DNA
<213> ORGANISM: Homo sapien
<220> FEATURE:
<221> NAME/KEY: misc_feature
<222> LOCATION: (500)..(500)
<223> OTHER INFORMATION: n= a, c, g or t
<220> FEATURE:
<221> NAME/KEY: misc_feature
<222> LOCATION: (538)..(585)
<223> OTHER INFORMATION: n= a, c, g or t
<220> FEATURE:
<221> NAME/KEY: misc_feature
<222> LOCATION: (877)..(877)
<223> OTHER INFORMATION: n= a, c, g or t

<400> SEQUENCE: 42
agttcatggg   cttgagggtg   tggtaattgt   atttaggtcc   tgtgaaaagg   cagaagccct    60
agtaaacaac   ctaggctttc   attgagaacc   ctgagtctag   gtgaatcaga   aataaaacat   120
aggtagtgaa   gccaaaactc   aaataatttc   agattagtgc   ccctagccta   gatgtctgcc   180
tgaagccaga   ataaaaattc   tctttggagg   aagatgcttt   tcccagaaac   tcaggttatc   240
actgtagttt   tcatgtgact   atatctgtca   gtcagtagaa   ataatagaca   catcacatga   300
```

```
gaagaccaga tatgattaaa aaaaacaata aaaaataaac aaattggata tacctacaag    360
agatccagat aatagataat caaatatggt ccctaccata actgtgatta atatgtttca    420
aggattaaaa gataagattg aaaactctgc cagagaactg aaaattgtaa ataagaccaa    480
atggaccttc tggaactgan aaatacaatt actgcagtta aaatctaaat gagtgaannn    540
nnnnnnnnnn nnnnnnnnnn nnnnnnnnnn nnnnnnnnnn nnnnatggt tgcataaatg     600 aattaatgac taaaaccatt gaatgtgtac ttacaatggg tgaattttat gctgtgtaaa    660
ttgtacttta aaaattaagc tttaaaaaaa ccaaatgaat tggttcaata gagtagatgc    720
aattgaggag agagttagtg aaccagaaga taaagcagaa gaaatatca acaataaagc     780 attttgaggc ttttagatgg aaaataaata tcagattgtg aaagacatat taaatatggt    840
ggaaaggcct aatatatgtg taactggagg ttcagcngga gaggagagag aaagtgggac    900
ataaaaaata attggaaaaa aatagctgag atagttctaa aactaacaaa tcacacaaag    960
ccacagaatc cagaagccct agggcaccaa gcaggataaa tacaaagatt caacatagta   1020
aaatttctga taacaaagct aacgagaaca acatagggac aacatggtaa catttataaa   1080
agaaaaagag aaaagctgaa aagcatcatg gttggggagt gggtacctct tatc         1134
```

<210> SEQ ID NO 43
<211> LENGTH: 161
<212> TYPE: DNA
<213> ORGANISM: Homo sapien

<400> SEQUENCE: 43

```
atgtgcttat ttctagtata tgtgctgctg aagcgagcag taaaatgtgc ttatttctat     60
taatgaattc tttattataa aagtggtaca ttattacaaa agtagtaaat gtttattaag    120
attagaaaca aattctaatt atacagaaga gtacttactg a                        161
```

<210> SEQ ID NO 44
<211> LENGTH: 413
<212> TYPE: DNA
<213> ORGANISM: Homo sapien
<220> FEATURE:
<221> NAME/KEY: misc_feature
<222> LOCATION: (220)..(221)
<223> OTHER INFORMATION: n= a, c, g or t

<400> SEQUENCE: 44

```
agctcactgc agcttcaaac tccaaagctg aagcaatctt cccacctcag cctctcaagt     60
agctgggact acaggcagac gccaccaggc caggccaatt tttgtatttt ttgtagagac    120
gaggtttcgc catattgccc aggctggtct cgaactcctg agctcaagtg atccaaccac    180
ctcatcctcc caaagtgctg ggattatagg cgtgacactn ngtgctgggt ctcagtaagt    240
actcttctgt ataattagaa tttgtttcta atcttaataa acatttacta cttttgtaat    300
aatgtaccac ttttataata aagaattcat taatagaaat aagcacattt tactgctcgc    360
ttcagcagca catatactag aaataagcac attttataat atagaagata tat           413
```

<210> SEQ ID NO 45
<211> LENGTH: 470
<212> TYPE: DNA
<213> ORGANISM: Homo sapien

<400> SEQUENCE: 45

```
atcaaatgct gagaccaaga tattgcgaga tggaagtgat ggtaatggaa agaacaatga     60
tgaccttgga agagatactg tgaggaatta acaagaggtc aaatagaaat aaatcaaagg    120
```

```
gctgacaggt agcactgagg tgagtaagca caaattaaca cagtttcatg gctttctcca    180
gcaaagctca tcagcaaaag ccagagactc tgggagtacc caggtttaga gaacatgcct    240
atggaatcag tttacaatgt ctttaaatcc agttaacccg tttcctccta aaatatcttt    300
aaaatattct ttctccatgc tattagtatt cagaattaaa atgttgttac tgatgtcaaa    360
gcaaagagaa taaactacgg agaaattaac tcttcatttc cagatacaga aggacctgat    420
tttgtagaga ccaccaactc aatagtttgg agcaggagtt ggcaaactac                470
```

<210> SEQ ID NO 46
<211> LENGTH: 410
<212> TYPE: DNA
<213> ORGANISM: Homo sapien

<400> SEQUENCE: 46

```
ccctcctgtg tcttttaaaa cagcatcacc ttccccccat gtttcccctt ctccccagat     60
ccattccact tagtctcacc agttcagttt tccttcatct gtctatttta ctggaagaca    120
gaactgtgtg atgattaaga ccctggtatt ggagccaaac acagctaaat ctgacttacc    180
acagcactta ctaagttact tggtctcact gagcctcagt tctctaataa aatgaggata    240
atatctacct tttgtagtta tggtaaggat ttaaaagctg atgcctgtgc ccgggatatg    300
gtagacacta cttacattgc tgtcatgatt ctattgtatt actcagtact ctatcttctc    360
cttcatacac ttcctttgcc aataatgaca aaaataatca cagcttatgt                410
```

<210> SEQ ID NO 47
<211> LENGTH: 411
<212> TYPE: DNA
<213> ORGANISM: Homo sapien
<220> FEATURE:
<221> NAME/KEY: misc_feature
<222> LOCATION: (254)..(276)
<223> OTHER INFORMATION: n= a, c, g or t
<220> FEATURE:
<221> NAME/KEY: misc_feature
<222> LOCATION: (333)..(333)
<223> OTHER INFORMATION: n= a, c, g or t
<220> FEATURE:
<221> NAME/KEY: misc_feature
<222> LOCATION: (393)..(393)
<223> OTHER INFORMATION: n= a, c, g or t

<400> SEQUENCE: 47

```
gtctaacttc agtgcattgc aacacatcag atatggttaa atgtaggagt ttataatgat     60
actttaaaga gagaaatcta gtccctaatt gcttgatctt ctctctggta attattaggg    120
agattaagag tcacaagtac aagaagccac agagaaacag gcatagtcta aagggcagt    180 gtatcccatg cccatagctg tgccctgccc atggcccatt aaacagcggc catgagacct    240 ttcctgttg tacnnnnnnn nnnnnnnnnn nnnnngtct tcaccagcgg ggaagctgca    300
gtcctacttt gtctgttctt actgtgctgg aangtttaac atatgggatt taattgtggt    360
tttatctcca aatttttaa ttatacagat gcntcttgac atacaatggc g              411
```

<210> SEQ ID NO 48
<211> LENGTH: 1022
<212> TYPE: DNA
<213> ORGANISM: Homo sapien
<220> FEATURE:
<221> NAME/KEY: misc_feature
<222> LOCATION: (254)..(276)
<223> OTHER INFORMATION: n= a, c, g or t
<220> FEATURE:

```
<221> NAME/KEY: misc_feature
<222> LOCATION: (333)..(333)
<223> OTHER INFORMATION: n= a, c, g or t

<400> SEQUENCE: 48
gtctaacttc agtgcattgc aacacatcag atatggttaa atgtaggagt ttataatgat      60
actttaaaga gagaaatcta gtccctaatt gcttgatctt ctctctggta attattaggg     120
agattaagag tcacaagtac aagaagccac agagaaacag gcatagtcta gaagggcagt    180
gtatcccatg cccatagctg tgccctgccc atggcccatt aaacagcggc catgagacct     240
tttcctgttg tacnnnnnnn nnnnnnnnnn nnnnnngtct tcaccagcgg ggaagctgca     300
gtcctacttt gtctgttctt actgtgctgg aangtttaac atatgggatt taattgtggt     360
tttatctcca aattttttaa ttatacagat gcgtcttgac atacaatggc gttatgtccc     420
aataaactca ttgtaggttg tagatattgt aagttgaaaa tgcattcaat acacctaccc     480
tactgaacat catagcttag cctagtctac cttaaatgtg cttagaacat ttacattagc     540
ctacagtctg gcaaaagcat ataacacaaa gcctatttta taataaagtg ttgaatagct     600
catgtaattt attgaatatg gttctaaaag tgaacagcag gatggttgca tgggtattca     660
aagtatggtt tctactgaat gcaagtggct ttctcaccaa cataaaatca aaaaaaaaa     720 aaaaaaatct ccttgtagct atcaggagac ttcagtgact taaatgcaag attgaattcc     780
agtgctcttt gcgctctttc tatccctgtg tccctatgt ataactataa taagtgacac     840
caggaaaatg ttatgagagt ataaaacagg gattaaaaat aatttggggg taaaaggagt    900
gggtcataaa tacttcccag ggaagatgac atttatacta ggccatgaat gatgtaagat     960
tttaacaggc attcatgggg gtggggcagg cattccaggc ttagggaaca ataggagcaa    1020
aa                                                                  1022

<210> SEQ ID NO 49
<211> LENGTH: 631
<212> TYPE: DNA
<213> ORGANISM: Homo sapien

<400> SEQUENCE: 49
gcaatcatat tcagcctgaa gtgaaaggat tgacctgtct cgttgcctgt tgcaccctcc      60
tgagctgatt aggaaaccta actttccacc aaagggctac cgcagtgctg ggaaacagca     120
cctcccctac ttcctcctgt tgctttgggg aggccatgcc aggtgtgctt gatgccctct     180 gccataccctg aatataccag tgctggcttc cggaattagg ggcaataggc agagacatga    240
gcggggtgct tgtgagaagg gagaaagcaa aaacccggag ggagaattgt ggggaagaca    300
tttacaaatt gactgatttt tcttatacat tttcaagagt cctgattttc agtttttaaa    360
aacattactt taaaaaaacc aatgcatttc aaagttgatt acaaaatgat tttaaactcc     420
tggattttac ccaaattttg tttacttaaa ttatagatga tcttaatatg ctattatttt     480
aaaaaaacat atcctactct attgtaatgt attatcagtt taaaaaatta ggaaactgcc     540
tatttcactt ttttaattta aagcacatat caaagatcat ggcaaaaaag gaggggctca    600
ataaatgtta gcccttcagt tgcttcaaaa g                                   631

<210> SEQ ID NO 50
<211> LENGTH: 797
<212> TYPE: DNA
<213> ORGANISM: Homo sapien
<220> FEATURE:
<221> NAME/KEY: misc_feature
```

<222> LOCATION: (569)..(569)
<223> OTHER INFORMATION: n= a, c, g or t

<400> SEQUENCE: 50

```
tgtgtagctt ccatgtttcc tgtattaaca atgctaatgg gagaagcgat taatttatgt    60
aaactttaca tttttatgca aatgaagctg atatttatta gagctaaaac aattatactg   120
gcacttagtg gagtaacctt gtgtgcctgg gaaatgttag aggagagcag ttgatgttcc   180
actaatacct ctgctgtaaa caaatatgca tttatgccac tttttagaat taaagacaa    240
aaagaagagc tcggagagca ttgctggaga ttgcttatta gggttgataa cctgaaataa   300
ctcctgattg gcaggcgagc cttggcctta caattttttt gtgaaagaaa gatagccttt   360
cttgatagaa tgtaataaac aaaatgataa aaaatgaaat gctaattgca ttttaaagag   420
gtcttttgaa aaaaatttt taatagttgg ttgtattgtt actgagagaa ctgttatgct    480
aatgactgac tacctagatg attttgcatt aatataataa ccattacctg ccttagtgct   540
ttgtacagta ttgtggcaaa atagctaanc ctaaggagt tatacaaaaa gcagaattcc    600
ataatgaaac agaattttac tttccacata aatagcatgc cttttttttt tatttttta    660
agaccgaaat attatatcag aagtgtgttt tctttcctgt atgatagtta cttgcatggt   720
acctggttgg ttcattttgt tttgtttttt taataccagg agaaagaagc ttctaacttt   780
tctgttgcca tacacgt                                                  797
```

<210> SEQ ID NO 51
<211> LENGTH: 527
<212> TYPE: DNA
<213> ORGANISM: Homo sapien

<400> SEQUENCE: 51

```
ggatggagga agggcagttg cgaaagtggt ggaaaaggag atccagcaga gcatggcaca    60
ttctcaggca aatcagattt ttttttcctt tttaaagagc ccttacaaaa gattgatggt   120
ctgaacattt atttccttca cacttttcac ataatcatgt accccttagt tcatggaagg   180
ccttcaagta tttctagggg ccaagtacac cttgtcagag cgcagaagct acacagtcag   240
actaatgaat catctcagaa cattttcctt agactttggg tatacctcta cagaaatcac   300
tggatgttat taagccttt tagtttttaa atatttcaaa tgatttattt atatgtgtag    360
aattcgtttc cttaagattt tcttctatat ggtcttaaat gatcctcata acagccctca   420
caatgaaaca agtgaggtat tgttatccac atttctaaat gactgagatt atgtgatttg   480
tctaaggtca cacagtatta gagtcaggac ttgctgccat ttttctt                  527
```

<210> SEQ ID NO 52
<211> LENGTH: 579
<212> TYPE: DNA
<213> ORGANISM: Homo sapien

<400> SEQUENCE: 52

```
ggatggagga agggcagttg cgaaagtggt ggaaaaggag atccagcaga gcatggcaca    60
ttctcaggca aatcagattt ttttttcctt tttaaagagc acatacaaaa gattgatggt   120
ctgaacattt atttccttca cacttttcac ataatcatgt accccttagt tcatggaagg   180
ccttcaagta tttctagggg ccaagtacac cttgtcagag cgcagaagct acacagtcag   240
actaatgaat catctcagaa cattttcctt agactttggg tatacctcta cagaaatcac   300
tggatgttat taagccttt tagtttttaa atatttcaaa tgatttattt atatgtgtag    360
```

| | |
|---|---|
| aattcgtttc cttaagatttt tcttctatat tgtcttaaat gatcctcata acagccctca | 420 |
| caatgaaaca agtgaggtat tgttatccac atttctaaat gactgagatt atgtgatttg | 480 |
| tctaaggtca cacagtatta gagtcaggac ttgctgccat tttcttttc tgtaaattcc | 540 |
| ttgttctttc tgccacttca agctgcatta tatatcatt | 579 |

```
<210> SEQ ID NO 53
<211> LENGTH: 1033
<212> TYPE: DNA
<213> ORGANISM: Homo sapien
<220> FEATURE:
<221> NAME/KEY: misc_feature
<222> LOCATION: (108)..(144)
<223> OTHER INFORMATION: n= a, c, g or t
<220> FEATURE:
<221> NAME/KEY: misc_feature
<222> LOCATION: (193)..(193)
<223> OTHER INFORMATION: n= a, c, g or t
<220> FEATURE:
<221> NAME/KEY: misc_feature
<222> LOCATION: (943)..(943)
<223> OTHER INFORMATION: n= a, c, g or t
<220> FEATURE:
<221> NAME/KEY: misc_feature
<222> LOCATION: (946)..(946)
<223> OTHER INFORMATION: n= a, c, g or t
<220> FEATURE:
<221> NAME/KEY: misc_feature
<222> LOCATION: (991)..(991)
<223> OTHER INFORMATION: n= a, c, g or t

<400> SEQUENCE: 53
```

| | |
|---|---|
| ttcatgtttc tgtgtttcca taaacttgtt ggtcttcacc caaggacaaa attaccctag | 60 |
| ggcaagactt tttgtttatc ttggtaacaa ttaggttttg gttttagnnn nnnnnnnnnn | 120 |
| nnnnnnnnnn nnnnnnnnnn nnnnggataa agaatgtata gctctataaa tgactgttaa | 180 |
| aaggatatta tcnattgttt agattttgtt ttttgtttt ttaaggaaaa gttgacaagg | 240 |
| ggtaaaaggg ttatcaaaca agaactttgt catcatatat agcattatat tatttaattg | 300 |
| acaaccagac aattagcttc tttttatcag catgatattc cagtgtactc aaaccccagc | 360 |
| cacagcaact acagtacagg aaagggccat gtaactaatt gagtcactga atttatgtaa | 420 |
| agctccttag aacacaaaca tgtatgttcc agcaagcagt acaaaattgg gcaggtgagt | 480 |
| catattacaa aaatgggcaa agaagcaata ttaattggcc ctagagaaca tgtaggcctt | 540 |
| tgtttagtgc ttgtgactgg aatactttac acttttatag ttggggaaaa agcagcaata | 600 |
| acctctgcca tgaaagtctt attgattcat gggcttaaca ttatagaaat gttgcttgtt | 660 |
| ctctgtaggg ctgattctag tagaacaaag gaatggcagt ctgatgagct aagcacatc | 720 |
| agagatccta cagtgcagat gatgacacag aatcttttc tcttatagac aactgacttt | 780 |
| tggcttattt taagtgattt gtcagacttt taagtacttc atctggtttt tttttccccc | 840 |
| tttcatttga taccatcaca gattggatgt ggcttatagc aatggtagcc tagtgtagag | 900 |
| agagatacat atatatgtag aatttggaat gccaagttaa ganttnaaat gtaattttag | 960 |
| taaggaaggc aatgctccat taacatttat nccagttgat aattataaag aatattaaga | 1020 |
| acagtatagg gaa | 1033 |

```
<210> SEQ ID NO 54
<211> LENGTH: 403
<212> TYPE: DNA
<213> ORGANISM: Homo sapien

<400> SEQUENCE: 54
```

```
cgaactcctg gttgccctt tctttcatag ttccccagtg ggagccctct atgtgtggta      60
aagacactgg ggagtagggt acagttagcc cagaaaggct tttctgaggc agagggaggt    120
ggaaccgact agttgggagg ggaatctgta gtcctagaga gtttatgaga actgcccaac   180
agtgcatcca aagacatgag cacctcgcag ccctggaatc tgggccacat aaatttggtg   240
ggatccaggc tttgccaaaa agagctggtg gatgctcatt cctgctccac ttcctatccc   300
agcgccccag agagctgtct ccccaaacca aaggcaaggg aaggttacaa agttccctat   360
acctggcctt gaatgcaagt tccctctgtg gtccagctcg agc                     403
```

<210> SEQ ID NO 55
<211> LENGTH: 360
<212> TYPE: DNA
<213> ORGANISM: Homo sapien
<220> FEATURE:
<221> NAME/KEY: misc_feature
<222> LOCATION: (58)..(289)
<223> OTHER INFORMATION: n= a, c, g or t

<400> SEQUENCE: 55

```
ttattaccag agatgacagg tccatttgtg gtagttccct gaagaccttc tagtgggnnn    60 nnnnnnnnn nnnnnnnnnn nnnnnnnnnn nnnnnnnnnn nnnnnnnnnn nnnnnnnnnn   120 nnnnnnnnn nnnnnnnnnn nnnnnnnnnn nnnnnnnnnn nnnnnnnnnn nnnnnnnnnn   180 nnnnnnnnn nnnnnnnnnn nnnnnnnnnn nnnnnnnnnn nnnnnnnnnn nnnnnnnnnn   240 nnnnnnnnn nnnnnnnnnn nnnnnnnnnn nnnnnnnnnn nnnnnnnna agttttaaaa    300 agaaacagaa aaaatacaga ataaagctta cagaataagg atataaagaa aatatttttt   360
```

<210> SEQ ID NO 56
<211> LENGTH: 247
<212> TYPE: DNA
<213> ORGANISM: Homo sapien

<400> SEQUENCE: 56

```
tgtctgattc caaagcccat gctttctcca aacttaccat gttggctgaa gagaaggaga    60
tctgagaagc ccagagagac tctcacttct taactaaggg ggaagaagct tctctgttac   120 tggcccctt tcatctgctg aacccatggt gtccttacat gtagggtgcc cattcatccc   180
catttgcctg gaacagtccc actctatgtc tgtcatagtg tcagtatggc agtattgtta   240
aaattcc                                                             247
```

<210> SEQ ID NO 57
<211> LENGTH: 250
<212> TYPE: DNA
<213> ORGANISM: Homo sapien

<400> SEQUENCE: 57

```
gcctgtctga ttccaaagcc catgctttct ccaaacttac catgttggct gaagagaagg    60
agatctgaga agcccagaga gactctcact tcttaactaa ggggaagaa gcttctctgt   120 tactggcccc atttcatctg ctgaacccat ggtgtcctta catgtagggt gcccattcat   180
ccccatttgc ctggaacagt cccactctat gtctgtcata gtgtcagtat ggcagtattg   240
ttaaaattcc                                                          250
```

<210> SEQ ID NO 58
<211> LENGTH: 598
<212> TYPE: DNA

<213> ORGANISM: Homo sapien

<400> SEQUENCE: 58

| | | | | | |
|---|---|---|---|---|---|
| gggctggaga | aatcactagc | agggaggagc | cctgaggttg | ccgaggggga | tcggagctac | 60 |
| ttcccaaggc | gcctacaccg | cccgtagact | gggaaactac | ggtcacaaag | ggtcagcgca | 120 |
| ttccccaagg | tcccagagcc | acacgcagca | tggctggcat | ttgaaagtca | aagcagagga | 180 |
| agcaggcagg | tggctcttgt | tgaactggct | tccagagtct | gtgttgggca | gagagatcct | 240 |
| tccccgagag | tggagtggcc | tcgtgctcac | ctgggttcag | cgtcaaggtt | cacctggaat | 300 |
| cacctgcact | cttgtccttg | accaaggcag | ggtggttagc | catgggctga | tagccttgga | 360 |
| gagcctgatt | cagcctttgg | gtagagctgg | gtcagtccag | cctcagggcc | atcactcacc | 420 |
| cgaagcattg | tggtaacctg | cctgcccctg | agaccccgg | gtgtggggca | gggtgaccgt | 480 |
| ggtggagagt | gggagctggc | agaggtaagg | aggcacacag | tcatgccaca | gcaccagagc | 540 |
| tcagggcgcc | tgagaagcaa | ggtcatagcg | tcctgttctt | ggaccccgtc | agtctcca | 598 |

<210> SEQ ID NO 59
<211> LENGTH: 594
<212> TYPE: DNA
<213> ORGANISM: Homo sapien

<400> SEQUENCE: 59

| | | | | | |
|---|---|---|---|---|---|
| gccctgtctg | aagggcgtg | tgggtttgca | ctcagcatct | gtcctccag | aattctggcc | 60 |
| ggctcaccca | ggccggggtc | tctgtaggct | ccaggttatt | gcccagaggc | ctgagtccat | 120 |
| gaatggatcc | aggacagtgg | ggaggctggg | cagctccagt | gcctgcttgc | ctcattgcac | 180 |
| attgttggtc | tgtttacctg | gggggcccctt | tgccttagca | catgtgtgac | ctctgtgatc | 240 |
| ggttagagtc | ctgcgggaaa | ccagtcctag | tcagggagag | tctggggccc | tttccccaca | 300 |
| gggctctgtt | ctcaaagtcc | catagctggg | tgaccaatgt | agatgcaggt | cccatgcctt | 360 |
| gcccaggagg | cctggctcct | gggagcccag | aaaataccag | tgggagatgg | gaggtatggt | 420 |
| ggggcagcct | ggctagggtg | gatatggggc | agagatcggg | aagaggctct | tcctggaagg | 480 |
| catgggcac | cttcagggagt | ctaggggct | agggacctg | aagcctaggc | ccaagccaga | 540 |
| ccctgaccct | gtacctccca | tccccacagg | acatcaacaa | tgcctggggc | tgct | 594 |

<210> SEQ ID NO 60
<211> LENGTH: 2848
<212> TYPE: DNA
<213> ORGANISM: Homo sapien

<400> SEQUENCE: 60

| | | | | | |
|---|---|---|---|---|---|
| gccctgtctg | aagggcgtg | tgggtttgca | ctcagcatct | gtcctccag | aattctggcc | 60 |
| ggctcaccca | ggccggggtc | tctgtaggct | ccaggttatt | gcccagaggc | ctgagtccat | 120 |
| gaatggatcc | aggacagtgg | ggaggctggg | cagctccagt | gcctgcttgc | ctcattgcac | 180 |
| attgttggtc | tgtttacctg | gggggcccctt | tgccttagca | catgtgtgac | ctctgtgatc | 240 |
| ggttagagtc | ctgcgggaaa | ccagtcctag | tcagggagag | tctggggccc | tttccccaca | 300 |
| gggctctgtt | ctcaaagtcc | catagctggg | tgaccaatgt | agatgcaggt | cccatgcctt | 360 |
| gcccaggagg | cctggctcct | gggagcccag | aaaataccag | tgggagatgg | gaggtatggt | 420 |
| ggggcagcct | ggctagggtg | gatatggggc | agagatcggg | aagaggctct | tcctggaagg | 480 |
| catgggcac | cttcagggagt | ctaggggct | agggacctg | aagcctaggc | ccaagccaga | 540 |
| ccctgaccct | gtacctccca | tccccacagg | acatcaacaa | tgcctggggc | tgcctggagc | 600 |

-continued

```
aggtggagaa gggctatgag gagtggttgc tgaatgagat ccggaggctg gagcgactgg    660
accacctggc agagaagttc cggcagaagg cctccatcca cgaggcctgg actgacggga    720
aggaagccat gctgaagcac cgggactacg agacggccac actatcggac atcaaagccc    780
tcattcgcaa gcacgaggcc ttcgagagcg acctgcctga gcaccaggac cgcgcggagc    840
agatcgccgc cattgcccag gagctcaacg agctggatta ctacgactcc cacaatgtca    900
acacccggtg ccagaagatc tgtgaccagt gggacgccct cggctctctg acacatagtc    960
gcagggaagc cctggagaaa acagagaagc agctggaggc catcgaccag ctgcacctgg   1020
aatacgccaa gcgcgcggcc cccttcaaca actggatgga gagcgccatg gaggacctcc   1080
aggacatgtt catcgtccat accatcgagg agattgaggg cctgatctca gcccatgacc   1140
agttcaagtc caccctgccg gacgcccgat agggagcgcg aggccatcct ggccatccac   1200
aaggaggccc agaggatcgc tgagagcaac cacatcaagc tgtcgggcag caaccccctac   1260 accaccgtca ccccgcaaat catcaactcc aagtgggaga aggtgcagca gctggtgcca   1320
aaacgggacc atgccctcct ggaggagcag agcaagcagc agtccaacga gcacctgcgc   1380
cgccagttcg ccagccaggc caatgttgtg gggccctgga tccagaccaa gatggaggag   1440
atcgggcgca tctccattga gatgaacggg accctggagg accagctgag ccacctgaag   1500
cagtatgaac gcagcatcgt ggactacaag cccaacctgg acctgctgga gcagcagcac   1560
cagctcatcc aggaggccct catcttcgac aacaagcaca ccaactatac catggagcac   1620
atccgcgtgg gctgggagca gctgctcacc accattgccc gcaccatcaa cgaggtggag   1680
aaccagatcc tcacccgcga cgccaagggc atcagccagg agcagatgca ggagttccgg   1740
gcgtccttca accacttcga caagaagcag acaggcagca tggactccga tgacttcagg   1800
gctctgctta tctccacagg atacagcctg ggtgaggccg agttcaaccg catcatgagc   1860
ctggtcgacc ccaaccatag cggccttgtg accttccaag ccttcatcga cttcatgtcg   1920
cgggagacca ccgacacgga cacggctgac caggtcatcg cttccttcaa ggtcttagca   1980
ggggacaaga acttcatcac agctgaggag ctgcggagag agctgccccc cgaccaggcc   2040
gagtactgca tcgcccgcat ggcgccatac cagggccctg acgccgtgcc cggtgccctc   2100
gactacaagt ccttctccac ggcccttgtat ggcgagagcg acctgtgagg ccccagagac   2160
ctgacccaac accccgacg gcctccagga ggggcctggg cagccccaca gtcccattcc   2220
tccactctgt atctatgcaa agcactctct gcagtcctcc ggggtgggtg ggtgggtggg   2280
cagggagggg ctgggggcagg ctctctcctc tctctctttg tgggttggcc aggaggttcc   2340
cccgaccagg ttggggagac ttggggccag cgcttctggt ctggtaaata tgtatgatgt   2400 gttgtgctttt tttaaccaag gaggggccag tggattccca cagcacaacc ggtcccttcc   2460
atgccctggg atgcctcacc acacccaggt ctcttccttt gctctgaggt cccttcaagg   2520
cctccccaat ccaggccaaa gccccatgtg ccttgtccag gaactgcctg gccatgcga    2580 gggcagcag agggcgccac caccacctga cggctggga cccacccagc ccctctcccc   2640
tctctgctcc agactcactt gccattgcca ggagatggcc ccaaccaagc aaccccgctt   2700
ttgcagcaga ggagctgagt tggcagaccg gggccccctg aacggaccca tccaacagcc   2760
ggcctgctta gtcggctcac ggtctcaaga attgctagaa ccaaaaaaaa agggacaaga   2820
gcaaaaacga agacgaaaca acaggggg                                      2848
```

<210> SEQ ID NO 61

```
<211> LENGTH: 572
<212> TYPE: DNA
<213> ORGANISM: Homo sapien

<400> SEQUENCE: 61
accctgggta atggtggaga cgaggggttc cagcctcctg gctcctgtcc cattcactgc      60
atcatcgcct gcaatgacag ctctgtcgga ccacggccca tgcaacagca gcagaggggc     120
ccaacagtct aatgaaaagg ccccatactt gaagtcagaa aatttggtcc cagtcctggc     180
tctcttgaga attcactatg tggcctggtg tgggacagaa aaatctacat aaggacagaa     240
ttctattttc tgaagcaaaa aacagtcgag gggctaccat aagattttt tcagcagttc     300 agttgcaaga gatgttaggc atctcctaca actcacacct gtcaaagaca tacccaggaa     360
gatgttcagc gttttcacat ttaggtgctg aacaaccta tatagctgtc tatatcttga     420
cctatttccc tgacttcctt ggtggttgac cttggtcagt tccggccttg ctgacacctg     480
gtctccatgg ctgggtatat ctctaagtta tcttgtttcc aggtcagccc tgtttcctgt     540
aacaaataat tctttcccct cagtgagcag aa                                    572

<210> SEQ ID NO 62
<211> LENGTH: 650
<212> TYPE: DNA
<213> ORGANISM: Homo sapien
<220> FEATURE:
<221> NAME/KEY: misc_feature
<222> LOCATION: (581)..(581)
<223> OTHER INFORMATION: n= a, c, g or t

<400> SEQUENCE: 62
accctgggta atggtggaga cgaggggttc cagcctcctg gctcctgtcc cattcactgc      60
atcatcgcct gcaatgacag ctctgtcgga ccacggccca tgcaacagca gcagaggggc     120
ccaacagtct aatgaaaagg ccccatactt gaagtcagaa aatttggtcc cagtcctggc     180
tctcttgaga attcactatg tggcctggtg tgggacagaa aaatctacat aaggacagaa     240
ttctattttc tgaagcaaaa aacagtcgag gggctaccat aagattttt tcagcagttc     300 agttgcaaga gatgttaggc atctcctaca actcacacct gtcaaagaca tacccaggaa     360
gatgttcagc gttttcacat ttaggtgctg aacaaccta tatagctgtc tatatcttga     420
cctatttccc tgacttcctt ggtggttgac cttggtcagt tccggccttg ctgacacctg     480
gtctccatgg ctgggtatat ctctaagtta tcttgtttcc agggtcagcc ctgtttcctg     540
taacaaataa ttctttcccc tcagtgagca gaagtaatgg nctcatctgg cctgatccag     600
catttgggga gaagccggtg aaagagggca tctaagagat atgtttaatg                650

<210> SEQ ID NO 63
<211> LENGTH: 591
<212> TYPE: DNA
<213> ORGANISM: Homo sapien

<400> SEQUENCE: 63
acaaggtgag ttgggatttt aatcatggtt tcagtttaaa ggcaaaggtt taatcatgtt      60
ttcggtttaa agatcatgcc gttcagttag ccctttgtta tgatctaaag gtgtttgaca     120
gcttgaaatc caaaggagg tcaactgagg tatggagagc tccacatatt gggctaaaag     180
ccagtcacat ttagcatttt ggaaagttat gtgaaaaatt gatatcgtct gttgtaaaac     240
tgaagcaatt gccaagcttg tccattgttc ttttgcactg aattaactca ctcttaataa     300
aaggaccgac acagggcctt acacggggtgg tctttgtgca gggcccacct gtgtatcttg     360
```

| | |
|---|---|
| ctctgatggt tgtctttgct catagctcaa tgatgctgat taaatgagtt taagtgtgct | 420 |
| ggacagtgtt gcacaaacta ggccatttgt gtgtcttttc tctttctctt cctttgtaga | 480 |
| ttataaattc agcctgtatt ctaacaaaag attttcattc cagaatttaa ggcagtgttc | 540 |
| ttctctcaaa atgatattgc ctcacagatg gtctagggcc agccagtgga t | 591 |

<210> SEQ ID NO 64
<211> LENGTH: 542
<212> TYPE: DNA
<213> ORGANISM: Homo sapien

<400> SEQUENCE: 64

| | |
|---|---|
| ctcaactagc attaacattg gaggtcaatt ttggtattga acataaatgt gagattaaag | 60 |
| ttgaagggcc cagatatctc tcagagatga ctacaaccac gggagatgtc tctgttttgt | 120 |
| tttcccatgc atgtaaattc aagtatctat aaacagcatg ggccaaaagg cagtcatgaa | 180 |
| gaggtcacag gacaaagctt tcactttag catacactgc tataataatc aaacttatgt | 240 |
| gacctgagtg cttcccagga attattattg atttatgtgc caaatattg atacagtccc | 300 |
| tgaggaagcc tcaaagcata taagtgtta cttcagacac aagcttcagg actccttaac | 360 |
| aattcctgcg tgtctaattg gctagctcct caggctgact gcccttttcc tgtttccaga | 420 |
| caaatcttcc ctaaaactca tggtcagatt aattttcctc aaatacagtt tacctcaaca | 480 |
| actttccatc accgcgctcg agccgattcg gctcgagggc gattgatgaa ccaggcggtt | 540 |
| ga | 542 |

<210> SEQ ID NO 65
<211> LENGTH: 586
<212> TYPE: DNA
<213> ORGANISM: Homo sapien

<400> SEQUENCE: 65

| | |
|---|---|
| aaattctttt tgacatctct cagggttata ttttttttcct ttaactcata tgtcaccatt | 60 |
| aggtttttaa aatccttta aatatttat ttctagtgta ccttggagtt ccctttttcc | 120 |
| tccttttgg ggaaagtttt gaaaatgttt tgttttgtg tatgaaaaga atagctcacc | 180 |
| aaggaagaag gggagtgttt ttggtgaaat aggaagaag tctgaaactg taggagagga | 240 |
| ggggaatatg gccgctgata aaaagcacta gaggaggggg gaaatactct tccataggaa | 300 |
| ggcttccagc tacaaagatt tgaagacatt tttctgggga agtaaaacac taaatcagca | 360 |
| ttattttcca aagcccagaa ataaacttaa tagattgttt ttaaattact gttttaattc | 420 |
| agcttgtgaa gatattctga atagttcatg tagaatatct tactattttg cagatactttt | 480 |
| tgtataaata gttgccagtg agaaatgttg caactgtgtc ttttcaaatg aagtaaatag | 540 |
| gagagctagt atagcgcctg aaagaagtaa gtgagttata ttgtac | 586 |

<210> SEQ ID NO 66
<211> LENGTH: 858
<212> TYPE: DNA
<213> ORGANISM: Homo sapien

<400> SEQUENCE: 66

| | |
|---|---|
| gtcaaaattc tttttgacat ctctcagggt tatattttttt tcctttaact catatgtcac | 60 |
| cattaggttt ttaaaatcct tttaaatatt ttatttctag tgtaccttgg agttcccttt | 120 |
| ttcctccttt tgggggaaag ttttgaaaat gttttgtttt tgtgtatgaa aagaatagct | 180 |

```
caccaaggaa gaaggggagt gttttttggtg aaataggaaa gaagtctgaa actgtaggag      240 aggagggaa tatggccgct gataaaaagc actagaggag gggggaaata ctcttccata        300
ggaaggcttc cagctacaaa gatttgaaga cattttttctg gggaagtaaa acactaaatc      360
agcattattt tccaaagccc agaaaataac ttaatagatt gttttttaaat tactgttttta    420 attcagcttg tgaagatatt ctgaatagtt catgtagaat atcttactat tttgcagata       480
cttttgtata aatagttgcc agtgagaaat gttgcaactg tgtctttttca aatgaagtaa      540 ataggagagc tagtatagcg cctgaaagaa gtaagtgagt tatattgtaa cttcttgctc      600
tacctcaggg taagcactcc ttttagcatt tattaaactc tcattatttg tagagaaatt     660
atttagatgt aggttgagta ttcctaatct gaaatctga aacacaagat gctctaaaat      720
tcaaaacagg atgctcaaag gagatacttg tttgagcatt tcagacttca gattttcaga     780
ttagggatgc tgaactggta agtataatgc agatattcca aaatctggaa gaaaaaaaaa     840 aaaaaaaat gagcggtc                                                   858

<210> SEQ ID NO 67
<211> LENGTH: 593
<212> TYPE: DNA
<213> ORGANISM: Homo sapien

<400> SEQUENCE: 67 gtgccttttta tgctcatatg caagtttaaa cacaatatga atctcccatt ctcttaaact     60
agaggctaaa aagaggacca ggtgttcaca cagaacttgg cagatgatgt tggccagttt    120
gaacgtggag aggattgaaa atggctgagt agggagggat gctgagcggt gcttgggcct    180
ctagcagctg ctaattttat agaatgcgct aaaataaacc ttgtggatag atcttgcctc    240
agccttttct atctctggtc cttggacaga gaattgttta agtcatttca tgtttattga    300
gttattttgg ttaatcatca gtacagattg cctctaagtg gttttttgcat cttttttttta  360 ttatcgcttg gtcacataac ttctcggaac ctcagtttcc ttatttaata ctctcaaggt    420
tgaatattaa atcatatgaa caggatttgc aaactataaa gcaatgctat gcatgtaagg   480
tgtcttttat ttgccagtta ctgagtcttt aagggcaaat tgtctactca atacttggtt   540
tactgtgtta ggattccatt agggaagcag aacccttata aatattgtgg aat           593

<210> SEQ ID NO 68
<211> LENGTH: 578
<212> TYPE: DNA
<213> ORGANISM: Homo sapien

<400> SEQUENCE: 68
gggaacagaa gagagaaaac aaacactggc ttcactaaag agacaaaagc tgaagcaaag    60
ttgggattgg tccacagccc agggcggaac tcactgtgtc ccgagagtac cctgccacac    120
agtgcctgcg tgtgcctctc catcacccag atggaagaga acgtgttccg aaaggcagag    180
caaacaacag agcctcaaag ctgttataac gggccctcgc cttggggttc ctagcaagtc    240
aatgacaaaa agcaccctct cgggagcaca ctggagagct gcagtcagcc tacggctatc    300
caacacactt gttttttccat aatcacggga aacctctgct taaagatggt ggattgaact    360
cacatattta tctcctttct caccagaaac cgtactaaaa cgaagggatt ttttttttaa    420
ggcacaaatc acaatgacaa aataacagga agagagatgg tggagcacgc atcatcttgg   480
gggaacctga agaatccaac agccaaaagc agggcagccg gagagcagga caggtggaaa   540
ctgactgaaa aggcccagga aagccagtga cccacctg                           578
```

<210> SEQ ID NO 69
<211> LENGTH: 730
<212> TYPE: DNA
<213> ORGANISM: Homo sapien

<400> SEQUENCE: 69

| | |
|---|---|
| gggaacagaa gagagaaaac aaacactggc ttcactaaag agacaaaagc tgaagcaaag | 60 |
| ttgggattgg tccacagccc agggcggaac tcactgtgtc ccgagagtac cctgccacac | 120 |
| agtgcctgcg tgtgcctctc catcacccag atggaagaga acgtgttccg aaaggcagag | 180 |
| caaacaacag agcctcaaag ctgttataac gggccctcgc cttggggttc ctagcaagtc | 240 |
| aatgacaaaa agcaccctct cgggagcaca ctggagagct gcagtcagcc tacggctatc | 300 |
| caacacactt gtttttccat aatcacggga aacctctgct taaagatggt ggattgaact | 360 |
| cacatattta tctcctttct caccagaaac cgtactaaaa cgaagggatt ttttttttaa | 420 |
| ggcacaaatc acaatgacaa ataacagga agagagatgg tggagcacgc atcatctttg | 480 |
| gggaacctga agaatccaac agccaaaagc agggcagccg agagcagga caggtggaaa | 540 |
| ctgactgaga aggcccagga aagccagtga cccacctgct gcatcccgaa gaactgccca | 600 |
| gaagctcagg ccctggaggt gctgagcggc tctggaagtg tgggcaaggt gacagtgaag | 660 |
| agagctgaac tgtttgaaag tctctttcag aagcaatgag ctcatcccgg cacaaactcg | 720 |
| ccagttacgc | 730 |

<210> SEQ ID NO 70
<211> LENGTH: 408
<212> TYPE: DNA
<213> ORGANISM: Homo sapien

<400> SEQUENCE: 70

| | |
|---|---|
| ggggcttgtg gttaccgatg gaaacctgga gaagtgtgcg ggctacatca ttctttcttt | 60 |
| caacagactc ggagtgtctg ccctgggcca ggaactctgc ctgacctccc agatgaggtg | 120 |
| tgtgtctaga accttcctt gggaagggaa ggagagggct ggggtatggg ggagcctgga | 180 |
| catgaaaaag aactaccctc tgacagtaac atttccctct acttattcaa ggtctgtatg | 240 |
| tgccagacgg tgcctagcac tttgtataca ttagcttatc cggtgctcac aaacatctct | 300 |
| gagatgggca ttacagttca atttccagac atcgtgtcaa aagccaaacc caagcctgtc | 360 |
| tgcaccagag cctgtgccct tcacacagac tggttaatat aaatctga | 408 |

<210> SEQ ID NO 71
<211> LENGTH: 430
<212> TYPE: DNA
<213> ORGANISM: Homo sapien

<400> SEQUENCE: 71

| | |
|---|---|
| ggggcttgtg gttaccgatg gaaacctgga gaagtgtgcg ggctacatca ttctttcttt | 60 |
| caacagactc ggagtgtctg ccctgggcca ggaactctgc ctgacctccc agatgaggtg | 120 |
| tgtgtctaga accgttccct tgggaaggga aggagagggc tggggtatgg gggagcctgg | 180 |
| acatgaaaaa ggactaccct ctgacagtaa catttcccct ctacttattc aaggtctgta | 240 |
| tgtgcccaga cggtgcctag caccttgtat acattagctt atcccggtgc tcacaaacca | 300 |
| tctctgagat gggccattac cagtgtccaa atttccagac atcgtgtcca aaagcccaac | 360 |
| ccaagcctgt ctgcaccacg agcctgtgcc ccttcaacac caagaactgg ttaaataatt | 420 |

```
aaaatctgaa                                                           430

<210> SEQ ID NO 72
<211> LENGTH: 239
<212> TYPE: DNA
<213> ORGANISM: Homo sapien

<400> SEQUENCE: 72
tgggagacaa acatacccctc ctgaccttgg ggaagtgttt tccctgctct tgtgtccaag    60
ggggagttgg caggactgtt agaaatgagg gatgggcctc catttggccc accatgggcc   120
aaatctccag agctggagag tagtaatttc tcccccttgg gagtggtgtt gattctcttc   180
tctctagagc tcaagtcctg ggctagcagc tggagaacag gactctgagg gactttcat   239

<210> SEQ ID NO 73
<211> LENGTH: 333
<212> TYPE: DNA
<213> ORGANISM: Homo sapien

<400> SEQUENCE: 73
tgggagacaa acatacccctc ctgaccttgg ggaagtgttt tccctgctct tgtgtccaag    60
ggggagttgg caggactgtt agaaatgagg gatgggcctc catttggccc accatgggcc   120
aaatctccag agctggagag tagtaatttc tcccccttgg gagtggtgtt gattctcttc   180
tctctagagc tcaaggtcct gggctagcag ctggagaaca ggactctgag gactttcat   240 ccagccatgc attcagggac ccagtgaggg tgatgggcca gctgcacacc ctacagaatc   300
tgggctgagt gtgaagaggg acaactggtg ccc                                333

<210> SEQ ID NO 74
<211> LENGTH: 636
<212> TYPE: DNA
<213> ORGANISM: Homo sapien

<400> SEQUENCE: 74
ggtactccca atattagagt ctgctttata caatataaga gaatagtaac tattcaagta    60
cttgttaaga gtataaaaag gagaaaatga ttgttcttca cttagagaag tacataatgt   120
agcgaaggat acaaaaacaa atataaaaga aagaatataa aaataagtgc agctataaat   180
attataaaac aaattataag aggagtttttt tagcatttat tctatgttaa agttttaca   240 ttaatgtgtt tgaagtttat tttatttctc agtaactctc tgaggaagct acttaatgaa   300
taataaaact gagacttgga actattaagt tttttgcccc tatagctctc aagttgagaa   360
ctgagattta aagctggtcc atgggagaac aaagttttc ctctttctgc aacattactt   420
ggggcataaa aaagcaagag gctagttggt atggatgagg ttttatagag aaggcttttc   480
agggaaaatg aaacttgaag aacaaaacaa taagagatat aagaagttga acctccttgc   540
tttgactatt tgtgggaagt gggaagatta tagattattc aggaatatta gaggtaaaat   600
tcagttattc agcaatattt gttgagtgta tactga                             636

<210> SEQ ID NO 75
<211> LENGTH: 244
<212> TYPE: DNA
<213> ORGANISM: Homo sapien

<400> SEQUENCE: 75 ggattattttt ttttcactt tgaaatgctt aagaacagcc tcagtaaaat gtttatatcc    60
taggcagtga atgatttgat ctctataggaa atgagctggt tgttatcata tcagaatttg   120
```

```
ggggtaagct acagatgcta atatagggac atagaagatt ttttcccctc aaaattagtt    180
aagattagca aatagcatta aggcagttaa ccttgatgaa atacctagca gaaatgggtg    240
atgt                                                                 244
```

<210> SEQ ID NO 76
<211> LENGTH: 359
<212> TYPE: DNA
<213> ORGANISM: Homo sapien

<400> SEQUENCE: 76

```
ggattatttt tttttcactt tgaaatgctt aagaacagcc tcagtaaaat gtttatatcc    60
taggcagtga atgatttgat ctctatagga atgagctggt tgttatcata tcagaatttg    120
ggggtaagct acagatgcta atatagggac atagaagatt tttcccctca aaattagtta    180
agattagcaa atagcattaa ggcagttaac cttgatgaaa tacctagcaa gaaatgggtg    240
atgttatcct ggaactgcta ttctcctccc atctcttctc tcagcatttg ccatccaaac    300
catttggaag ctttggtgct tgatgcattg cagtatttt tttttctttt ctttgagaa     359
```

<210> SEQ ID NO 77
<211> LENGTH: 142
<212> TYPE: DNA
<213> ORGANISM: Homo sapien

<400> SEQUENCE: 77

```
cagtgcggga ccagccgagc tctgcaggt gggcacaggc tgctgcggct ttctcccgag     60
gcagttctgg gagcttctgt ctgcagagca ccccacccac agcctcagag agtggggcga    120
ctgtggagtg gggtgctctg ca                                             142
```

<210> SEQ ID NO 78
<211> LENGTH: 72
<212> TYPE: DNA
<213> ORGANISM: Homo sapien

<400> SEQUENCE: 78

```
ctgaatgaca gagcaagact ctctctctct caaaaaaaaa cagagagaga gagtttagag    60
accaggcaca gt                                                        72
```

<210> SEQ ID NO 79
<211> LENGTH: 529
<212> TYPE: DNA
<213> ORGANISM: Homo sapien
<220> FEATURE:
<221> NAME/KEY: misc_feature
<222> LOCATION: (234)..(388)
<223> OTHER INFORMATION: n= a, c, g or t

<400> SEQUENCE: 79

```
gtttttataa agcctgaaac tcacagaatt ggaagtctga gtgacacaga tatgttaaca    60
gaataaccca attgtttctc aacaatggaa agatgtggga tccagagagc agttttttgct  120 tttgtttctg ctatcaagtg actgccctcc atgtgataaa attggagagg tgaactgaga   180
gttcttcatt acaaatacag ctgactttat tgcttactga attttgatac tgannnnnnn   240
nnnnnnnnnn nnnnnnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnag taccagaatg ctaaccaagg caatctgact   420
```

```
tggttcactt ggctcttgtg agccccacaa tggaagggct ctgtccatta cttgctgaca      480
agaacaagac ctcaaacata cacggcactc aagaaatatc tgttgatgg                  529
```

<210> SEQ ID NO 80
<211> LENGTH: 567
<212> TYPE: DNA
<213> ORGANISM: Homo sapien
<220> FEATURE:
<221> NAME/KEY: misc_feature
<222> LOCATION: (12)..(12)
<223> OTHER INFORMATION: n= a, c, g or t
<220> FEATURE:
<221> NAME/KEY: misc_feature
<222> LOCATION: (34)..(34)
<223> OTHER INFORMATION: n= a, c, g or t
<220> FEATURE:
<221> NAME/KEY: misc_feature
<222> LOCATION: (46)..(46)
<223> OTHER INFORMATION: n= a, c, g or t
<220> FEATURE:
<221> NAME/KEY: misc_feature
<222> LOCATION: (101)..(101)
<223> OTHER INFORMATION: n= a, c, g or t
<220> FEATURE:
<221> NAME/KEY: misc_feature
<222> LOCATION: (107)..(107)
<223> OTHER INFORMATION: n= a, c, g or t
<220> FEATURE:
<221> NAME/KEY: misc_feature
<222> LOCATION: (137)..(137)
<223> OTHER INFORMATION: n= a, c, g or t
<220> FEATURE:
<221> NAME/KEY: misc_feature
<222> LOCATION: (140)..(140)
<223> OTHER INFORMATION: n= a, c, g or t
<220> FEATURE:
<221> NAME/KEY: misc_feature
<222> LOCATION: (202)..(202)
<223> OTHER INFORMATION: n= a, c, g or t
<220> FEATURE:
<221> NAME/KEY: misc_feature
<222> LOCATION: (210)..(210)
<223> OTHER INFORMATION: n= a, c, g or t
<220> FEATURE:
<221> NAME/KEY: misc_feature
<222> LOCATION: (237)..(237)
<223> OTHER INFORMATION: n= a, c, g or t

<400> SEQUENCE: 80

```
atcaagtgaa gnctccctca atgaatgaga tggnaactga actgantctc agggttaacc      60
aggttggaga ataaagtgtg gcgtgttcta ggcagagggg ncaacantgt gatcacaagc      120
agagagggaa ggaaacnacn tggtgtgcag aaggaattat gagcacttag gtgttgctgg     180
agcttaaagc tgaataggaa gnactaattn tgtagccaga gataattggc aaaggtngaa     240
tcatgaaggc ccgtgtttgc caggtgaaga catattgtgt acacacagct tgttattttc     300
attattgttg tattgcattt tggattggag ctgtctgatc aggtttgtgt tttagacaaa     360
tccttctatc agcagtgggg aaggtggatt tcagggtatg aattctgaag catgaagacc     420
agtcagatgg ccgttgcagc agttcaggca aggacaatga ggcctaaatt aagactgcga     480
gggtgaggat ggggaagaga aactagagtc aagaaatagg tggttttaaa aagaagtatt     540
tagagggtaa aaagaatact aactggc                                          567
```

<210> SEQ ID NO 81
<211> LENGTH: 4158
<212> TYPE: DNA
<213> ORGANISM: Homo sapien

<400> SEQUENCE: 81

-continued

```
atgagccacg gcgcccggcc cttaagaagt cttaaagtca tctatgatgg gctaatggca      60
ctcttcacga caagcctgat tgcactgtta agctccagag gaaaaaatgt ggctatagag     120
tatattaaaa tacatacaat tgaaaaggaa gatgttcatt tttgcaagca gaagattacc     180
aacagaatgc taaaattaaa gttggactat gaagagagcc cagtgtacca agtgtacgtg     240
caagccaagg acctgggccc caacgccgtg cctgcgcact gcaaggtgat agtgcgagta     300
ctggatgcta atgacaacgc gccagagatc agcttcagca ccgtgaagga agcggtgagt     360
gagggcgcgc cgcccggcac tgtggtggcc cttttcagcg tgactgaccg cgactcagag     420
gagaatgggc aggtgcagtg cgagctactg ggagacgtgc ctttccgcct caagtcttcc     480
tttaagaatt actacaccat cgttaccgaa gccccctgg accgagaggc gggggactcc      540
tacaccctga ctgtagtggc tcgggaccgg ggcgagcctg cgctctccac cagtaagtcg     600
atccaggtac aagtgtcgga tgtgaacgac aacgcgccgc gtttcagcca gccggtctac     660
gacgtgtatg tgactgaaaa caacgtgcct ggcgcctaca tctacgcggt gagcgccacc     720
gaccgggatg agggcgccaa cgcccagctt gcctactcta tcctcgagtg ccagatccag     780
ggcatgagcg tcttcaccta cgtttctatc aactctgaga acggctactt gtacgccctg     840
cgctccttcg actatgagca gctgaaggac ttcagttttc aggtggaagc ccggacgct      900
ggcagccccc aggcgctggc tggtaacgcc actgtcaaca tcctcatagt ggatcaaaat     960
gacaacgccc ctgccatcgt ggcgcctcta ccagggcgca acgggactcc agcgcgtgag    1020
gtgctgcccc gctcggcgga gccgggttac ctgctcaccc cgctggccgc cgtggacgcg    1080
gacgacggcg agaacgcccg gctcacttac agcatcgtgc gtggcaacga atgaacctc     1140
tttcgcatgg actggcgcac cggggagctg cgcacagcac gccgagtccc ggccaagcgc    1200
gaccccagc ggccttatga gctggtgatc gaggtgcgcg accatgggca gccgcccctt    1260
tcctccaccg ccaccctggt ggttcagctg gtggatggcg ccgtggagcc ccagggcggg    1320
ggcgggagcg gaggcggagg gtcaggagag caccagcgcc ccagtcgctc tggcggcggg    1380
gaaacctcgc tagacctcac cctcatcctc atcatcgcgt tgggctcggt gtccttcatc    1440
ttcctgctgg ccatgatcgt gctggccgtg cgttgccaaa agagaagaa gctcaacatc    1500
tatacttgtc tggccagcga ttgctgcctc tgctgctgct gctgcggtgg cggaggttcg    1560
acctgctgtg gccgccaagc ccgggcgcgc aagaagaaac tcagcaagtc agacatcatg    1620
ctggtgcaga gctccaatgt acccagtaac ccggcccagg tgccgataga ggagtccggg    1680
ggctttggct cccaccacca caaccagaat tactgctatc aggtatgcct gaccctgag     1740
tccgccaaga ccgacctgat gttcttaag ccctgcagcc cttcgcggag tacgacact      1800
gagcacaacc cctgcggggc catcgtcacc ggttacaccg accagcagcc tgatatcatc    1860
tccaacggaa gcatttttgtc caacgagact aaacaccagc gagcagagct cagctatcta    1920
gttgacagac ctcgccgagt taacagttct gcattccagg aagccgacat agtaagctct    1980
aaggacagtg tcatggaga cagtgaacag ggagatagtg atcatgatgc caccaaccgt     2040
gcccagtcag ctggtatgga tctcttctcc aattgcactg aggaatgtaa agctctgggc    2100
cactcagatc ggtgctggat gccttctttt gtcccttctg atggacgcca ggctgctgat    2160
tatcgcagca atctgcatgt tcctggcatg gactctgttc cagacactga ggtgtttgaa    2220
actccagaag cccagcctgg ggcagagcgg tccttttcca cctttggcaa agagaaggcc    2280
cttcacagca ctctggagag gaaggagctg gatggactgc tgactaatac gcgagcgcct    2340
```

-continued

```
tacaaaccac catatttgag tgatccacct gcctcagcct cccaaagtgc tgggattaca      2400
ggcgtgagcc accacatccg gccagttagt attctttta ccctctaaat acttctttt       2460 aaaaccacct atttcttgac tctagtttct cttccccatc ctcaccctcg cagtcttaat     2520
ttaggcctca ttgtccttgc ctgaactgct gcaacggcca tctgactggt cttcatgctt     2580
cagaattcat accctgaaat ccaccttccc cactgctgat agaaggattt gtctaaaaca     2640
caaacctgat cagacagctc caatccaaaa tgcaatacaa caataatgaa aataacaagc    2700
tgtgtgtaca caatatgtct tcacctggca aacacgggcc ttcatgattc aacctttgcc     2760
aattatctct ggctacataa ttagtacttc ctattccagc tttaagctcc agcaacacct    2820
aagtgctcat aattccttct gcacaccatg ttgtttcctt cctctctgct tgtgatcaca    2880
ctgttgtccc ctctgcctag aacacgccac cctttattct ccaacctggt taacctgaga    2940
ttcagttcag ttgccatctc attcattgag ggagtcttcc ttgatgatga aggaaggatt    3000
aggtgtctcg actcagtgtt cctgtgatac gtagtaaata tcactgtcat tgtaatctac    3060
attgcttcaa aattgtttat gtgtctacct ccttgttcca gcaacaaatc attcctaaac   3120
tctatggctt aactcaacag tcatttattt tgctcacaaa cttggaaagg gcacagtggg    3180
gatggatgac tgatgacttg tctctgtttc atgtagcatt aactggggca gctctcctgg   3240
aactggagaa tccacctcca agatggctca ttcatacagc tgacaagttg gttcctctct    3300
gcttgggtct ttaggcttca tcacagcatg gtagctgggt tccaagagtg agcatacaag    3360
gagacaggaa gtggacgctg ctaggttctt aaggtctggg cccagaaact gatacaatgc    3420
gtcatttctg ccatattcta ttggcaggca gttacagagc tcagatccaa gtggaagggg    3480
cagagtccca cttgctaatg agaagagtgt caaataattt tgggggacat gttgtaaaac   3540
aactatattc ctttacgtgc ccatgagctc tttcaggact cagctggcat ggcatttgtt   3600
tgctgaatga aaggattcat tcccggacca aactgcttcc atagaacgtc acagtctcag    3660
tcatttgcac caaggaggtt gattccagac aactcagtca catcaattag caagaggatt    3720
aaggctcaaa ggaaattagg cttaaagtct tatagcatgt tagaaatggg aagaatttac    3780
aagccaatca aattatagtc ctttattaaa aaaaaaaat ctgaggtaaa cagataaaag     3840
aaaaagcaaa gaacccatgt gggtcagtta tataaaaaat ggcagtgatt caggatttgc    3900
tatatatggt gaagtacatg ctatttactt gttcaatttc tttcttttag caagttaaag   3960
ctaattaaac ttcagaatct gaatgagcat ggttaatttt ctttcttgta aaagggaca     4020 ctatttactt ttgtaaattg ggtcccgttt acagctacca ttgtaattca actatttgat    4080
gacgcaccat ttcttggtaa aatgttttgt ggcacactaa tgactcaaat cctatgcact    4140
gacatgcatc cagccatt                                                  4158
```

<210> SEQ ID NO 82
<211> LENGTH: 270
<212> TYPE: DNA
<213> ORGANISM: Homo sapien

<400> SEQUENCE: 82

```
caagaacaat ttttgcatt gtcatcattt atgtataaga gacgaagttg taaaatagcc       60
cccatagaat cagaattaga gaacctggaa gagtgtgctc taaccaatgc accatttcc     120 agcaaagcac attttttttt tctacaaacg aaactcttgg aacaagtaga ctacactttc    180
tgtcattccc atgtatggaa gaataaaaat ggccacaagt tatttgcagc tccttacgtc    240
aagagttgga gtccattggc tgggtgtggt                                     270
```

```
<210> SEQ ID NO 83
<211> LENGTH: 612
<212> TYPE: DNA
<213> ORGANISM: Homo sapien
<220> FEATURE:
<221> NAME/KEY: misc_feature
<222> LOCATION: (349)..(456)
<223> OTHER INFORMATION: n= a, c, g or t

<400> SEQUENCE: 83
caaaaccaaa caaaactgac cactacattt agctgcgtgg agggaactgt taagttttgt      60
tgaagtgacg gagacaaaaa cctaaatgga gtgggagaga aattggagac agaaagaacc     120
cttcagaggt ctgttgtaaa aggatgcaaa gaaacaggga actagaaggg attgtggggt     180
ccaaaggaga ataccagca cgtttgtatg ttgtcaataa tgtttcagta gaaaggtaaa      240
aattgagaca agagagaaga aagtgtagct ggctagtcca acatcctaga atagccaaga     300
agggatggga catagtgcaa aactaggctg cccaaagcag agttttcann nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnaact ccaagaattt gcgtttctag     480
caagttcccg gatgattcta ttgctagcta ggtcccagaa acctcatatt tggagaacca     540
ctgtatcaaa aggagggaag acagaaaaga tgagtatata cattagtaca aatgctgaac     600
acctgggtta tc                                                         612

<210> SEQ ID NO 84
<211> LENGTH: 342
<212> TYPE: DNA
<213> ORGANISM: Homo sapien
<220> FEATURE:
<221> NAME/KEY: misc_feature
<222> LOCATION: (268)..(268)
<223> OTHER INFORMATION: n= a, c, g or t

<400> SEQUENCE: 84
gcttcagttt catcccacag gtgttgctat tgttattta tggttcagtt caaatatttt       60
tctcaatacc attgactctg tctctgtgtt attcaggctt gtttttacag ttctttattg     120
atttctatct taaatgcact gtagtaaaaa atgacaatta tttcaatttt caaaatttct     180
tgagttgctt tataactaag tatgtggttg actgtggtga tgtgtctgct ttcaaaaaac     240
tgtacattct gattttggtc gtgttgtnct gtacatatta attgcgtcat ttttacatca     300
tgttattcac gtttcctata tccttaactt ttctcttgct ag                        342

<210> SEQ ID NO 85
<211> LENGTH: 1035
<212> TYPE: DNA
<213> ORGANISM: Homo sapien
<220> FEATURE:
<221> NAME/KEY: misc_feature
<222> LOCATION: (97)..(179)
<223> OTHER INFORMATION: n= a, c, g or t

<400> SEQUENCE: 85
attttctgtc ttatttttgct gtcctttttc taacttcttg aaaagggatt ttcagctcaa     60
gacttttcag actcttctaa tacacttact tatggcnnnn nnnnnnnnnn nnnnnnnnnn     120
nnnnnnnnnn nnnnnnnnnn nnnnnnnnnn nnnnnnnnnn nnnnnnnnnn nnnnnnnnnc    180
tcaataccat tgactctgtc tctgtgttat tcaggcttgt ttttacagtt ctttattgat     240
```

-continued

```
ttctatctta aatgcactgt agtaaaaaat gacaattatt tcaattttca aaatttcttg      300
agttgcttta taactaagta tgtggttgac tgtggtgatg tgtctgcttt caaaaaactg      360
tacattctga ttttggtcgt gttgttctgt acatattaat tgcgtcattt ttacatcatg      420
ttattcacgt ttcctatatc cttaattttt ctcttgctag tcttaacgat tagtgagaaa      480
gtcctgttaa aattacccaa tatgaccagg catttttttt ctttgtaatt ctgtcacttc      540
actttgtttc atatgtattt ttcattaggt acttataaat tttaaattta aaacacattt      600
cctttttaga ctcagaagtc atctaagact ctttcctttc attccttttta tatcccatca      660 gtcatattta aaagatatct atatgtaaac tgacgtcaat agacatgatg taaaagaagg      720
gggtggctct ggtaaagcta aagtaactcc actatgagag tgcattaact atggggggaaa     780 tactttctat attgcagaac acatatttgg tggtacgtag cctcacatcg ccacccggaa      840
aagtctgcat atattgaatt tggaatggat caaactgcac tgagtgcaaa attgtaaatt      900
gcatcttata taaatgtttt agaactagat gatggagcag atgggatcta ttaagagaac      960
ggggtgccag atgactgacc ataaacatgc ttttaataa agactctgct gagagattaa     1020
ctcataaaaa aaaaa                                                     1035
```

<210> SEQ ID NO 86
<211> LENGTH: 662
<212> TYPE: DNA
<213> ORGANISM: Homo sapien

<400> SEQUENCE: 86

```
aaagaacaag acaaaggaat tcagagcttt caagaaccaa gtatgtcagg atagttgtgg       60
aaaacagatc ttttttctcat tttctttgag atgaagatag gcaacatttg ctgcccatta     120 aatacctaa aagtatacag gtgtatctgc aggattcttt ttgctgcttt taaatagtat       180
attgttttaa aaggtctgtt tttatcttgc ctttacaatt atatagactt ttattgacta     240
gctgatcata tagggcctta gtatagacta ccatattcgc cagcatttaa gaaatagtcc     300
ccttccctcc aggagagtat ttatctggta ctcccatatt atggattgaa ggatgagaca     360
agagactgag tattgctaat agttctgtgt gagcctgcag tgttaagtaa aacctattga     420
gtgcacaaaa aaatcatgtt acaattacta caaaatagag aaaccaccta ggttaccaag     480
atgtcaaata atggattaat ggaagaaagt aatgtacctc cttggtagcc tacataatcc     540
accttaattt gttatttctt atttaactat tttgctatgt cttaagaaat gtatattaag     600
tgaaaatgga tgcataaaaa taaaaaaga gaaatgtata tatacaagct acatgaaaat     660
ac                                                                  662
```

<210> SEQ ID NO 87
<211> LENGTH: 884
<212> TYPE: DNA
<213> ORGANISM: Homo sapien

<400> SEQUENCE: 87

```
tcatttctga attcttcctt cttcatttct ggactttaca gctatgaaag aacaagacaa       60
aggaattcag agctttcaag aaccaagtat gtcaggatag ttgtggaaaa cagatctttt     120
tctcattttc tttgagatga agataggcaa catttgctgc ccattaaata ccttaaaagt     180
atacaggtgt atctgcagga ttcttttgc tgcttttaaa tagtatattg ttttaaaagg     240
tctgttttta tcttgccttt acaattatat agactttat tgactagctg atcatatagg     300
gccttagtat agactaccat attcgccagc atttaagaaa tagtcccctt ccctccagga     360
```

```
gagtatttat ctggtactcc catattatgg attgaaggat gagacaagag actgagtatt    420
gctaatagtt ctgtgtgagc ctgcagtgtt aagtaaaacc tattgagtgc acaaaaaaat    480
catgttacaa ttactacaaa atagagaaac cacctaggtt accaagatgt caaataatgg    540
attaatggaa gaaagtaatg tacctccttg gtagcctaca taatccacct taatttgtta    600
tttcttattt aactattttg ctatgtctta agaaatgtat attaagtgaa aatggatgca    660
taaaaataaa aaagagaaa tgtatatata caagctacat gaaaattggt cctgggaata    720
aatcaagaaa ttcaaccaac aaggctacca gttatttagt aaataccaaa agataggtg     780 gatgtagcag taccgaatat cacagtaaga tatgagtagg tagttccact ccctcctacc    840
caactcagtt ttattagaaa attcccgctg ccaaaggggc aagg                     884

<210> SEQ ID NO 88
<211> LENGTH: 528
<212> TYPE: DNA
<213> ORGANISM: Homo sapien

<400> SEQUENCE: 88
caccactggg tgcctgggca gttacccacg gtggacaaag ggcaagagcg ctggttttgg    60
agtcagatag atgtgctctg ccctcccgcc tccagggctg ggctcccagg ttggctgtgg   120
atccagagag ttgtgaggga gaggtaaaat gtgtgtgaaa gttcttggta acacccagc    180 cactatatat tatgagtggt agcacctaat ctccttaatg atatttcagg tgccatattg   240
ggtcatcctc actaaagacc cttcaagagg gttttcctcc aatagcccca gtattaacat   300
tggtctggcc ttattatttg tatctaatgg ggttagactt tcccttccat gctgagaaaa   360
agttgtcttt aagagaatgt gctgaacaat cagggcccag aaaggcaaca acgaatattt   420
tgcatgccaa gaaggaggca aaagaggaag tggaattgta cccaaatatg cttataatag   480
gtgttatttt agctgagctt gtaaggcctc caggagggca gggtatta                528

<210> SEQ ID NO 89
<211> LENGTH: 1282
<212> TYPE: DNA
<213> ORGANISM: Homo sapien

<400> SEQUENCE: 89
gttacttatt tcattctgat cacatttttcc agtacaaata catggaggtc ccaagtgcca    60
aagttacaaa aaaaaaaaca cagttcctgg tccagtttgg gaagacatgt agggactttt   120
tctttaaaca cttgggacca agtggggagt aagcctgcat tgagggaggt gacccagttg   180
ctaagagacg gggaggccag ccaggatgaa aacttggcct gtataatctg tggtcaccac   240
tgggtgcctg ggagttaccc acggtggaca aagggcaaga gcgctggttt tggagtcaga   300
tagatgtgct ctgccctccc gcctccaggg ctgggctccc aggttggctg tggatccaga   360
gagttgtgag ggagaggtaa aatgtgtgtg aaagttcttg gtaaacaccc agccactata   420
tattatgagt ggtagcacct aatctcctta atgatatttc aggtgccata ttgggtcatc   480
ctcactaaag acccttcaag agggttttcc tccaatagcc ccagtattaa cattggtctg   540
gccttattat ttgtatctaa tggggttaga ctttcccttc catgctgaga aaaagttgtc   600
tttaagagaa tgtgctgaac aatcagggcc agaaaggca acaacgaata ttttgcatgc   660
caagaaggag gcaaaagagg aagtggaatt gtacccaaat aatgcttata ataggtgtta   720
ttttagctga gctgtaagct ccaggagggc agggtattaa tatattgagg tgttggctga   780
```

```
gcactgtggc tcactcctat aatctcaaca ctttgggagg ccaaggtggg aggatgactt      840
gagaccagga gttcgagacc agcctgggca acatagcaag acctcgtctc tacacataat      900
ttaaaaaaat aggcatggta gcgtgcgcct gtgattccca actactcaag aggctgaaga      960
aggatcaccg gagactggga ggtcaaggct gcagtgagct gtgtttgcac cactgcactc     1020
cagcctgggg gacagagcat gaccctgtct caaaaaacaa acaaaaaaag aagcggaaga     1080
agaggaagaa gaggaagaag aggaagaaga ggaagagag gaagaggaag aggaagaaga     1140
agagaagaaa gaaggaaga agaagaagaa agaagaagaa gaagaagaag aagaagaaga     1200
agaagaagaa gaagaagaag aagaagaaga agaagaagaa agaaagaaag aaagaaagaa     1260
agagggagga ctctacaaat aa                                              1282

<210> SEQ ID NO 90
<211> LENGTH: 286
<212> TYPE: DNA
<213> ORGANISM: Homo sapien
<220> FEATURE:
<221> NAME/KEY: misc_feature
<222> LOCATION: (259)..(259)
<223> OTHER INFORMATION: n= a, c, g or t
<220> FEATURE:
<221> NAME/KEY: misc_feature
<222> LOCATION: (263)..(264)
<223> OTHER INFORMATION: n= a, c, g or t
<220> FEATURE:
<221> NAME/KEY: misc_feature
<222> LOCATION: (268)..(268)
<223> OTHER INFORMATION: n= a, c, g or t
<220> FEATURE:
<221> NAME/KEY: misc_feature
<222> LOCATION: (271)..(271)
<223> OTHER INFORMATION: n= a, c, g or t
<220> FEATURE:
<221> NAME/KEY: misc_feature
<222> LOCATION: (277)..(277)
<223> OTHER INFORMATION: n= a, c, g or t

<400> SEQUENCE: 90
gctcgagggc aggtgaataa caggcaatgg aaatgcatgg aaatgcattt gtgagcacag       60
ttttggaacg attaaagcat tttatttagg taatagagtc ttctgtctta tttttctagt      120
agaggaattt tagtttatgc tacaatatca agatatctga tttaatccat gcatctctga      180
aggatgtatt ggtttcttat ttcttttaat tgagagagtt gttgaatgat ttaatagaac      240
tttggaattt tcaaaaaana aannaaanta nattaanaaa atttt                      286

<210> SEQ ID NO 91
<211> LENGTH: 644
<212> TYPE: DNA
<213> ORGANISM: Homo sapien

<400> SEQUENCE: 91
acagttggaa atgcagttat tctgtagcat acaggttagg taaagtttct ttcttctgtt       60
tctagagctt gtaaacatag gagcgattgg aatagtttaa gcaaagtcaa agtgagaaaa      120
tatgcagtgc cagaagcttg tgtgagggag tggaaatttt tgcacaaaag ccagaatttg      180
actagataat acttttcaaa ttgtggtccc tgcagtggca ttacatggga acctggtata      240
aaagcaaatt attgggtctc aactaaaatc cactgaatca aaaaccttag ggggttttg      300 agcccagaga tccatgtttt aacaagcccc tcagtgattt tgttatgcat taaactttga      360
gaaccactgg actaaattat gttggttttt caatggcagg tgaataacag gcaatggaaa      420
tgcatggaaa tgcatttgtg agcacagttt tggaacgatt aaagcatttt atttaggtaa      480
```

| | |
|---|---|
| tagagtcttc tgtcttattt ttctagtaga ggaattttag tttatgctac aatatcaaga | 540 |
| tatctgattt aatccatgca tctctgaagg atgtattggt ttcttatttc ttttaattga | 600 |
| gagagttgtt gaatgattta atagaacttt ggaattttca aaaa | 644 |

<210> SEQ ID NO 92
<211> LENGTH: 870
<212> TYPE: DNA
<213> ORGANISM: Homo sapien

<400> SEQUENCE: 92

| | |
|---|---|
| cttacttcag ctgcaaatta cttatattaa taaagtagga tctatcaaat tagagaaatg | 60 |
| atatatggca tcattgggat tttcatattt aatacaattt atcattttc tggtctgaca | 120 |
| ttaagcgatt tatttggaat ttttccctt atgacaaaat ttatcaatca atggtaactc | 180 |
| ctttagtacc ttggtcattt gatgaggtgt tttctaggga atttggtcgt tcttagtata | 240 |
| taattcagct attttcagtc agatccaatc tttagatata aaaatatatc atttgattaa | 300 |
| tggtagttac aagagggtga aagcggtact gtttatcaga ttctactcct tctcgctctt | 360 |
| aggacggcct catctgacag cctcctgact aattatggcc acttgttact acttctctgt | 420 |
| gttccaagtg cgtaaaacac atgcaaggtc ccaacaatga gaagtcactc tctccagcca | 480 |
| ggatttccct cattgtgttg gcacaacgaa tcaaaattaa tgtataatgt tcattttttt | 540 |
| agaactctcc ggtctttgaa ctttcctctt tgaaataaaa atttctcttc tgcccattgt | 600 |
| gaattagagc ctcatttcca cataaagcat ttgtatttgc ttttagtgat ttaatactgc | 660 |
| ttttagtttt tgctttatct gtactaacca atagtcatag cttttgact ccttttgact | 720 |
| tttacatttg tttgtaattt cagtatctca agtggattta tgttaccatt tcaaataagg | 780 |
| agtttatata gcccgggcaa tgttaaggtg ttttaataaa ccaaaggaca aaaattaagt | 840 |
| aaacttgaaa gaatgtcaac tgaaatatct | 870 |

<210> SEQ ID NO 93
<211> LENGTH: 499
<212> TYPE: DNA
<213> ORGANISM: Homo sapien

<400> SEQUENCE: 93

| | |
|---|---|
| ggcagccaag cacaatagcc atacactaca caaggcaaca tcttcctcag gggttattct | 60 |
| tcttttaaag gaagtagtgc agccttcctg ttggttgcct tctcaattac actttactag | 120 |
| gttctgccct ttctacagtc tttctactta gttaacgtag ttctcctagg ccacaatgct | 180 |
| tttaccacat acaacatctg tttaacagtg gttatttatt caagagctgt tatctctttg | 240 |
| acataagctg gaaggtagga ggcattggtg acttttctct gggtattcag tattagatat | 300 |
| gtccttggtg gccatatttt ccacagtgtt tacaaattag acaaatcagg gtttctgggt | 360 |
| ggctaggaag gtgagagttg atgaatgtga gagagaaata aaacaaactg gcagaaggaa | 420 |
| ggagaggtta aagaaatcct gttcatttca aaggcttgtc tgattctctg gccgtgtatt | 480 |
| ctatgaaaca tccttgaat | 499 |

<210> SEQ ID NO 94
<211> LENGTH: 654
<212> TYPE: DNA
<213> ORGANISM: Homo sapien

<400> SEQUENCE: 94

```
ggcagccaag cacaatagcc atacactaca caaggcaaca tcttcctcag gggttattct      60
tcttttaaag gaagtagtgc agccttcctg ttggttgcct tctcaattac actttactag     120
gttctgccct ttctacagtc tttctactta gttaacgtag ttctcctagg ccacaatgct     180
tttaccacat acaacatctg tttaacagtg gttatttatt caagagctgt tatctctttg     240
acataagctg gaaggtagga ggcattggtg acttttctct gggtattcag tattagatat     300
gtccttggtg gccatatttt ccacagtgtt tacaaattag acaaatcagg gtttctgggt     360
ggctaggaag gtgagagttg atgaatgtga gagagaaata aaacaaactg gcagaaggaa     420
ggagaggtta aagaaatcct gttcatttca aaggcttgtc tgattctctg gccgtgtatt     480
ctatgaaaca tccttgaatc ctgggttcct taagttggct ggagtgggct gctgtaattt     540
gaggttaaga aaagtccaaa ttaatatact atccctccag tgagctgcaa atattattca     600
tatatactat aaataaactg ggtgataagt tggttttaat taatgatatt ccaa           654

<210> SEQ ID NO 95
<211> LENGTH: 431
<212> TYPE: DNA
<213> ORGANISM: Homo sapien

<400> SEQUENCE: 95
gtttgagcca ctgtgtccag cctgaaagtt cttgactcaa gtggtgggaa acacataatt      60
tgagccttta tgaactctaa aatctatttt gtcagctaca tgattttact tgcaattgca     120
ttgacacaga tctattcatt gaacatttaa gaattgtctt ttcatcatat cgtatatctc     180
atatatatga gagaacatct tttagtaaac tttacaagtg gtcttctttt tacatattaa     240
catgttgatg aatgttaaag tagcaaagac tcaagccctt accatactaa tgtttcttct     300
tttcaagaca gatctttatg ggcagaaaca cagaaatgga agtagcagat tttaagaaaa     360
ctgattcaga ctttgaactt gtatgacctt atatttattg atttatttga gtcataagat     420
ttctgggttt t                                                          431

<210> SEQ ID NO 96
<211> LENGTH: 616
<212> TYPE: DNA
<213> ORGANISM: Homo sapien
<220> FEATURE:
<221> NAME/KEY: misc_feature
<222> LOCATION: (15)..(15)
<223> OTHER INFORMATION: n= a, c, g or t
<220> FEATURE:
<221> NAME/KEY: misc_feature
<222> LOCATION: (61)..(61)
<223> OTHER INFORMATION: n= a, c, g or t
<220> FEATURE:
<221> NAME/KEY: misc_feature
<222> LOCATION: (191)..(191)
<223> OTHER INFORMATION: n= a, c, g or t

<400> SEQUENCE: 96
ccagggttcc ggttngtttt cctgtgtgct ggttcggggc catggctgcc aacggcaact      60 ncctggggg cacagagtag gtttcctgtg agctggtcgg ggccatggct tgccgccttg     120
caattgcccc tgggggcaac agacttaggt tttcatgtga gcttggtcgg ggccatggct     180
gccgccggca nctgccctg gggcaacaga gtaggtttcc tgtgagctgg tcggggccat     240
ggctgccgcc tgcacctgcc ccggggcaca gagtaggttt cctgtgtgct ggtcgggccc     300
atggctgcca ccggcacctg ccctgggca cagagtaggt ttcctgtgag ttggtcgggg     360
ccacggctgc cgcctgcact gccctggggc acagactagg tttcatgtga gctggtcggg     420
```

```
gccatggctg ccgccggcac ctgccctggg gcacagagta ggtttcgtgt tgcttggaac      480
attaaggcgt aattttgatt cagttttcc taaagaagca ttttgcattt ttatggcttt       540
tgcagttcgg gagaaagctt ctctattttg gatgcatttc agaagggcgt tctattaaac      600
atgaatctgc aaacag                                                      616

<210> SEQ ID NO 97
<211> LENGTH: 1636
<212> TYPE: DNA
<213> ORGANISM: Homo sapien

<400> SEQUENCE: 97
ctgtttgcag attcatgttt aatagaacgc ccttctgaaa tgcatccaaa atagagaagc       60
tttctcccga actgcaaaag ccataaaaat gcaaaatgct tctttaggaa aaactgaatc      120
aaaattacgc cttaatgttc caagcaacac gaaacctact ctgtgcccca gggcaggtgc      180
cggcggcagc catggccccg accagctcac atgaaaccta gtctgtgccc cagggcagtg      240
caggcggcag ccgtggcccc gaccaactca caggaaacct actctgtgcc cagggcagg      300 tgccggtggc agccatggcc ccgaccagca cacaggaaac ctactctgtg ccccggggca      360
ggtgcaggcg gcagccatgg ccccgaccag ctcacaggaa acctactctg tccccgggg      420 caggtgcagg cagcagccat ggccccgacc agctcacagg aaacctagtc tgtgcccag      480 ggcagtgcag gcggcagccg tggccccgac cagctcacag gaaacctact ctgtgcccca      540
gggcaggtgc cggtggcagc cgtggcccg accagctcac aggaaaccta ctctgtgccc      600
cagggcaggt gccggcggca gccgtggccc cgaccagctc acaggaaacc tactctgtgc      660
cctgggtcag gcaggtgcc ggcggcagcc gtggccccga ccagccccca ccagcctcag      720
ttgttctcga tctgctccag gtccagctcc cagcgggccc cggggaaga cgccctcctc      780 cccgacactg tccccatcac gggggtcccc gctgctcctg cggagccat cactggtcac      840 cgactcccta gaggcccaca gggggagcct ggcacctgga gtcctctgga cttcaggcac      900
tgcttctggc agcaaagctg caccccccacc ccaggagggg ctgatgactg agctcgagtc      960
ctgtggaggc aggacagcca caggaccctg cctgcccact ggctcagaaa gaccctccct     1020
tcggctgcca gggccctgcc cgagtgtggg gcactccag gccctgggcc agcggaagca     1080
gttccgggag actgcgcagg ccaggaaagc ccaggtggcc tgggagcccc ggtcagctga     1140
aatagaactg gagaaacaag aagcttggcc ggggcccccg gcaagcaagg gggagcggca     1200
ggctcctgga gtgggaagtg gggtcctggg tccccaccaa actggaatct tccctccact     1260
cccaggaggt ggggcaggca gagccagccc agcagaggcc cccggaagcg tcaggaacaa     1320
caggaaaggc agccggggca cagggacttc ccacactccc caccccgtcc accccatcgg     1380
ccccatccac cccgtgcacc ctgtctaccc catctaccgt cacttccctc tgcactctca     1440
actttcccga ctcctgacct tggaggagct gaactccggc ctggccagct gtctgcagtg     1500
tgggaccctg tgctcctcca cgtgggagcc ccagggtgcc cgctcagtgg ggatctgtac     1560
cctgcccctc acagagatct accatgcaga gacctcagac ttgcgtggga cctcggcagg     1620 ccccctgggtc cattga                                                    1636

<210> SEQ ID NO 98
<211> LENGTH: 638
<212> TYPE: DNA
<213> ORGANISM: Homo sapien
```

```
<400> SEQUENCE: 98
gcagagatta tctcagagag ctctttgacc atttaattta taaataattc tacttgtgtt        60
ttctttctac tttcactagt tttctctttc cacttttaaa aaatgttgtg tttcttattc       120
agggttttgt tttggactgt aatatttat  agaaatttta ggattacttt cataaaaatt       180
tcttaatact tcagagctaa ttcaagaaac ctgtgtgcat taacgtcagg aagttaactg       240
tcccacataa ttgccttgga gttgttctga attgttgatt atggtctcaa ataattatct       300
gacaggtttt tggttaggaa ttttttctgct gccacacact gttcctgttg agaatgtaga       360
ggtacatttc ggactttata ttttatgaa  acatttggaa ggttggggtg gtggatgcca       420
ggtttctaaa tccagaaaaa tgtattttgt tagactatga gtatccctaa tctttaacat       480
gggttaattg gatggtgggg agtatttgct ttgatttcct gtgtataact caccgatggg       540
tttccattgt ttgattttct tcgcggatag gttttttcaga ttacaattag tctaaattag       600
ctggtgcggt ggacatgact gtaatcccag cacgttga                              638

<210> SEQ ID NO 99
<211> LENGTH: 1253
<212> TYPE: DNA
<213> ORGANISM: Homo sapien

<400> SEQUENCE: 99
aaggtactgc ctaaaggttg tcatcttaaa tagcaactgc tgttttttcac tcataagttt       60 ggatgtatgt agcaaataat gtaggttttc tattgagatt tttggataaa ctattatttt      120
ttctaataga gtgataagat attctctact ttgctctcat tctgaaaatc agctaccatg      180
aatattataa cttacatctg ttatcttgct tcagcatagt aatatttaaa gtgattaaag      240
gaaacaaatg tttaccttcc aaaagatgca ttcatttat  tcatttatat aaaaaaactg      300
cacgtttaat atatacattt tgagtgaagt cattgttaat taagggatgt tacagcccct      360
tttgtactat gaagagactt tatgattttc tttctgttaa gggtagtatt tacataaaaa      420
ataatttcat caaaccagag agaggccaac agacattaca tgtcatctca ggtggttcca      480
agcagagatt atctcagaga gctctttgac catttaattt ataaataatt ctacttgtgt      540
ttctttctta ctttcactag ttttctcttt ccacttttaa aaaatgttgt gtttcttatt      600
cagggttttg ttttggactg taatatttta tagaaatttt aggattactt tcataaaaat      660
ttcttaatac ttcagagcta attcaagaaa cctgtgtgca ttaacgtcag gaagttaact      720
gtcccacata attgccttgg agttgttctg aattgttgat tatggtctca ataattatc      780 tgacaggttt tggttagga  ttttttctgc tgccacacac tgttcctgtt gagaatgtag      840
aggtacattt cggactttat attttatga  acatttgga  aggttgggt  ggtggatgcc      900 aggtttctaa atccagaaaa atgtattttg ttagactatg agtatcccta atctttaaca      960
tgggttaatt ggatggtggg gagtatttgc tttgatttcc tgtgtataac tcaccgatgg     1020
gtttccattg tttgattttc ttcgcggata ggttttttcag attacaatta gtctaaatta     1080
gcctggtgcg gtggcacatg actgtaatcc cagcactttg aggaaggcta aggcaagcgg     1140
atcgcttgag ctcgaattca agaccagcct gggcaacatg gcgaaaccct gtctctacca     1200
aaaaaacctc atgccgaatt cttgcctcgg ggccaaatcc ctatgtggac aat            1253

<210> SEQ ID NO 100
<211> LENGTH: 1479
<212> TYPE: DNA
<213> ORGANISM: Homo sapien
```

<220> FEATURE:
<221> NAME/KEY: misc_feature
<222> LOCATION: (778)..(778)
<223> OTHER INFORMATION: n= a, c, g or t

<400> SEQUENCE: 100

| | | |
|---|---|---|
| gtctttggta gaattctatg attctaaagt gctgtgacta caagtgtgga caggtgtaat | 60 |
| cactttacct ctacactgcc cgctgcatgc tgacactgcc tttcatatgg tgggcattca | 120 |
| acagcaacat tcctgtggag tatagatggc tatgactaag gtagtgtaag tggtggtcct | 180 |
| tataaaatat gctctgcttg ccttagggga aaatagttcc ttaaaaacgt tctcatccaa | 240 |
| ctcctcagtg ttaagatatc taaacaaaag tgaccacatc tatacacaac agtaatgaca | 300 |
| cctgaaagaa ttttttaaca gataaagaac agtactccca tggttatgta accaaccaac | 360 |
| taggaaggag agactttaaa attgacaaca tcccagagat gttatatcct aagttatgaa | 420 |
| tgtgctgccg ttgaagaaaa atcagctttc tcatattact cacatatata tattattaca | 480 |
| taacaatgtg ttaaattgga ctacagtgaa tcaaagagtt attgcagctt ctgaaggtga | 540 |
| cagactttta actttcagat attgcttaat gcctgggaaa ccctgggaac cacgccaagt | 600 |
| caatttaacc aagcttttgc ttttagcca gctgtgatgg tggtttctac atagtctgga | 660 |
| taaatccaag aatactttca tggccctagt gaaatttgcc ttttgaaat tattaggaaa | 720 |
| acgaaataca cattatgaaa cttctatcac tcctaaagaa aggggaaaac ctattaanaa | 780 |
| tgaagctctt atttactaat gcatttctat ttcaggagca tttggctaaa ctggggacaa | 840 |
| aaaacaaaaa cttgttctta attaacaaaa gaactagaaa gaagctcata tgaaagcacc | 900 |
| accttgtgtt cagtaagctt caggatagct ctgttgacag cagggcattt agagagtccc | 960 |
| aagtatagtc atgtatcact ggggagggaa gaatctttga ggacatctag tttacaatct | 1020 |
| ttattatttt tcaggtgtag aaaagagatt aaagatcata gaagtcagaa taaatttgta | 1080 |
| aaagttctca tagtcaaaac agctaagtaa tggcattgcc cagactccaa aatcctgacc | 1140 |
| agaatataaa tcaccaattg ttggtttaaa ggggttattt gtgaatcatt ttccaaaaaa | 1200 |
| agaagtacac ttttgtgtt acttaccatt tcaaagaaac ttattcttca agaccatttc | 1260 |
| agatttcctt aggaatgtat gtgttaccca taattgacca cttcaaactt gtaagaaaaa | 1320 |
| aaatgttatg gtcattttgt tattttaga gacaaagtat ttctaatcta ggtttgcata | 1380 |
| caaccttgag gctgtgagat cattagtcaa ttgctttaat tataagccct gtttttttt | 1440 |
| aaatctaaaa actaataaac atctataagg ttaaaaaaa | 1479 |

<210> SEQ ID NO 101
<211> LENGTH: 2313
<212> TYPE: DNA
<213> ORGANISM: Homo sapien

<400> SEQUENCE: 101

| | | |
|---|---|---|
| gtactctcga tgttgaatgg gagccagctg attaggagag ttaatgagag ctacaataga | 60 |
| cttgttttaa aagaatagga caaggcaaac actaactcga caagtattca acaagaatgt | 120 |
| ccttagataa ccttagaata tatcacttta tacagcattg tatttaaga tacaaaaatt | 180 |
| ggagatagtt ctcaagcatc tttccagtcc tgcttgtgaa tcttagccca agataggttc | 240 |
| aataatggat tttaagtcct cctaggcgtt ggagtgcaac ttaacaaaca ccaatcagga | 300 |
| cttttattag taagaagaaa actaggaaag ctgttgtttt ataacattaa tggtctgcta | 360 |
| cttttaactt tgatttttca tggatttttt aaaagtaatt tcaagtgtaa gagacaattt | 420 |

```
aggcaaatca taacatattt tatcagagac tgtgcacaaa gggcactttt aggtagcttc      480
attctccaca ggttctatac ataaatcatg aggtgttacg agaatattgg tccaggaatc      540
agaaaagtgt ggaatttaca atcacctaaa gcaatatgac tttaagaaaa tctgttacct      600
cccatcatct ccctttccca tcctgttaac atttggtggt gatagattta gataagttga      660
cattagtata gatactttac tattataaga ggttgtcttt ggtagaattc tatgattcta      720
aagtgctgtg actacaagtg tggacaggtg taatcacttt acctctacac tgcccgctgc      780
atgctgacac tgcctttcat atggtgggca ttcaacagca acattcctgt ggagtataga      840
tggctatgac taaggtagtg taagtggtgg tccttataaa atatgctctg cttgccttag      900
gggaaaatag ttccttaaaa acgttctcat ccaactcctc agtgttaaga tatctaaaca      960
aaagtgacca catctataca caacagtaat gacacctgaa agaattttt aacagataaa      1020 gaacagtact cccatggtta tgtaaccaac caactaggaa ggagagactt taaaattgac      1080
aacatcccag agatgttata tcctaagtta tgaatgtgct gccgttgaag aaaaatcagc      1140
tttctcatat tactcacata tatatattat tacataacaa tgtgttaaat tggactacag      1200
tgaatcaaag agttattgca gcttctgaag gtgacagact tttaactttc agatattgct      1260
taatgcctgg gaaaccctgg gaaccacgcc aagtcaattt aaccaagctt ttgctttta       1320 gccagctgtg atggtggttt ctacatagtc tggataaatc caagaatact ttcatggccc      1380
tagtgaaatt tgcctttttg aaattattag gaaaacgaaa tacacattat gaaacttcta      1440
tcactcctaa agaaaggga aaacctatta aaatgaagc tcttatttac taatgcattt        1500
ctatttcagg agcatttggc taaactgggg acaaaaaaca aaaacttgtt cttaattaac      1560
aaaagaacta gaaagaagct catatgaaag caccaccttg tgttcagtaa gcttcaggat      1620
agctctgttg acagcagggc atttagagag tcccaagtat agtcatgtat cactggggag      1680
ggaagaatct ttgaggacat ctagtttaca atctttatta ttttcaggt gtagaaaaga      1740 gattaaagat catagaagtc agaataaatt tgtaaaagtt ctcatagtca aaacagctaa      1800
gtaatggcat tgcccagact ccaaaatcct gaccagaata taaatcacca attgttggtt      1860 taaggggtt atttgtgaat cattttccaa aaaagaagt acactttttg tgttacttac        1920
catttcaaag aaacttattc ttcaagacca tttcagattt ccttaggaat gtatgtgtta      1980
cccataattg accacttcaa acttgtaaga aaaaaatgt tatggtcatt ttgttatttt       2040
tagagacaaa gtatttctaa tctaggtttg catacaacct tgaggctgtg agatcattag      2100
tcaattgctt taattataag ccctgttttt tttttaaatc taaaaactaa taaacatcta      2160
taagaattat aacagattat tttcttcatt aaattacttt gtaatcaagt tctagattaa      2220
atgtttaaac atgcattaaa ggattagttc tatctcaaaa gacaaaataa aactcgaggg      2280
gggctccgta ccctattctg ccgatagtga ctt                                   2313
```

<210> SEQ ID NO 102
<211> LENGTH: 217
<212> TYPE: DNA
<213> ORGANISM: Homo sapien
<220> FEATURE:
<221> NAME/KEY: misc_feature
<222> LOCATION: (138)..(154)
<223> OTHER INFORMATION: n= a, c, g or t
<220> FEATURE:
<221> NAME/KEY: misc_feature
<222> LOCATION: (159)..(159)
<223> OTHER INFORMATION: n= a, c, g or t
<220> FEATURE:
<221> NAME/KEY: misc_feature

```
<222> LOCATION: (172)..(172)
<223> OTHER INFORMATION: n= a, c, g or t
<220> FEATURE:
<221> NAME/KEY: misc_feature
<222> LOCATION: (182)..(182)
<223> OTHER INFORMATION: n= a, c, g or t
<220> FEATURE:
<221> NAME/KEY: misc_feature
<222> LOCATION: (188)..(188)
<223> OTHER INFORMATION: n= a, c, g or t
<220> FEATURE:
<221> NAME/KEY: misc_feature
<222> LOCATION: (190)..(190)
<223> OTHER INFORMATION: n= a, c, g or t
<220> FEATURE:
<221> NAME/KEY: misc_feature
<222> LOCATION: (192)..(192)
<223> OTHER INFORMATION: n= a, c, g or t
<220> FEATURE:
<221> NAME/KEY: misc_feature
<222> LOCATION: (198)..(198)
<223> OTHER INFORMATION: n= a, c, g or t

<400> SEQUENCE: 102
agaaatggca aacttcctct aaaacttgcc acacaaagat tattttcct tctctgtctg        60
cacctgagat ctcacactca atttatccat tgctgaaatc tgtggcaaag ctacccctga      120
tcgagagatt ccatctcnnn nnnnnnnnn nnnngtcant tttaaaggct ancatccaag       180
anttgggngn gnatgtgngc atgtttatat ttagaag                               217

<210> SEQ ID NO 103
<211> LENGTH: 667
<212> TYPE: DNA
<213> ORGANISM: Homo sapien
<220> FEATURE:
<221> NAME/KEY: misc_feature
<222> LOCATION: (231)..(542)
<223> OTHER INFORMATION: n= a, c, g or t

<400> SEQUENCE: 103
acacaaaagc gtattgtggg ggagaaacgc cagcaaaagg aacacagaga aagatcttaa        60
agtttcactg ctaaagggat ttattacata acacggccac cttttgccag ccagaccaaa      120
ccgaaagagc aatggctgta tttctgaaag tagcattctg tccggccgaa atatggtaat      180
gagatttaaa aagatttttt taaaggagct caatggttaa aagtcagctt nnnnnnnnnn      240
nnnnnnnnnn nnnnnnnnnn nnnnnnnnnn nnnnnnnnnn nnnnnnnnnn nnnnnnnnnn      300
nnnnnnnnnn nnnnnnnnnn nnnnnnnnnn nnnnnnnnnn nnnnnnnnnn nnnnnnnnnn      360
nnnnnnnnnn nnnnnnnnnn nnnnnnnnnn nnnnnnnnnn nnnnnnnnnn nnnnnnnnnn      420
nnnnnnnnnn nnnnnnnnnn nnnnnnnnnn nnnnnnnnnn nnnnnnnnnn nnnnnnnnnn      480
nnnnnnnnnn nnnnnnnnnn nnnnnnnnnn nnnnnnnnnn nnnnnnnnnn nnnnnnnnnn      540
nncttcctct aaaacttgcc acacaaagat tattttcct tctctgtctg cacctgagat       600
ctcacactca atttatccat tgctgaaatc tgtggcaaag ctacccctga tcgagagatt      660
ccatctc                                                                667

<210> SEQ ID NO 104
<211> LENGTH: 451
<212> TYPE: DNA
<213> ORGANISM: Homo sapien

<400> SEQUENCE: 104
ataacattct agaaataaat tgtttaatat aaaatacact aatatataat aatgtattac        60
```

| | |
|---|---|
| ctaacatatg attatatata actataatgt gtactgtttt acatatatat ttccaaagta | 120 |
| tactataaat gcacttccgc actttgctct ttttactaaa tatatcttgg aaatcatcct | 180 |
| ttattcgtac ataaaaagct tcatagttcc tttttatggc tgcaaaatgt tccagcttat | 240 |
| ggatggactg attctctatc gagcaacatt aagattgtgt cctattttac tattcctaat | 300 |
| tttgctgaag tgaatttctt ttgccatgtg atttccacag gtgtatatat gtagcgtaat | 360 |
| tagtactagt agaaagtaga attgctagat caaagagtat gtgccttgta attttgatga | 420 |
| tattgtgaaa tctcttccac agaagttgtt g | 451 |

```
<210> SEQ ID NO 105
<211> LENGTH: 852
<212> TYPE: DNA
<213> ORGANISM: Homo sapien
<220> FEATURE:
<221> NAME/KEY: misc_feature
<222> LOCATION: (557)..(557)
<223> OTHER INFORMATION: n= a, c, g or t
<220> FEATURE:
<221> NAME/KEY: misc_feature
<222> LOCATION: (821)..(821)
<223> OTHER INFORMATION: n= a, c, g or t

<400> SEQUENCE: 105
```

| | |
|---|---|
| ggacggagtc tcaggtcagg aactgcagtc atctcctttg ctgggtttca gcatttccct | 60 |
| ccttgggaat ctacttctat ctgcaggttt tttatacctt atgttcacct ttggttgtat | 120 |
| ggaagtcgtt ctcttactgt ttaatccaac ctccagtgac agaagtagaa ttaactaaaa | 180 |
| cacaagttag gctccatgct agccaagaac tcagtttttc ttggtctgca gatgagggga | 240 |
| tgttcagtat cctaacctgt tctctggtca caggatggtg tttctctggg tgtggctcac | 300 |
| gagcctccca tcttagaatc ttctaggagc cgggaagtgt gcaagctcta gagccctact | 360 |
| ccggacttgt tgaatctgaa tgtgttagtg ctggggctca ggacctgtga taggaaagtc | 420 |
| acagaaagca tagatctgtc tgaagaaact gctgcagcct ccattcattt ctttcttcat | 480 |
| cttccaggcc atgacttcga actttgttag gatccaacct gcaggagat ttcatgtcag | 540 |
| ttcagtcaca cacacantca cccactagca tcgctgtatc caatatcttc tctggatgtc | 600 |
| aggagagctc tgtgctggcg ctcaaggacc tcagggtcta gttgaaggaa tgaagtgtgc | 660 |
| tcatattaaa agaaaagtag caatgcaaag caaagaaggc caagtgcaaa tgtgcagtgt | 720 |
| aaacttgatt ttaagggagg ggagaggctt tggccttggc caggatccca aggaaggagc | 780 |
| tgaagacatg gaattggagg cagtgagaaa ggtggtcttt ncagagggag cagtgttgac | 840 |
| aaggcccctg ta | 852 |

```
<210> SEQ ID NO 106
<211> LENGTH: 456
<212> TYPE: DNA
<213> ORGANISM: Homo sapien
<220> FEATURE:
<221> NAME/KEY: misc_feature
<222> LOCATION: (84)..(129)
<223> OTHER INFORMATION: n= a, c, g or t

<400> SEQUENCE: 106
```

| | |
|---|---|
| taggttactt tctctactaa tagtctttcc agaaatcttt catatttcat ggggttattt | 60 |
| ggggattcag aaagccaccc agannnnnnn nnnnnnnnnn nnnnnnnnnn nnnnnnnnnn | 120 |
| nnnnnnnnnc actgcatttt aggaaggtga gaatttagag aagagaacac cacttggaat | 180 |
| ccctgcttag cggtgaatgt gaaagtagac atagtggttt ccctttctc aagtgactgg | 240 |

```
gtcttacttc aagtaaatta gacatttcct ggagatcagg ggttgtgtat tttcacttct    300
ctatatagcc atagtactct ttaagagttc actaactacg tgttaaatgg gaactcatga    360
tggttaacaa tagctcagtg gagatgttct acagttattt catacatgct actttgaagt    420
agctcagctt attttgtgaa gtgagtgtat gtgcca                              456
```

<210> SEQ ID NO 107
<211> LENGTH: 501
<212> TYPE: DNA
<213> ORGANISM: Homo sapien
<220> FEATURE:
<221> NAME/KEY: misc_feature
<222> LOCATION: (393)..(393)
<223> OTHER INFORMATION: n= a, c, g or t

<400> SEQUENCE: 107

```
cacagaacgt catagggagt agtgcaccat ctgggataca aaacaaggtc ctaagctagg     60
attgtggatc acaacggatg aatccaggat ctagtttcta gtgatacaag agagggactt    120
ggttatgaat aactagataa aatcttagtg cctgaaacta ggtcacaata tcagagcagg    180
atcagcagaa tgactgatcc tactgagcag ataagctacc agtctgaggc ttctaaaaat    240
tcctccagta tagagcacca gcccaggccc tgaggccaag ataagattcc aggtggaact    300
tcatggttcc aggtggccaa agggctggag ggctttgcct gaaaagatca ctgcagatag    360
tatttgagaa aattactcaa aaccagcctt ggntatatct taggcaagaa ggaaagtatt    420
ttaaaagact ttgtgaattt gtttcagttc acttgttttt tgtggagtac attttactca    480
tctgatacac aaacttcata g                                              501
```

<210> SEQ ID NO 108
<211> LENGTH: 377
<212> TYPE: DNA
<213> ORGANISM: Homo sapien
<220> FEATURE:
<221> NAME/KEY: misc_feature
<222> LOCATION: (317)..(317)
<223> OTHER INFORMATION: n= a, c, g or t
<220> FEATURE:
<221> NAME/KEY: misc_feature
<222> LOCATION: (333)..(333)
<223> OTHER INFORMATION: n= a, c, g or t
<220> FEATURE:
<221> NAME/KEY: misc_feature
<222> LOCATION: (341)..(341)
<223> OTHER INFORMATION: n= a, c, g or t
<220> FEATURE:
<221> NAME/KEY: misc_feature
<222> LOCATION: (354)..(355)
<223> OTHER INFORMATION: n= a, c, g or t
<220> FEATURE:
<221> NAME/KEY: misc_feature
<222> LOCATION: (369)..(369)
<223> OTHER INFORMATION: n= a, c, g or t
<220> FEATURE:
<221> NAME/KEY: misc_feature
<222> LOCATION: (374)..(374)
<223> OTHER INFORMATION: n= a, c, g or t

<400> SEQUENCE: 108

```
actgtgcctg gcctgttctt taaaatatga gataatatat ctgttggatg gatgcctaaa     60
agtggaattg cttggtcaaa gaaatgtttt tttagttgcc ctctatagag actgtaccaa    120
ttaacagaat aggagtcttg ctgcatggga tattgttaag acttggtggg cctttgttaa    180
tataagagaa aattggtggc ctttcagaat ttaagtagta ttttttgtaga tacatattta    240
```

| | | |
|---|---|---|
| agagtgattt tgtgtgtgtga actgtttatt ttttgtcatt tattctatttt gattgtggtt | 300 | |
| tatctcattg attgtangaa ctctttgcct tcnttttctt ncgatctgac aaannttttc | 360 | |
| ttttcatgng gatntcc | 377 | |

<210> SEQ ID NO 109
<211> LENGTH: 884
<212> TYPE: DNA
<213> ORGANISM: Homo sapien
<220> FEATURE:
<221> NAME/KEY: misc_feature
<222> LOCATION: (108)..(108)
<223> OTHER INFORMATION: n= a, c, g or t
<220> FEATURE:
<221> NAME/KEY: misc_feature
<222> LOCATION: (140)..(140)
<223> OTHER INFORMATION: n= a, c, g or t
<220> FEATURE:
<221> NAME/KEY: misc_feature
<222> LOCATION: (300)..(300)
<223> OTHER INFORMATION: n= a, c, g or t

<400> SEQUENCE: 109

| | |
|---|---|
| aactgaggtc cagaggagct tgggtgcctt gcccgaggtc acacagcttg tgagtgctgg | 60 |
| ttggagctga ggaaacgtga gaaaattgtt gttcccaagc tgtgaagntg ccacatgggg | 120 |
| gccagataaa attattcttn ttcttttag agatagggtc tcaccatcat tcaggttgta | 180 |
| gtacagtggc gcaatcatgg ctcactgcca cctccaactc ctgggcttaa gggatcctcc | 240 |
| cacctcagcc tcctgagtag ctgggtctac aggccagtgc caccatggtg ggctaatttn | 300 |
| taaaagtttt tattttccat agagattggg ctttgccatt tgcccaggc tggtcttgaa | 360 |
| ctcgtgggct gaagcaatcc ggctccgtca acctcccaaa gccctgggat tacaggcgtg | 420 |
| agccactgtg cctggcctgt tctttaaaat atgagataat atatctgttg gatggatgcc | 480 |
| taaaagtgga attgcttggt caaagaaatg ttttttttagt tgccctctat agagactgta | 540 |
| ccaattaaca gaataggagt cttgctgcat gggatattgt taagacttgg tgggcctttg | 600 |
| ttaatataag agaaaattgg tggccttca gaatttaagt agtatttttg tagatacata | 660 |
| tttaagagtg attttttgtgt gtgaactgtt tatttttgt catttattct atttgattgt | 720 |
| ggtttatctc attgattgta ggagctcttt gccttcattt tattacgata tgacaaaaat | 780 |
| tttcttttca taggatatca ttgttttggg tatttttttc ccccatatgg tgtcttcttt | 840 |
| tcttaaaaaa aaatcctcgt gccgaatgta tcgtcgaggc cagt | 884 |

<210> SEQ ID NO 110
<211> LENGTH: 471
<212> TYPE: DNA
<213> ORGANISM: Homo sapien

<400> SEQUENCE: 110

| | |
|---|---|
| ggtccattgg tgagtgaaag gtcattatgt ggtatatgac tatatttcca ggctgggttg | 60 |
| agggagaggt acacagggat tcttgggtta agaaatcttt atattctcat cttctcttaa | 120 |
| aagccaagag ccctgtagga taattttcat agaaccagtg gtctcaggct ccagactcta | 180 |
| gatactttaa atactataat aatttattat atgcaaaaat aaccctcatt taactttagc | 240 |
| taatttataa agcagtccta gcaattcatc ttttgttggt agctatatat agggaatgcc | 300 |
| tttgtcaaaa ggaaaattac tgtggtgtcc cagcataacc aaggcatttg atcactgtgt | 360 |
| tcagtagtga ttttagagtg atgctgtctg ataaggtgac tgattttta ctttaagtct | 420 |
| tgtttactat gataataaca gttaatattt attattttta ctagatattg t | 471 |

<210> SEQ ID NO 111
<211> LENGTH: 233
<212> TYPE: DNA
<213> ORGANISM: Homo sapien
<220> FEATURE:
<221> NAME/KEY: misc_feature
<222> LOCATION: (96)..(121)
<223> OTHER INFORMATION: n= a, c, g or t

<400> SEQUENCE: 111 aatataggggg tgatgaagcc agctcttgct acatatattc tttactaaat atttaacaga     60
attgaatgtt cactgatgtg ttagagttga aggtgnnnnn nnnnnnnnnn nnnnnnnnnn    120
ngcaagatat gtccaagtat gcatggttgt tttctataat gtgtatgttg agtatatctc    180
tattatctgt gttgggggta gaactaactg ttttgggcca ctttattgag ttt           233

<210> SEQ ID NO 112
<211> LENGTH: 771
<212> TYPE: DNA
<213> ORGANISM: Homo sapien
<220> FEATURE:
<221> NAME/KEY: misc_feature
<222> LOCATION: (342)..(410)
<223> OTHER INFORMATION: n= a, c, g or t

<400> SEQUENCE: 112
ttaaggcaat aaaagcatta tttgggataa ataaggtaat taggtaatga taaaaagaac     60
taagtaggaa gatagtaaca atttcaaact tctactcagt tcataaaata gccttaattt    120
ttaaaagcac aacttgacaa aactgtaaga acttttcaaa tgtacaacaa aggtggaaga    180
acttaatatt tttctcaata attgatagat caggaagaca aaataaaagt aagtaaataa    240
ttatctgaat agagttaaca agctacctaa tacaaacata ataattatt cagcacattt     300 tagggagcat tgtctatgat ctagacactt ctctaatcac tnnnnnnnnn nnnnnnnnnn    360
nnnnnnnnnn nnnnnnnnnn nnnnnnnnnn nnnnnnnnnn nnnnnnnnnn taatagacaa    420
caataagtaa ctgataaata tatgatatgc taaatggtga aaaatgccat gaagaaaat     480 aaagcagatt aaaggaggta aggagatgca aaatggtagg gaggagggtt gctattttac    540
atattcagtg atcagggatg cttaactcat aagattatat ttgaggagag acctgaaaga    600
agtaaagggt gagccatgtg agaagaatgt cccaggcaga aggaacagca gttaaaaagc    660
cctgatgcaa gaatgtgctt ggcctatttg agaaacagca agactagttt gcctggagta    720
gagtgaggaa cggggaaagt tgaagaagat gttaccaggg aacatgcgga g              771

<210> SEQ ID NO 113
<211> LENGTH: 453
<212> TYPE: DNA
<213> ORGANISM: Homo sapien

<400> SEQUENCE: 113
cgttaactga tcatccaaat acaatcctaa agatatatca gaagctttat tttggtacaa     60
agtcataaga atcaaaactt ttttaaccat tcacattagg tatcaacagt aattgtttga    120 gatacttta tatcaattct gttacactga gcctttagtc atactaagag aatgcagaag     180
aagttatagg aaaacgaatc ttcactgaaa ctagtattat ataatcttga attagatgtt    240 taaaaactt tatagcttga tataaaatga gttgaaaatt attatttaat aggaagcagc     300
attagatttt tgtcacctgt tttcagataa tatttctagt ctatgtatgt tatttaattt    360

```
ttacactttg gcccattgtt tattttcctt aaggaattca tcaaatgcaa tgaaatttga    420
ataaaattga tcatagcaat aaataatttt taa                                 453

<210> SEQ ID NO 114
<211> LENGTH: 810
<212> TYPE: DNA
<213> ORGANISM: Homo sapien

<400> SEQUENCE: 114
caagaatcat aacataaagg gattcatgct tagaaaaaat ccataaactc ccttctaaat     60
attgagacac tccaggcttc tttcagacaa ataacttcta attattccat atttttcaag   120
ttattaacca agataaagaa tctctcagtt agtggggaaa atgaaaatta ttaagaatag   180
aattgtcttc tgactttaaa aacaatttag actttaaaac atgaacgttt actcaggctg   240
gtgatactct agttgttagt ataccatact tgaagatatc atcaagatca ctatagttgt   300
atatattctc tattttata tgtaaatgtt aacttagttc aagtattttt gcttgtatcg    360
ttaactgatc atcaaataca atcctaaaga tatatcagaa gctttatttt ggtacaaagt   420
cataagaatc aaaactttt taaccattca cattaggtat caacagtaat tgtttgagat    480
acttttatat caattctgtt acactgagcc tttagtcata ctaagagaat gcagaagaag   540
ttataggaaa acgaatcttc actgaaacta gtattatata atcttgaatt agatgtttaa   600
aaaactttat agcttgatat aaaatgagtt gaaaattatt atttaatagg aagcagcatt   660 agattttgt cacctgtttt cagataatat ttctagtcta tgtatgttat ttaatttta    720 cactttggcc cattgtttat tttccttaag gaattcatca aatgcaatga aatttgaata   780
aaattgatca tagcaataaa taatttttaa                                     810

<210> SEQ ID NO 115
<211> LENGTH: 155
<212> TYPE: DNA
<213> ORGANISM: Homo sapien

<400> SEQUENCE: 115
ctctaactct aggagtaaca gccgctccta acatctgctc ttcctatgtg ctttagagtt     60
ctctctgctt attagccaat tcctcattac tccaatcccc catcaccaaa tagagttgat   120
aactctttac agtaaactat ccctgttgat attgt                              155

<210> SEQ ID NO 116
<211> LENGTH: 160
<212> TYPE: DNA
<213> ORGANISM: Homo sapien

<400> SEQUENCE: 116
ctctaactct aggagtaaca gccgctccta acatctgctc ttcctatgtg ctttagagtt     60
ctctctgctt attagccaat tcctcattac tccaatcccc catcaccaaa tagagttgat   120
aactctttac agtaaactat ccctgttgat attgtaaaag                         160

<210> SEQ ID NO 117
<211> LENGTH: 553
<212> TYPE: DNA
<213> ORGANISM: Homo sapien

<400> SEQUENCE: 117
accacgtccg gcccctcttc tcttaattta aatgttttct tcagcaaaca gtatcctagg     60
agcattgctc atatgggccg gaatgtcctg gctgcccatc gaggctgtct gtagataccc   120
```

-continued

```
tttgcctgct tcagtgccaa gtgaacatcg cagagatctg ccttgtgtct ccctgcaccc    180
ctggctgcag gggagctcct gctgcctcct ctggagctgg tggggcctc actgccatcc     240 ttggatccct tcctgccgtc agcctgctgt cctcagtgca ctgggaggag ggggtgcgct    300
gtggttgtgt tgagccttca taggtgtcct ctggtgggct tagaatgggg gttcttaatc    360 cccccccagta tgtggataga attcagggt ctgtgaacat ggatgaggaa aaataacat    420 tattatttat tactaatgta gctaaaatat gtagtgtgac ctttgattat aaatgtagac    480
aataaacctc acagcattag aaaggcctgt gactacccac ataacaaaca agcacattgt    540
tgtccctgaa ccc                                                      553
```

<210> SEQ ID NO 118
<211> LENGTH: 593
<212> TYPE: DNA
<213> ORGANISM: Homo sapien

<400> SEQUENCE: 118

```
accacgtccg gcccctcttc tcttaattta aatgttttct tcagcaaaca gtatcctagg    60
agcattgctc atacgggccg gaatgtcctg gctgcccatc gaggctgtct gtagataccc    120
tttgcctgct tcagtgccaa gtgaacatcg cagagatctg ccttgtgtct ccctgcaccc    180
ctggctgcag gggagctcct gctgcctcct ctggagctgg tggggcctc actgccatcc     240 ttggatccct tcctgccgtc agccctgctg tcctcagtgc actgggagga ggggtgcgc    300 tgtggttgtg ttgagccttc ataggtgtcc tctggtgggc ttagaatggg ggttcttaat    360 ccccccagt atgtggatag aattcagggg tctgtgaaca tggatgagga aaaaataaca    420
ttattattta ttactaatgt agctaaaata tgtagtgtga cctttgatta taaatgtaga    480
caataaacct cacagcatta gaaaggcctg tgactaccca cataacaaac aagcacatgt    540
agtccctgaa cccaaaaaaa aaaaaaaaa aaaagatctt taattaagcg gtc            593
```

<210> SEQ ID NO 119
<211> LENGTH: 94
<212> TYPE: DNA
<213> ORGANISM: Homo sapien

<400> SEQUENCE: 119

```
ttaaaatttt taaaaaaata aaaagaaaat cttgtgactt tatccccagt ggaaatcaca    60
ggtatttcat atgaagttat agttactgct gata                                94
```

<210> SEQ ID NO 120
<211> LENGTH: 82
<212> TYPE: DNA
<213> ORGANISM: Homo sapien

<400> SEQUENCE: 120

```
gaaaaagcc attctgcaac atgaaagtgc aaggtgctga tgtagcagct gcagcaagtt    60
atcaagaata tctaactaag at                                            82
```

<210> SEQ ID NO 121
<211> LENGTH: 431
<212> TYPE: DNA
<213> ORGANISM: Homo sapien

<400> SEQUENCE: 121

```
gcagtgttca ggacagggg ataagctgag gccttagcaa tcaggagagg catcgtggag     60
```

```
ggggtggccc tgagcagtcc caactgccac cagcccagag ggcacatcaa taccagtgat    120
aaaaagcatc ttcctcctcg cttcatgaga ggggctggag tggactcagc tcccacccag    180
cccaccaccc aagctggcat cattggccag ggcacaaccc acgtagctct cagcagtggc    240
cctgggctgc tccttgctgg acaggatagg ctaaggttgg taaaggaaaa gggaagggag    300
aaccaggtaa caatcccata agcagggtac cacgcgactc atcacaacag aggcaaaagg    360
ctgtcatggg ggcatctgat tccgaattga cctgtttcta atggcttccg tgtttccttt    420
cttttccagc a                                                         431
```

<210> SEQ ID NO 122
<211> LENGTH: 750
<212> TYPE: DNA
<213> ORGANISM: Homo sapien

<400> SEQUENCE: 122

```
agacaaaacc caagaatcag cttcctcttc cttcattact cttgcatggg tgttggctct     60
aatttctcca tctagttagg cagtcctttg ctttttattg cttgtttatt gatgacattt    120
gccatttgta gcaatagtaa tagaatcatc tatatatttg tggccttgtt gaatgtagaa    180
aaaggatagt ggcattttct aattgtgtaa ccctataaca ccttgacggg ggactacagt    240
tcatatgctg gacctttgt gtttgttcat ggcgtgtggg ttgctttaat atacttagca    300
cattgtccta attgccatcc ttttggggag ggctatatat ccaagctaat atggtagcat    360
ttttgtttta acatagagct gacccaaggt agacgtaagt gttgttcatt ttcgcctaat    420
actaataaaa ttacctaatt gttgaagctt ggagcttgaa tctaggcatt ttatgtcatt    480
tcaagtacac cctagtattt taaagcataa atatcctact atcctcaaca actttagaac    540
aaaaataaat attttaacaa gaaaaaagca tgccatgaca agctgtaact taataaagaa    600
agacaaggaa tggtctctat agaccgagaa aaaataggtc ctcagatata tttatagcaa    660
aggaaagtta ggaagttaaa aaacagtgga ctcccccccc ccgccaaaaa ctcacaacct    720
atatattggt tatcacaagc tgttttagtg                                     750
```

<210> SEQ ID NO 123
<211> LENGTH: 55
<212> TYPE: DNA
<213> ORGANISM: Homo sapien

<400> SEQUENCE: 123

```
ctaatagcct gctgttgact gaaagcctta ctgatagcaa aaccagttga ttaac          55
```

<210> SEQ ID NO 124
<211> LENGTH: 450
<212> TYPE: DNA
<213> ORGANISM: Homo sapien
<220> FEATURE:
<221> NAME/KEY: misc_feature
<222> LOCATION: (292)..(292)
<223> OTHER INFORMATION: n= a, c, g or t
<220> FEATURE:
<221> NAME/KEY: misc_feature
<222> LOCATION: (384)..(386)
<223> OTHER INFORMATION: n= a, c, g or t
<220> FEATURE:
<221> NAME/KEY: misc_feature
<222> LOCATION: (384)..(386)
<223> OTHER INFORMATION: n= a, c, g or t
<220> FEATURE:
<221> NAME/KEY: misc_feature
<222> LOCATION: (396)..(396)
<223> OTHER INFORMATION: n= a, c, g or t
<220> FEATURE:
<221> NAME/KEY: misc_feature
<222> LOCATION: (398)..(398)
<223> OTHER INFORMATION: n= a, c, g or t
<220> FEATURE:
<221> NAME/KEY: misc_feature
<222> LOCATION: (405)..(405)
<223> OTHER INFORMATION: n= a, c, g or t

<400> SEQUENCE: 124

```
taattatttg catgaaataa atcatcagtt gaaacttact atattaaaaa acataaaaat      60
aagccctttt tttacacaca ccagtgcctt gaaaaactgg cttgccaaat tcaaaatggc    120
aaaattaata aaatgagtag ctaagcattt tatttgcaat tgtatctttg catttatttt    180
tagagcataa tcgagaaata tatttattga ttcctaaagg aaatgtttac tttcctttat    240
ctggtaatta cggaaacaaa ttgcctggtc acatttgaaa taaatgaatc anatttgagt    300
caatgtgtta tagataacta aagttacatg attgcaattt attcacagag tgttttttta    360
aaaaaatcat tgaagtgact ggannnaatg tacttnantg aaatnttaaa aaatggagaa    420
gagtctcagc atgaagtgct gaaggcttct                                     450
```

<210> SEQ ID NO 125
<211> LENGTH: 398
<212> TYPE: DNA
<213> ORGANISM: Homo sapien

<400> SEQUENCE: 125

```
gtcttctagc tcccggacct gagcgttctt gccttgcttt ctctctttcc tctcatttat      60
gctatttctg gcgtgtcatc actggcttac ccattatgta agctttaagt gaaaaaatca    120
gatgttattt tcatgagctc tgagggcact tctgcatttg ttctcatttg actcttctga    180
agcctggaga tgcacaggaa ggcagtttcc actgcagatg agcagcatgg aggaggcttt    240
tggaagtgaa atgaattgtc caaggtccag aggtgaggag ctgggaccag gcctcacagg    300
cttctgttct gtggtcctgt cccgtccctg gtttctgctc tatccaggtg gtgccttcta    360
gttccttcct aaccaacaag tgtgggaggc tgggtgtg                            398
```

<210> SEQ ID NO 126
<211> LENGTH: 658
<212> TYPE: DNA
<213> ORGANISM: Homo sapien

<400> SEQUENCE: 126

```
gattttattg ttgatgggaa atgacaccaa atgtcatttc aggaataaat aaccatggca      60
gttctaaaaa cttggcacaa atatatgagt tgcgctgaga ctggggtagc tccatccttt    120
atccatggag attggcaagt gacaactcct gctccggctc cttcgtgcat tccccttatt    180
gtgaggaagc gagaggggcc ctcctgtctg tgtccccatg cctgtgtcac tgcctctctt    240
ttcacccagc gtgttgtctt ctagctcccg gacctgagcg ttcttgcctt gctttctctc    300
tttcctctca tttatgctat ttctggcgtg tcatcactgg cttacccatt atgtaagctt    360
taagtgaaaa aatcagatgt tatttcatg agctctgagg gcacttctgc atttgttctc    420
atttgactct tctgaagcct ggagatgcac aggaaggcag tttccactgc agatgagcag    480
catggaggag gcttttggaa gtgaaatgaa ttgtccaagg tccagaggtg aggagctggg    540
accaggcctc acaggcttct gttctgtggt cctgtcccgt ccctggtttc tgctctatcc    600
aggtggtgcc ttctagttcc ttcctaacca acaagtgtgg gaggctgggt gtggtggc     658
```

```
<210> SEQ ID NO 127
<211> LENGTH: 430
<212> TYPE: DNA
<213> ORGANISM: Homo sapien
<220> FEATURE:
<221> NAME/KEY: misc_feature
<222> LOCATION: (142)..(142)
<223> OTHER INFORMATION: n= a, c, g or t
<220> FEATURE:
<221> NAME/KEY: misc_feature
<222> LOCATION: (152)..(152)
<223> OTHER INFORMATION: n= a, c, g or t
<220> FEATURE:
<221> NAME/KEY: misc_feature
<222> LOCATION: (167)..(167)
<223> OTHER INFORMATION: n= a, c, g or t
<220> FEATURE:
<221> NAME/KEY: misc_feature
<222> LOCATION: (171)..(171)
<223> OTHER INFORMATION: n= a, c, g or t
<220> FEATURE:
<221> NAME/KEY: misc_feature
<222> LOCATION: (183)..(183)
<223> OTHER INFORMATION: n= a, c, g or t
<220> FEATURE:
<221> NAME/KEY: misc_feature
<222> LOCATION: (195)..(195)
<223> OTHER INFORMATION: n= a, c, g or t
<220> FEATURE:
<221> NAME/KEY: misc_feature
<222> LOCATION: (241)..(241)
<223> OTHER INFORMATION: n= a, c, g or t
<220> FEATURE:
<221> NAME/KEY: misc_feature
<222> LOCATION: (243)..(243)
<223> OTHER INFORMATION: n= a, c, g or t
<220> FEATURE:
<221> NAME/KEY: misc_feature
<222> LOCATION: (283)..(283)
<223> OTHER INFORMATION: n= a, c, g or t
<220> FEATURE:
<221> NAME/KEY: misc_feature
<222> LOCATION: (296)..(296)
<223> OTHER INFORMATION: n= a, c, g or t
<220> FEATURE:
<221> NAME/KEY: misc_feature
<222> LOCATION: (315)..(315)
<223> OTHER INFORMATION: n= a, c, g or t

<400> SEQUENCE: 127
cagaaaatat ttggccagaa gaaataaagt atgatcctaa tagaatccag aagcgtaagc      60
atagcactaa atgatgccct taggcctgat cttcaagcca gtcatactgt ataacgtaag     120
atttgagccg gtgtcggtat cntcagacat gnaggaggaa gtgattnaac natgaacagt     180
tgnaaagtgg cagcngttag gacaacccaa attgtttttc caagagaaaa caatccacac     240
ntnaaaaaaa aaattgggcc cttttctttt ttgtcctggc ttntgtcttg gccacnttgg     300
ccacatagtg ttgtntgtta aatataataa aactcattag ggcagtcctt cattaaaaat     360
ggcatcagct ctagaaactc actatttaag cttaaaggac tacatattca tgatagagtc     420
gagatgcccg                                                            430

<210> SEQ ID NO 128
<211> LENGTH: 113
<212> TYPE: DNA
<213> ORGANISM: Homo sapien

<400> SEQUENCE: 128
tacaaaacaa aaatgatcag tgagaagcta ggtggcgtca aatgcccggg caaaaggggg      60
ttaggtctgc agcgctatac tcagatgtaa cttacagatg caactagcgg aaa            113
```

```
<210> SEQ ID NO 129
<211> LENGTH: 689
<212> TYPE: DNA
<213> ORGANISM: Homo sapien

<400> SEQUENCE: 129
cacaactcta gaaggtgcct gtcacaccgt tttgtatgaa aggtgcctcc tagagtatag      60
ctgtacagta gactcatttt tgatataaga agggataaag cacacttgac agatgatatc     120
aaaatgtaaa agaaaagaag tgtctgtttt agaaggaagc tgtatgagat aataggccaa     180
ggttagggtg gtggtagcca tggtggtaaa aataggatca cttaatctag attacttaat     240
cagtaagttg attccagggg ccagtgggaa ttgctgaaag tttcatctga atacatggaa     300
tttttagcag tgattagggg aatggtgctg gtatttatag ccatgaactt attacttgaa     360
agcatcctag ggacccaagt cttaatcaag gggcagttct tccaagtagt ggttgaggaa     420
gttgggtatg ctttccaaaa cttctttcct cactaaagat tgcagatata ctctgtaagt     480
gacttcacag aatatactca attgtcatat tttaatttac atgtttcttc tgattatagg     540
tcccacgtga ttataagttc tgagatcaag ggtcatcttt gtgggggtgt gtgtgtgcac     600
ttaaaatttt tatgtgctgg taatagttat cttgtggata tttaagaaat aggaatgtgt     660
gccatatttt aaatacacct tatatgcaa                                        689

<210> SEQ ID NO 130
<211> LENGTH: 1901
<212> TYPE: DNA
<213> ORGANISM: Homo sapien
<220> FEATURE:
<221> NAME/KEY: misc_feature
<222> LOCATION: (1582)..(1837)
<223> OTHER INFORMATION: n= a, c, g or t

<400> SEQUENCE: 130
tcttttaaac tgtcttacc ttgctcccat taatattcac atttaaggta accgctttca      60 taaaacatc actgaataac tcccctggt cctgtcagtc cagcattatt ctcaccattt      120
atagagtttc aaatattgtt aaactgtagt ggctatcttg cttttatgta ttttgggttt     180
atgcacattt cctccacaga ataggaattg ttttcggtat tgttctctat ctcttctcca     240
agtacctagt cagcaacccc ccatgggtgc tcagtaaata ttgaatgatt atacttaacc     300
tcccttcata gctcagacta ttccatgaac aatttatgga cataaaaatc tatgccagta     360
gacatttaag gatatttttt atggtgacta tggaaattgc ctggttacaa atttatatat     420
agagtcagta acattgataa aaacataaca aattactgtt tcatggaact catgaggcat     480
taagaggctt atttagtttt gtttagatac aaggtagtgt cttccaaaac attgttactt     540
caaaattttt gtagctgctc cagttgaaca ctatattaaa atgcacattt ttgaggacat     600
attcttgaaa ttaggaatgt aatttttaag aattaaacag aggaccagaa atagatctga     660
ggagtttatc agagctgctt ccttgcacaa ctctagaagg tgcctgtcac acctttttgt     720
atgaaaggtg cctcctagag tataactgta cagtagactc atttttgata taagaaggga     780
taaagcacac ttaacagatg atatcaaaat gtaaagaaaa agaagtgtct gttttagaag     840
gaagctgtat gagataatag gcaaaggtta gggtggtggt agcaatggtg gtaaaaatag     900
gatcacttaa tctagattac ttaatcagta agttgattcc aggggccagt gggaattgct     960
gaaagtttca tctgaataca tggaattttt agcagtgatt aggggaatgg tgctggtatt    1020
```

```
tatagccatg aacttattac ttgaaagcat cctagggacc caagtcttaa tcaaggggca       1080
gttcttccaa gtagtggttg aggaagttgg gtatgctttc caaaacttct ttcctcacta       1140
aagattgcag atatactctg taagtgactt cacagaatat actcaattgt catattttaa       1200
tttacatgtt tcttctgatt ataggtccca cgtgattata agttctgaga tcaagggtca       1260
tctttgtggg ggtgtgtgtg tgcacttaaa attttatgt gctggtaata gttatcttgt        1320
ggatatttaa gaaataggaa tgtgtgccat attttaaata caccttatat gcaaaaattt       1380
taatgtaatt taagtatatc gcaaaaaata aatagcgggt ggtattcaca ctgcagagga       1440
ttggcaagtc ttttactat acttcaaaca attgttggca gaaatccgcc tcatgcactg        1500
tattgaataa tttgaaacat tagcatttaa ctaatccaaa gctaagataa agagattttg       1560
aggtgaggta ataatatat gnnnnnnnnn nnnnnnnnn nnnnnnnnnn nnnnnnnnnn         1620
nnnnnnnnnn nnnnnnnnnn nnnnnnnnnn nnnnnnnnnn nnnnnnnnnn nnnnnnnnnn      1680
nnnnnnnnnn nnnnnnnnnn nnnnnnnnnn nnnnnnnnnn nnnnnnnnnn nnnnnnnnnn      1740
nnnnnnnnnn nnnnnnnnnn nnnnnnnnnn nnnnnnnnnn nnnnnnnnnn nnnnnnnnnn      1800
nnnnnnnnnn nnnnnnnnnn nnnnnnnnnn nnnnnnnttt aataggtata ttttcgattc      1860
atgattgaat ccatgataat ggaacccatt gatatggagg g                          1901

<210> SEQ ID NO 131
<211> LENGTH: 436
<212> TYPE: DNA
<213> ORGANISM: Homo sapien

<400> SEQUENCE: 131
gctcgagtaa ggcattcaat aatgtctttt tgcttccgat tctagctgta taacataggt        60
aaatctctta aattctcaga acttcaattc atttatatgt aaagtgagga gttgtaccat       120
attggtagtt attaacatgt actgtactta tgaatcagtc tgaaaatctt gctaaactgc       180
atattctgag cttttcttaa ttttttttg ttttctcgga aacgctgatt ctctaggtct        240
tggttggagt ccaggtatct gcaaattaaa taagcacttg aagtgatagt atctgagtgt       300
ccgtaggcaa atgttaggag aactgaatca gatgttcttt gaaagatttt catggttcta       360
aaatgttctg atttaaaatc cacaaagaaa aaaagcattg aaaatgaatc agcaaactag       420
atgtaattaa agcttc                                                      436

<210> SEQ ID NO 132
<211> LENGTH: 498
<212> TYPE: DNA
<213> ORGANISM: Homo sapien
<220> FEATURE:
<221> NAME/KEY: misc_feature
<222> LOCATION: (434)..(434)
<223> OTHER INFORMATION: n= a, c, g or t
<220> FEATURE:
<221> NAME/KEY: misc_feature
<222> LOCATION: (488)..(488)
<223> OTHER INFORMATION: n= a, c, g or t

<400> SEQUENCE: 132 gaaaaaagt ggaaacattt ttttaaatca agatttaaaa aaaaattaca tttgtgatag         60
gtagaaaaca atctgtcaca cactgctttt ggtagttgtg taagtttgta caacctacca       120
aaatgtaaat ctgacagtat acatcaaagc cttatgatgg tcggcagtcc atcgaggaat       180
ctattctatg ttgtacaatc aaggcgtact atgatattta ttgcagaaca gagagaaata       240
gcatatacat tgctagttaa ttgattaaat aaagcatgat tccttcaaaa attgagtaat       300
```

```
atgacattaa aaaccacaat ttcaaactat atttaagaag atacaaataa ttctttatta        360
ttacttttac tctcaggaat gtgtttgagt gatgcatctc caggcatcaa gtgagtaatc        420
caatattgaa gaanattaaa attttccaca aagtccccct tctagaagaa tgtgctcata        480
tcttttgnac agaaatga                                                      498

<210> SEQ ID NO 133
<211> LENGTH: 422
<212> TYPE: DNA
<213> ORGANISM: Homo sapien

<400> SEQUENCE: 133
tagaggagga aatcagggct gcttaggaat gttacataat gtattctgat ttgagttaaa         60
taaaaaaatc attatttgct catacatcag atgaagaaac ctgggaagat gaaatgtggc        120
ttgagtgagt gggtaactgg atgaacgagt gattgagttg tcaactgttg gttagcggtc        180
atggtgaaca cgaagggagg catctgggga tatgccatat agctctgttc ttggccagca        240
cttgtaaaag acattttaaa caatgacata atcaggtca ttggtggcac acttatcaaa         300
tatataaatg tcccaaagct caggggatg gtgaatgtaa gatgacagaa ttaacacttc        360
ccaattattt ccaaccaggc tagaatgaat acttagccaa agtccataaa ataacattca        420
ct                                                                       422

<210> SEQ ID NO 134
<211> LENGTH: 441
<212> TYPE: DNA
<213> ORGANISM: Homo sapien
<220> FEATURE:
<221> NAME/KEY: misc_feature
<222> LOCATION: (307)..(307)
<223> OTHER INFORMATION: n= a, c, g or t

<400> SEQUENCE: 134
tagtacataa aactgaaatg gcccaaaaaa catgaaaaga tgcccaactg tttattcttc         60
agtctcattt tttgctcatt tcttttcctt tgctttacta tagtaaaagt gactccagtc        120
cctacattaa attttgattt tgaattttg catcttttcc ataaacttct tttctacagt        180 gtttttttaat tcaaatgtac gtgtcttcat cttctctttt tttctcctgt agtttctttt        240
attcggagtt attttaatga aggcaccaag gttcctgggt aatctcatgc tggctgatat        300 tttttttntaa catttaatat aaaatttttc acacataggc aaatttgaaa tgtttgcaat        360
gaaatttttt atacctgcca cctagctatt accatgaata ttttagtata cttgctttat        420
cacatatctg gtccatttat c                                                  441

<210> SEQ ID NO 135
<211> LENGTH: 499
<212> TYPE: DNA
<213> ORGANISM: Homo sapien

<400> SEQUENCE: 135
tagcttccct aacatgccag tctacagttt actccaaatc ccaccaggag aagccacttt         60
aaaaatacct gataaattaa aattcattaa tttaattcta ttaagtcctg ttagtcctat        120
cattgtgccc attgctgaca caataccaaa tttacacagt tgcagtgccc gccatgagtc        180
aagaaaatgg ggtctaatcc ttcctgccac cttagtatcg aattattctg aaaaagaagt        240
ggatgtactg atagatggaa agatcgaaat gattttttta ggagagattt tcttgcgctc        300
```

```
atgataaaat aatcctgttg gaatagatat tgtatccatg cctcctcaag tacagggtcc    360
caaagtcaag gccagacagt aagccaagtg ctatagaaat ttgtggtatg ggtacaatta    420
gcaatacata ataaatttga gctcttagga tggttaaaga atttgaggga aaaaacttaa    480
aaccacctct taaaagcaa                                                 499
```

<210> SEQ ID NO 136
<211> LENGTH: 701
<212> TYPE: DNA
<213> ORGANISM: Homo sapien

<400> SEQUENCE: 136

```
ctccttgagg atttccatat aacgctagcc ttgatattct ggcccacacc atttgtatga     60
aagaagaatg attgttcttt actgagtaag agaactacag agaccaatgg attcaagtag    120
tggaacagct ttaatatgta acccatacct gtaccaatgg gtattggttc tctagctcac    180
ctttaggctg actagtatgc ctatgctgga tgttcaatcg cgggattaga cgggattgag    240
ctttatttag tatctctatt agtcactatg agctataatc ttttagcccc tggatcatta    300
tgaagtgcac caagaataag atacagtggt tcccaaggac tggatatcat agctaaccaa    360
ctcagatggc taaaatacta ttcttgtatt ttatacctag tattttggc ttgctttata     420 atgggagtag tcattctggg aatctgatct tctaaatgaa agacaacttt atgcctatat    480
tatttctatc ctgccaaaga tatgtaccaa acttgatttc tggggtttct gtgggattat    540
acatttttct tggactttct cccccttttac tgaagaagtg attttttctaa aagcaccaa    600 tcacttttttc tttttttctgt agggaggatg gtggtggtga ggtgttcttt gcaaggaggg    660
tagacaatga gatgaattgc actgaactag tgttaaagaa t                         701
```

<210> SEQ ID NO 137
<211> LENGTH: 274
<212> TYPE: DNA
<213> ORGANISM: Homo sapien

<400> SEQUENCE: 137

```
gtaaaaacct aaatgcccaa taataggaat taaactggta aaataatatt gtcattttaa     60
taatcagata aaatgatata gatgaatatt caatgacacg agaagatatt tataaatatt    120
ttattataaa aactatttta attggttaca ttatatgtcg ctatgccttc agagtagaga    180
gaagtgacag tttcaacaca aactgaaaaa tttgtaagat aatggctgct atttctaggc    240
ctgtaaaaat tcatttaccc aaagaaaatc atag                                274
```

<210> SEQ ID NO 138
<211> LENGTH: 352
<212> TYPE: DNA
<213> ORGANISM: Homo sapien

<400> SEQUENCE: 138

```
gtaaaaacct aaatgcccaa taataggaat taaactggta aaataatatt gtcattttaa     60
taatcagata aaatgatata gatgaatatt caatgacacg agaagatatt tataaatatt    120
ttattataaa aactatttta attggttaca ttatatgtcg ctatgccttc agagtagaga    180
gaagtgacag tttcaacaca aactgaaaaa tttgtaagat aatggctgct atttctaggc    240
ctgtaaaaat tcatttaccc aaagaaaatc atagttttt tttttttttc tggagatgga    300
gtttcgctct tgttgcccag gctggagtac ctcggccgcg accacgctaa gc            352
```

<210> SEQ ID NO 139
<211> LENGTH: 647
<212> TYPE: DNA
<213> ORGANISM: Homo sapien
<220> FEATURE:
<221> NAME/KEY: misc_feature
<222> LOCATION: (319)..(552)
<223> OTHER INFORMATION: n= a, c, g or t

<400> SEQUENCE: 139

```
acagattcat ctgttatact cgtatagatt gaaactgatc tactgttaag tcaacaataa      60
cgaaggggag gacattgcag aaaactatga gaaggatctc aattttgcaa attatacatg     120
tatacacaca tatcctacat ctattctctg tgagcatttg tttctgttaa tatgtagatc     180
aagttctagg cacagaaagt tctagaagta tctattaaca gttgggtttg agttaagtaa     240
ataacttact ttctaaccac attttcatt gatatgcgtt gtgaattttt tatactttgt      300
gtgtgtgtgt atacacacnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnaaacaatg aaaattaggt agtatgattt ttctaaacat atgagagtta     600
gagaaaaggc ttggatctca gaacaccctc tttgacagcc gggtgca                   647
```

<210> SEQ ID NO 140
<211> LENGTH: 334
<212> TYPE: DNA
<213> ORGANISM: Homo sapien
<220> FEATURE:
<221> NAME/KEY: misc_feature
<222> LOCATION: (44)..(44)
<223> OTHER INFORMATION: n= a, c, g or t
<220> FEATURE:
<221> NAME/KEY: misc_feature
<222> LOCATION: (214)..(214)
<223> OTHER INFORMATION: n= a, c, g or t
<220> FEATURE:
<221> NAME/KEY: misc_feature
<222> LOCATION: (300)..(300)
<223> OTHER INFORMATION: n= a, c, g or t
<220> FEATURE:
<221> NAME/KEY: misc_feature
<222> LOCATION: (306)..(306)
<223> OTHER INFORMATION: n= a, c, g or t
<220> FEATURE:
<221> NAME/KEY: misc_feature
<222> LOCATION: (308)..(308)
<223> OTHER INFORMATION: n= a, c, g or t
<220> FEATURE:
<221> NAME/KEY: misc_feature
<222> LOCATION: (315)..(315)
<223> OTHER INFORMATION: n= a, c, g or t
<220> FEATURE:
<221> NAME/KEY: misc_feature
<222> LOCATION: (323)..(323)
<223> OTHER INFORMATION: n= a, c, g or t
<220> FEATURE:
<221> NAME/KEY: misc_feature
<222> LOCATION: (320)..(320)
<223> OTHER INFORMATION: n= a, c, g or t

<400> SEQUENCE: 140

```
tgctacagaa catggcttca attaagagtg aattcagttt tttnttatta aagtcataac      60
ttacgtgcca cttttatgtt attctggact ttgggcagtg tgatttatta tgtctgtccc     120
tccattgaag tgtcactaac tttgtcaaaa ataccttca ctaattagag gtgccagaat      180
```

| | |
|---|---|
| ttttatactc gctactcagg aattggtcac ttcnataatc tgaattacta taaccttggt | 240 |
| cctcttttca tgaacagctt gagccactga cattctgttg tctaggtgat tacgtgaagn | 300 |
| ttctangnta taatntggan acnagtcacc agtc | 334 |

<210> SEQ ID NO 141
<211> LENGTH: 990
<212> TYPE: DNA
<213> ORGANISM: Homo sapien
<220> FEATURE:
<221> NAME/KEY: misc_feature
<222> LOCATION: (105)..(105)
<223> OTHER INFORMATION: n= a, c, g or t
<220> FEATURE:
<221> NAME/KEY: misc_feature
<222> LOCATION: (116)..(117)
<223> OTHER INFORMATION: n= a, c, g or t
<220> FEATURE:
<221> NAME/KEY: misc_feature
<222> LOCATION: (132)..(132)
<223> OTHER INFORMATION: n= a, c, g or t
<220> FEATURE:
<221> NAME/KEY: misc_feature
<222> LOCATION: (143)..(143)
<223> OTHER INFORMATION: n= a, c, g or t

<400> SEQUENCE: 141

| | |
|---|---|
| ggccgatggg ggcatgcagt ttgtcttctg ggaactgctt tccagctgtt tggctatgag | 60 |
| gaaaacgcag tccaatctct acagcatctc ttgaagttta tgtcnagtaa taaganngca | 120 |
| gcagatgata anagtgtagc aanagcagca cagagtttct tccaacgatt ggaactgggc | 180 |
| gatatgcaag cactttcact gtggcaaaaa tttcgggact tgagcattga agagtacatt | 240 |
| cgggtttaca agcgtctggg agtatatttt gatgaatatt caggagaatc attttatcgt | 300 |
| gaaaaatctc aagaggtctt aaagttgctg agagtaaag gactcctact gaaaacaata | 360 |
| aaaggaacgg ctgtagtaga tctctctggg aatggcgacc cctcctcaat ttgtactgta | 420 |
| atgcgaagtg atgggacttc tctctatgca accagagatc ttgcagctgc tatagatcga | 480 |
| atggacaagt ataattttga tacaatgata tatgtgacag ataaaggaca aaaaaagcat | 540 |
| tttcagcaag tattccaaat gctgaagatc atgggatatg actgggcaga aaggtgccag | 600 |
| cacgtgccct ttggagtagt acagggaatg aagactcgaa gaggagatgt cactttcctg | 660 |
| gaagatgttt taaatgagat tcaattaagg atgctacaga acatggcttc aattaagagt | 720 |
| gaattcagtt ttttcttatt aaagtcataa cttacgtgcc acttttatgt tattctggac | 780 |
| tttgggcagt gtgatttatt atgtctgtcc ctccattgaa gtgtcactaa ctttgtcaaa | 840 |
| aatacctttc actaattaga ggtgccagaa tttttatact cgctactcag gaattggtca | 900 |
| cttcaataat ctgaattact ataaccttgg tcctcttttc atgaacagct tgagccactg | 960 |
| acattctgtt gtctaggtga ttacgtgaag | 990 |

<210> SEQ ID NO 142
<211> LENGTH: 195
<212> TYPE: DNA
<213> ORGANISM: Homo sapien

<400> SEQUENCE: 142

| | |
|---|---|
| ccaaaatcct atcattttaa caagtacaac taccctattt ccctcagaat gtagcattgc | 60 |
| ctctggtttg ctgtggatcc tgtattggac cactcagctg tagagtcctg tgggatccaa | 120 |
| gcttcaagga gacccatcat gcatgtttag ggccagttcc aggtgtcctt gacatgacac | 180 |
| taaacctcca tttcc | 195 |

<210> SEQ ID NO 143
<211> LENGTH: 57
<212> TYPE: PRT
<213> ORGANISM: Homo sapien

<400> SEQUENCE: 143

Met Asn Leu His Cys Ser Ser Met Thr Gly Pro Leu Ala Ser Lys Thr
1               5                   10                  15
Ser Glu Asp Leu Leu Ser Leu Glu Ser Lys Phe Leu Ser Leu Phe Asn
            20                  25                  30
Gln Ile Phe Leu Arg Ser Glu Glu Thr Val Thr Pro Tyr Tyr Thr
        35                  40                  45
Leu Gly Ser Gln Met Cys Asn Leu Ile
    50                  55

<210> SEQ ID NO 144
<211> LENGTH: 57
<212> TYPE: PRT
<213> ORGANISM: Homo sapien

<400> SEQUENCE: 144

Met Asn Leu His Cys Ser Ser Met Thr Gly Pro Leu Ala Ser Lys Thr
1               5                   10                  15
Ser Glu Asp Leu Leu Ser Leu Glu Ser Lys Phe Leu Ser Leu Phe Asn
            20                  25                  30
Gln Ile Phe Leu Arg Ser Glu Glu Thr Val Thr Pro Tyr Tyr Thr
        35                  40                  45
Leu Gly Ser Gln Met Cys Asn Leu Ile
    50                  55

<210> SEQ ID NO 145
<211> LENGTH: 45
<212> TYPE: PRT
<213> ORGANISM: Homo sapien

<400> SEQUENCE: 145

Met Arg Ser Ala Gly Ser Asp Phe Ser Leu Val Lys Trp Val Phe
1               5                   10                  15
Lys Leu Cys Arg Trp Thr Gly Asp Ile Phe Pro Leu Leu His Glu
            20                  25                  30
Glu Ile Cys Leu Asn Val Asp Arg Leu Glu Ile Phe Phe
        35                  40                  45

<210> SEQ ID NO 146
<211> LENGTH: 30
<212> TYPE: PRT
<213> ORGANISM: Homo sapien

<400> SEQUENCE: 146

Met Ser His Arg Ala Arg Pro Arg Trp Cys Val Phe Ser Arg Asn Lys
1               5                   10                  15
Tyr Ile Leu Leu His His Arg Ile Thr Leu Ile Lys Val Gly
            20                  25                  30

<210> SEQ ID NO 147
<211> LENGTH: 85
<212> TYPE: PRT
<213> ORGANISM: Homo sapien -continued

```
<400> SEQUENCE: 147

Gly Ala Val Leu Ala His Cys Asn Ser His Leu Pro Gly Ser Ser Asp
1               5                   10                  15

Ser Pro Ala Ser Val Ser Ala Val Ala Gly Ile Asn Gly Ala Ala His
            20                  25                  30

His Thr Trp Leu Ile Phe Val Phe Leu Val Glu Thr Gly Phe His His
        35                  40                  45

Val Gly Gln Asp Gly Ile Glu Leu Leu Thr Ser Asp Leu Pro Ala Ser
    50                  55                  60

Ala Ser Gln Ser Ala Gly Ile Ile Gly Met Ser His Arg Ala Arg Pro
65                  70                  75                  80

Arg Trp Cys Val Phe
                85

<210> SEQ ID NO 148
<211> LENGTH: 47
<212> TYPE: PRT
<213> ORGANISM: Homo sapien

<400> SEQUENCE: 148

Met Pro Lys Leu Leu Pro Gly Phe Gln Gly Asn Arg Ala Arg Trp Leu
1               5                   10                  15

Asn Gln Arg Ser Asp Ser Gln Ala Ala Arg Glu Lys Val Phe Asn Pro
            20                  25                  30

Leu Ile Pro Val Cys Asn Arg Arg Asn Gln Gly Leu His Thr Leu
        35                  40                  45

<210> SEQ ID NO 149
<211> LENGTH: 166
<212> TYPE: PRT
<213> ORGANISM: Homo sapien

<400> SEQUENCE: 149

Met Leu Val Gly Arg Lys Arg Arg Glu Ser Ser Val Lys Glu Asn
1               5                   10                  15

Thr Gly Met Glu Thr Leu Gln Arg Leu Arg Gln Lys His Pro Met Gly
            20                  25                  30

Lys Ser Arg Arg Thr Ile Ser Cys Leu Trp Arg Thr Gly Ser Arg Glu
            35                  40                  45

Gln Ser Thr Ser Pro Asp Thr Ser Leu Gly Ser Thr Thr Pro Ser Ser
    50                  55                  60

His Thr Leu Glu Leu Val Ala Leu Asp Ser Glu Val Leu Arg Asp Ser
65                  70                  75                  80

Leu Gln Cys Gln Asp His Leu Ser Pro Gly Val Ser Ser Leu Cys Asp
                85                  90                  95

Asp Asp Pro Gly Ser Asn Lys Pro Leu Ser Ser Asn Leu Arg Arg Leu
            100                 105                 110

Leu Glu Ala Gly Ser Leu Lys Leu Asp Ala Ala Thr Ala Asn Gly
            115                 120                 125

Arg Val Glu Ser Pro Val Asn Val Gly Ser Lys Pro Leu Leu Phe Pro
```

```
            130                 135                 140
Ala Phe Pro Pro Arg Pro Ala Ala Gln Cys Ser Gly Gln Glu Val Gly
145                 150                 155                 160

Arg Glu Ala Gly Thr Glu
                165

<210> SEQ ID NO 150
<211> LENGTH: 352
<212> TYPE: PRT
<213> ORGANISM: Homo sapien

<400> SEQUENCE: 150

Pro Arg Asp Val Ser Arg Gln Glu Ala Glu Gly Glu Leu Ser Glu
1               5                   10                  15

Gly Glu His Trp Tyr Gly Asn Ser Ser Glu Thr Pro Ser Glu Ala Ser
                20                  25                  30

Tyr Gly Glu Val Gln Glu Asn Tyr Lys Leu Ser Leu Glu Asp Arg Ile
                35                  40                  45

Gln Glu Gln Ser Thr Ser Pro Asp Thr Ser Leu Gly Ser Thr Thr Pro
50                  55                  60

Ser Ser His Thr Leu Glu Leu Val Ala Leu Asp Ser Glu Val Leu Arg
65                  70                  75                  80

Asp Ser Leu Gln Cys Gln Asp His Leu Ser Pro Gly Val Ser Ser Leu
                85                  90                  95

Cys Asp Asp Pro Gly Ser Asn Lys Pro Leu Ser Ser Asn Leu Arg
                100                 105                 110

Arg Leu Leu Glu Ala Gly Ser Leu Lys Leu Asp Ala Ala Ala Thr Ala
                115                 120                 125

Asn Gly Arg Val Glu Ser Pro Val Asn Val Gly Ser Asn Leu Ser Phe
                130                 135                 140

Ser Pro Pro Ser His His Ala Gln Gln Leu Ser Val Leu Ala Arg Lys
145                 150                 155                 160

Leu Ala Glu Lys Gln Glu Gln Asn Asp Gln Tyr Thr Pro Ser Asn Arg
                165                 170                 175

Phe Ile Trp Asn Gln Gly Lys Trp Leu Pro Asn Ser Thr Thr Thr Cys
                180                 185                 190

Ser Leu Ser Pro Asp Ser Ala Ile Leu Lys Leu Lys Ala Ala Ala Asn
                195                 200                 205

Ala Val Leu Gln Asp Lys Ser Leu Thr Arg Thr Glu Thr Met Arg
                210                 215                 220

Phe Glu Ser Phe Ser Ser Pro Phe Ser Ser Gln Ser Ala Ser Ser Thr
225                 230                 235                 240

Leu Ala Ala Leu Ser Lys Lys Val Ser Glu Arg Ser Leu Thr Pro Gly
                245                 250                 255

Gln Glu His Pro Pro Ala Ser Ser Phe Leu Ser Leu Ala Ser Met
                260                 265                 270

Thr Ser Ser Ala Ala Leu Leu Lys Glu Val Ala Ala Arg Ala Ala Gly
                275                 280                 285

Ser Leu Leu Ala Glu Lys Ser Ser Leu Leu Pro Glu Asp Pro Leu Pro
                290                 295                 300

Pro Pro Pro Ser Glu Lys Lys Pro Glu Lys Val Thr Pro Pro Pro
305                 310                 315                 320

Pro Pro Pro Pro Pro Pro Pro Pro Pro Gln Ser Leu Glu Leu
                325                 330                 335
```

```
Leu Leu Leu Pro Val Pro Lys Gly Arg Val Ser Lys Pro Ser Asn Ser
        340                 345                 350
```

<210> SEQ ID NO 151
<211> LENGTH: 67
<212> TYPE: PRT
<213> ORGANISM: Homo sapien

<400> SEQUENCE: 151

```
Met Gly Tyr Gln Trp Tyr Arg Leu Arg Val Asn Ser Ile Ser Gly Phe
1               5                   10                  15

His Gly Ser Leu Glu Gln His Leu Pro Val Ser Ser Ala Phe His Gln
            20                  25                  30

Arg Trp Asp Leu Trp Ser Thr Gly Cys Leu Thr Pro Gly Ala Ile Glu
        35                  40                  45

Lys Gly Glu Asp Leu Trp Lys Ala Phe Val Leu Ala Pro Val His Leu
    50                  55                  60

Val Leu Asn
65
```

<210> SEQ ID NO 152
<211> LENGTH: 52
<212> TYPE: PRT
<213> ORGANISM: Homo sapien

<400> SEQUENCE: 152

```
Met Lys Glu Gly Val Leu Gly Ser Val Phe Arg Pro Lys Cys Pro Gln
1               5                   10                  15

Gly Pro Ser Gly Cys Leu Tyr Leu Leu Met Ser Pro His Thr Cys Trp
            20                  25                  30

Gln Ser Trp Asp Lys Ser Leu Thr Leu Cys Val Thr Ser Asp Ser Pro
        35                  40                  45

Trp Lys Lys Glu
    50
```

<210> SEQ ID NO 153
<211> LENGTH: 63
<212> TYPE: PRT
<213> ORGANISM: Homo sapien

<400> SEQUENCE: 153

```
Met Arg Thr Glu Ile Ser Trp Ser Val His Glu Glu Trp Ile Gln
1               5                   10                  15

Leu Leu Val Leu Ala Leu Cys Ser Leu Asn Ala Leu Tyr Phe Leu Leu
            20                  25                  30

Phe Tyr Leu Thr Ile Phe Phe Trp Phe Ala Phe Thr Val Asn Asn Ile
        35                  40                  45

Phe Ser Ser Phe Leu Ala Leu Ala Phe Leu Ala Asp Arg Lys Trp
    50                  55                  60
```

<210> SEQ ID NO 154
<211> LENGTH: 98
<212> TYPE: PRT
<213> ORGANISM: Homo sapien

<400> SEQUENCE: 154

```
Met Lys Asn Gln Pro Leu Gly Gly Leu Leu Leu Leu Gly Gln Ile
1               5                   10                  15

Phe Met Trp Pro Thr Arg Leu Cys Ala Ala Gln Leu Cys Leu Pro Ala
```

```
                20                  25                  30
Ser Leu Val Leu His Thr Val Leu Ser Ile Val Ser Val Ala Trp Pro
            35                  40                  45

Tyr Pro Ser Ser Cys Leu Pro Ile Leu Asn Tyr Ile Thr Cys Phe Leu
    50                  55                  60

Ala Ser Gly Pro Leu His Met Leu Phe Met Leu Leu Gly Val Phe Cys
65                  70                  75                  80

Ser Phe Leu His Pro Gln Pro Leu Pro Leu Asp Cys Thr Pro Gln Gly
                85                  90                  95

Arg Ser

<210> SEQ ID NO 155
<211> LENGTH: 57
<212> TYPE: PRT
<213> ORGANISM: Homo sapien

<400> SEQUENCE: 155

Met Val Tyr Thr Phe Ser Cys Phe Phe Ser Ser Phe Leu Glu Ser Gly
1               5                   10                  15

Asp Thr His Arg Arg Ile Asn Gly Ser Gly Lys Val Pro Gly Leu Met
            20                  25                  30

His Glu Glu Asp Leu Val Arg Leu Glu Thr Cys Leu Ala Ser Gln Gly
        35                  40                  45

Ser Ala Val Ser Tyr Pro Cys Ala Lys
    50                  55

<210> SEQ ID NO 156
<211> LENGTH: 89
<212> TYPE: PRT
<213> ORGANISM: Homo sapien

<400> SEQUENCE: 156

Asp Thr Glu Ser Gly Trp Asp Thr Ala Val Val Asn Asp Leu Ser
1               5                   10                  15

Ser Thr Ser Ser Gly Thr Glu Ser Gly Pro Gln Ser Pro Leu Thr Pro
            20                  25                  30

Asp Gly Lys Arg Asn Pro Lys Gly Ile Lys Lys Ser Trp Gly Lys Ile
        35                  40                  45

Arg Arg Thr Gln Ser Gly Asn Phe Tyr Thr Asp Thr Leu Gly Met Ala
    50                  55                  60

Glu Phe Arg Arg Gly Gly Leu Arg Ala Thr Ala Gly Pro Gly Leu Ser
65                  70                  75                  80

Arg Thr Arg Asp Phe Lys Gly Gln Lys
                85

<210> SEQ ID NO 157
<211> LENGTH: 65
<212> TYPE: PRT
<213> ORGANISM: Homo sapien

<400> SEQUENCE: 157

Met Ser His Ser Pro Val Leu Pro Ala Pro Gln Ser Ser Val Gly Tyr
1               5                   10                  15

Pro Val Arg Pro Ser Pro Cys Thr Pro Phe Phe Ser Leu Ile Glu Ile
            20                  25                  30

Pro Ala Thr Cys Cys Leu Leu Pro Cys Arg Ile Thr Asn Ala Cys Pro
        35                  40                  45
```

```
Val Pro Gly Ile Glu Ala Ala Ile Ala Gly Leu Leu Pro Cys Ser Arg
    50                  55                  60

His
65

<210> SEQ ID NO 158
<211> LENGTH: 51
<212> TYPE: PRT
<213> ORGANISM: Homo sapien

<400> SEQUENCE: 158

Met Val Ala Arg Ile Lys Ser Glu Lys Pro Gly Asn Ser Lys Leu Leu
1               5                   10                  15

Glu Ile Leu Val Ile Leu Thr Arg Arg Val Glu Val Lys Val Met Lys
                20                  25                  30

Cys Gly Lys Phe Trp Lys Pro Phe Glu Ser Lys Ala Glu Ser Ile Cys
            35                  40                  45

Cys Tyr Ile
        50

<210> SEQ ID NO 159
<211> LENGTH: 116
<212> TYPE: PRT
<213> ORGANISM: Homo sapien
<220> FEATURE:
<221> NAME/KEY: MISC_FEATURE
<222> LOCATION: (33)..(33)
<223> OTHER INFORMATION: X=any amino acid

<400> SEQUENCE: 159

Met Ala Gly Leu Leu Asn Val Thr Phe Ile Tyr Leu Leu Glu Cys
1               5                   10                  15

Leu Ser Leu Tyr Thr His Val Thr Cys Ser Ser Leu Pro Ser Ser Leu
                20                  25                  30

Xaa Leu Tyr Ile Tyr Tyr Tyr His Arg Gly Leu Gly Lys Lys Thr Pro
            35                  40                  45

Thr Ala Ala Pro His Thr His Pro Pro Ala Leu Tyr His Leu Leu Gly
        50                  55                  60

Phe Val Phe Leu Cys Arg Ile His Asp Phe Leu Lys Tyr Asn Phe Phe
65                  70                  75                  80

Asn Val Tyr Ile Leu Tyr Ala Phe Ser His Ser Tyr Val Lys Ser Gly
                85                  90                  95

Arg His Arg Leu Val Phe Leu Phe Thr Val Asp Ala Ser Val Pro Lys
                100                 105                 110

Ile Cys Ile Ala
        115

<210> SEQ ID NO 160
<211> LENGTH: 81
<212> TYPE: PRT
<213> ORGANISM: Homo sapien
<220> FEATURE:
<221> NAME/KEY: MISC_FEATURE
<222> LOCATION: (23)..(31)
<223> OTHER INFORMATION: X=any amino acid

<400> SEQUENCE: 160

Met Gln Asn His His Ile Pro His Cys Ile Ala Val Ala Ser Trp Pro
1               5                   10                  15

Leu Ile Asn Cys Lys Lys Xaa Xaa Xaa Xaa Xaa Xaa Xaa Xaa Val
                20                  25                  30
```

```
Tyr Ile Cys Ile His Val Phe Ile Tyr Ala Tyr Val Met Tyr Met Pro
            35                  40                  45

Thr Tyr Leu Cys Thr Cys Asn Val Tyr Ala Tyr Ile Cys Ile Tyr Lys
        50                  55                  60

Gly Ile Gln Ile Cys Ile Tyr Leu Arg Lys Thr Ile Lys Asn Leu Cys
65                  70                  75                  80

Ser

<210> SEQ ID NO 161
<211> LENGTH: 39
<212> TYPE: PRT
<213> ORGANISM: Homo sapien

<400> SEQUENCE: 161

Met His Thr Gln Val His Met Phe Thr Glu Ser Gln Val Gln Glu Arg
1               5                   10                  15

Ser Lys Glu Pro Lys Leu Glu Ala Thr His Met Phe Ile Asn Ser Arg
            20                  25                  30

Asp Asp Lys Ile Tyr Leu Asp
        35

<210> SEQ ID NO 162
<211> LENGTH: 40
<212> TYPE: PRT
<213> ORGANISM: Homo sapien

<400> SEQUENCE: 162

Met Phe Ala Ser Gly Pro Pro Cys His Val Lys Ser Thr Leu Tyr Ser
1               5                   10                  15

Leu Phe Leu Glu Arg Thr Tyr Tyr Val Asn Leu Asp Phe His Met Val
            20                  25                  30

Ile Thr Leu Tyr Glu Ala Asn Ile
        35                  40

<210> SEQ ID NO 163
<211> LENGTH: 73
<212> TYPE: PRT
<213> ORGANISM: Homo sapien

<400> SEQUENCE: 163

Met Gln Asn Ser Val Ser Thr Gln Arg Phe Asn Val Tyr Ser Phe Lys
1               5                   10                  15

Gln Ile Ser Phe Asp Ser Leu Glu Tyr Phe Phe Leu Asn Ile Leu Ser
            20                  25                  30

Pro Ser Met Glu Ser Cys Pro Lys Ala Glu Arg Lys Glu Lys Lys
            35                  40                  45

Lys Arg Lys Leu Asn Phe Leu Asn Ser Ile Ser His Cys Leu Gly His
        50                  55                  60

Val Cys Lys Trp Pro Thr Leu Pro Arg
65                  70

<210> SEQ ID NO 164
<211> LENGTH: 37
<212> TYPE: PRT
<213> ORGANISM: Homo sapien

<400> SEQUENCE: 164

Met Lys Cys Phe Asp Ile Trp Asn Phe Leu Pro Leu Phe His Phe Ala
1               5                   10                  15
```

-continued

Val Asn Gln Ser Glu Phe Arg Ser Ile Met Trp Ile Tyr Glu Asn Val
            20                  25                  30

Ser Asn Gly Leu Phe
        35

<210> SEQ ID NO 165
<211> LENGTH: 55
<212> TYPE: PRT
<213> ORGANISM: Homo sapien
<220> FEATURE:
<221> NAME/KEY: MISC_FEATURE
<222> LOCATION: (8)..(42)
<223> OTHER INFORMATION: X=any amino acid

<400> SEQUENCE: 165

Met Gln Ile Leu Trp Leu Leu Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Ser Asn Pro Arg Leu Cys
        35                  40                  45

Leu Leu Val Ala Leu Lys Pro
    50                  55

<210> SEQ ID NO 166
<211> LENGTH: 48
<212> TYPE: PRT
<213> ORGANISM: Homo sapien

<400> SEQUENCE: 166

Met Cys Ala Lys Val Leu Val Leu Ser Arg Lys Asp Thr Asp Glu Cys
1               5                   10                  15

Tyr Arg Leu Leu Lys Asn Ile Tyr Leu Asn Lys Tyr Val Lys Tyr Lys
            20                  25                  30

Gly Ile Gln Tyr Ser Asn Arg Asn Ile Glu Ile Glu Gly Thr Ser Pro
        35                  40                  45

<210> SEQ ID NO 167
<211> LENGTH: 95
<212> TYPE: PRT
<213> ORGANISM: Homo sapien

<400> SEQUENCE: 167

Met Cys Leu Phe Cys Ser His Ser Val Tyr Lys Pro Leu Tyr Glu Thr
1               5                   10                  15

Gly Ser Ser Gln Leu Phe Phe Tyr Ser Thr Leu Lys Ile Leu Val Ser
            20                  25                  30

Phe Leu Val Ser Thr Val Ala Lys Ala Tyr Cys Gln Phe Asp Tyr His
        35                  40                  45

Ser Ile Ile Gln Asn Phe Phe Leu Tyr Leu Tyr Ser Glu Phe Gln Ile
    50                  55                  60

Phe Ser Leu Ser Leu Ile Ser Tyr Asp Phe Ile Ile Met Tyr Val Val
65                  70                  75                  80

Val Asp Leu Ser Ile Leu Cys Tyr Ile Trp Gln His Phe Leu Phe
                85                  90                  95

<210> SEQ ID NO 168
<211> LENGTH: 89
<212> TYPE: PRT
<213> ORGANISM: Homo sapien

```
<400> SEQUENCE: 168

Met Asn Asn Arg Trp Met Leu Pro Pro Phe Ser Pro Arg Arg Asn Lys
1               5                   10                  15

Gly Lys Gly Glu Gly Leu Gly Gly Trp Ile Ser Arg Gln Thr Gly Glu
            20                  25                  30

Cys Glu Gly Thr Ile Arg Arg Glu Val His Pro Glu Ile Arg Tyr Val
            35                  40                  45

Ser Pro Leu Arg Phe Pro Thr Ile Asp Ser Glu Leu Leu Glu Ser Val
        50                  55                  60

Ser Ser Ile Ser Asp Ala Val Gly Ser Ser Lys Ser Gly Lys Tyr Ser
65                  70                  75                  80

Cys Thr Phe Val Pro Glu Ser Ser Asn
                85

<210> SEQ ID NO 169
<211> LENGTH: 42
<212> TYPE: PRT
<213> ORGANISM: Homo sapien

<400> SEQUENCE: 169

Met Glu Ser Ser Leu Glu Thr Cys Ala Ser Ser Asn Pro Leu Arg Leu
1               5                   10                  15

Lys Lys Thr Ser Phe Leu Ser Gln Glu Thr Pro Gly Arg Leu Phe Ile
            20                  25                  30

Leu Pro Thr Thr Trp Pro Asn Ala His Asn
            35                  40

<210> SEQ ID NO 170
<211> LENGTH: 132
<212> TYPE: PRT
<213> ORGANISM: Homo sapien

<400> SEQUENCE: 170

Met Gly Arg Arg Thr Arg Thr Val Arg Val Ser Arg Leu Pro Pro Ala
1               5                   10                  15

Thr His Ser Cys Ser Pro Pro Ile Tyr Ala Leu Ala Leu Pro Ala
            20                  25                  30

Phe Trp Pro Ser Gly Ala Val Leu Val Pro Ala Leu Ala Gln Ala Cys
        35                  40                  45

Phe Ser Ser Leu Pro Thr Asn Phe Leu Ser Ser Cys Gly Cys Ala Tyr
        50                  55                  60

Leu Val Trp Val Trp Phe Trp Leu Leu Asn Glu Gln Arg Gln Asn Glu
65                  70                  75                  80

Gly Ala Met Ser Thr Asp Glu Ala Phe Gly Lys Arg Pro Pro Ser Ile
            85                  90                  95

Ala Leu Leu Glu Gly Ser Val Glu Ala Ala Val Phe Pro Gly Ala Gly
            100                 105                 110

His Leu Asp Thr Val Pro Ala Cys Thr Gln Pro Pro Ser Thr Leu Leu
            115                 120                 125

His Gln Pro Ala
        130

<210> SEQ ID NO 171
<211> LENGTH: 121
<212> TYPE: PRT
<213> ORGANISM: Homo sapien
```

-continued

```
<400> SEQUENCE: 171

Met Val Ser Cys Asn Tyr Gly Tyr Val Arg Val Gln Arg Arg Glu Ser
1               5                   10                  15

Cys Val Gly Trp Ser Gly Leu Glu Arg Leu Gly Thr Glu Leu Gly Val
            20                  25                  30

Glu Leu Gly Trp Pro Ala Ala Glu Gly Ala Glu Met Gly Trp Gly Gly
        35                  40                  45

Pro Ser Ser Gln Pro Pro Gly Thr Phe Pro Glu Gly Pro Ala Val Gly
    50                  55                  60

Leu Cys Thr Arg Glu Ile Ala Ser Leu Phe Arg Thr Pro Ser Leu Pro
65                  70                  75                  80

Ala Leu His Leu Pro Thr Gly Ala Leu Glu Gln Ala Arg Leu Gln Leu
                85                  90                  95

Arg His Val Gln Pro Gln Thr Phe Ala Pro Ala Ser Pro Pro Arg Leu
            100                 105                 110

Pro Arg Glu Leu Gly Lys Gly Leu Cys
        115                 120

<210> SEQ ID NO 172
<211> LENGTH: 107
<212> TYPE: PRT
<213> ORGANISM: Homo sapien

<400> SEQUENCE: 172

Met Val Leu Pro Gln Asp Phe Leu Ala Glu Pro Gly Ile Leu Leu Thr
1               5                   10                  15

Leu Pro Ser His Gly Asn Met Ala Leu Ala Cys Trp Arg Leu Trp Ala
            20                  25                  30

Pro Phe Leu Ala Ala Val Leu Pro Gly Val Ala Lys Asp Ser Ser Tyr
        35                  40                  45

Pro Leu Pro Arg Ile Leu Val Ser Arg Leu Ser Leu Leu Val Thr Gly
    50                  55                  60

Ser Glu Trp Asn Thr Val Gln Val Arg Glu Gly Thr Asn Arg Pro Cys
65                  70                  75                  80

Phe Asn Ser Pro Cys Phe Pro Pro Val Pro Tyr Arg Pro Ser Leu Ser
                85                  90                  95

Pro Gly Val Ser Ile Glu Asn Ser Ala Tyr Leu
            100                 105

<210> SEQ ID NO 173
<211> LENGTH: 107
<212> TYPE: PRT
<213> ORGANISM: Homo sapien

<400> SEQUENCE: 173

Met Val Leu Pro Gln Asp Phe Leu Ala Glu Pro Gly Ile Leu Leu Thr
1               5                   10                  15

Leu Pro Ser His Gly Asn Met Ala Leu Ala Cys Trp Arg Leu Trp Ala
            20                  25                  30

Pro Phe Leu Ala Ala Val Leu Pro Gly Val Ala Lys Asp Ser Ser Tyr
        35                  40                  45

Pro Leu Pro Arg Ile Leu Val Ser Arg Leu Ser Leu Leu Val Thr Gly
    50                  55                  60

Ser Glu Trp Asn Thr Val Gln Val Arg Glu Gly Thr Asn Arg Pro Cys
65                  70                  75                  80

Phe Asn Ser Pro Cys Phe Pro Pro Val Pro Tyr Arg Pro Ser Leu Ser
```

Pro Gly Val Ser Ile Glu Asn Ser Ala Tyr Leu
            100                 105

<210> SEQ ID NO 174
<211> LENGTH: 65
<212> TYPE: PRT
<213> ORGANISM: Homo sapien

<400> SEQUENCE: 174

Met Val Trp Trp Ser Leu Gly Leu Thr Leu Thr Arg Glu Arg Asn Ala
1               5                   10                  15

Asp Phe Ser Phe Thr Ile Pro Ser Gly Leu His Arg Tyr Pro Ser Lys
            20                  25                  30

Val Arg Arg Asp Phe Cys Cys Tyr Leu Ser Ser Cys Phe Ser Ala Glu
        35                  40                  45

Ala Leu Thr Lys Ile Gln Ile Asn Ile Ser Gln Met Gly Ile Val Leu
    50                  55                  60

Ile
65

<210> SEQ ID NO 175
<211> LENGTH: 65
<212> TYPE: PRT
<213> ORGANISM: Homo sapien

<400> SEQUENCE: 175

Met Val Trp Trp Ser Leu Gly Leu Thr Leu Thr Arg Glu Arg Asn Ala
1               5                   10                  15

Asp Phe Ser Phe Thr Ile Pro Ser Gly Leu His Arg Tyr Pro Ser Lys
            20                  25                  30

Val Arg Arg Asp Phe Cys Cys Tyr Leu Ser Ser Cys Phe Ser Ala Glu
        35                  40                  45

Ala Leu Thr Lys Ile Gln Ile Asn Ile Ser Gln Met Gly Ile Val Leu
    50                  55                  60

Ile
65

<210> SEQ ID NO 176
<211> LENGTH: 92
<212> TYPE: PRT
<213> ORGANISM: Homo sapien

<400> SEQUENCE: 176

Met Tyr Lys Arg Lys Val Tyr Pro Val Ser Ser Pro Leu Met Val Thr
1               5                   10                  15

Leu Glu Thr His Val Leu Lys Thr Arg Ser Gly Pro Gly Thr Ala Pro
            20                  25                  30

Asp Pro Ala Phe Pro Ser Tyr Thr Ala His Phe Cys Leu Ser Thr His
        35                  40                  45

Gly Gly Cys His Ser Ala Glu Met Pro Ala Gly Leu Thr Ser Thr Pro
    50                  55                  60

Phe Ile Asn Asn Ala Ala Pro Thr Ser Thr His Val Trp Ile Ser Thr
65                  70                  75                  80

His Leu Ser Ser Phe Leu Arg Ile Asp Phe Lys Met
            85                  90

<210> SEQ ID NO 177

-continued

<211> LENGTH: 114
<212> TYPE: PRT
<213> ORGANISM: Homo sapien

<400> SEQUENCE: 177

Met Phe Ser Asn Tyr Tyr Cys Lys Lys Val Ile His Ala Tyr Gln Lys
1               5                   10                  15

Asn Leu Tyr Asn Thr Thr Met Tyr Lys Arg Lys Val Tyr Pro Val Ser
            20                  25                  30

Ser Pro Leu Met Val Thr Leu Glu Thr His Val Leu Lys Thr Arg Ser
        35                  40                  45

Gly Pro Gly Thr Ala Pro Asp Pro Thr Phe Pro Ser Tyr Thr Ala His
    50                  55                  60

Phe Cys Leu Ser Thr His Gly Cys His Ser Ala Glu Met Pro Ala
65                  70                  75                  80

Gly Leu Thr Ser Thr Pro Phe Ile Asn Asn Ala Ala Pro Thr Ser Thr
                85                  90                  95

His Val Trp Ile Ser Thr His Leu Ser Ser Phe Leu Arg Ile Asp Phe
            100                 105                 110

Lys Met

<210> SEQ ID NO 178
<211> LENGTH: 47
<212> TYPE: PRT
<213> ORGANISM: Homo sapien

<400> SEQUENCE: 178

Met Glu Leu Pro Phe Cys Lys Gln Phe Ile Ser Asp Asp Ile Thr Thr
1               5                   10                  15

Phe Leu Tyr Val Ser Leu Tyr Ile His Leu Ile Val Leu Leu Lys Trp
            20                  25                  30

Phe Leu Lys Cys Ile His Arg Tyr Phe Gly Tyr Leu Gly Arg Gly
            35                  40                  45

<210> SEQ ID NO 179
<211> LENGTH: 42
<212> TYPE: PRT
<213> ORGANISM: Homo sapien

<400> SEQUENCE: 179

Met Asn Leu Leu Ile Leu Ser Leu Ser Asn Tyr Pro Lys Asn Gln Phe
1               5                   10                  15

Val Phe Leu Val Ile Ala Gly Asn Arg Gly Leu Cys Leu Ile Asn Gln
            20                  25                  30

Lys Gly Ser Ser Leu Gly Ala Val Ile Tyr
            35                  40

<210> SEQ ID NO 180
<211> LENGTH: 24
<212> TYPE: PRT
<213> ORGANISM: Homo sapien

<400> SEQUENCE: 180

Met Lys Arg Val Leu Ser Tyr Asp Leu Asn Leu Thr Ala Glu Lys Ser
1               5                   10                  15

Ser Ile Phe Gln Leu Ser Ala Val
            20

<210> SEQ ID NO 181

```
<211> LENGTH: 69
<212> TYPE: PRT
<213> ORGANISM: Homo sapien

<400> SEQUENCE: 181

Met Ser Leu Ser Val His Gln Glu Gln Cys Thr Ala Gln Arg Asp Pro
1               5                   10                  15

Gly Gln Leu Glu Gly Arg Gly Phe Ala Glu Val Pro Glu Pro Asp Gly
            20                  25                  30

Thr Leu Trp Cys Leu Gly Arg Asn Leu Asp Phe Gly Leu Arg Gly Ser
        35                  40                  45

Arg His Val Gln Trp Gln Gln Phe Gly Gln Gly Gly Asp Glu Leu Ser
    50                  55                  60

Cys Phe Leu Leu Arg
65

<210> SEQ ID NO 182
<211> LENGTH: 20
<212> TYPE: PRT
<213> ORGANISM: Homo sapien

<400> SEQUENCE: 182

Met Lys Gln Glu Ser Gln Leu Glu Ser Leu Tyr Thr Ile Cys Thr Val
1               5                   10                  15

Gly Ile Phe Lys
            20

<210> SEQ ID NO 183
<211> LENGTH: 136
<212> TYPE: PRT
<213> ORGANISM: Homo sapien

<400> SEQUENCE: 183

Asn Glu Tyr Lys Ala Glu Ile Ala Glu Val Glu Arg Gln Ile Leu Gln
1               5                   10                  15

Gly Glu Gln Ser Tyr Ser Ser Ala Leu Glu Gly Met Lys Met Glu Ile
            20                  25                  30

Ser His Leu Thr Gln Glu Leu His Gln Arg Asp Ile Thr Ile Ala Ser
        35                  40                  45

Thr Lys Gly Ser Ser Ser Asp Met Glu Lys Arg Leu Arg Ala Glu Met
    50                  55                  60

Gln Lys Ala Glu Asp Lys Ala Val Glu His Lys Glu Ile Leu Asp Gln
65                  70                  75                  80

Leu Glu Ser Leu Lys Leu Glu Asn Arg His Leu Ser Glu Met Val Met
                85                  90                  95

Lys Leu Glu Leu Gly Leu His Glu Arg Trp Gly Phe Thr Met Leu Ser
            100                 105                 110

Ser Leu Val Leu Asn Phe Gly Ile Gln Ala Ile Arg Gln Pro Gln Arg
        115                 120                 125

Pro Lys Val Leu Glu Leu Gln Val
    130                 135

<210> SEQ ID NO 184
<211> LENGTH: 47
<212> TYPE: PRT
<213> ORGANISM: Homo sapien
<220> FEATURE:
<221> NAME/KEY: MISC_FEATURE
<222> LOCATION: (8)..(8)
<223> OTHER INFORMATION: X=any amino acid
```

```
<400> SEQUENCE: 184

Met Cys Asn Trp Arg Phe Ser Xaa Arg Gly Glu Arg Lys Trp Asp Ile
1               5                   10                  15

Lys Asn Asn Trp Lys Lys Ile Ala Glu Ile Val Leu Lys Leu Thr Asn
            20                  25                  30

His Thr Lys Pro Gln Asn Pro Glu Ala Leu Gly His Gln Ala Gly
        35                  40                  45

<210> SEQ ID NO 185
<211> LENGTH: 30
<212> TYPE: PRT
<213> ORGANISM: Homo sapien

<400> SEQUENCE: 185

Met Tyr His Phe Tyr Asn Lys Glu Phe Ile Asn Arg Asn Lys His Ile
1               5                   10                  15

Leu Leu Leu Ala Ser Ala Ala His Ile Leu Glu Ile Ser Thr
            20                  25                  30

<210> SEQ ID NO 186
<211> LENGTH: 86
<212> TYPE: PRT
<213> ORGANISM: Homo sapien

<400> SEQUENCE: 186

Ala His Cys Ser Phe Lys Leu Gln Ser Ala Ser Asn Leu Pro Thr Ser
1               5                   10                  15

Ala Ser Gln Val Ala Gly Thr Thr Gly Arg Arg His Gln Ala Arg Pro
            20                  25                  30

Ile Phe Val Phe Phe Val Glu Thr Arg Phe Arg His Ile Ala Gln Ala
        35                  40                  45

Gly Leu Glu Leu Leu Ser Ser Ser Asp Pro Thr Thr Ser Ser Ser Gln
    50                  55                  60

Ser Ala Gly Ile Ile Gly Val Thr Ala Ala Gly Ser Gln Ala Val
65                  70                  75                  80

Leu Phe Cys Ile Ile Arg
                85

<210> SEQ ID NO 187
<211> LENGTH: 40
<212> TYPE: PRT
<213> ORGANISM: Homo sapien

<400> SEQUENCE: 187

Met Phe Ser Lys Pro Gly Tyr Ser Gln Ser Leu Trp Leu Leu Leu Met
1               5                   10                  15

Ser Phe Ala Gly Glu Ser His Glu Thr Val Leu Ile Cys Ala Tyr Ser
            20                  25                  30

Pro Gln Cys Tyr Leu Ser Ala Leu
        35                  40

<210> SEQ ID NO 188
<211> LENGTH: 59
<212> TYPE: PRT
<213> ORGANISM: Homo sapien

<400> SEQUENCE: 188

Met Arg Ile Ile Ser Thr Phe Cys Ser Tyr Gly Lys Asp Leu Lys Ala
1               5                   10                  15
```

-continued

Asp Ala Cys Ala Arg Asp Met Val Asp Thr Thr Tyr Ile Ala Val Met
            20                  25                  30

Ile Leu Leu Tyr Tyr Ser Val Leu Tyr Leu Leu His Thr Leu Pro
            35                  40                  45

Leu Pro Ile Met Thr Lys Ile Ile Thr Ala Tyr
    50                  55

<210> SEQ ID NO 189
<211> LENGTH: 35
<212> TYPE: PRT
<213> ORGANISM: Homo sapien
<220> FEATURE:
<221> NAME/KEY: MISC_FEATURE
<222> LOCATION: (8)..(15)
<223> OTHER INFORMATION: X=any amino acid
<220> FEATURE:
<221> NAME/KEY: MISC_FEATURE
<222> LOCATION: (34)..(34)
<223> OTHER INFORMATION: X=any amino acid

<400> SEQUENCE: 189

Met Arg Pro Phe Pro Val Val Xaa Xaa Xaa Xaa Xaa Xaa Xaa Val
1               5                   10                  15

Phe Thr Ser Gly Glu Ala Ala Val Leu Leu Cys Leu Phe Leu Leu Cys
            20                  25                  30

Trp Xaa Val
    35

<210> SEQ ID NO 190
<211> LENGTH: 46
<212> TYPE: PRT
<213> ORGANISM: Homo sapien

<400> SEQUENCE: 190

Met Val Leu Lys Val Asn Ser Arg Met Val Ala Trp Val Phe Lys Val
1               5                   10                  15

Trp Phe Leu Leu Asn Ala Ser Gly Phe Leu Thr Asn Ile Lys Ser Lys
            20                  25                  30

Lys Lys Lys Lys Asn Leu Leu Val Ala Ile Arg Arg Leu Gln
        35                  40                  45

<210> SEQ ID NO 191
<211> LENGTH: 96
<212> TYPE: PRT
<213> ORGANISM: Homo sapien

<400> SEQUENCE: 191

Met Ser Ser Pro Gln Phe Ser Leu Arg Val Phe Ala Phe Ser Leu Leu
1               5                   10                  15

Thr Ser Thr Pro Leu Met Ser Leu Pro Ile Ala Pro Asn Ser Gly Ser
            20                  25                  30

Gln His Trp Tyr Ile Gln Val Trp Gln Arg Ala Ser Ser Thr Pro Gly
        35                  40                  45

Met Ala Ser Pro Lys Gln Gln Glu Glu Val Gly Glu Val Leu Phe Pro
    50                  55                  60

Ser Thr Ala Val Ala Leu Trp Trp Lys Val Arg Phe Pro Asn Gln Leu
65                  70                  75                  80

Arg Arg Val Gln Gln Ala Thr Arg Gln Val Asn Pro Phe Thr Ser Gly
            85                  90                  95

-continued

```
<210> SEQ ID NO 192
<211> LENGTH: 54
<212> TYPE: PRT
<213> ORGANISM: Homo sapien
<220> FEATURE:
<221> NAME/KEY: MISC_FEATURE
<222> LOCATION: (24)..(24)
<223> OTHER INFORMATION: X=any amino acid

<400> SEQUENCE: 192

Met Leu Phe Met Trp Lys Val Lys Phe Cys Phe Ile Met Glu Phe Cys
1               5                   10                  15

Phe Leu Tyr Asn Ser Phe Arg Xaa Ser Tyr Phe Ala Thr Ile Leu Tyr
            20                  25                  30

Lys Ala Leu Arg Gln Val Met Val Ile Ile Leu Met Gln Asn His Leu
        35                  40                  45

Gly Ser Gln Ser Leu Ala
    50

<210> SEQ ID NO 193
<211> LENGTH: 57
<212> TYPE: PRT
<213> ORGANISM: Homo sapien

<400> SEQUENCE: 193

Met Tyr Pro Leu Val His Gly Arg Pro Ser Ser Ile Ser Arg Gly Gln
1               5                   10                  15

Val His Leu Val Arg Ala Gln Lys Leu His Ser Gln Thr Asn Glu Ser
            20                  25                  30

Ser Gln Asn Ile Phe Leu Arg Leu Trp Val Tyr Leu Tyr Arg Asn His
        35                  40                  45

Trp Met Leu Leu Ser Leu Phe Ser Phe
    50                  55

<210> SEQ ID NO 194
<211> LENGTH: 57
<212> TYPE: PRT
<213> ORGANISM: Homo sapien

<400> SEQUENCE: 194

Met Tyr Pro Leu Val His Gly Arg Pro Ser Ser Ile Ser Arg Gly Gln
1               5                   10                  15

Val His Leu Val Arg Ala Gln Lys Leu His Ser Gln Thr Asn Glu Ser
            20                  25                  30

Ser Gln Asn Ile Phe Leu Arg Leu Trp Val Tyr Leu Tyr Arg Asn His
        35                  40                  45

Trp Met Leu Leu Ser Leu Phe Ser Phe
    50                  55

<210> SEQ ID NO 195
<211> LENGTH: 91
<212> TYPE: PRT
<213> ORGANISM: Homo sapien

<400> SEQUENCE: 195

Met Gly Lys Glu Ala Ile Leu Ile Gly Pro Arg Glu His Val Gly Leu
1               5                   10                  15

Cys Leu Val Leu Val Thr Gly Ile Leu Tyr Thr Phe Ile Val Gly Glu
            20                  25                  30

Lys Ala Ala Ile Thr Ser Ala Met Lys Val Leu Leu Ile His Gly Leu
        35                  40                  45
```

```
Asn Ile Ile Glu Met Leu Leu Val Leu Cys Arg Ala Asp Ser Ser Arg
 50                  55                  60

Thr Lys Glu Trp Gln Ser Asp Glu Leu Arg His Ile Arg Asp Pro Thr
 65                  70                  75                  80

Val Gln Met Met Thr Gln Asn Leu Phe Leu Leu
                 85                  90

<210> SEQ ID NO 196
<211> LENGTH: 79
<212> TYPE: PRT
<213> ORGANISM: Homo sapien

<400> SEQUENCE: 196

Met Arg Thr Ala Gln Gln Cys Ile Gln Arg His Glu His Leu Ala Ala
 1               5                  10                  15

Leu Glu Ser Gly Pro His Lys Phe Gly Gly Ile Gln Ala Leu Pro Lys
                 20                  25                  30

Arg Ala Gly Gly Cys Ser Phe Leu Leu His Phe Leu Ser Gln Arg Pro
             35                  40                  45

Arg Glu Leu Ser Pro Gln Thr Lys Gly Lys Gly Arg Leu Gln Ser Ser
         50                  55                  60

Leu Tyr Leu Ala Leu Asn Ala Ser Ser Leu Cys Gly Pro Ala Arg
 65                  70                  75

<210> SEQ ID NO 197
<211> LENGTH: 40
<212> TYPE: PRT
<213> ORGANISM: Homo sapien

<400> SEQUENCE: 197

Met Thr Asp Ile Glu Trp Asp Cys Ser Arg Gln Met Gly Met Asn Gly
 1               5                  10                  15

His Pro Thr Cys Lys Asp Thr Met Gly Ser Ala Asp Glu Met Gly Pro
                 20                  25                  30

Val Thr Glu Lys Leu Leu Pro Pro
             35                  40

<210> SEQ ID NO 198
<211> LENGTH: 40
<212> TYPE: PRT
<213> ORGANISM: Homo sapien

<400> SEQUENCE: 198

Met Thr Asp Ile Glu Trp Asp Cys Ser Arg Gln Met Gly Met Asn Gly
 1               5                  10                  15

His Pro Thr Cys Lys Asp Thr Met Gly Ser Ala Asp Glu Met Gly Pro
                 20                  25                  30

Val Thr Glu Lys Leu Leu Pro Pro
             35                  40

<210> SEQ ID NO 199
<211> LENGTH: 76
<212> TYPE: PRT
<213> ORGANISM: Homo sapien

<400> SEQUENCE: 199

Met Thr Leu Leu Leu Arg Arg Pro Glu Leu Trp Cys Cys Gly Met Thr
 1               5                  10                  15

Val Cys Leu Leu Thr Ser Ala Ser Ser His Ser Pro Pro Arg Ser Pro
```

```
                   20                  25                  30
Cys Pro Thr Pro Gly Val Ser Arg Gly Arg Gln Val Thr Met Leu
                35                  40                  45
Arg Val Ser Asp Gly Pro Glu Ala Gly Leu Thr Gln Leu Tyr Pro Lys
 50                  55                  60
Ala Glu Ser Gly Ser Pro Arg Leu Ser Ala His Gly
 65                  70                  75

<210> SEQ ID NO 200
<211> LENGTH: 78
<212> TYPE: PRT
<213> ORGANISM: Homo sapien

<400> SEQUENCE: 200

Met Cys Asp Leu Cys Asp Arg Leu Glu Ser Cys Gly Lys Pro Val Leu
  1               5                  10                  15
Val Arg Glu Ser Leu Gly Pro Phe Pro His Arg Ala Leu Phe Ser Lys
                 20                  25                  30
Ser His Ser Trp Val Thr Asn Val Asp Ala Gly Pro Met Pro Cys Pro
                 35                  40                  45
Gly Gly Leu Ala Pro Gly Ser Pro Glu Asn Thr Ser Gly Arg Trp Glu
             50                  55                  60
Val Trp Trp Gly Ser Leu Ala Arg Val Asp Met Gly Gln Arg
 65                  70                  75

<210> SEQ ID NO 201
<211> LENGTH: 525
<212> TYPE: PRT
<213> ORGANISM: Homo sapien

<400> SEQUENCE: 201

Asp Ile Asn Asn Ala Trp Gly Cys Leu Glu Gln Val Glu Lys Gly Tyr
  1               5                  10                  15
Glu Glu Trp Leu Leu Asn Glu Ile Arg Arg Leu Glu Arg Leu Asp His
                 20                  25                  30
Leu Ala Glu Lys Phe Arg Gln Lys Ala Ser Ile His Glu Ala Trp Thr
                 35                  40                  45
Asp Gly Lys Glu Ala Met Leu Lys His Arg Asp Tyr Glu Thr Ala Thr
             50                  55                  60
Leu Ser Asp Ile Lys Ala Leu Ile Arg Lys His Glu Ala Phe Glu Ser
 65                  70                  75                  80
Asp Leu Pro Glu His Gln Asp Arg Ala Glu Gln Ile Ala Ala Ile Ala
                 85                  90                  95
Gln Glu Leu Asn Glu Leu Asp Tyr Tyr Asp Ser His Asn Val Asn Thr
                100                 105                 110
Arg Cys Gln Lys Ile Cys Asp Gln Trp Asp Ala Leu Gly Ser Leu Thr
                115                 120                 125
His Ser Arg Arg Glu Ala Leu Glu Lys Thr Glu Lys Gln Leu Glu Ala
             130                 135                 140
Ile Asp Gln Leu His Leu Glu Tyr Ala Lys Arg Ala Ala Pro Phe Asn
145                 150                 155                 160
Asn Trp Met Glu Ser Ala Met Glu Asp Leu Gln Asp Met Phe Ile Val
                165                 170                 175
His Thr Ile Glu Glu Ile Glu Gly Leu Ile Ser Ala His Asp Gln Phe
                180                 185                 190
Lys Ser Thr Leu Pro Asp Ala Asp Arg Glu Arg Glu Ala Ile Leu Ala
```

```
                195                 200                 205
Ile His Lys Glu Ala Gln Arg Ile Ala Glu Ser Asn His Ile Lys Leu
    210                 215                 220

Ser Gly Ser Asn Pro Tyr Thr Val Thr Pro Gln Ile Ile Asn Ser
225                 230                 235                 240

Lys Trp Glu Lys Val Gln Gln Leu Val Pro Lys Arg Asp His Ala Leu
                245                 250                 255

Leu Glu Glu Gln Ser Lys Gln Ser Asn Glu His Leu Arg Arg Gln
                260                 265                 270

Phe Ala Ser Gln Ala Asn Val Val Gly Pro Trp Ile Gln Thr Lys Met
            275                 280                 285

Glu Glu Ile Gly Arg Ile Ser Ile Glu Met Asn Gly Thr Leu Glu Asp
    290                 295                 300

Gln Leu Ser His Leu Lys Gln Tyr Glu Arg Ser Ile Val Asp Tyr Lys
305                 310                 315                 320

Pro Asn Leu Asp Leu Glu Gln Gln His Gln Leu Ile Gln Glu Ala
                325                 330                 335

Leu Ile Phe Asp Asn Lys His Thr Asn Tyr Thr Met Glu His Ile Arg
            340                 345                 350

Val Gly Trp Glu Gln Leu Leu Thr Thr Ile Ala Arg Thr Ile Asn Glu
        355                 360                 365

Val Glu Asn Gln Ile Leu Thr Arg Asp Ala Lys Gly Ile Ser Gln Glu
    370                 375                 380

Gln Met Gln Glu Phe Arg Ala Ser Phe Asn His Phe Asp Lys Lys Gln
385                 390                 395                 400

Thr Gly Ser Met Asp Ser Asp Phe Arg Ala Leu Leu Ile Ser Thr
                405                 410                 415

Gly Tyr Ser Leu Gly Glu Ala Glu Phe Asn Arg Ile Met Ser Leu Val
            420                 425                 430

Asp Pro Asn His Ser Gly Leu Val Thr Phe Gln Ala Phe Ile Asp Phe
        435                 440                 445

Met Ser Arg Glu Thr Thr Asp Thr Asp Thr Ala Asp Gln Val Ile Ala
    450                 455                 460

Ser Phe Lys Val Leu Ala Gly Asp Lys Asn Phe Ile Thr Ala Glu Glu
465                 470                 475                 480

Leu Arg Arg Glu Leu Pro Pro Asp Gln Ala Glu Tyr Cys Ile Ala Arg
                485                 490                 495

Met Ala Pro Tyr Gln Gly Pro Asp Ala Val Pro Gly Ala Leu Asp Tyr
            500                 505                 510

Lys Ser Phe Ser Thr Ala Leu Tyr Gly Glu Ser Asp Leu
        515                 520                 525

<210> SEQ ID NO 202
<211> LENGTH: 83
<212> TYPE: PRT
<213> ORGANISM: Homo sapien

<400> SEQUENCE: 202

Met Trp Pro Gly Val Gly Gln Lys Asn Leu His Lys Asp Arg Ile Leu
1               5                   10                  15

Phe Ser Glu Ala Lys Asn Ser Arg Gly Ala Thr Ile Arg Phe Phe Ser
            20                  25                  30

Ala Val Gln Leu Gln Glu Met Leu Gly Ile Ser Tyr Asn Ser His Leu
        35                  40                  45
```

-continued

Ser Lys Thr Tyr Pro Gly Arg Cys Ser Ala Phe Ser His Leu Gly Ala
        50                  55                  60

Glu Gln Pro Tyr Ile Ala Val Tyr Ile Leu Thr Tyr Phe Pro Asp Phe
65                  70                  75                  80

Leu Gly Gly

<210> SEQ ID NO 203
<211> LENGTH: 83
<212> TYPE: PRT
<213> ORGANISM: Homo sapien

<400> SEQUENCE: 203

Met Trp Pro Gly Val Gly Gln Lys Asn Leu His Lys Asp Arg Ile Leu
1               5                   10                  15

Phe Ser Glu Ala Lys Asn Ser Arg Gly Ala Thr Ile Arg Phe Phe Ser
                20                  25                  30

Ala Val Gln Leu Gln Glu Met Leu Gly Ile Ser Tyr Asn Ser His Leu
            35                  40                  45

Ser Lys Thr Tyr Pro Gly Arg Cys Ser Ala Phe Ser His Leu Gly Ala
        50                  55                  60

Glu Gln Pro Tyr Ile Ala Val Tyr Ile Leu Thr Tyr Phe Pro Asp Phe
65                  70                  75                  80

Leu Gly Gly

<210> SEQ ID NO 204
<211> LENGTH: 62
<212> TYPE: PRT
<213> ORGANISM: Homo sapien

<400> SEQUENCE: 204

Met Ser Leu Ser Val Leu Asp Ser Val Ala Gln Thr Arg Pro Phe Val
1               5                   10                  15

Cys Leu Phe Ser Phe Ser Ser Phe Val Asp Tyr Lys Phe Ser Leu Tyr
                20                  25                  30

Ser Asn Lys Arg Phe Ser Phe Gln Asn Leu Arg Gln Cys Ser Ser Leu
            35                  40                  45

Lys Met Ile Leu Pro His Arg Trp Ser Arg Ala Ser Gln Trp
        50                  55                  60

<210> SEQ ID NO 205
<211> LENGTH: 36
<212> TYPE: PRT
<213> ORGANISM: Homo sapien

<400> SEQUENCE: 205

Met Cys Gln Asn Ile Asp Thr Val Pro Glu Glu Ala Ser Lys His Asn
1               5                   10                  15

Lys Cys Tyr Phe Arg His Lys Leu Gln Asp Ser Leu Thr Ile Pro Ala
                20                  25                  30

Cys Leu Ile Gly
            35

<210> SEQ ID NO 206
<211> LENGTH: 78
<212> TYPE: PRT
<213> ORGANISM: Homo sapien

<400> SEQUENCE: 206

Met Ser Ser Asn Leu Cys Ser Trp Lys Pro Ser Tyr Gly Arg Val Phe

```
                1               5                   10                  15
            Pro Pro Ser Ser Ser Ala Phe Tyr Gln Arg Pro Tyr Ser Pro Pro Leu
                            20                  25                  30

Leu Gln Phe Gln Thr Ser Phe Leu Phe His Gln Lys His Ser Pro Ser
                        35                  40                  45

Ser Leu Val Ser Tyr Ser Phe His Thr Gln Lys Gln Asn Ile Phe Lys
                    50                  55                  60

Thr Phe Pro Lys Lys Glu Glu Lys Gly Asn Ser Lys Val His
            65                  70                  75

<210> SEQ ID NO 207
<211> LENGTH: 78
<212> TYPE: PRT
<213> ORGANISM: Homo sapien

<400> SEQUENCE: 207

Met Ser Ser Asn Leu Cys Ser Trp Lys Pro Ser Tyr Gly Arg Val Phe
            1               5                   10                  15

Pro Pro Ser Ser Ser Ala Phe Tyr Gln Arg Pro Tyr Ser Pro Pro Leu
                            20                  25                  30

Leu Gln Phe Gln Thr Ser Phe Leu Phe His Gln Lys His Ser Pro Ser
                        35                  40                  45

Ser Leu Val Ser Tyr Ser Phe His Thr Gln Lys Gln Asn Ile Phe Lys
                    50                  55                  60

Thr Phe Pro Lys Lys Glu Glu Lys Gly Asn Ser Lys Val His
            65                  70                  75

<210> SEQ ID NO 208
<211> LENGTH: 15
<212> TYPE: PRT
<213> ORGANISM: Homo sapien

<400> SEQUENCE: 208

Met Phe Ile Glu Leu Phe Trp Leu Ile Ile Ser Thr Asp Cys Leu
            1               5                   10                  15

<210> SEQ ID NO 209
<211> LENGTH: 47
<212> TYPE: PRT
<213> ORGANISM: Homo sapien

<400> SEQUENCE: 209

Met Glu Arg His Thr Gln Ala Leu Cys Gly Arg Val Leu Ser Gly His
            1               5                   10                  15

Ser Glu Phe Arg Pro Gly Leu Trp Thr Asn Pro Asn Phe Ala Ser Ala
                            20                  25                  30

Phe Val Ser Leu Val Lys Pro Val Phe Val Phe Ser Leu Leu Phe
                        35                  40                  45

<210> SEQ ID NO 210
<211> LENGTH: 77
<212> TYPE: PRT
<213> ORGANISM: Homo sapien

<400> SEQUENCE: 210

Met Ser Ser Leu Leu Leu Lys Glu Thr Phe Lys Gln Phe Ser Ser Leu
            1               5                   10                  15

His Cys His Leu Ala His Thr Ser Arg Ala Ala Gln His Leu Gln Gly
                            20                  25                  30
```

-continued

```
Leu Ser Phe Trp Ala Val Leu Arg Asp Ala Gly Gly Ser Leu Ala
         35                  40                  45

Phe Leu Gly Leu Leu Ser Gln Phe Pro Val Leu Leu Ser Gly Cys
     50                  55                  60

Pro Ala Phe Gly Cys Trp Ile Leu Gln Val Pro Gln Arg
 65              70                  75
```

<210> SEQ ID NO 211
<211> LENGTH: 78
<212> TYPE: PRT
<213> ORGANISM: Homo sapien

<400> SEQUENCE: 211

```
Met Gly Glu Pro Gly His Glu Lys Glu Leu Pro Ser Asp Ser Asn Ile
 1               5                  10                  15

Ser Leu Tyr Leu Phe Lys Val Cys Met Cys Gln Thr Val Pro Ser Thr
             20                  25                  30

Leu Tyr Thr Leu Ala Tyr Pro Val Leu Thr Asn Ile Ser Glu Met Gly
         35                  40                  45

Ile Thr Val Gln Phe Pro Asp Ile Val Ser Lys Ala Lys Pro Lys Pro
 50                  55                  60

Val Cys Thr Arg Ala Cys Ala Leu His Thr Asp Trp Leu Ile
 65              70                  75
```

<210> SEQ ID NO 212
<211> LENGTH: 61
<212> TYPE: PRT
<213> ORGANISM: Homo sapien

<400> SEQUENCE: 212

```
Met Ser Arg Leu Pro His Thr Pro Ala Leu Ser Phe Pro Ser Gln Gly
 1               5                  10                  15

Asn Gly Ser Arg His Thr Pro His Leu Gly Gly Gln Ala Glu Phe Leu
             20                  25                  30

Ala Gln Gly Arg His Ser Glu Ser Val Glu Arg Lys Asn Asp Val Ala
         35                  40                  45

Arg Thr Leu Leu Gln Val Ser Ile Gly Asn His Lys Pro
     50                  55                  60
```

<210> SEQ ID NO 213
<211> LENGTH: 79
<212> TYPE: PRT
<213> ORGANISM: Homo sapien

<400> SEQUENCE: 213

```
Met Lys Val Pro Gln Ser Pro Val Leu Gln Leu Leu Ala Gln Asp Leu
 1               5                  10                  15

Ser Ser Arg Glu Lys Arg Ile Asn Thr Thr Pro Lys Gly Glu Lys Leu
             20                  25                  30

Leu Leu Ser Ser Ser Gly Asp Leu Ala His Gly Gly Pro Asn Gly Gly
         35                  40                  45

Pro Ser Leu Ile Ser Asn Ser Pro Ala Asn Ser Pro Leu Asp Thr Arg
     50                  55                  60

Ala Gly Lys Thr Leu Pro Gln Gly Gln Glu Gly Met Phe Val Ser
 65              70                  75
```

<210> SEQ ID NO 214
<211> LENGTH: 40
<212> TYPE: PRT

<213> ORGANISM: Homo sapien

<400> SEQUENCE: 214

Met Arg Asp Gly Pro Pro Phe Gly Pro Pro Trp Ala Lys Ser Pro Glu
1               5                   10                  15

Leu Glu Ser Ser Asn Phe Ser Pro Leu Gly Val Val Leu Ile Leu Phe
            20                  25                  30

Ser Leu Glu Leu Lys Val Leu Gly
        35                  40

<210> SEQ ID NO 215
<211> LENGTH: 72
<212> TYPE: PRT
<213> ORGANISM: Homo sapien

<400> SEQUENCE: 215

Met Leu Lys Asn Ser Ser Tyr Asn Leu Phe Tyr Asn Ile Tyr Ser Cys
1               5                   10                  15

Thr Tyr Phe Tyr Ile Leu Ser Phe Ile Phe Val Phe Val Ser Phe Ala
            20                  25                  30

Thr Leu Cys Thr Ser Leu Ser Glu Glu Gln Ser Phe Ser Pro Phe Tyr
        35                  40                  45

Thr Leu Asn Lys Tyr Leu Asn Ser Tyr Tyr Ser Leu Ile Leu Tyr Lys
    50                  55                  60

Ala Asp Ser Asn Ile Gly Ser Thr
65                  70

<210> SEQ ID NO 216
<211> LENGTH: 16
<212> TYPE: PRT
<213> ORGANISM: Homo sapien

<400> SEQUENCE: 216

Met Ser Trp Leu Leu Ser Tyr Gln Asn Leu Gly Val Ser Tyr Arg Cys
1               5                   10                  15

<210> SEQ ID NO 217
<211> LENGTH: 39
<212> TYPE: PRT
<213> ORGANISM: Homo sapien

<400> SEQUENCE: 217

Met Leu Ser Trp Asn Cys Tyr Ser Pro Pro Ile Ser Ser Leu Ser Ile
1               5                   10                  15

Cys His Pro Asn His Leu Glu Ala Leu Val Leu Asp Ala Leu Gln Tyr
            20                  25                  30

Phe Phe Phe Leu Phe Phe Glu
        35

<210> SEQ ID NO 218
<211> LENGTH: 24
<212> TYPE: PRT
<213> ORGANISM: Homo sapien

<400> SEQUENCE: 218

Met Asn Asp Arg Ala Arg Leu Ser Leu Ser Gln Lys Lys Thr Glu Arg
1               5                   10                  15

Glu Ser Leu Glu Thr Arg His Ser
            20

```
<210> SEQ ID NO 219
<211> LENGTH: 84
<212> TYPE: PRT
<213> ORGANISM: Homo sapien
<220> FEATURE:
<221> NAME/KEY: MISC_FEATURE
<222> LOCATION: (28)..(79)
<223> OTHER INFORMATION: X=any amino acid

<400> SEQUENCE: 219

Met Asp Arg Ala Leu Pro Leu Trp Gly Ser Gln Glu Pro Ser Glu Pro
1               5                   10                  15

Ser Gln Ile Ala Leu Val Ser Ile Leu Val Leu Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Ser
65                  70                  75                  80

Ile Lys Ile Gln

<210> SEQ ID NO 220
<211> LENGTH: 32
<212> TYPE: PRT
<213> ORGANISM: Homo sapien
<220> FEATURE:
<221> NAME/KEY: MISC_FEATURE
<222> LOCATION: (31)..(31)
<223> OTHER INFORMATION: X=any amino acid

<400> SEQUENCE: 220

Met Lys Ile Thr Ser Cys Val Tyr Thr Ile Cys Leu His Leu Ala Asn
1               5                   10                  15

Thr Gly Leu His Asp Ser Thr Phe Ala Asn Tyr Leu Trp Leu Xaa Asn
            20                  25                  30

<210> SEQ ID NO 221
<211> LENGTH: 786
<212> TYPE: PRT
<213> ORGANISM: Homo sapien

<400> SEQUENCE: 221

Arg Pro Leu Arg Ser Leu Lys Val Ile Tyr Asp Gly Leu Met Ala Leu
1               5                   10                  15

Phe Thr Thr Ser Leu Ile Ala Leu Leu Ser Ser Arg Gly Lys Asn Val
            20                  25                  30

Ala Ile Glu Tyr Ile Lys Ile His Thr Ile Glu Lys Glu Asp Val His
        35                  40                  45

Phe Cys Lys Gln Lys Ile Thr Asn Arg Met Leu Lys Leu Lys Leu Asp
    50                  55                  60

Tyr Glu Glu Ser Pro Val Tyr Gln Val Tyr Val Gln Ala Lys Asp Leu
65                  70                  75                  80

Gly Pro Asn Ala Val Pro Ala His Cys Lys Val Ile Val Arg Val Leu
            85                  90                  95

Asp Ala Asn Asp Asn Ala Pro Glu Ile Ser Phe Ser Thr Val Lys Glu
            100                 105                 110

Ala Val Ser Glu Gly Ala Ala Pro Gly Thr Val Val Ala Leu Phe Ser
        115                 120                 125

Val Thr Asp Arg Asp Ser Glu Glu Asn Gly Gln Val Gln Cys Glu Leu
```

-continued

```
            130                 135                 140
Leu Gly Asp Val Pro Phe Arg Leu Lys Ser Ser Phe Lys Asn Tyr Tyr
145                 150                 155                 160

Thr Ile Val Thr Glu Ala Pro Leu Asp Arg Glu Ala Gly Asp Ser Tyr
                165                 170                 175

Thr Leu Thr Val Val Ala Arg Asp Arg Gly Glu Pro Ala Leu Ser Thr
                180                 185                 190

Ser Lys Ser Ile Gln Val Gln Val Ser Asp Val Asn Asp Asn Ala Pro
                195                 200                 205

Arg Phe Ser Gln Pro Val Tyr Asp Val Tyr Val Thr Glu Asn Asn Val
210                 215                 220

Pro Gly Ala Tyr Ile Tyr Ala Val Ser Ala Thr Asp Arg Asp Glu Gly
225                 230                 235                 240

Ala Asn Ala Gln Leu Ala Tyr Ser Ile Leu Glu Cys Gln Ile Gln Gly
                245                 250                 255

Met Ser Val Phe Thr Tyr Val Ser Ile Asn Ser Glu Asn Gly Tyr Leu
                260                 265                 270

Tyr Ala Leu Arg Ser Phe Asp Tyr Glu Gln Leu Lys Asp Phe Ser Phe
                275                 280                 285

Gln Val Glu Ala Arg Asp Ala Gly Ser Pro Gln Ala Leu Ala Gly Asn
                290                 295                 300

Ala Thr Val Asn Ile Leu Ile Val Asp Gln Asn Asp Asn Ala Pro Ala
305                 310                 315                 320

Ile Val Ala Pro Leu Pro Gly Arg Asn Gly Thr Pro Ala Arg Glu Val
                325                 330                 335

Leu Pro Arg Ser Ala Glu Pro Gly Tyr Leu Leu Thr Arg Val Ala Ala
                340                 345                 350

Val Asp Ala Asp Asp Gly Glu Asn Ala Arg Leu Thr Tyr Ser Ile Val
                355                 360                 365

Arg Gly Asn Glu Met Asn Leu Phe Arg Met Asp Trp Arg Thr Gly Glu
                370                 375                 380

Leu Arg Thr Ala Arg Arg Val Pro Ala Lys Arg Asp Pro Gln Arg Pro
385                 390                 395                 400

Tyr Glu Leu Val Ile Glu Val Arg Asp His Gly Gln Pro Pro Leu Ser
                405                 410                 415

Ser Thr Ala Thr Leu Val Val Gln Leu Val Asp Gly Ala Val Glu Pro
                420                 425                 430

Gln Gly Gly Gly Gly Ser Gly Gly Gly Ser Gly Glu His Gln Arg
                435                 440                 445

Pro Ser Arg Ser Gly Gly Glu Thr Ser Leu Asp Leu Thr Leu Ile
450                 455                 460

Leu Ile Ile Ala Leu Gly Ser Val Ser Phe Ile Phe Leu Leu Ala Met
465                 470                 475                 480

Ile Val Leu Ala Val Arg Cys Gln Lys Glu Lys Lys Leu Asn Ile Tyr
                485                 490                 495

Thr Cys Leu Ala Ser Asp Cys Cys Leu Cys Cys Cys Cys Gly Gly
                500                 505                 510

Gly Gly Ser Thr Cys Cys Gly Arg Gln Ala Arg Ala Arg Lys Lys Lys
                515                 520                 525

Leu Ser Lys Ser Asp Ile Met Leu Val Gln Ser Ser Asn Val Pro Ser
                530                 535                 540

Asn Pro Ala Gln Val Pro Ile Glu Glu Ser Gly Gly Phe Gly Ser His
545                 550                 555                 560
```

```
His His Asn Gln Asn Tyr Cys Tyr Gln Val Cys Leu Thr Pro Glu Ser
                565                 570                 575
Ala Lys Thr Asp Leu Met Phe Leu Lys Pro Cys Ser Pro Ser Arg Ser
                580                 585                 590
Thr Asp Thr Glu His Asn Pro Cys Gly Ala Ile Val Thr Gly Tyr Thr
                595                 600                 605
Asp Gln Gln Pro Asp Ile Ile Ser Asn Gly Ser Ile Leu Ser Asn Glu
                610                 615                 620
Thr Lys His Gln Arg Ala Glu Leu Ser Tyr Leu Val Asp Arg Pro Arg
625                 630                 635                 640
Arg Val Asn Ser Ser Ala Phe Gln Glu Ala Asp Ile Val Ser Ser Lys
                645                 650                 655
Asp Ser Gly His Gly Asp Ser Glu Gln Gly Asp Ser Asp His Asp Ala
                660                 665                 670
Thr Asn Arg Ala Gln Ser Ala Gly Met Asp Leu Phe Ser Asn Cys Thr
                675                 680                 685
Glu Glu Cys Lys Ala Leu Gly His Ser Asp Arg Cys Trp Met Pro Ser
                690                 695                 700
Phe Val Pro Ser Asp Gly Arg Gln Ala Ala Asp Tyr Arg Ser Asn Leu
705                 710                 715                 720
His Val Pro Gly Met Asp Ser Val Pro Asp Thr Glu Val Phe Glu Thr
                725                 730                 735
Pro Glu Ala Gln Pro Gly Ala Glu Arg Ser Phe Ser Thr Phe Gly Lys
                740                 745                 750
Glu Lys Ala Leu His Ser Thr Leu Glu Arg Lys Glu Leu Asp Gly Leu
                755                 760                 765
Leu Thr Asn Thr Arg Ala Pro Tyr Lys Pro Pro Tyr Leu Ser Pro Tyr
                770                 775                 780
Leu Thr
785

<210> SEQ ID NO 222
<211> LENGTH: 80
<212> TYPE: PRT
<213> ORGANISM: Homo sapien

<400> SEQUENCE: 222

Met Tyr Lys Arg Arg Ser Cys Lys Ile Ala Pro Ile Glu Ser Glu Leu
1               5                   10                  15
Glu Asn Leu Glu Glu Cys Ala Leu Thr Asn Ala Pro Phe Ser Ser Lys
                20                  25                  30
Ala His Phe Phe Phe Leu Gln Thr Lys Leu Leu Glu Gln Val Asp Tyr
                35                  40                  45
Thr Phe Cys His Ser His Val Trp Lys Asn Lys Asn Gly His Lys Leu
                50                  55                  60
Phe Ala Ala Pro Tyr Val Lys Ser Trp Ser Pro Leu Ala Gly Cys Gly
65                  70                  75                  80

<210> SEQ ID NO 223
<211> LENGTH: 87
<212> TYPE: PRT
<213> ORGANISM: Homo sapien

<400> SEQUENCE: 223

Met Ser His Pro Phe Leu Ala Ile Leu Gly Cys Trp Thr Ser Gln Leu
1               5                   10                  15
```

-continued

```
His Phe Leu Leu Ser Cys Leu Asn Phe Tyr Leu Ser Thr Glu Thr Leu
            20                  25                  30

Leu Thr Thr Tyr Lys Arg Ala Gly Ile Ser Pro Leu Asp Pro Thr Ile
            35                  40                  45

Pro Ser Ser Ser Leu Phe Leu Cys Ile Leu Leu Gln Gln Thr Ser Glu
 50                  55                      60

Gly Phe Phe Leu Ser Pro Ile Ser Leu Pro Leu His Leu Gly Phe Cys
 65                  70                      75                  80

Leu Arg His Phe Asn Lys Thr
                85

<210> SEQ ID NO 224
<211> LENGTH: 61
<212> TYPE: PRT
<213> ORGANISM: Homo sapien
<220> FEATURE:
<221> NAME/KEY: MISC_FEATURE
<222> LOCATION: (8)..(8)
<223> OTHER INFORMATION: X=any amino acid

<400> SEQUENCE: 224

Met Thr Gln Leu Ile Cys Thr Xaa Gln His Asp Gln Asn Gln Asn Val
 1               5                  10                  15

Gln Phe Phe Glu Ser Arg His Ile Thr Thr Val Asn His Ile Leu Ser
            20                  25                  30

Tyr Lys Ala Thr Gln Glu Ile Leu Lys Ile Glu Ile Ile Val Ile Phe
            35                  40                  45

Tyr Tyr Ser Ala Phe Lys Ile Glu Ile Asn Lys Glu Leu
 50                  55                      60

<210> SEQ ID NO 225
<211> LENGTH: 78
<212> TYPE: PRT
<213> ORGANISM: Homo sapien

<400> SEQUENCE: 225

Met Phe Met Val Ser His Leu Ala Pro Arg Ser Leu Asn Arg Ser His
 1               5                  10                  15

Leu Leu His His Leu Val Leu Lys His Leu Tyr Lys Met Gln Phe Thr
            20                  25                  30

Ile Leu His Ser Val Gln Phe Asp Pro Phe Gln Ile Gln Tyr Met Gln
            35                  40                  45

Thr Phe Pro Gly Gly Asp Val Arg Leu Arg Thr Thr Lys Tyr Val Phe
 50                  55                      60

Cys Asn Ile Glu Ser Ile Ser Pro Ile Val Asn Ala Leu Ser
 65                  70                      75

<210> SEQ ID NO 226
<211> LENGTH: 38
<212> TYPE: PRT
<213> ORGANISM: Homo sapien

<400> SEQUENCE: 226

Met Leu Ala Asn Met Val Val Tyr Thr Lys Ala Leu Tyr Asp Gln Leu
 1               5                  10                  15

Val Asn Lys Ser Leu Tyr Asn Cys Lys Gly Lys Ile Lys Thr Asp Leu
            20                  25                  30

Leu Lys Gln Tyr Thr Ile
            35
```

```
<210> SEQ ID NO 227
<211> LENGTH: 45
<212> TYPE: PRT
<213> ORGANISM: Homo sapien

<400> SEQUENCE: 227

Met Pro Leu Trp Gln Arg Glu Phe Ser Asn Lys Thr Glu Leu Gly Arg
1               5                   10                  15

Arg Glu Trp Asn Tyr Leu Leu Ile Ser Tyr Cys Asp Ile Arg Tyr Cys
                20                  25                  30

Tyr Ile His Leu Ser Leu Trp Tyr Leu Leu Asn Asn Trp
                35                  40                  45

<210> SEQ ID NO 228
<211> LENGTH: 67
<212> TYPE: PRT
<213> ORGANISM: Homo sapien

<400> SEQUENCE: 228

Met Gly Leu Asp Phe Pro Phe His Ala Glu Lys Lys Leu Ser Leu Arg
1               5                   10                  15

Glu Cys Ala Glu Gln Ser Gly Pro Arg Lys Ala Thr Thr Asn Ile Leu
                20                  25                  30

His Ala Lys Lys Glu Ala Lys Glu Glu Val Glu Leu Tyr Pro Asn Met
                35                  40                  45

Leu Ile Ile Gly Val Ile Leu Ala Glu Leu Val Arg Pro Pro Gly Gly
            50                  55                  60

Gln Gly Ile
65

<210> SEQ ID NO 229
<211> LENGTH: 76
<212> TYPE: PRT
<213> ORGANISM: Homo sapien

<400> SEQUENCE: 229

Lys Asn Lys Gln Lys Lys Arg Lys Lys Arg Lys Lys Arg Lys Lys Lys
1               5                   10                  15

Arg Lys Lys Arg Lys Lys Arg Lys Arg Lys Arg Lys Lys Lys Arg Arg
                20                  25                  30

Lys Lys Gly Arg Arg Arg Lys Lys Lys Lys Lys Lys Lys
                35                  40                  45

Lys Lys Lys Lys Lys Lys Lys Lys Lys Lys Lys Lys Lys Lys Lys Glu
            50                  55                  60

Arg Lys Lys Glu Arg Lys Arg Glu Asp Ser Thr Asn
65                  70                  75

<210> SEQ ID NO 230
<211> LENGTH: 20
<212> TYPE: PRT
<213> ORGANISM: Homo sapien

<400> SEQUENCE: 230

Met Glu Met His Gly Asn Ala Phe Val Ser Thr Val Leu Glu Arg Leu
1               5                   10                  15

Lys His Phe Ile
                20
```

-continued

<210> SEQ ID NO 231
<211> LENGTH: 61
<212> TYPE: PRT
<213> ORGANISM: Homo sapien

<400> SEQUENCE: 231

Met Pro Leu Gln Gly Pro Gln Phe Glu Lys Tyr Tyr Leu Val Lys Phe
1               5                   10                  15

Trp Leu Leu Cys Lys Asn Phe His Ser Leu Thr Gln Ala Ser Gly Thr
            20                  25                  30

Ala Tyr Phe Leu Thr Leu Thr Leu Leu Lys Leu Phe Gln Ser Leu Leu
        35                  40                  45

Cys Leu Gln Ala Leu Glu Thr Glu Glu Arg Asn Phe Thr
    50                  55                  60

<210> SEQ ID NO 232
<211> LENGTH: 39
<212> TYPE: PRT
<213> ORGANISM: Homo sapien

<400> SEQUENCE: 232

Met Ile Tyr Gly Ile Ile Gly Ile Phe Ile Phe Asn Thr Ile Tyr His
1               5                   10                  15

Phe Ser Gly Leu Thr Leu Ser Asp Leu Phe Gly Ile Phe Ser Leu Met
            20                  25                  30

Thr Lys Phe Ile Asn Gln Trp
        35

<210> SEQ ID NO 233
<211> LENGTH: 42
<212> TYPE: PRT
<213> ORGANISM: Homo sapien

<400> SEQUENCE: 233

Met Phe His Arg Ile His Gly Gln Arg Ile Arg Gln Ala Phe Glu Met
1               5                   10                  15

Asn Arg Ile Ser Leu Thr Ser Pro Ser Phe Cys Gln Phe Val Leu Phe
            20                  25                  30

Leu Ser His Ile His Gln Leu Ser Pro Ser
        35                  40

<210> SEQ ID NO 234
<211> LENGTH: 42
<212> TYPE: PRT
<213> ORGANISM: Homo sapien

<400> SEQUENCE: 234

Met Phe His Arg Ile His Gly Gln Arg Ile Arg Gln Ala Phe Glu Met
1               5                   10                  15

Asn Arg Ile Ser Leu Thr Ser Pro Ser Phe Cys Gln Phe Val Leu Phe
            20                  25                  30

Leu Ser His Ile His Gln Leu Ser Pro Ser
        35                  40

<210> SEQ ID NO 235
<211> LENGTH: 37
<212> TYPE: PRT
<213> ORGANISM: Homo sapien

<400> SEQUENCE: 235

Met Leu Met Asn Val Lys Val Ala Lys Thr Gln Ala Leu Thr Ile Leu

```
                1               5                   10                  15
Met Phe Leu Leu Phe Lys Thr Asp Leu Tyr Gly Gln Lys His Arg Asn
                20                  25                  30

Gly Ser Ser Arg Phe
            35

<210> SEQ ID NO 236
<211> LENGTH: 135
<212> TYPE: PRT
<213> ORGANISM: Homo sapien
<220> FEATURE:
<221> NAME/KEY: MISC_FEATURE
<222> LOCATION: (72)..(72)
<223> OTHER INFORMATION: X=any amino acid
<220> FEATURE:
<221> NAME/KEY: MISC_FEATURE
<222> LOCATION: (116)..(116)
<223> OTHER INFORMATION: X=any amino acid
<220> FEATURE:
<221> NAME/KEY: MISC_FEATURE
<222> LOCATION: (131)..(131)
<223> OTHER INFORMATION: X=any amino acid

<400> SEQUENCE: 236

Met Lys Pro Ser Leu Cys Pro Arg Ala Val Gln Ala Ala Val Ala
1               5                   10                  15

Pro Thr Asn Ser Gln Glu Thr Tyr Ser Val Pro Gln Gly Arg Cys Arg
                20                  25                  30

Trp Gln Pro Trp Pro Arg Pro Ala His Arg Lys Pro Thr Leu Cys Pro
                35                  40                  45

Gly Ala Gly Ala Gly Gly Ser His Gly Pro Asp Gln Leu Thr Gly Asn
            50                  55                  60

Leu Leu Cys Cys Pro Arg Gly Xaa Cys Arg Arg Gln Pro Trp Pro Arg
65                  70                  75                  80

Pro Ser Ser His Glu Asn Leu Ser Leu Leu Pro Pro Gly Ala Ile Ala
                85                  90                  95

Arg Arg Gln Ala Met Ala Pro Thr Ser Ser Gln Glu Thr Tyr Ser Val
                100                 105                 110

Pro Pro Gly Xaa Leu Pro Leu Ala Ala Met Ala Pro Asn Gln His Thr
            115                 120                 125

Gly Lys Xaa Thr Gly Thr Leu
            130             135

<210> SEQ ID NO 237
<211> LENGTH: 419
<212> TYPE: PRT
<213> ORGANISM: Homo sapien

<400> SEQUENCE: 237

Met Ala Pro Thr Ser Ser Gln Glu Thr Tyr Ser Val Pro Arg Gly Arg
1               5                   10                  15

Cys Arg Gln Gln Pro Trp Pro Arg Pro Ala His Arg Lys Pro Ser Leu
                20                  25                  30

Cys Pro Arg Ala Val Gln Ala Ala Val Ala Pro Thr Ser Ser Gln
            35                  40                  45

Glu Thr Tyr Ser Val Pro Gln Gly Arg Cys Arg Trp Gln Pro Trp Pro
        50                  55                  60

Arg Pro Ala His Arg Lys Pro Thr Leu Cys Pro Arg Ala Gly Ala Gly
65                  70                  75                  80

Gly Ser Arg Gly Pro Asp Gln Leu Thr Gly Asn Leu Leu Cys Ala Leu
```

```
                    85                  90                  95
Gly Gln Gly Arg Cys Arg Arg Gln Pro Trp Pro Arg Pro Ala Pro Thr
            100                 105                 110
Ser Leu Ser Cys Ser Arg Ser Ala Pro Gly Pro Ala Pro Ser Gly Pro
            115                 120                 125
Arg Gly Lys Thr Pro Ser Ser Pro Thr Leu Ser Pro Ser Arg Gly Ser
            130                 135                 140
Pro Leu Leu Leu Arg Glu Pro Ser Leu Val Thr Asp Ser Leu Glu Ala
145                 150                 155                 160
His Arg Gly Ser Leu Ala Pro Gly Val Leu Trp Thr Ser Gly Thr Ala
                165                 170                 175
Ser Gly Ser Lys Ala Ala Pro Pro Gln Glu Gly Leu Met Thr Glu
                180                 185                 190
Leu Glu Ser Cys Gly Gly Arg Thr Ala Thr Gly Pro Cys Leu Pro Thr
                195                 200                 205
Gly Ser Glu Arg Pro Ser Leu Arg Leu Pro Gly Pro Cys Pro Ser Val
            210                 215                 220
Gly His Ser Gln Ala Leu Gly Gln Arg Lys Gln Phe Arg Glu Thr Ala
225                 230                 235                 240
Gln Ala Arg Lys Ala Gln Val Ala Trp Glu Pro Arg Ser Ala Glu Ile
                245                 250                 255
Glu Leu Glu Lys Gln Glu Ala Trp Pro Gly Pro Pro Ala Ser Lys Gly
                260                 265                 270
Glu Arg Gln Ala Pro Gly Val Gly Ser Gly Val Leu Gly Pro His Gln
            275                 280                 285
Thr Gly Ile Phe Pro Pro Leu Pro Gly Gly Ala Gly Arg Ala Ser
        290                 295                 300
Pro Ala Glu Ala Pro Gly Ser Val Arg Asn Asn Arg Lys Gly Ser Arg
305                 310                 315                 320
Gly Thr Gly Thr Ser His Thr Pro His Pro Val His Pro Ile Gly Pro
                325                 330                 335
Ile His Pro Val His Pro Val Tyr Pro Ile Tyr Arg His Phe Pro Leu
                340                 345                 350
His Ser Gln Leu Ser Arg Leu Leu Thr Leu Glu Glu Leu Asn Ser Gly
                355                 360                 365
Leu Ala Ser Cys Leu Gln Cys Gly Thr Leu Cys Ser Ser Thr Trp Glu
            370                 375                 380
Pro Gln Gly Ala Arg Ser Val Gly Ile Cys Thr Leu Pro Leu Thr Glu
385                 390                 395                 400
Ile Tyr His Ala Glu Thr Ser Asp Leu Arg Gly Thr Ser Ala Gly Pro
                405                 410                 415
Trp Val His

<210> SEQ ID NO 238
<211> LENGTH: 59
<212> TYPE: PRT
<213> ORGANISM: Homo sapien

<400> SEQUENCE: 238

Met Val Ser Asn Asn Tyr Leu Thr Gly Phe Trp Leu Gly Ile Phe Leu
1               5                   10                  15
Leu Pro His Thr Val Pro Val Glu Asn Val Glu Val His Phe Gly Leu
            20                  25                  30
Tyr Ile Phe Met Lys His Leu Glu Gly Trp Gly Gly Gly Cys Gln Val
```

```
                35                  40                  45

Ser Lys Ser Arg Lys Met Tyr Phe Val Arg Leu
    50                  55

<210> SEQ ID NO 239
<211> LENGTH: 59
<212> TYPE: PRT
<213> ORGANISM: Homo sapien

<400> SEQUENCE: 239

Met Val Ser Asn Asn Tyr Leu Thr Gly Phe Trp Leu Gly Ile Phe Leu
1               5                   10                  15

Leu Pro His Thr Val Pro Val Glu Asn Val Glu Val His Phe Gly Leu
            20                  25                  30

Tyr Ile Phe Met Lys His Leu Glu Gly Trp Gly Gly Cys Gln Val
        35                  40                  45

Ser Lys Ser Arg Lys Met Tyr Phe Val Arg Leu
    50                  55

<210> SEQ ID NO 240
<211> LENGTH: 73
<212> TYPE: PRT
<213> ORGANISM: Homo sapien

<400> SEQUENCE: 240

Met Asn Val Leu Pro Leu Lys Lys Asn Gln Leu Ser His Ile Thr His
1               5                   10                  15

Ile Tyr Ile Leu Leu His Asn Asn Val Leu Asn Trp Thr Thr Val Asn
            20                  25                  30

Gln Arg Val Ile Ala Ala Ser Glu Gly Asp Arg Leu Leu Thr Phe Arg
        35                  40                  45

Tyr Cys Leu Met Pro Gly Lys Pro Trp Glu Pro Arg Gln Val Asn Leu
    50                  55                  60

Thr Lys Leu Leu Leu Phe Ser Gln Leu
65                  70

<210> SEQ ID NO 241
<211> LENGTH: 73
<212> TYPE: PRT
<213> ORGANISM: Homo sapien

<400> SEQUENCE: 241

Met Asn Val Leu Pro Leu Lys Lys Asn Gln Leu Ser His Ile Thr His
1               5                   10                  15

Ile Tyr Ile Leu Leu His Asn Asn Val Leu Asn Trp Thr Thr Val Asn
            20                  25                  30

Gln Arg Val Ile Ala Ala Ser Glu Gly Asp Arg Leu Leu Thr Phe Arg
        35                  40                  45

Tyr Cys Leu Met Pro Gly Lys Pro Trp Glu Pro Arg Gln Val Asn Leu
    50                  55                  60

Thr Lys Leu Leu Leu Phe Ser Gln Leu
65                  70

<210> SEQ ID NO 242
<211> LENGTH: 39
<212> TYPE: PRT
<213> ORGANISM: Homo sapien
<220> FEATURE:
<221> NAME/KEY: MISC_FEATURE
<222> LOCATION: (2)..(2)
```

```
<223> OTHER INFORMATION: X=any amino acid
<220> FEATURE:
<221> NAME/KEY: MISC_FEATURE
<222> LOCATION: (4)..(5)
<223> OTHER INFORMATION: X=any amino acid
<220> FEATURE:
<221> NAME/KEY: MISC_FEATURE
<222> LOCATION: (7)..(7)
<223> OTHER INFORMATION: X=any amino acid
<220> FEATURE:
<221> NAME/KEY: MISC_FEATURE
<222> LOCATION: (11)..(11)
<223> OTHER INFORMATION: X=any amino acid
<220> FEATURE:
<221> NAME/KEY: MISC_FEATURE
<222> LOCATION: (15)..(15)
<223> OTHER INFORMATION: X=any amino acid
<220> FEATURE:
<221> NAME/KEY: MISC_FEATURE
<222> LOCATION: (17)..(22)
<223> OTHER INFORMATION: X=any amino acid

<400> SEQUENCE: 242

Met Xaa Thr Xaa Xaa Pro Xaa Ser Trp Met Xaa Ala Phe Lys Xaa Asp
1               5                   10                  15

Xaa Xaa Xaa Xaa Xaa Xaa Arg Trp Asn Leu Ser Ile Arg Gly Ser Phe
            20                  25                  30

Ala Thr Asp Phe Ser Asn Gly
        35

<210> SEQ ID NO 243
<211> LENGTH: 81
<212> TYPE: PRT
<213> ORGANISM: Homo sapien

<400> SEQUENCE: 243

Met Ile Ile Tyr Asn Tyr Asn Val Tyr Cys Phe Thr Tyr Ile Phe Pro
1               5                   10                  15

Lys Tyr Thr Ile Asn Ala Leu Pro His Phe Ala Leu Phe Thr Lys Tyr
            20                  25                  30

Ile Leu Glu Ile Ile Leu Tyr Ser Tyr Ile Lys Ser Phe Ile Val Pro
        35                  40                  45

Phe Tyr Gly Cys Lys Met Phe Gln Leu Met Asp Gly Leu Ile Leu Tyr
    50                  55                  60

Arg Ala Thr Leu Arg Leu Cys Pro Ile Leu Leu Phe Leu Ile Leu Leu
65                  70                  75                  80

Lys

<210> SEQ ID NO 244
<211> LENGTH: 85
<212> TYPE: PRT
<213> ORGANISM: Homo sapien
<220> FEATURE:
<221> NAME/KEY: MISC_FEATURE
<222> LOCATION: (76)..(76)
<223> OTHER INFORMATION: X=any amino acid

<400> SEQUENCE: 244

Met Ser Gly Glu Leu Cys Ala Gly Ala Gln Gly Pro Gln Gly Leu Val
1               5                   10                  15

Glu Gly Met Lys Cys Ala His Ile Lys Arg Lys Val Ala Met Gln Ser
            20                  25                  30

Lys Glu Gly Gln Val Gln Met Cys Ser Val Asn Leu Ile Leu Arg Glu
        35                  40                  45
```

```
Gly Arg Gly Phe Gly Leu Gly Gln Asp Pro Lys Glu Gly Ala Glu Asp
            50                  55                  60

Met Glu Leu Glu Ala Val Arg Lys Val Val Phe Xaa Glu Gly Ala Val
 65                  70                  75                  80

Leu Thr Arg Pro Leu
                85

<210> SEQ ID NO 245
<211> LENGTH: 70
<212> TYPE: PRT
<213> ORGANISM: Homo sapien
<220> FEATURE:
<221> NAME/KEY: MISC_FEATURE
<222> LOCATION: (28)..(43)
<223> OTHER INFORMATION: X=any amino acid

<400> SEQUENCE: 245

Met Ser Thr Phe Thr Phe Thr Ala Lys Gln Gly Phe Gln Val Val Phe
 1               5                  10                  15

Ser Ser Leu Asn Ser His Leu Pro Lys Met Gln Xaa Xaa Xaa Xaa Xaa
            20                  25                  30

Xaa Xaa Xaa Xaa Xaa Xaa Xaa Xaa Xaa Xaa Ser Gly Trp Leu Ser
        35                  40                  45

Glu Ser Pro Asn Asn Pro Met Lys Tyr Glu Arg Phe Leu Glu Arg Leu
    50                  55                  60

Leu Val Glu Lys Val Thr
 65                  70

<210> SEQ ID NO 246
<211> LENGTH: 60
<212> TYPE: PRT
<213> ORGANISM: Homo sapien
<220> FEATURE:
<221> NAME/KEY: MISC_FEATURE
<222> LOCATION: (31)..(31)
<223> OTHER INFORMATION: X=any amino acid

<400> SEQUENCE: 246

Met Val Pro Gly Gly Gln Arg Ala Gly Gly Leu Cys Leu Lys Arg Ser
 1               5                  10                  15

Leu Gln Ile Val Phe Glu Lys Ile Thr Gln Asn Gln Pro Trp Xaa Tyr
            20                  25                  30

Leu Arg Gln Glu Gly Lys Tyr Phe Lys Arg Leu Cys Glu Phe Val Ser
        35                  40                  45

Val His Leu Phe Phe Val Glu Tyr Ile Leu Leu Ile
    50                  55                  60

<210> SEQ ID NO 247
<211> LENGTH: 48
<212> TYPE: PRT
<213> ORGANISM: Homo sapien

<400> SEQUENCE: 247

Met Gln Gln Asp Ser Tyr Ser Val Asn Trp Tyr Ser Leu Tyr Arg Gly
 1               5                  10                  15

Gln Leu Lys Lys His Phe Phe Asp Gln Ala Ile Pro Leu Leu Gly Ile
            20                  25                  30

His Pro Thr Asp Ile Leu Ser His Ile Leu Lys Asn Arg Pro Gly Thr
        35                  40                  45

<210> SEQ ID NO 248
```

```
<211> LENGTH: 103
<212> TYPE: PRT
<213> ORGANISM: Homo sapien

<400> SEQUENCE: 248

Ile Ile Leu Ala Leu Phe Arg Asp Arg Val Ser Pro Ser Phe Arg Leu
1               5                   10                  15

Ala Tyr Ser Gly Ala Ile Met Ala His Cys His Leu Gln Leu Leu Gly
            20                  25                  30

Leu Arg Asp Pro Pro Thr Ser Ala Ser Ala Val Ala Gly Ser Thr Gly
        35                  40                  45

Gln Cys His His Gly Trp Ala Asn Ala Ala Lys Phe Leu Phe Ser Ile
    50                  55                  60

Glu Ile Gly Leu Cys His Phe Ala Gln Ala Gly Leu Glu Leu Val Gly
65                  70                  75                  80

Ala Ser Asn Pro Ala Pro Ser Thr Ser Gln Ser Pro Gly Ile Thr Gly
                85                  90                  95

Val Ser His Cys Ala Trp Pro
            100

<210> SEQ ID NO 249
<211> LENGTH: 38
<212> TYPE: PRT
<213> ORGANISM: Homo sapien

<400> SEQUENCE: 249

Met Trp Tyr Met Thr Ile Phe Pro Gly Trp Val Glu Gly Glu Val His
1               5                   10                  15

Arg Asp Ser Trp Val Lys Lys Ser Leu Tyr Ser His Leu Leu Leu Lys
            20                  25                  30

Ala Lys Ser Pro Val Gly
        35

<210> SEQ ID NO 250
<211> LENGTH: 56
<212> TYPE: PRT
<213> ORGANISM: Homo sapien
<220> FEATURE:
<221> NAME/KEY: MISC_FEATURE
<222> LOCATION: (11)..(19)
<223> OTHER INFORMATION: X=any amino acid

<400> SEQUENCE: 250

Met Phe Thr Asp Val Leu Glu Leu Lys Val Xaa Xaa Xaa Xaa Xaa
1               5                   10                  15

Xaa Xaa Xaa Gln Asp Met Ser Lys Tyr Ala Trp Leu Phe Ser Ile Met
            20                  25                  30

Cys Met Leu Ser Ile Ser Leu Leu Ser Val Leu Gly Val Glu Leu Thr
        35                  40                  45

Val Leu Gly His Phe Ile Glu Phe
    50                  55

<210> SEQ ID NO 251
<211> LENGTH: 37
<212> TYPE: PRT
<213> ORGANISM: Homo sapien

<400> SEQUENCE: 251

Met Phe Pro Gly Asn Ile Phe Phe Asn Phe Pro Arg Ser Ser Leu Tyr
1               5                   10                  15
```

-continued

Ser Arg Gln Thr Ser Leu Ala Val Ser Gln Ile Gly Gln Ala His Ser
            20                  25                  30

Cys Ile Arg Ala Phe
         35

<210> SEQ ID NO 252
<211> LENGTH: 30
<212> TYPE: PRT
<213> ORGANISM: Homo sapien

<400> SEQUENCE: 252

Met Val Lys Lys Val Leu Ile Leu Met Thr Leu Tyr Gln Asn Lys Ala
1               5                   10                  15

Ser Asp Ile Ser Leu Gly Leu Tyr Leu Asp Asp Gln Leu Thr
            20                  25                  30

<210> SEQ ID NO 253
<211> LENGTH: 28
<212> TYPE: PRT
<213> ORGANISM: Homo sapien

<400> SEQUENCE: 253

Met Val Lys Lys Val Leu Ile Leu Met Thr Leu Tyr Gln Asn Lys Ala
1               5                   10                  15

Ser Asp Ile Ser Leu Gly Leu Tyr Leu Met Ile Ser
            20                  25

<210> SEQ ID NO 254
<211> LENGTH: 19
<212> TYPE: PRT
<213> ORGANISM: Homo sapien

<400> SEQUENCE: 254

Met Arg Asn Trp Leu Ile Ser Arg Glu Asn Ser Lys Ala His Arg Lys
1               5                   10                  15

Ser Arg Cys

<210> SEQ ID NO 255
<211> LENGTH: 19
<212> TYPE: PRT
<213> ORGANISM: Homo sapien

<400> SEQUENCE: 255

Met Arg Asn Trp Leu Ile Ser Arg Glu Asn Ser Lys Ala His Arg Lys
1               5                   10                  15

Ser Arg Cys

<210> SEQ ID NO 256
<211> LENGTH: 93
<212> TYPE: PRT
<213> ORGANISM: Homo sapien

<400> SEQUENCE: 256

Met Phe Ser Ser Ala Asn Ser Ile Leu Gly Ala Leu Leu Ile Trp Ala
1               5                   10                  15

Gly Met Ser Trp Leu Pro Ile Glu Ala Val Cys Arg Tyr Pro Leu Pro
            20                  25                  30

Ala Ser Val Pro Ser Glu His Arg Arg Asp Leu Pro Cys Val Ser Leu
        35                  40                  45

His Pro Trp Leu Gln Gly Ser Cys Cys Leu Leu Trp Ser Trp Trp
    50                  55                  60

Gly Pro His Cys His Pro Trp Ile Pro Ser Cys Arg Gln Pro Ala Val
65                  70                  75                  80

Leu Ser Ala Leu Gly Gly Gly Ala Leu Trp Leu Cys
                85                  90

<210> SEQ ID NO 257
<211> LENGTH: 121
<212> TYPE: PRT
<213> ORGANISM: Homo sapien

<400> SEQUENCE: 257

Met Phe Ser Ser Ala Asn Ser Ile Leu Gly Ala Leu Leu Ile Arg Ala
1               5                   10                  15

Gly Met Ser Trp Leu Pro Ile Glu Ala Val Cys Arg Tyr Pro Leu Pro
            20                  25                  30

Ala Ser Val Pro Ser Glu His Arg Arg Asp Leu Pro Cys Val Ser Leu
        35                  40                  45

His Pro Trp Leu Gln Gly Ser Ser Cys Cys Leu Leu Trp Ser Trp Trp
    50                  55                  60

Gly Pro His Cys His Pro Trp Ile Pro Ser Cys Arg Gln Pro Cys Cys
65                  70                  75                  80

Pro Gln Cys Thr Gly Arg Arg Gly Cys Ala Val Val Leu Ser Leu
                85                  90                  95

His Arg Cys Pro Leu Val Gly Leu Glu Trp Gly Phe Leu Ile Pro Pro
            100                 105                 110

Ser Met Trp Ile Glu Phe Arg Gly Leu
        115                 120

<210> SEQ ID NO 258
<211> LENGTH: 20
<212> TYPE: PRT
<213> ORGANISM: Homo sapien

<400> SEQUENCE: 258

Met Lys Val Gln Gly Ala Asp Val Ala Ala Ala Ser Tyr Gln Glu
1               5                   10                  15

Tyr Leu Thr Lys
            20

<210> SEQ ID NO 259
<211> LENGTH: 67
<212> TYPE: PRT
<213> ORGANISM: Homo sapien

<400> SEQUENCE: 259

Met Met Pro Ala Trp Val Val Gly Trp Val Gly Ala Glu Ser Thr Pro
1               5                   10                  15

Ala Pro Leu Met Lys Arg Gly Gly Arg Cys Phe Leu Ser Leu Val Leu
            20                  25                  30

Met Cys Pro Leu Gly Trp Trp Gln Leu Gly Leu Leu Arg Ala Thr Pro
        35                  40                  45

Ser Thr Met Pro Leu Leu Ile Ala Lys Ala Ser Ala Tyr Pro Pro Val
    50                  55                  60

Leu Asn Thr
65

<210> SEQ ID NO 260
<211> LENGTH: 49

```
<212> TYPE: PRT
<213> ORGANISM: Homo sapien

<400> SEQUENCE: 260

Met Ser Phe Gln Val His Pro Ser Ile Leu Lys His Lys Tyr Pro Thr
1               5                   10                  15

Ile Leu Asn Asn Phe Arg Thr Lys Ile Asn Ile Leu Thr Arg Lys Lys
                20                  25                  30

His Ala Met Thr Ser Cys Asn Leu Ile Lys Lys Asp Lys Glu Trp Ser
            35                  40                  45

Leu

<210> SEQ ID NO 261
<211> LENGTH: 32
<212> TYPE: PRT
<213> ORGANISM: Homo sapien
<220> FEATURE:
<221> NAME/KEY: MISC_FEATURE
<222> LOCATION: (24)..(24)
<223> OTHER INFORMATION: X=any amino acid

<400> SEQUENCE: 261

Met Phe Thr Phe Leu Tyr Leu Val Ile Thr Glu Thr Asn Cys Leu Val
1               5                   10                  15

Thr Phe Glu Ile Asn Glu Ser Xaa Leu Ser Gln Cys Val Ile Asp Asn
                20                  25                  30

<210> SEQ ID NO 262
<211> LENGTH: 47
<212> TYPE: PRT
<213> ORGANISM: Homo sapien

<400> SEQUENCE: 262

Met Ser Ser Met Glu Glu Ala Phe Gly Ser Glu Met Asn Cys Pro Arg
1               5                   10                  15

Ser Arg Gly Glu Glu Leu Gly Pro Gly Leu Thr Gly Phe Cys Ser Val
                20                  25                  30

Val Leu Ser Arg Pro Trp Phe Leu Leu Tyr Pro Gly Gly Ala Phe
            35                  40                  45

<210> SEQ ID NO 263
<211> LENGTH: 69
<212> TYPE: PRT
<213> ORGANISM: Homo sapien

<400> SEQUENCE: 263

Met Ala Val Leu Lys Thr Trp His Lys Tyr Met Ser Cys Ala Glu Thr
1               5                   10                  15

Gly Val Ala Pro Ser Phe Ile His Gly Asp Trp Gln Val Thr Thr Pro
                20                  25                  30

Ala Pro Ala Pro Ser Cys Ile Pro Leu Ile Val Arg Lys Arg Glu Gly
            35                  40                  45

Pro Ser Cys Leu Cys Pro His Ala Cys Val Thr Ala Ser Leu Phe Thr
    50                  55                  60

Gln Arg Val Val Phe
65

<210> SEQ ID NO 264
<211> LENGTH: 79
<212> TYPE: PRT
<213> ORGANISM: Homo sapien
```

```
<220> FEATURE:
<221> NAME/KEY: MISC_FEATURE
<222> LOCATION: (4)..(4)
<223> OTHER INFORMATION: X=any amino acid
<220> FEATURE:
<221> NAME/KEY: MISC_FEATURE
<222> LOCATION: (8)..(8)
<223> OTHER INFORMATION: X=any amino acid
<220> FEATURE:
<221> NAME/KEY: MISC_FEATURE
<222> LOCATION: (22)..(22)
<223> OTHER INFORMATION: X=any amino acid
<220> FEATURE:
<221> NAME/KEY: MISC_FEATURE
<222> LOCATION: (38)..(38)
<223> OTHER INFORMATION: X=any amino acid
<220> FEATURE:
<221> NAME/KEY: MISC_FEATURE
<222> LOCATION: (42)..(42)
<223> OTHER INFORMATION: X=any amino acid
<220> FEATURE:
<221> NAME/KEY: MISC_FEATURE
<222> LOCATION: (46)..(47)
<223> OTHER INFORMATION: X=any amino acid
<220> FEATURE:
<221> NAME/KEY: MISC_FEATURE
<222> LOCATION: (52)..(52)
<223> OTHER INFORMATION: X=any amino acid
<220> FEATURE:
<221> NAME/KEY: MISC_FEATURE
<222> LOCATION: (55)..(55)
<223> OTHER INFORMATION: X=any amino acid

<400> SEQUENCE: 264

Met Trp Pro Xaa Trp Pro Arg Xaa Lys Pro Gly Gln Lys Glu Lys Gly
1               5                   10                  15

Pro Asn Phe Phe Phe Xaa Val Trp Ile Val Phe Ser Trp Lys Asn Asn
            20                  25                  30

Leu Gly Cys Pro Asn Xaa Cys His Phe Xaa Thr Val His Xaa Xaa Ile
        35                  40                  45

Thr Ser Ser Xaa Met Ser Xaa Asp Thr Asp Thr Gly Ser Asn Leu Thr
    50                  55                  60

Leu Tyr Ser Met Thr Gly Leu Lys Ile Arg Pro Lys Gly Ile Ile
65                  70                  75

<210> SEQ ID NO 265
<211> LENGTH: 25
<212> TYPE: PRT
<213> ORGANISM: Homo sapien

<400> SEQUENCE: 265

Met Ile Ser Glu Lys Leu Gly Gly Val Lys Cys Pro Gly Lys Lys Gly
1               5                   10                  15

Leu Gly Leu Gln Arg Tyr Thr Gln Met
            20                  25

<210> SEQ ID NO 266
<211> LENGTH: 59
<212> TYPE: PRT
<213> ORGANISM: Homo sapien

<400> SEQUENCE: 266

Met Ala Thr Thr Thr Leu Thr Leu Ala Tyr Tyr Leu Ile Gln Leu Pro
1               5                   10                  15

Ser Lys Thr Asp Thr Ser Phe Leu Leu His Phe Asp Ile Ile Cys Gln
            20                  25                  30

Val Cys Phe Ile Pro Ser Tyr Ile Lys Asn Glu Ser Thr Val Gln Leu
```

```
                35                  40                  45
Tyr Ser Arg Arg His Leu Ser Tyr Lys Thr Val
     50                  55
```

<210> SEQ ID NO 267
<211> LENGTH: 88
<212> TYPE: PRT
<213> ORGANISM: Homo sapien

<400> SEQUENCE: 267

```
Met Leu Phe Phe Phe Val Asp Phe Lys Ser Glu His Phe Arg Thr Met
1               5                   10                  15

Lys Ile Phe Gln Arg Thr Ser Asp Ser Val Leu Leu Thr Phe Ala Tyr
            20                  25                  30

Gly His Ser Asp Thr Ile Thr Ser Ser Ala Tyr Leu Ile Cys Arg Tyr
        35                  40                  45

Leu Asp Ser Asn Gln Asp Leu Glu Asn Gln Arg Phe Arg Glu Asn Lys
    50                  55                  60

Lys Lys Leu Arg Lys Ala Gln Asn Met Gln Phe Ser Lys Ile Phe Arg
65                  70                  75                  80

Leu Ile His Lys Tyr Ser Thr Cys
                85
```

<210> SEQ ID NO 268
<211> LENGTH: 46
<212> TYPE: PRT
<213> ORGANISM: Homo sapien

<400> SEQUENCE: 268

```
Met His His Ser Asn Thr Phe Leu Arg Val Lys Val Ile Ile Lys Asn
1               5                   10                  15

Tyr Leu Tyr Leu Leu Lys Tyr Ser Leu Lys Leu Trp Phe Leu Met Ser
            20                  25                  30

Tyr Tyr Ser Ile Phe Glu Gly Ile Met Leu Tyr Leu Ile Asn
        35                  40                  45
```

<210> SEQ ID NO 269
<211> LENGTH: 60
<212> TYPE: PRT
<213> ORGANISM: Homo sapien

<400> SEQUENCE: 269

```
Met Ser Leu Phe Lys Met Ser Phe Thr Ser Ala Gly Gln Glu Gln Ser
1               5                   10                  15

Tyr Met Ala Tyr Pro Gln Met Pro Pro Phe Val Phe Thr Met Thr Ala
            20                  25                  30

Asn Gln Gln Leu Thr Thr Gln Ser Leu Val His Pro Val Thr His Ser
        35                  40                  45

Leu Lys Pro His Phe Ile Phe Pro Gly Phe Phe Ile
    50                  55                  60
```

<210> SEQ ID NO 270
<211> LENGTH: 69
<212> TYPE: PRT
<213> ORGANISM: Homo sapien
<220> FEATURE:
<221> NAME/KEY: MISC_FEATURE
<222> LOCATION: (10)..(10)
<223> OTHER INFORMATION: X=any amino acid

<400> SEQUENCE: 270

-continued

Met Cys Glu Lys Phe Tyr Ile Lys Cys Xaa Lys Lys Ile Ser Ala Ser
1               5                   10                  15

Met Arg Leu Pro Arg Asn Leu Gly Ala Phe Ile Lys Ile Thr Pro Asn
            20                  25                  30

Lys Arg Asn Tyr Arg Arg Lys Lys Glu Lys Met Lys Thr Arg Thr Phe
            35                  40                  45

Glu Leu Lys Asn Thr Val Glu Lys Lys Phe Met Glu Lys Met Gln Lys
    50                  55                  60

Phe Lys Ile Lys Ile
65

<210> SEQ ID NO 271
<211> LENGTH: 96
<212> TYPE: PRT
<213> ORGANISM: Homo sapien

<400> SEQUENCE: 271

Met Pro Val Tyr Ser Leu Leu Gln Ile Pro Pro Gly Glu Ala Thr Leu
1               5                   10                  15

Lys Ile Pro Asp Lys Leu Lys Phe Ile Asn Leu Ile Leu Leu Ser Pro
            20                  25                  30

Val Ser Pro Ile Ile Val Pro Ile Ala Asp Thr Ile Pro Asn Leu His
            35                  40                  45

Ser Cys Ser Ala Arg His Glu Ser Arg Lys Trp Gly Leu Ile Leu Pro
    50                  55                  60

Ala Thr Leu Val Ser Asn Tyr Ser Glu Lys Glu Val Asp Val Leu Ile
65                  70                  75                  80

Asp Gly Lys Ile Glu Met Ile Phe Leu Gly Glu Ile Phe Leu Arg Ser
                85                  90                  95

<210> SEQ ID NO 272
<211> LENGTH: 48
<212> TYPE: PRT
<213> ORGANISM: Homo sapien

<400> SEQUENCE: 272

Met Gly Tyr Ile Leu Lys Leu Phe His Tyr Leu Asn Pro Leu Val Ser
1               5                   10                  15

Val Val Leu Leu Leu Ser Lys Glu Gln Ser Phe Phe His Thr Asn
            20                  25                  30

Gly Val Gly Gln Asn Ile Lys Ala Ser Val Ile Trp Lys Ser Ser Arg
            35                  40                  45

<210> SEQ ID NO 273
<211> LENGTH: 38
<212> TYPE: PRT
<213> ORGANISM: Homo sapien

<400> SEQUENCE: 273

Met Asn Phe Tyr Arg Pro Arg Asn Ser Ser His Tyr Leu Thr Asn Phe
1               5                   10                  15

Ser Val Cys Val Glu Thr Val Thr Ser Leu Tyr Ser Glu Gly Ile Ala
            20                  25                  30

Thr Tyr Asn Val Thr Asn
            35

<210> SEQ ID NO 274
<211> LENGTH: 42

```
<212> TYPE: PRT
<213> ORGANISM: Homo sapien

<400> SEQUENCE: 274

Met Ala Ala Ile Ser Arg Pro Val Lys Ile His Leu Pro Lys Glu Asn
1               5                   10                  15

His Ser Phe Phe Phe Phe Trp Arg Trp Ser Phe Ala Leu Val Ala
            20                  25                  30

Gln Ala Gly Val Pro Arg Pro Arg
        35                  40

<210> SEQ ID NO 275
<211> LENGTH: 30
<212> TYPE: PRT
<213> ORGANISM: Homo sapien

<400> SEQUENCE: 275

Met Leu Phe Trp Thr Leu Gly Ser Val Ile Tyr Tyr Val Cys Pro Ser
1               5                   10                  15

Ile Glu Val Ser Leu Thr Leu Ser Lys Ile Pro Phe Thr Asn
            20                  25                  30

<210> SEQ ID NO 276
<211> LENGTH: 244
<212> TYPE: PRT
<213> ORGANISM: Homo sapien

<400> SEQUENCE: 276

Leu Leu Gly Thr Ala Phe Gln Leu Phe Gly Tyr Glu Glu Asn Ala Val
1               5                   10                  15

Gln Ser Leu Gln His Leu Leu Lys Phe Met Ala Ser Asn Lys Ala Ala
            20                  25                  30

Ala Asp Asp Ala Ser Val Ala Ala Ala Ala Gln Ser Phe Phe Gln Arg
        35                  40                  45

Leu Glu Leu Gly Asp Met Gln Ala Leu Ser Leu Trp Gln Lys Phe Arg
50                  55                  60

Asp Leu Ser Ile Glu Glu Tyr Ile Arg Val Tyr Lys Arg Leu Gly Val
65                  70                  75                  80

Tyr Phe Asp Glu Tyr Ser Gly Glu Ser Phe Tyr Arg Glu Lys Ser Gln
                85                  90                  95

Glu Val Leu Lys Leu Leu Glu Ser Lys Gly Leu Leu Lys Thr Ile
            100                 105                 110

Lys Gly Thr Ala Val Val Asp Leu Ser Gly Asn Gly Asp Pro Ser Ser
        115                 120                 125

Ile Cys Thr Val Met Arg Ser Asp Gly Thr Ser Leu Tyr Ala Thr Arg
130                 135                 140

Asp Leu Ala Ala Ala Ile Asp Arg Met Asp Lys Tyr Asn Phe Asp Thr
145                 150                 155                 160

Met Ile Tyr Val Thr Asp Lys Gly Gln Lys Lys His Phe Gln Gln Val
                165                 170                 175

Phe Gln Met Leu Lys Ile Met Gly Tyr Asp Trp Ala Glu Arg Cys Gln
            180                 185                 190

His Val Pro Phe Gly Val Val Gln Gly Met Lys Thr Arg Arg Gly Asp
        195                 200                 205

Val Thr Phe Leu Glu Asp Val Leu Asn Glu Ile Gln Leu Arg Met Leu
210                 215                 220
```

-continued

```
Gln Asn Met Ala Ser Ile Lys Ser Glu Phe Ser Phe Phe Leu Leu Lys
225                 230                 235                 240

Ser Leu Lys Ser

<210> SEQ ID NO 277
<211> LENGTH: 35
<212> TYPE: PRT
<213> ORGANISM: Homo sapien

<400> SEQUENCE: 277

Met Met Gly Leu Leu Glu Ala Trp Ile Pro Gln Asp Ser Thr Ala Glu
1               5                   10                  15

Trp Ser Asn Thr Gly Ser Thr Ala Asn Gln Arg Gln Cys Tyr Ile Leu
                20                  25                  30

Arg Glu Ile
            35
```

COMPOSITIONS AND METHODS RELATING TO LUNG SPECIFIC GENES AND PROTEINS

This application claims the benefit of priority from U.S. Provisional Application Ser. No. 60/242,998 filed Oct. 25, 2000, which is herein incorporated by reference in its entirety.

FIELD OF THE INVENTION

The present invention relates to newly identified nucleic acid molecules and polypeptides present in normal and neoplastic lung cells, including fragments, variants and derivatives of the nucleic acids and polypeptides. The present invention also relates to antibodies to the polypeptides of the invention, as well as agonists and antagonists of the polypeptides of the invention. The invention also relates to compositions comprising the nucleic acids, polypeptides, antibodies, variants, derivatives, agonists and antagonists of the invention and methods for the use of these compositions. These uses include identifying, diagnosing, monitoring, staging, imaging and treating lung cancer and non-cancerous disease states in lung, identifying lung tissue and monitoring and identifying and/or designing agonists and antagonists of polypeptides of the invention. The uses also include gene therapy, production of transgenic animals and cells, and production of engineered lung tissue for treatment and research.

BACKGROUND OF THE INVENTION

Throughout the last hundred years, the incidence of lung cancer has steadily increased, so much so that now in many countries, it is the most common cancer. In fact, lung cancer is the second most prevalent type of cancer for both men and women in the United States and is the most common cause of cancer death in both sexes. Lung cancer deaths have increased ten-fold in both men and women since 1930, primarily due to an increase in cigarette smoking, but also due to an increased exposure to arsenic, asbestos, chromates, chloromethyl ethers, nickel, polycyclic aromatic hydrocarbons and other agents. See Scott, *Lung Cancer: A Guide to Diagnosis and Treatment*, Addicus Books (2000) and Alberg et al., in Kane et al (eds.) *Biology of Lung Cancer*, pp. 11–52, Marcel Dekker, Inc. (1998). Lung cancer may result from a primary tumor originating in the lung or a secondary tumor which has spread from another organ such as the bowel or breast. Although there are over a dozen types of lung cancer, over 90% fall into two categories: small cell lung cancer (SCLC) and non-small cell lung cancer (NSCLC). See Scott, supra. About 20–25% of all lung cancers are characterized as SCLC, while 70–80% are diagnosed as NSCLC. Id. A rare type of lung cancer is mesothelioma, which is generally caused by exposure to asbestos, and which affects the pleura of the lung. Lung cancer is usually diagnosed or screened for by chest x-ray, CAT scans, PET scans, or by sputum cytology. A diagnosis of lung cancer is usually confirmed by biopsy of the tissue. Id.

SCLC tumors are highly metastatic and grow quickly. By the time a patient has been diagnosed with SCLC, the cancer has usually already spread to other parts of the body, including lymph nodes, adrenals, liver, bone, brain and bone marrow. See Scott, supra; Van Houtte et al. (eds.), *Progress and Perspective in the Treatment of Lung Cancer*, Springer-Verlag (1999). Because the disease has usually spread to such an extent that surgery is not an option, the current treatment of choice is chemotherapy plus chest irradiation. See Van Houtte, supra. The stage of disease is a principal predictor of long-term survival. Less than 5% of patients with extensive disease that has spread beyond one lung and surrounding lymph nodes, live longer than two years. Id. However, the probability of five-year survival is three to four times higher if the disease is diagnosed and treated when it is still in a limited stage, i.e., not having spread beyond one lung. Id.

NSCLC is generally divided into three types: squamous cell carcinoma, adenocarcinoma and large cell carcinoma. Both squamous cell cancer and adenocarcinoma develop from the cells that line the airways; however, adenocarcinoma develops from the goblet cells that produce mucus. Large cell lung cancer has been thus named because the cells look large and rounded when viewed microscopically, and generally are considered relatively undifferentiated. See Yesner, *Atlas of Lung Cancer*, Lippincott-Raven (1998).

Secondary lung cancer is a cancer initiated elsewhere in the body that has spread to the lungs. Cancers that metastasize to the lung include, but are not limited to, breast cancer, melanoma, colon cancer and Hodgkin's lymphoma. Treatment for secondary lung cancer may depend upon the source of the original cancer. In other words, a lung cancer that originated from breast cancer may be more responsive to breast cancer treatments and a lung cancer that originated from the colon cancer may be more responsive to colon cancer treatments.

The stage of a cancer indicates how far it has spread and is an important indicator of the prognosis. In addition, staging is important because treatment is often decided according to the stage of a cancer. SCLC is divided into two stages: limited disease, i.e., cancer that can only be seen in one lung and in nearby lymph nodes; and extensive disease, i.e., cancer that has spread outside the lung to the chest or to other parts of the body. For most patients with SCLC, the disease has already progressed to lymph nodes or elsewhere in the body at the time of diagnosis. See Scott, supra. Even if spreading is not apparent on the scans, it is likely that some cancer cells may have spread away and traveled through the bloodstream or lymph system. In general, chemotherapy with or without radiotherapy is often the preferred treatment. The initial scans and tests done at first will be used later to see how well a patient is responding to treatment.

In contrast, non-small cell cancer may be divided into four stages. Stage I is highly localized cancer with no cancer in the lymph nodes. Stage II cancer has spread to the lymph nodes at the top of the affected lung. Stage III cancer has spread near to where the cancer started. This can be to the chest wall, the covering of the lung (pleura), the middle of the chest (mediastinum) or other lymph nodes. Stage IV cancer has spread to another part of the body. Stage I-III cancer is usually treated with surgery, with or without chemotherapy. Stage IV cancer is usually treated with chemotherapy and/or palliative care.

A number of chromosomal and genetic abnormalities have been observed in lung cancer. In NSCLC, chromosomal aberrations have been described on 3p, 9p, 11p, 15p and 17p, and chromosomal deletions have been seen on chromosomes 7, 11, 13 and 19. See Skarin (ed.), *Multimodality Treatment of Lung Cancer*, Marcel Dekker, Inc. (2000); Gemmill et al., pp. 465–502, in Kane, supra; Bailey-Wilson et al., pp. 53–98, in Kane, supra. Chromosomal abnormalities have been described on 1p, 3p, 5q, 6q, 8q, 13q and 17p in SCLC. Id. The loss of the short arm of chromosome 3p has also been seen in greater than 90% of SCLC tumors and approximately 50% of NSCLC tumors. Id.

A number of oncogenes and tumor suppressor genes have been implicated in lung cancer. See Mabry, pp. 391–412, in Kane, supra and Sclafani et al., pp. 295–316, in Kane, supra. In both SCLC and NSCLC, the p53 tumor suppressor gene is mutated in over 50% of lung cancers. See Yesner, supra. Another tumor suppressor gene, FHIT, which is found on chromosome 3p, is mutated by tobacco smoke. Id.; Skarin, supra. In addition, more than 95% of SCLCs and approximately 20–60% of NSCLCs have an absent or abnormal retinoblastoma (Rb) protein, another tumor suppressor gene. The ras oncogene (particularly K-ras) is mutated in 20–30% of NSCLC specimens and the c-erbB2 oncogene is expressed in 18% of stage 2 NSCLC and 60% of stage 4 NSCLC specimens. See Van Houtte, supra. Other tumor suppressor genes that are found in a region of chromosome 9, specifically in the region of 9p21, are deleted in many cancer cells, including $p16^{INK4A}$ and $p15^{INK4B}$. See Bailey-Wilson, supra; Sclafani et al., supra. These tumor suppressor genes may also be implicated in lung cancer pathogenesis.

In addition, many lung cancer cells produce growth factors that may act in an autocrine fashion on lung cancer cells. See Siegfried et al., pp. 317–336, in Kane, supra; Moody, pp. 337–370, in Kane, supra and Heasley et al., 371–390, in Kane, supra. In SCLC, many tumor cells produce gastrin-releasing peptide (GRP), which is a proliferative growth factor for these cells. See Skarin, supra. Many NSCLC tumors express epidermal growth factor (EGF) receptors, allowing NSCLC cells to proliferate in response to EGF. Insulin-like growth factor (IGF-I) is elevated in greater than 95% of SCLC and greater than 80% of NSCLC tumors; it is thought to function as an autocrine growth factor. Id. Finally, stem cell factor (SCF, also known as steel factor or kit ligand) and c-Kit (a proto-oncoprotein tyrosine kinase receptor for SCF) are both expressed at high levels in SCLC, and thus may form an autocrine loop that increases proliferation. Id.

Although the majority of lung cancer cases are attributable to cigarette smoking, most smokers do not develop lung cancer. Epidemiological evidence has suggested that susceptibility to lung cancer may be inherited in a Mendelian fashion, and thus have an inherited genetic component. Bailey-Wilson, supra. Thus, it is thought that certain allelic variants at some genetic loci may affect susceptibility to lung cancer. Id. One way to identify which allelic variants are likely to be involved in lung cancer susceptibility, as well as susceptibility to other diseases, is to look at allelic variants of genes that are highly expressed in lung.

The lung is susceptible to a number of other debilitating diseases as well, including, without limitation, emphysema, pneumonia, cystic fibrosis and asthma. See Stockley (ed.), *Molecular Biology of the Lung, Volume I: Emphysema and Infection*, Birkhauser Verlag (1999), hereafter Stockley I, and Stockley (ed.), *Molecular Biology of the Lung, Volume II: Asthma and Cancer*, Birkhauser Verlag (1999), hereafter Stockley II. The cause of many these disorders is still not well understood and there are few, if any, good treatment options for many of these noncancerous lung disorders. Thus, there also remains a need for understanding of various noncancerous lung disorders and for identify treatments for these diseases.

The development and differentiation of the lung tissue during embryonic development is also very important. All of the epithelial cells of the respiratory tract, including those of the lung and bronchi, are derived from the primitive endodermal cells that line the embryonic outpouching. See Yesner, supra. During embryonic development, multipotent endodermal stem cells differentiate into many different types of specialized cells, which include ciliated cells for moving inhaled particles, goblet cells for producing mucus, Kulchitsky's cells for endocrine function, and Clara cells and type II pneumocytes for secreting surfactant protein. Id. Improper development and differentiation may cause respiratory disorders and distress in infants, particularly in premature infants, whose lungs cannot produce sufficient surfactant when they are born. Further, some lung cancer cells, particularly small cell carcinomas, appear multipotent, and can spontaneously differentiate into a number of cell types, including small cell carcinoma, adenocarcinoma and squamous cell carcinoma. Id. Thus, a better understanding of lung development and differentiation may help facilitate understanding of lung cancer initiation and progression.

Accordingly, there is a great need for more sensitive and accurate methods for predicting whether a person is likely to develop lung cancer, for diagnosing lung cancer, for monitoring the progression of the disease, for staging the lung cancer, for determining whether the lung cancer has metastasized and for imaging the lung cancer. There is also a need for better treatment of lung cancer. There is also a great need for diagnosing and treating noncancerous lung disorders such as emphysema, pneumonia, lung infection, pulmonary fibrosis, cystic fibrosis and asthma. There is also a need for compositions and methods of using compositions that are capable of identifying lung tissue for forensic purposes and for determining whether a particular cell or tissue exhibits lung-specific characteristics.

SUMMARY OF THE INVENTION

The present invention solves these and other needs in the art by providing nucleic acid molecules and polypeptides as well as antibodies, agonists and antagonists, thereto that may be used to identify, diagnose, monitor, stage, image and treat lung cancer and non-cancerous disease states in lung; identify and monitor lung tissue; and identify and design agonists and antagonists of polypeptides of the invention. The invention also provides gene therapy, methods for producing transgenic animals and cells, and methods for producing engineered lung tissue for treatment and research.

Accordingly, one object of the invention is to provide nucleic acid molecules that are specific to lung cells, lung tissue and/or the lung organ. These lung specific nucleic acids (LSNAs) may be a naturally-occurring cDNA, genomic DNA, RNA, or a fragment of one of these nucleic acids, or may be a non-naturally-occurring nucleic acid molecule. If the LSNA is genomic DNA, then the LSNA is a lung specific gene (LSG). In a preferred embodiment, the nucleic acid molecule encodes a polypeptide that is specific to lung. In a more preferred embodiment, the nucleic acid molecule encodes a polypeptide that comprises an amino acid sequence of SEQ ID NO: 143 through 277. In another highly preferred embodiment, the nucleic acid molecule comprises a nucleic acid sequence of SEQ ID NO: 1 through 142. By nucleic acid molecule, it is also meant to be inclusive of sequences that selectively hybridize or exhibit substantial sequence similarity to a nucleic acid molecule encoding an LSP, or that selectively hybridize or exhibit substantial sequence similarity to an LSNA, as well as allelic variants of a nucleic acid molecule encoding an LSP, and allelic variants of an LSNA. Nucleic acid molecules comprising a part of a nucleic acid sequence that encodes an LSP or that comprises a part of a nucleic acid sequence of an LSNA are also provided.

A related object of the present invention is to provide a nucleic acid molecule comprising one or more expression control sequences controlling the transcription and/or translation of all or a part of an LSNA. In a preferred embodiment, the nucleic acid molecule comprises one or more expression control sequences controlling the transcription and/or translation of a nucleic acid molecule that encodes all or a fragment of an LSP.

Another object of the invention is to provide vectors and/or host cells comprising a nucleic acid molecule of the instant invention. In a preferred embodiment, the nucleic acid molecule encodes all or a fragment of an LSP. In another preferred embodiment, the nucleic acid molecule comprises all or a part of an LSNA.

Another object of the invention is to provided methods for using the vectors and host cells comprising a nucleic acid molecule of the instant invention to recombinantly produce polypeptides of the invention.

Another object of the invention is to provide a polypeptide encoded by a nucleic acid molecule of the invention. In a preferred embodiment, the polypeptide is an LSP. The polypeptide may comprise either a fragment or a full-length protein as well as a mutant protein (mutein), fusion protein, homologous protein or a polypeptide encoded by an allelic variant of an LSP.

Another object of the invention is to provide an antibody that specifically binds to a polypeptide of the instant invention.

Another object of the invention is to provide agonists and antagonists of the nucleic acid molecules and polypeptides of the instant invention.

Another object of the invention is to provide methods for using the nucleic acid molecules to detect or amplify nucleic acid molecules that have similar or identical nucleic acid sequences compared to the nucleic acid molecules described herein. In a preferred embodiment, the invention provides methods of using the nucleic acid molecules of the invention for identifying, diagnosing, monitoring, staging, imaging and treating lung cancer and non-cancerous disease states in lung. In another preferred embodiment, the invention provides methods of using the nucleic acid molecules of the invention for identifying and/or monitoring lung tissue. The nucleic acid molecules of the instant invention may also be used in gene therapy, for producing transgenic animals and cells, and for producing engineered lung tissue for treatment and research.

The polypeptides and/or antibodies of the instant invention may also be used to identify, diagnose, monitor, stage, image and treat lung cancer and non-cancerous disease states in lung. The invention provides methods of using the polypeptides of the invention to identify and/or monitor lung tissue, and to produce engineered lung tissue.

The agonists and antagonists of the instant invention may be used to treat lung cancer and non-cancerous disease states in lung and to produce engineered lung tissue.

Yet another object of the invention is to provide a computer readable means of storing the nucleic acid and amino acid sequences of the invention. The records of the computer readable means can be accessed for reading and displaying of sequences for comparison, alignment and ordering of the sequences of the invention to other sequences.

DETAILED DESCRIPTION OF THE INVENTION

Definitions and General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well-known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press (1989) and Sambrook et al., *Molecular Cloning: A Laboratory Manual*, 3d ed., Cold Spring Harbor Press (2001); Ausubel et al., *Current Protocols in Molecular Biology*, Greene Publishing Associates (1992, and Supplements to 2000); Ausubel et al, *Short Protocols in Molecular Biology: A Compendium of Methods from Current Protocols in Molecular Biology*—$4^{th}$ Ed., Wiley & Sons (1999); Harlow and Lane, *Antibodies: A Laboratory Manual*, Cold Spring Harbor Laboratory Press (1990); and Harlow and Lane, *Using Antibodies: A Laboratory Manual*, Cold Spring Harbor Laboratory Press (1999); each of which is incorporated herein by reference in its entirety.

Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

A "nucleic acid molecule" of this invention refers to a polymeric form of nucleotides and includes both sense and antisense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." The term "nucleic acid molecule" usually refers to a molecule of at least 10 bases in length, unless otherwise specified. The term includes single- and double-stranded forms of DNA. In addition, a polynucleotide may include either or both naturally-occurring and modified nucleotides linked together by naturally-occurring and/or non-naturally occurring nucleotide linkages.

The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) The term "nucleic acid molecule" also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

A "gene" is defined as a nucleic acid molecule that comprises a nucleic acid sequence that encodes a polypeptide and the expression control sequences that surround the nucleic acid sequence that encodes the polypeptide. For instance, a gene may comprise a promoter, one or more enhancers, a nucleic acid sequence that encodes a polypeptide, downstream regulatory sequences and, possibly, other nucleic acid sequences involved in regulation of the expression of an RNA. As is well-known in the art, eukaryotic genes usually contain both exons and introns. The term "exon" refers to a nucleic acid sequence found in genomic DNA that is bioinformatically predicted and/or experimentally confirmed to contribute a contiguous sequence to a mature mRNA transcript. The term "intron" refers to a nucleic acid sequence found in genomic DNA that is predicted and/or confirmed to not contribute to a mature mRNA transcript, but rather to be "spliced out" during processing of the transcript.

A nucleic acid molecule or polypeptide is "derived" from a particular species if the nucleic acid molecule or polypeptide has been isolated from the particular species, or if the nucleic acid molecule or polypeptide is homologous to a nucleic acid molecule or polypeptide isolated from a particular species.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, or genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, (4) does not occur in nature as part of a larger sequence or (5) includes nucleotides or internucleoside bonds that are not found in nature. The term "isolated" or "substantially pure" also can be used in reference to recombinant or cloned DNA isolates, chemically synthesized polynucleotide analogs, or polynucleotide analogs that are biologically synthesized by heterologous systems. The term "isolated nucleic acid molecule" includes nucleic acid molecules that are integrated into a host cell chromosome at a heterologous site, recombinant fusions of a native fragment to a heterologous sequence, recombinant vectors present as episomes or as integrated into a host cell chromosome.

A "part" of a nucleic acid molecule refers to a nucleic acid molecule that comprises a partial contiguous sequence of at least 10 bases of the reference nucleic acid molecule. Preferably, a part comprises at least 15 to 20 bases of a reference nucleic acid molecule. In theory, a nucleic acid sequence of 17 nucleotides is of sufficient length to occur at random less frequently than once in the three gigabase human genome, and thus to provide a nucleic acid probe that can uniquely identify the reference sequence in a nucleic acid mixture of genomic complexity. A preferred part is one that comprises a nucleic acid sequence that can encode at least 6 contiguous amino acid sequences (fragments of at least 18 nucleotides) because they are useful in directing the expression or synthesis of peptides that are useful in mapping the epitopes of the polypeptide encoded by the reference nucleic acid. See, e.g., Geysen et al., *Proc. Natl. Acad. Sci. USA* 81:3998–4002 (1984); and U.S. Pat. Nos. 4,708,871 and 5,595,915, the disclosures of which are incorporated herein by reference in their entireties. A part may also comprise at least 25, 30, 35 or 40 nucleotides of a reference nucleic acid molecule, or at least 50, 60, 70, 80, 90, 100, 150, 200, 250, 300, 350, 400 or 500 nucleotides of a reference nucleic acid molecule. A part of a nucleic acid molecule may comprise no other nucleic acid sequences. Alternatively, a part of a nucleic acid may comprise other nucleic acid sequences from other nucleic acid molecules.

The term "oligonucleotide" refers to a nucleic acid molecule generally comprising a length of 200 bases or fewer. The term often refers to single-stranded deoxyribonucleotides, but it can refer as well to single- or double-stranded ribonucleotides, RNA:DNA hybrids and double-stranded DNAs, among others. Preferably, oligonucleotides are 10 to 60 bases in length and most preferably 12, 13, 14, 15, 16, 17, 18, 19 or 20 bases in length. Other preferred oligonucleotides are 25, 30, 35, 40, 45, 50, 55 or 60 bases in length. Oligonucleotides may be single-stranded, e.g. for use as probes or primers, or may be double-stranded, e.g. for use in the construction of a mutant gene. Oligonucleotides of the invention can be either sense or antisense oligonucleotides. An oligonucleotide can be derivatized or modified as discussed above for nucleic acid molecules.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms. Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP. The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well-known, this reaction can be prevented selectively, where desired, by removing the 5' phosphates of the other polynucleotide(s) prior to ligation.

The term "naturally-occurring nucleotide" referred to herein includes naturally-occuring deoxyribonucleotides and ribonucleotides. The term "modified nucleotides" referred to herein includes nucleotides with modified or substituted sugar groups and the like. The term "nucleotide linkages" referred to herein includes nucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081–9093 (1986); Stein et al. *Nucl Acids Res.* 16:3209–3221 (1988); Zon et al. *Anti-Cancer Drug Design* 6:539–568 (1991); Zon et al., in Eckstein (ed.) *Oligonucleotides and Analogues: A Practical Approach*, pp. 87–108, Oxford University Press (1991); U.S. Pat. No.

5,151,510; Uhlmann and Peyman *Chemical Reviews* 90:543 (1990), the disclosures of which are hereby incorporated by reference.

Unless specified otherwise, the left hand end of a polynucleotide sequence in sense orientation is the 5' end and the right hand end of the sequence is the 3' end. In addition, the left hand direction of a polynucleotide sequence in sense orientation is referred to as the 5' direction, while the right hand direction of the polynucleotide sequence is referred to as the 3' direction. Further, unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

The term "allelic variant" refers to one of two or more alternative naturally-occuring forms of a gene, wherein each gene possesses a unique nucleotide sequence. In a preferred embodiment, different alleles of a given gene have similar or identical biological properties.

The term "percent sequence identity" in the context of nucleic acid sequences refers to the residues in two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183: 63–98 (1990); Pearson, *Methods Mol. Biol.* 132: 185–219 (2000); Pearson, *Methods Enzymol.* 266: 227–258 (1996); Pearson, *J. Mol. Biol.* 276: 71–84 (1998); herein incorporated by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers.

In the molecular biology art, researchers use the terms "percent sequence identity", "percent sequence similarity" and "percent sequence homology" interchangeably. In this application, these terms shall have the same meaning with respect to nucleic acid sequences only.

The term "substantial similarity" or "substantial sequence similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95–98% of the nucleotide bases, as measured by any well-known algorithm of sequence identity, such as FASTA, BLAST or Gap, as discussed above.

Alternatively, substantial similarity exists when a nucleic acid or fragment thereof hybridizes to another nucleic acid, to a strand of another nucleic acid, or to the complementary strand thereof, under selective hybridization conditions. Typically, selective hybridization will occur when there is at least about 55% sequence identity, preferably at least about 65%, more preferably at least about 75%, and most preferably at least about 90% sequence identity, over a stretch of at least about 14 nucleotides, more preferably at least 17 nucleotides, even more preferably at least 20, 25, 30, 35, 40, 50, 60, 70, 80, 90 or 100 nucleotides.

Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. "Stringent hybridization conditions" and "stringent wash conditions" in the context of nucleic acid hybridization experiments depend upon a number of different physical parameters. The most important parameters include temperature of hybridization, base composition of the nucleic acids, salt concentration and length of the nucleic acid. One having ordinary skill in the art knows how to vary these parameters to achieve a particular stringency of hybridization. In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook (1989), supra, p. 9.51, hereby incorporated by reference.

The $T_m$ for a particular DNA-DNA hybrid can be estimated by the formula:

$$T_m = 81.5° C. + 16.6 \, (\log_{10}[Na^+]) + 0.41 \, (\text{fraction } G+C) - 0.63 \, (\% \text{ formamide}) - (600/l)$$

where l is the length of the hybrid in base pairs.

The $T_m$ for a particular RNA-RNA hybrid can be estimated by the formula:

$$T_m = 79.8° C. + 18.5 \, (\log_{10}[Na^{+1}] + 0.58 \, (\text{fraction } G+C) + 11.8 \, (\text{fraction } G+C)^2 - 0.35 \, (\% \text{ formamide}) - (820/l).$$

The $T_m$ for a particular RNA-DNA hybrid can be estimated by the formula:

$$T_m = 79.8° C. + 18.5 (\log_{10}[Na^{+1}] + 0.58 \, (\text{fraction } G+C) + 11.8 \, (\text{fraction } G+C)^2 - 0.50 \, (\% \text{ formamide}) - (820/l).$$

In general, the $T_m$ decreases by 1–1.5° C. for each 1% of mismatch between two nucleic acid sequences. Thus, one having ordinary skill in the art can alter hybridization and/or washing conditions to obtain sequences that have higher or lower degrees of sequence identity to the target nucleic acid. For instance, to obtain hybridizing nucleic acids that contain up to 10% mismatch from the target nucleic acid sequence, 10–15° C. would be subtracted from the calculated $T_m$ of a perfectly matched hybrid, and then the hybridization and washing temperatures adjusted accordingly. Probe sequences may also hybridize specifically to duplex DNA under certain conditions to form triplex or other higher order DNA complexes. The preparation of such probes and suitable hybridization conditions are well-known in the art.

An example of stringent hybridization conditions for hybridization of complementary nucleic acid sequences having more than 100 complementary residues on a filter in a Southern or Northern blot or for screening a library is 50% formamide/6×SSC at 42° C. for at least ten hours and preferably overnight (approximately 16 hours). Another example of stringent hybridization conditions is 6×SSC at 68° C. without formamide for at least ten hours and preferably overnight. An example of moderate stringency hybridization conditions is 6×SSC at 55° C. without formamide for at least ten hours and preferably overnight. An example of low stringency hybridization conditions for hybridization of complementary nucleic acid sequences having more than 100 complementary residues on a filter in a Southern or Northern blot or for screening a library is 6×SSC at 42° C. for at least ten hours. Hybridization conditions to identify nucleic acid sequences that are similar but not identical can be identified by experimentally changing the hybridization temperature from 68° C. to 42° C. while keeping the salt concentration constant (6×SSC), or keeping the hybridization temperature and salt concentration constant (e.g. 42° C. and 6×SSC) and varying the formamide concentration from 50% to 0%. Hybridization buffers may also include blocking agents to lower background. These agents are well-known in the art. See Sambrook et al. (1989), supra, pages 8.46 and 9.46–9.58, herein incorporated by reference. See also Ausubel (1992), supra, Ausubel (1999), supra, and Sambrook (2001), supra.

Wash conditions also can be altered to change stringency conditions. An example of stringent wash conditions is a 0.2×SSC wash at 65° C. for 15 minutes (see Sambrook (1989), supra, for SSC buffer). Often the high stringency wash is preceded by a low stringency wash to remove excess probe. An exemplary medium stringency wash for duplex DNA of more than 100 base pairs is 1×SSC at 45° C. for 15 minutes. An exemplary low stringency wash for such a duplex is 4×SSC at 40° C. for 15 minutes. In general, signal-to-noise ratio of 2× or higher than that observed for an unrelated probe in the particular hybridization assay indicates detection of a specific hybridization.

As defined herein, nucleic acid molecules that do not hybridize to each other under stringent conditions are still substantially similar to one another if they encode polypeptides that are substantially identical to each other. This occurs, for example, when a nucleic acid molecule is created synthetically or recombinantly using high codon degeneracy as permitted by the redundancy of the genetic code.

Hybridization conditions for nucleic acid molecules that are shorter than 100 nucleotides in length (e.g., for oligonucleotide probes) may be calculated by the formula:

$$T_m = 81.5° C. + 16.6(\log_{10}[Na+]) + 0.41(\text{fraction } G+C) - (600/N),$$

wherein N is change length and the $[Na^{+1}]$ is 1 M or less. See Sambrook (1989), supra, p. 11.46. For hybridization of probes shorter than 100 nucleotides, hybridization is usually performed under stringent conditions (5–10° C. below the $T_m$) using high concentrations (0.1–1.0 pmol/ml) of probe. Id. at p. 11.45. Determination of hybridization using mismatched probes, pools of degenerate probes or "guessmers," as well as hybridization solutions and methods for empirically determining hybridization conditions are well-known in the art. See, e.g., Ausubel (1999), supra; Sambrook (1989), supra, pp. 11.45–11.57.

The term "digestion" or "digestion of DNA" refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan. For analytical purposes, typically, 1 µg of plasmid or DNA fragment is digested with about 2 units of enzyme in about 20 µl of reaction buffer. For the purpose of isolating DNA fragments for plasmid construction, typically 5 to 50 µg of DNA are digested with 20 to 250 units of enzyme in proportionately larger volumes. Appropriate buffers and substrate amounts for particular restriction enzymes are described in standard laboratory manuals, such as those referenced below, and they are specified by commercial suppliers. Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well-known methods that are routine for those skilled in the art.

The term "ligation" refers to the process of forming phosphodiester bonds between two or more polynucleotides, which most often are double-stranded DNAS. Techniques for ligation are well-known to the art and protocols for ligation are described in standard laboratory manuals and references, such as, e.g., Sambrook (1989), supra.

Genome-derived "single exon probes," are probes that comprise at least part of an exon ("reference exon") and can hybridize detectably under high stringency conditions to transcript-derived nucleic acids that include the reference exon but do not hybridize detectably under high stringency conditions to nucleic acids that lack the reference exon. Single exon probes typically further comprise, contiguous to a first end of the exon portion, a first intronic and/or intergenic sequence that is identically contiguous to the exon in the genome, and may contain a second intronic and/or intergenic sequence that is identically contiguous to the exon in the genome. The minimum length of genome-derived single exon probes is defined by the requirement that the exonic portion be of sufficient length to hybridize under high stringency conditions to transcript-derived nucleic acids, as discussed above. The maximum length of genome-derived single exon probes is defined by the requirement that the probes contain portions of no more than one exon. The single exon probes may contain priming sequences not found in contiguity with the rest of the probe sequence in the genome, which priming sequences are useful for PCR and other amplification-based technologies.

The term "microarray" or "nucleic acid microarray" refers to a substrate-bound collection of plural nucleic acids, hybridization to each of the plurality of bound nucleic acids being separately detectable. The substrate can be solid or porous, planar or non-planar, unitary or distributed. Microarrays or nucleic acid microarrays include all the devices so called in Schena (ed.), *DNA Microarrays: A Practical Approach (Practical Approach Series)*, Oxford University Press (1999); *Nature Genet.* 21 (1)(suppl.):1–60 (1999); Schena (ed.), *Microarray Biochip: Tools and Technology*, Eaton Publishing Company/BioTechniques Books Division (2000). These microarrays include substrate-bound collections of plural nucleic acids in which the plurality of nucleic acids are disposed on a plurality of beads, rather than on a unitary planar substrate, as is described, inter alia, in Brenner et al., *Proc. Natl. Acad. Sci. USA* 97(4):1665–1670 (2000).

The term "mutated" when applied to nucleic acid molecules means that nucleotides in the nucleic acid sequence of the nucleic acid molecule may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. In a preferred embodiment, the nucleic acid molecule comprises the wild type nucleic acid sequence encoding an LSP or is an LSNA. The nucleic acid molecule may be mutated by any method known in the art including those mutagenesis techniques described infra.

The term "error-prone PCR" refers to a process for performing PCR under conditions where the copying fidelity of the DNA polymerase is low, such that a high rate of point mutations is obtained along the entire length of the PCR product. See, e.g., Leung et al., *Technique* 1: 11–15 (1989) and Caldwell et al., *PCR Methods Applic.* 2: 28–33 (1992).

The term "oligonucleotide-directed mutagenesis" refers to a process which enables the generation of site-specific mutations in any cloned DNA segment of interest. See, e.g., Reidhaar-Olson et al., *Science* 241: 53–57 (1988).

The term "assembly PCR" refers to a process which involves the assembly of a PCR product from a mixture of small DNA fragments. A large number of different PCR reactions occur in parallel in the same vial, with the products of one reaction priming the products of another reaction.

The term "sexual PCR mutagenesis" or "DNA shuffling" refers to a method of error-prone PCR coupled with forced homologous recombination between DNA molecules of different but highly related DNA sequence in vitro, caused by random fragmentation of the DNA molecule based on sequence similarity, followed by fixation of the crossover by primer extension in an error-prone PCR reaction. See, e.g., Stemmer, *Proc. Natl. Acad. Sci. U.S.A.* 91: 10747–10751 (1994). DNA shuffling can be carried out between several related genes ("Family shuffling").

The term "in vivo mutagenesis" refers to a process of generating random mutations in any cloned DNA of interest which involves the propagation of the DNA in a strain of bacteria such as *E. coli* that carries mutations in one or more of the DNA repair pathways. These "mutator" strains have a higher random mutation rate than that of a wild-type parent. Propagating the DNA in a mutator strain will eventually generate random mutations within the DNA.

The term "cassette mutagenesis" refers to any process for replacing a small region of a double-stranded DNA molecule with a synthetic oligonucleotide "cassette" that differs from the native sequence. The oligonucleotide often contains completely and/or partially randomized native sequence.

The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. See, e.g., Arkin et al, *Proc. Natl. Acad. Sci. U.S.A.* 89: 7811–7815 (1992).

The term "exponential ensemble mutagenesis" refers to a process for generating combinatorial libraries with a high percentage of unique and functional mutants, wherein small groups of residues are randomized in parallel to identify, at each altered position, amino acids which lead to functional proteins. See, e.g., Delegrave et al., *Biotechnology Research* 11: 1548–1552 (1993); Arnold, *Current Opinion in Biotechnology* 4: 450–455 (1993). Each of the references mentioned above are hereby incorporated by reference in its entirety.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include the promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "vector," as used herein, is intended to refer to a nucleic acid molecule capable of transporting another nucleic acid to which it has been linked. One type of vector is a "plasmid", which refers to a circular double-stranded DNA loop into which additional DNA segments may be ligated. Other vectors include cosmids, bacterial artificial chromosomes (SAC) and yeast artificial chromosomes (YAC). Another type of vector is a viral vector, wherein additional DNA segments may be ligated into the viral genome. Viral vectors that infect bacterial cells are referred to as bacteriophages. Certain vectors are capable of autonomous replication in a host cell into which they are introduced (e.g., bacterial vectors having a bacterial origin of replication). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include other forms of expression vectors that serve equivalent functions.

The term "recombinant host cell" (or simply "host cell"), as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the phrase "open reading frame" and the equivalent acronym "ORF" refer to that portion of a transcript-derived nucleic acid that can be translated in its entirety into a sequence of contiguous amino acids. As so defined, an ORF has length, measured in nucleotides, exactly divisible by 3. As so defined, an ORF need not encode the entirety of a natural protein.

As used herein, the phrase "ORF-encoded peptide" refers to the predicted or actual translation of an ORF.

As used herein, the phrase "degenerate variant" of a reference nucleic acid sequence intends all nucleic acid sequences that can be directly translated, using the standard genetic code, to provide an amino acid sequence identical to that translated from the reference nucleic acid sequence.

The term "polypeptide" encompasses both naturally-occurring and non-naturally-occurring proteins and polypeptides, polypeptide fragments and polypeptide mutants, derivatives and analogs. A polypeptide may be monomeric or polymeric. Further, a polypeptide may comprise a number of different modules within a single polypeptide each of which has one or more distinct activities. A preferred polypeptide in accordance with the invention comprises an LSP encoded by a nucleic acid molecule of the instant invention, as well as a fragment, mutant, analog and derivative thereof.

The term "isolated protein" or "isolated polypeptide" is a protein or polypeptide that by virtue of its origin or source of derivation (1) is not associated with naturally associated components that accompany it in its native state, (2) is free of other proteins from the same species (3) is expressed by a cell from a different species, or (4) does not occur in nature. Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well-known in the art.

A protein or polypeptide is "substantially pure," "substantially homogeneous" or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well-known in the art, such as polyacrylamide gel electrophoresis of a protein sample, followed by visualizing a single polypeptide band upon staining the gel with a stain well-known in the art. For certain purposes, higher resolution may be provided by using HPLC or other means well-known in the art for purification.

The term "polypeptide fragment" as used herein refers to a polypeptide of the instant invention that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "derivative" refers to polypeptides or fragments thereof that are substantially similar in primary structural sequence but which include, e.g., in vivo or in vitro chemical and biochemical modifications that are not found in the native polypeptide. Such modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Other modification include, e.g., labeling with radionuclides, and various enzymatic modifications, as will be readily appreciated by those skilled in the art. A variety of methods for labeling polypeptides and of substituents or labels useful for such purposes are well-known in the art, and include radioactive isotopes such as $^{125}$I, $^{32}$P, $^{35}$S, and $^{3}$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well-known in the art. See Ausubel (1992), supra; Ausubel (1999), supra, herein incorporated by reference.

The term "fusion protein" refers to polypeptides of the instant invention comprising polypeptides or fragments coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "analog" refers to both polypeptide analogs and non-peptide analogs. The term "polypeptide analog" as used herein refers to a polypeptide of the instant invention that is comprised of a segment of at least 25 amino acids that has substantial identity to a portion of an amino acid sequence but which contains non-natural amino acids or non-natural inter-residue bonds. In a preferred embodiment, the analog has the same or similar biological activity as the native polypeptide. Typically, polypeptide analogs comprise a conservative amino acid substitution (or insertion or deletion) with respect to the naturally-occurring sequence. Analogs typically are at least 20 amino acids long, preferably at least 50 amino acids long or longer, and can often be as long as a full-length naturally-occurring polypeptide.

The term "non-peptide analog" refers to a compound with properties that are analogous to those of a reference polypeptide of the instant invention. A non-peptide compound may also be termed a "peptide mimetic"or a "peptidomimetic." Such compounds are often developed with the aid of computerized molecular modeling. Peptide mimetics that are structurally similar to useful peptides may be used to produce an equivalent effect. Generally, peptidomimetics are structurally similar to a paradigm polypeptide (i.e., a polypeptide that has a desired biochemical property or pharmacological activity), but have one or more peptide linkages optionally replaced by a linkage selected from the group consisting of: —CH$_2$NH—, —CH$_2$S—, —CH$_2$—CH$_2$—, —CH=CH—(cis and trans), —COCH$_2$—, —CH(OH)CH$_2$—, and —CH$_2$SO—, by methods well-known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo et al., *Ann. Rev. Biochem.* 61:387–418 (1992), incorporated herein by reference). For example, one may add internal cysteine residues capable of forming intramolecular disulfide bridges which cyclize the peptide.

A "polypeptide mutant" or "mutein" refers to a polypeptide of the instant invention whose sequence contains substitutions, insertions or deletions of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. Further, a mutein may have the same or different biological activity as the naturally-occurring protein. For instance, a mutein may have an increased or decreased biological activity. A mutein has at least 50% sequence similarity to the wild type protein, preferred is 60% sequence similarity, more preferred is 70% sequence similarity. Even more preferred are muteins having 80%, 85% or 90% sequence similarity to the wild type protein. In an even more preferred embodiment, a mutein exhibits 95% sequence identity, even more preferably 97%, even more preferably 98% and even more preferably 99%. Sequence similarity may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs. For example, single or multiple amino acid substitutions (preferably conservative amino acid substitutions) may be made in the naturally-occurring sequence (preferably in the portion of the polypeptide outside the domain(s) forming intermolecular contacts. In a preferred embodiment, the amino acid substitutions are moderately conservative substitutions or conservative substitutions. In a more preferred embodiment, the amino acid substitutions are conservative substitutions. A conservative amino acid substitution should not substantially change the structural characteristics of the parent sequence (e.g., a replacement amino acid should not tend to disrupt a helix that occurs in the parent sequence, or disrupt other types of secondary structure that characterizes the parent sequence). Examples of art-recognized polypeptide secondary and tertiary structures are described in Creighton (ed.), *Proteins Structures and Molecular Principles*, W. H. Freeman and Company (1984); Branden et al. (ed.), *Introduction to Protein Structure*, Garland Publishing (1991); Thornton et al., *Nature* 354:105–106 (1991), each of which are incorporated herein by reference.

As used herein, the twenty conventional amino acids and their abbreviations follow conventional usage. See Golub et al. (eds.), *Immunology—A Synthesis* 2$^{nd}$ Ed., Sinauer Associates (1991), which is incorporated herein by reference. Stereoisomers (e.g., D-amino acids) of the twenty conventional amino acids, unnatural amino acids such as —, -disubstituted amino acids, N-alkyl amino acids, and other unconventional amino acids may also be suitable components for polypeptides of the present invention. Examples of unconventional amino acids include: 4-hydroxyproline, γ-carboxyglutamate, —N,N,N-trimethyllysine, —N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the lefthand direction is the amino terminal direction and the right hand direction is the carboxy-terminal direction, in accordance with standard usage and convention.

A protein has "homology" or is "homologous" to a protein from another organism if the encoded amino acid sequence of the protein has a similar sequence to the encoded amino acid sequence of a protein of a different organism and has a similar biological activity or function. Alternatively, a protein may have homology or be homologous to another protein if the two proteins have similar amino acid sequences and have similar biological activities or functions. Although two proteins are said to be "homologous," this does not imply that there is necessarily an evolutionary relationship between the proteins. Instead, the term "homologous" is defined to mean that the two proteins have similar amino acid sequences and similar biological activities or functions. In a preferred embodiment, a homologous protein is one that exhibits 50% sequence similarity to the wild type protein, preferred is 60% sequence similarity, more preferred is 70% sequence similarity. Even more preferred are homologous proteins that exhibit 80%, 85% or 90% sequence similarity to the wild type protein. In a yet more preferred embodiment, a homologous protein exhibits 95%, 97%, 98% or 99% sequence similarity.

When "sequence similarity" is used in reference to proteins or peptides, it is recognized that residue positions that are not identical often differ by conservative amino acid substitutions. In a preferred embodiment, a polypeptide that has "sequence similarity" comprises conservative or moderately conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.* 24: 307–31 (1994), herein incorporated by reference.

For instance, the following six groups each contain amino acids that are conservative substitutions for one another:

1) Serine (S), Threonine (T);
2) Aspartic Acid (D), Glutamic Acid (E);
3) Asparagine (N), Glutamine (Q);
4) Arginine (R), Lysine (K);

5) Isoleucine (I), Leucine (L), Methionine (M), Alanine (A), Valine (V), and

6) Phenylalanine (F), Tyrosine (Y), Tryptophan (W).

Alternatively, a conservative replacement is any change having a positive value in the PAM250 log-likelihood matrix disclosed in Gonnet et al., Science 256: 1443–45 (1992), herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Other programs include FASTA, discussed supra.

A preferred algorithm when comparing a sequence of the invention to a database containing a large number of sequences from different organisms is the computer program BLAST, especially blastp or tblastn. See, e.g., Altschul et al., J. Mol. Biol. 215: 403–410 (1990); Altschul et al., Nucleic Acids Res. 25:3389–402 (1997); herein incorporated by reference. Preferred parameters for blastp are:

| | |
|---|---|
| Expectation value: | 10 (default) |
| Filter: | seg (default) |
| Cost to open a gap: | 11 (default) |
| Cost to extend a gap: | 1 (default) |
| Max. alignments: | 100 (default) |
| Word size: | 11 (default) |
| No. of descriptions: | 100 (default) |
| Penalty Matrix: | BLOSUM62 |

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

Database searching using amino acid sequences can be measured by algorithms other than blastp are known in the art. For instance, polypeptide sequences can be compared using FASTA, a program in GCG Version 6.1. FASTA (e.g., FASTA2 and FASTA3) provides alignments and percent sequence identity of the regions of the best overlap between the query and search sequences (Pearson (1990), supra; Pearson (2000), supra. For example, percent sequence identity between amino acid sequences can be determined using FASTA with its default or recommended parameters (a word size of 2 and the PAM250 scoring matrix), as provided in GCG Version 6.1, herein incorporated by reference.

An "antibody" refers to an intact immunoglobulin, or to an antigen-binding portion thereof that competes with the intact antibody for specific binding to a molecular species, e.g., a polypeptide of the instant invention. Antigen-binding portions may be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. An Fab fragment is a monovalent fragment consisting of the VL, VH, CL and CH1 domains; an F(ab')$_2$ fragment is a bivalent fragment comprising two Fab fragments linked by a disulfide bridge at the hinge region; an Fd fragment consists of the VH and CH1 domains; an Fv fragment consists of the VL and VH domains of a single arm of an antibody; and a dAb fragment consists of a VH domain. See, e.g., Ward et al., Nature 341: 544–546 (1989).

By "bind specifically" and "specific binding" is here intended the ability of the antibody to bind to a first molecular species in preference to binding to other molecular species with which the antibody and first molecular species are admixed. An antibody is said specifically to "recognize" a first molecular species when it can bind specifically to that first molecular species.

A single-chain antibody (scFv) is an antibody in which a VL and VH region are paired to form a monovalent molecule via a synthetic linker that enables them to be made as a single protein chain. See, e.g., Bird et al., Science 242: 423–426 (1988); Huston et al., Proc. Natl. Acad. Sci. USA 85: 5879–5883 (1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites. See e.g., Holliger et al., Proc. Natl. Acad. Sci. USA 90: 6444–6448 (1993); Poljak et al., Structure 2: 1121–1123 (1994). One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest. A chimeric antibody is an antibody that contains one or more regions from one antibody and one or more regions from one or more other antibodies.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. It is known that purified proteins, including purified antibodies, may be stabilized with non-naturally-associated components. The non-naturally-associated component may be a protein, such as albumin (e.g., BSA) or a chemical such as polyethylene glycol (PEG).

A "neutralizing antibody" or "an inhibitory antibody" is an antibody that inhibits the activity of a polypeptide or blocks the binding of a polypeptide to a ligand that normally binds to it. An "activating antibody" is an antibody that increases the activity of a polypeptide.

The term "epitope" includes any protein determinant capable of specifically binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. An antibody is said to specifically bind an antigen when the dissociation constant is less than 1 µM, preferably less than 100 nM and most preferably less than 10 nM.

The term "patient" as used herein includes human and veterinary subjects.

Throughout this specification and claims, the word "comprise," or variations such as "comprises" or "comprising," will be understood to imply the inclusion of a stated integer or group of integers but not the exclusion of any other integer or group of integers.

The term "lung specific" refers to a nucleic acid molecule or polypeptide that is expressed predominantly in the lung as compared to other tissues in the body. In a preferred embodiment, a "lung specific" nucleic acid molecule or polypeptide is expressed at a level that is 5-fold higher than any other tissue in the body. In a more preferred embodiment, the "lung specific" nucleic acid molecule or polypeptide is expressed at a level that is 10-fold higher than any other tissue in the body, more preferably at least 15-fold, 20-fold, 25-fold, 50-fold or 100-fold higher than any other tissue in the body. Nucleic acid molecule levels may be measured by nucleic acid hybridization, such as Northern blot hybridization, or quantitative PCR. Polypeptide levels may be measured by any method known to accurately quantitate protein levels, such as Western blot analysis.

Nucleic Acid Molecules, Regulatory Sequences, Vectors, Host Cells and Recombinant Methods of Making Polypeptides Nucleic Acid Molecules One aspect of the invention provides isolated nucleic acid molecules that are specific to the lung or to lung cells or tissue or that are derived from such nucleic acid molecules. These isolated lung specific nucleic acids (LSNAs) may comprise a cDNA, a genomic DNA, RNA, or a fragment of one of these nucleic acids, or may be a non-naturally-occurring nucleic acid molecule. In a preferred embodiment, the nucleic acid molecule encodes a polypeptide that is specific to lung, a lung-specific polypeptide (LSP). In a more preferred embodiment, the nucleic acid molecule encodes a polypeptide that comprises an amino acid sequence of SEQ ID NO: 143 through 277. In another highly preferred embodiment, the nucleic acid molecule comprises a nucleic acid sequence of SEQ ID NO: 1 through 142.

An LSNA may be derived from a human or from another animal. In a preferred embodiment, the LSNA is derived from a human or other mammal. In a more preferred embodiment, the LSNA is derived from a human or other primate. In an even more preferred embodiment, the LSNA is derived from a human.

By "nucleic acid molecule" for purposes of the present invention, it is also meant to be inclusive of nucleic acid sequences that selectively hybridize to a nucleic acid molecule encoding an LSNA or a complement thereof. The hybridizing nucleic acid molecule may or may not encode a polypeptide or may not encode an LSP. However, in a preferred embodiment, the hybridizing nucleic acid molecule encodes an LSP. In a more preferred embodiment, the invention provides a nucleic acid molecule that selectively hybridizes to a nucleic acid molecule that encodes a polypeptide comprising an amino acid sequence of SEQ ID NO: 143 through 277. In an even more preferred embodiment, the invention provides a nucleic acid molecule that selectively hybridizes to a nucleic acid molecule comprising the nucleic acid sequence of SEQ ID NO: 1 through 142.

In a preferred embodiment, the nucleic acid molecule selectively hybridizes to a nucleic acid molecule encoding an LSP under low stringency conditions. In a more preferred embodiment, the nucleic acid molecule selectively hybridizes to a nucleic acid molecule encoding an LSP under moderate stringency conditions. In a more preferred embodiment, the nucleic acid molecule selectively hybridizes to a nucleic acid molecule encoding an LSP under high stringency conditions. In an even more preferred embodiment, the nucleic acid molecule hybridizes under low, moderate or high stringency conditions to a nucleic acid molecule encoding a polypeptide comprising an amino acid sequence of SEQ ID NO: 143 through 277. In a yet more preferred embodiment, the nucleic acid molecule hybridizes under low, moderate or high stringency conditions to a nucleic acid molecule comprising a nucleic acid sequence selected from SEQ ID NO: 1 through 142. In a preferred embodiment of the invention, the hybridizing nucleic acid molecule may be used to express recombinantly a polypeptide of the invention.

By "nucleic acid molecule" as used herein it is also meant to be inclusive of sequences that exhibits substantial sequence similarity to a nucleic acid encoding an LSP or a complement of the encoding nucleic acid molecule. In a preferred embodiment, the nucleic acid molecule exhibits substantial sequence similarity to a nucleic acid molecule encoding human LSP. In a more preferred embodiment, the nucleic acid molecule exhibits substantial sequence similarity to a nucleic acid molecule encoding a polypeptide having an amino acid sequence of SEQ ID NO: 143 through 277. In a preferred embodiment, the similar nucleic acid molecule is one that has at least 60% sequence identity with a nucleic acid molecule encoding an LSP, such as a polypeptide having an amino acid sequence of SEQ ID NO: 143 through 277, more preferably at least 70%, even more preferably at least 80% and even more preferably at least 85%. In a more preferred embodiment, the similar nucleic acid molecule is one that has at least 90% sequence identity with a nucleic acid molecule encoding an LSP, more preferably at least 95%, more preferably at least 97%, even more preferably at least 98%, and still more preferably at least 99%. In another highly preferred embodiment, the nucleic acid molecule is one that has at least 99.5%, 99.6%, 99.7%, 99.8% or 99.9% sequence identity with a nucleic acid molecule encoding an LSP.

In another preferred embodiment, the nucleic acid molecule exhibits substantial sequence similarity to an LSNA or its complement. In a more preferred embodiment, the nucleic acid molecule exhibits substantial sequence similarity to a nucleic acid molecule comprising a nucleic acid sequence of SEQ ID NO: 1 through 142. In a preferred embodiment, the nucleic acid molecule is one that has at least 60% sequence identity with an LSNA, such as one having a nucleic acid sequence of SEQ ID NO: 1 through 142, more preferably at least 70%, even more preferably at least 80% and even more preferably at least 85%. In a more preferred embodiment, the nucleic acid molecule is one that has at least 90% sequence identity with an LSNA, more preferably at least 95%, more preferably at least 97%, even more preferably at least 98%, and still more preferably at least 99%. In another highly preferred embodiment, the nucleic acid molecule is one that has at least 99.5%, 99.6%, 99.7%, 99.8% or 99.9% sequence identity with an LSNA.

A nucleic acid molecule that exhibits substantial sequence similarity may be one that exhibits sequence identity over its entire length to an LSNA or to a nucleic acid molecule encoding an LSP, or may be one that is similar over only a part of its length. In this case, the part is at least 50 nucleotides of the LSNA or the nucleic acid molecule encoding an LSP, preferably at least 100 nucleotides, more preferably at least 150 or 200 nucleotides, even more preferably at least 250 or 300 nucleotides, still more preferably at least 400 or 500 nucleotides.

The substantially similar nucleic acid molecule may be a naturally-occurring one that is derived from another species, especially one derived from another primate, wherein the similar nucleic acid molecule encodes an amino acid sequence that exhibits significant sequence identity to that of SEQ ID NO: 143 through 277 or demonstrates significant sequence identity to the nucleotide sequence of SEQ ID NO: 1 through 142. The similar nucleic acid molecule may also be a naturally-occurring nucleic acid molecule from a human, when the LSNA is a member of a gene family. The similar nucleic acid molecule may also be a naturally-occurring nucleic acid molecule derived from a non-primate, mammalian species, including without limitation, domesticated species, e.g., dog, cat, mouse, rat, rabbit, hamster, cow, horse and pig; and wild animals, e.g., monkey, fox, lions, tigers, bears, giraffes, zebras, etc. The substantially similar nucleic acid molecule may also be a naturally-occurring nucleic acid molecule derived from a non-mammalian species, such as birds or reptiles. The naturally-occurring substantially similar nucleic acid molecule may be isolated directly from humans or other species. In another embodiment, the substantially similar nucleic acid molecule may be one that is experimentally produced by random mutation of a nucleic acid molecule. In another embodiment, the substantially similar nucleic acid molecule may be one that is experimentally produced by directed mutation of an LSNA. Further, the substantially similar nucleic acid molecule may or may not be an LSNA. However, in a preferred embodiment, the substantially similar nucleic acid molecule is an LSNA.

By "nucleic acid molecule" it is also meant to be inclusive of allelic variants of an LSNA or a nucleic acid encoding an LSP. For instance, single nucleotide polymorphisms (SNPs) occur frequently in eukaryotic genomes. In fact, more than 1.4 million SNPs have already identified in the human genome, International Human Genome Sequencing Consortium, *Nature* 409: 860–921 (2001). Thus, the sequence determined from one individual of a species may differ from other allelic forms present within the population. Additionally, small deletions and insertions, rather than single nucleotide polymorphisms, are not uncommon in the general population, and often do not alter the function of the protein. Further, amino acid substitutions occur frequently among natural allelic variants, and often do not substantially change protein function.

In a preferred embodiment, the nucleic acid molecule comprising an allelic variant is a variant of a gene, wherein the gene is transcribed into an mRNA that encodes an LSP. In a more preferred embodiment, the gene is transcribed into an mRNA that encodes an LSP comprising an amino acid sequence of SEQ ID NO: 143 through 277. In another preferred embodiment, the allelic variant is a variant of a gene, wherein the gene is transcribed into an mRNA that is an LSNA. In a more preferred embodiment, the gene is transcribed into an mRNA that comprises the nucleic acid sequence of SEQ ID NO: 1 through 142. In a preferred embodiment, the allelic variant is a naturally-occurring allelic variant in the species of interest. In a more preferred embodiment, the species of interest is human.

By "nucleic acid molecule" it is also meant to be inclusive of a part of a nucleic acid sequence of the instant invention. The part may or may not encode a polypeptide, and may or may not encode a polypeptide that is an LSP. However, in a preferred embodiment, the part encodes an LSP. In one aspect, the invention comprises a part of an LSNA. In a second aspect, the invention comprises a part of a nucleic acid molecule that hybridizes or exhibits substantial sequence similarity to an LSNA. In a third aspect, the invention comprises a part of a nucleic acid molecule that is an allelic variant of an LSNA. In a fourth aspect, the invention comprises a part of a nucleic acid molecule that encodes an LSP. A part comprises at least 10 nucleotides, more preferably at least 15, 17, 18, 20, 25, 30, 35, 40, 50, 60, 70, 80, 90, 100, 150, 200, 250, 300, 350, 400 or 500 nucleotides. The maximum size of a nucleic acid part is one nucleotide shorter than the sequence of the nucleic acid molecule encoding the full-length protein.

By "nucleic acid molecule" it is also meant to be inclusive of sequence that encoding a fusion protein, a homologous protein, a polypeptide fragment, a mutein or a polypeptide analog, as described below.

Nucleotide sequences of the instantly-described nucleic acids were determined by sequencing a DNA molecule that had resulted, directly or indirectly, from at least one enzymatic polymerization reaction (e.g., reverse transcription and/or polymerase chain reaction) using an automated sequencer (such as the MegaBACE™ 1000, Molecular Dynamics, Sunnyvale, Calif., USA). Further, all amino acid sequences of the polypeptides of the present invention were predicted by translation from the nucleic acid sequences so determined, unless otherwise specified.

In a preferred embodiment of the invention, the nucleic acid molecule contains modifications of the native nucleic acid molecule. These modifications include nonnative internucleoside bonds, post-synthetic modifications or altered nucleotide analogues. One having ordinary skill in the art would recognize that the type of modification that can be made will depend upon the intended use of the nucleic acid molecule. For instance, when the nucleic acid molecule is used as a hybridization probe, the range of such modifications will be limited to those that permit sequence-discriminating base pairing of the resulting nucleic acid. When used to direct expression of RNA or protein in vitro or in vivo, the range of such modifications will be limited to those that permit the nucleic acid to function properly as a polymerization substrate. When the isolated nucleic acid is used as a therapeutic agent, the modifications will be limited to those that do not confer toxicity upon the isolated nucleic acid.

In a preferred embodiment, isolated nucleic acid molecules can include nucleotide analogues that incorporate labels that are directly detectable, such as radiolabels or fluorophores, or nucleotide analogues that incorporate labels that can be visualized in a subsequent reaction, such as biotin or various haptens. In a more preferred embodiment, the labeled nucleic acid molecule may be used as a hybridization probe.

Common radiolabeled analogues include those labeled with $^{33}$P, $^{32}$P, and $^{35}$S, such as $-^{32}$P-dATP, $-^{32}$P-dCTP, $-^{32}$P-dGTP, $-^{32}$P-dTTP, $-^{32}$P-3'dATP, $-^{32}$P-ATP, $-^{32}$P-CTP, $-^{32}$P-GTP, $-^{32}$P-UTP, $-^{35}$S-dATP, $\alpha-^{35}$S-GTP, $\alpha-^{33}$P-dATP, and the like.

Commercially available fluorescent nucleotide analogues readily incorporated into the nucleic acids of the present invention include Cy3-dCTP, Cy3-dUTP, Cy5-dCTP, Cy3-dUTP (Amersham Pharmacia Biotech, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY® TMR-14-dUTP, BODIPY® TR-14-dUTP, Rhodamine Green™-5-dUTP, Oregon Greene® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA). One may also custom synthesize nucleotides having other fluorophores. See Henegariu et al., Nature Biotechnol. 18: 345–348 (2000), the disclosure of which is incorporated herein by reference in its entirety.

Haptens that are commonly conjugated to nucleotides for subsequent labeling include biotin (biotin-11-dUTP, Molecular Probes, Inc., Eugene, Oreg., USA; biotin-21-UTP, biotin-21-dUTP, Clontech Laboratories, Inc., Palo Alto, Calif., USA), digoxigenin (DIG-11-dUTP, alkali labile, DIG-11-UTP, Roche Diagnostics Corp., Indianapolis, Ind., USA), and dinitrophenyl (dinitrophenyl-11-dUTP, Molecular Probes, Inc., Eugene, Oreg., USA).

Nucleic acid molecules can be labeled by incorporation of labeled nucleotide analogues into the nucleic acid. Such analogues can be incorporated by enzymatic polymerization, such as by nick translation, random priming, polymerase chain reaction (PCR), terminal transferase tailing, and end-filling of overhangs, for DNA molecules, and in vitro transcription driven, e.g., from phage promoters, such as T7, T3, and SP6, for RNA molecules. Commercial kits are readily available for each such labeling approach. Analogues can also be incorporated during automated solid phase chemical synthesis. Labels can also be incorporated after nucleic acid synthesis, with the 5' phosphate and 3' hydroxyl providing convenient sites for post-synthetic covalent attachment of detectable labels.

Other post-synthetic approaches also permit internal labeling of nucleic acids. For example, fluorophores can be attached using a cisplatin reagent that reacts with the N7 of guanine residues (and, to a lesser extent, adenine bases) in DNA, RNA, and PNA to provide a stable coordination complex between the nucleic acid and fluorophore label (Universal Linkage System) (available from Molecular Probes, Inc., Eugene, Oreg., USA and Amersham Pharmacia Biotech, Piscataway, N.J., USA); see Alers et al., Genes, Chromosomes & Cancer 25: 301–305 (1999); Jelsma et al., J. NIH Res. 5: 82 (1994); Van Belkum et al., BioTechniques 16: 148–153 (1994), incorporated herein by reference. As another example, nucleic acids can be labeled using a disulfide-containing linker (FastTag™ Reagent, Vector Laboratories, Inc., Burlingame, Calif., USA) that is photo- or thermally-coupled to the target nucleic acid using aryl azide chemistry; after reduction, a free thiol is available for coupling to a hapten, fluorophore, sugar, affinity ligand, or other marker.

One or more independent or interacting labels can be incorporated into the nucleic acid molecules of the present invention. For example, both a fluorophore and a moiety that in proximity thereto acts to quench fluorescence can be included to report specific hybridization through release of fluorescence quenching or to report exonucleotidic excision. See, e.g., Tyagi et al., Nature Biotechnol. 14: 303–308 (1996); Tyagi et al., Nature Biotechnol. 16: 49–53 (1998); Sokol et al., Proc. Natl. Acad. Sci. USA 95: 11538–11543 (1998); Kostrikis et al., Science 279: 1228–1229 (1998); Marras et al., Genet. Anal. 14: 151–156 (1999); U.S. Pat. No. 5,846,726; 5,925,517; 5,925,517; 5,723,591 and 5,538, 848; Holland et al., Proc. Natl. Acad. Sci. USA 88: 7276–7280 (1991); Heid et al., Genome Res. 6(10): 986–94 (1996); Kuimelis et al, Nucleic Acids Symp. Ser. (37): 255–6 (1997); the disclosures of which are incorporated herein by reference in their entireties.

Nucleic acid molecules of the invention may be modified by altering one or more native phosphodiester internucleoside bonds to more nuclease-resistant, internucleoside bonds. See Hartmann et al. (eds.), Manual of Antisense Methodology: Perspectives in Antisense Science, Kluwer Law International (1999); Stein et al. (eds.), Applied Antisense Oligonucleotide Technology, Wiley-Liss (1998); Chadwick et al. (eds.), Oligonucleotides as Therapeutic Agents-Symposium No. 209, John Wiley & Son Ltd (1997); the disclosures of which are incorporated herein by reference in their entireties. Such altered internucleoside bonds are often desired for antisense techniques or for targeted gene correction. See Gamper et al., Nucl. Acids Res. 28(21): 4332–4339 (2000), the disclosure of which is incorporated herein by reference in its entirety.

Modified oligonucleotide backbones include, without limitation, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, the disclosures of which are incorporated herein by reference in their entireties. In a preferred embodiment, the modified internucleoside linkages may be used for antisense techniques.

Other modified oligonucleotide backbones do not include a phosphorus atom, but have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above backbones include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307;

5,561,225; 5,596,086; 5,602,240; 5,610,289; 5,602,240; 5,608,046; 5,610,289; 5,618,704; 5,623,070; 5,663,312; 5,633,360; 5,677,437 and 5,677,439; the disclosures of which are incorporated herein by reference in their entireties.

In other preferred oligonucleotide mimetics, both the sugar and the internucleoside linkage are replaced with novel groups, such as peptide nucleic acids (PNA). In PNA compounds, the phosphodiester backbone of the nucleic acid is replaced with an amide-containing backbone, in particular by repeating N-(2-aminoethyl) glycine units linked by amide bonds. Nucleobases are bound directly or indirectly to aza nitrogen atoms of the amide portion of the backbone, typically by methylene carbonyl linkages. PNA can be synthesized using a modified peptide synthesis protocol. PNA oligomers can be synthesized by both Fmoc and tBoc methods. Representative U.S. patents that teach the preparation of PNA compounds include, but are not limited to, U.S. Pat. Nos. 5,539,082; 5,714,331; and 5,719,262, each of which is herein incorporated by reference. Automated PNA synthesis is readily achievable on commercial synthesizers (see, e.g., "PNA User's Guide," Rev. 2, February 1998, Perseptive Biosystems Part No. 60138, Applied Biosystems, Inc., Foster City, Calif.).

PNA molecules are advantageous for a number of reasons. First, because the PNA backbone is uncharged, PNA/DNA and PNA/RNA duplexes have a higher thermal stability than is found in DNA/DNA and DNA/RNA duplexes. The Tm of a PNA/DNA or PNA/RNA duplex is generally 1° C. higher per base pair than the Tm of the corresponding DNA/DNA or DNA/RNA duplex (in 100 mM NaCl). Second, PNA molecules can also form stable PNA/DNA complexes at low ionic strength, under conditions in which DNA/DNA duplex formation does not occur. Third, PNA also demonstrates greater specificity in binding to complementary DNA because a PNA/DNA mismatch is more destabilizing than DNA/DNA mismatch. A single mismatch in mixed a PNA/DNA 15-mer lowers the Tm by 8–20° C. (15° C. on average). In the corresponding DNA/DNA duplexes, a single mismatch lowers the Tm by 4–16° C. (11° C. on average). Because PNA probes can be significantly shorter than DNA probes, their specificity is greater. Fourth, PNA oligomers are resistant to degradation by enzymes, and the lifetime of these compounds is extended both in vivo and in vitro because nucleases and proteases do not recognize the PNA polyamide backbone with nucleobase sidechains. See, e.g., Ray et al, *FASEB J.* 14(9): 1041–60 (2000); Nielsen et al., *Pharmacol Toxicol.* 86(1): 3–7 (2000); Larsen et al., *Biochim Biophys Acta.* 1489(1): 159–66 (1999); Nielsen, *Curr. Opin. Struct. Biol.* 9(3): 353–7 (1999), and Nielsen, *Curr. Opin. Biotechnol.* 10(1): 71–5 (1999), the disclosures of which are incorporated herein by reference in their entireties.

Nucleic acid molecules may be modified compared to their native structure throughout the length of the nucleic acid molecule or can be localized to discrete portions thereof. As an example of the latter, chimeric nucleic acids can be synthesized that have discrete DNA and RNA domains and that can be used for targeted gene repair and modified PCR reactions, as further described in U.S. Pat. Nos. 5,760,012 and 5,731,181, Misra et al., *Biochem.* 37: 1917–1925 (1998); and Finn et al., *Nucl. Acids Res.* 24: 3357–3363 (1996), the disclosures of which are incorporated herein by reference in their entireties.

Unless otherwise specified, nucleic acids of the present invention can include any topological conformation appropriate to the desired use; the term thus explicitly comprehends, among others, single-stranded, double-stranded, triplexed, quadruplexed, partially double-stranded, partially-triplexed, partially-quadruplexed, branched, hairpinned, circular, and padlocked conformations. Padlock conformations and their utilities are further described in Banér et al., *Curr. Opin. Biotechnol.* 12: 11–15 (2001); Escude et al., *Proc. Natl. Acad. Sci. USA* 14: 96(19) :10603–7 (1999); Nilsson et al., *Science* 265(5181): 2085–8 (1994), the disclosures of which are incorporated herein by reference in their entireties. Triplex and quadruplex conformations, and their utilities, are reviewed in Praseuth et al., *Biochim. Biophys. Acta*. 1489(1): 181–206 (1999); Fox, *Curr. Med. Chem.* 7(1): 17–37 (2000); Kochetkova et al., *Methods Mol. Biol.* 130: 189–201 (2000); Chan et al., *J. Mol. Med.* 75(4): 267–82 (1997), the disclosures of which are incorporated herein by reference in their entireties.

Methods for Using Nucleic Acid Molecules as Probes and Primers

The isolated nucleic acid molecules of the present invention can be used as hybridization probes to detect, characterize, and quantify hybridizing nucleic acids in, and isolate hybridizing nucleic acids from, both genomic and transcript-derived nucleic acid samples. When free in solution, such probes are typically, but not invariably, detectably labeled; bound to a substrate, as in a microarray, such probes are typically, but not invariably unlabeled.

In one embodiment, the isolated nucleic acids of the present invention can be used as probes to detect and characterize gross alterations in the gene of an LSNA, such as deletions, insertions, translocations, and duplications of the LSNA genomic locus through fluorescence in situ hybridization (FISH) to chromosome spreads. See, e.g., Andreeff et al. (eds.), *Introduction to Fluorescence In Situ Hybridization: Principles and Clinical Applications*, John Wiley & Sons (1999), the disclosure of which is incorporated herein by reference in its entirety. The isolated nucleic acids of the present invention can be used as probes to assess smaller genomic alterations using, e.g., Southern blot detection of restriction fragment length polymorphisms. The isolated nucleic acid molecules of the present invention can be used as probes to isolate genomic clones that include the nucleic acid molecules of the present invention, which thereafter can be restriction mapped and sequenced to identify deletions, insertions, translocations, and substitutions (single nucleotide polymorphisms, SNPs) at the sequence level.

In another embodiment, the isolated nucleic acid molecules of the present invention can be used as probes to detect, characterize, and quantify LSNA in, and isolate LSNA from, transcript-derived nucleic acid samples. In one aspect, the isolated nucleic acid molecules of the present invention can be used as hybridization probes to detect, characterize by length, and quantify mRNA by Northern blot of total or poly-$A^+$-selected RNA samples. In another aspect, the isolated nucleic acid molecules of the present invention can be used as hybridization probes to detect, characterize by location, and quantify mRNA by in situ hybridization to tissue sections. See, e.g., Schwarchzacher et al., *In Situ Hybridization*, Springer-Verlag New York (2000), the disclosure of which is incorporated herein by reference in its entirety. In another preferred embodiment, the isolated nucleic acid molecules of the present invention can be used as hybridization probes to measure the representation of clones in a cDNA library or to isolate hybridizing nucleic acid molecules acids from cDNA libraries, permitting sequence level characterization of mRNAs that hybridize to LSNAs, including, without limitations, identification of deletions, insertions, substitutions, truncations, alternatively spliced forms and single nucleotide polymorphisms. In yet another preferred embodiment, the nucleic acid molecules of the instant invention may be used in microarrays.

All of the aforementioned probe techniques are well within the skill in the art, and are described at greater length in standard texts such as Sambrook (2001), supra; Ausubel (1999), supra; and Walker et al. (eds.), *The Nucleic Acids Protocols Handbook*, Humana Press (2000), the disclosures of which are incorporated herein by reference in their entirety.

Thus, in one embodiment, a nucleic acid molecule of the invention may be used as a probe or primer to identify or amplify a second nucleic acid molecule that selectively hybridizes to the nucleic acid molecule of the invention. In a preferred embodiment, the probe or primer is derived from a nucleic acid molecule encoding an LSP. In a more preferred embodiment, the probe or primer is derived from a nucleic acid molecule encoding a polypeptide having an amino acid sequence of SEQ ID NO: 143 through 277. In another preferred embodiment, the probe or primer is derived from an LSNA. In a more preferred embodiment, the probe or primer is derived from a nucleic acid molecule having a nucleotide sequence of SEQ ID NO: 1 through 142.

In general, a probe or primer is at least 10 nucleotides in length, more preferably at least 12, more preferably at least 14 and even more preferably at least 16 or 17 nucleotides in length. In an even more preferred embodiment, the probe or primer is at least 18 nucleotides in length, even more preferably at least 20 nucleotides and even more preferably at least 22 nucleotides in length. Primers and probes may also be longer in length. For instance, a probe or primer may be 25 nucleotides in length, or may be 30, 40 or 50 nucleotides in length. Methods of performing nucleic acid hybridization using oligonucleotide probes are well-known in the art. See, e.g., Sambrook et al., 1989, supra, Chapter 11 and pp. 11.31–11.32 and 11.40–11.44, which describes radiolabeling of short probes, and pp. 11.45–11.53, which describe hybridization conditions for oligonucleotide probes, including specific conditions for probe hybridization (pp. 11.50–11.51).

Methods of performing primer-directed amplification are also well-known in the art. Methods for performing the polymerase chain reaction (PCR) are compiled, inter alia, in McPherson, *PCR Basics: From Background to Bench*, Springer Verlag (2000); Innis et al (eds.), *PCR Applications: Protocols for Functional Genomics*, Academic Press (1999); Gelfand et al. (eds.), *PCR Strategies*, Academic Press (1998); Newton et al., PCR, Springer-Verlag New York (1997); Burke (ed.), *PCR: Essential Techniques*, John Wiley & Son Ltd (1996); White (ed.), *PCR Cloning Protocols: From Molecular Cloning to Genetic Engineering*, Vol. 67, Humana Press (1996); McPherson et al. (eds.), *PCR 2: A Practical Approach*, Oxford University Press, Inc. (1995); the disclosures of which are incorporated herein by reference in their entireties. Methods for performing RT-PCR are collected, e.g., in Siebert et al. (eds.), *Gene Cloning and Analysis by RT-PCR*, Eaton Publishing Company/Bio Techniques Books Division, 1998; Siebert (ed.), *PCR Technique:RT-PCR*, Eaton Publishing Company/ BioTechniques Books (1995); the disclosure of which is incorporated herein by reference in its entirety.

PCR and hybridization methods may be used to identify and/or isolate allelic variants, homologous nucleic acid molecules and fragments of the nucleic acid molecules of the invention. PCR and hybridization methods may also be used to identify, amplify and/or isolate nucleic acid molecules that encode homologous proteins, analogs, fusion protein or muteins of the invention. The nucleic acid primers of the present invention can be used to prime amplification of nucleic acid molecules of the invention, using transcript-derived or genomic DNA as template.

The nucleic acid primers of the present invention can also be used, for example, to prime single base extension (SBE) for SNP detection (See, e.g., U.S. Pat. No. 6,004,744, the disclosure of which is incorporated herein by reference in its entirety).

Isothermal amplification approaches, such as rolling circle amplification, are also now well-described. See, e.g., Schweitzer et al., *Curr. Opin. Biotechnol.* 12(1): 21–7 (2001); U.S. Pat. Nos. 5,854,033 and 5,714,320; and international patent publications WO 97/19193 and WO 00/15779, the disclosures of which are incorporated herein by reference in their entireties. Rolling circle amplification can be combined with other techniques to facilitate SNP detection. See, e.g., Lizardi et al., *Nature Genet.* 19(3): 225–32 (1998).

Nucleic acid molecules of the present invention may be bound to a substrate either covalently or noncovalently. The substrate can be porous or solid, planar or non-planar, unitary or distributed. The bound nucleic acid molecules may be used as hybridization probes, and may be labeled or unlabeled. In a preferred embodiment, the bound nucleic acid molecules are unlabeled.

In one embodiment, the nucleic acid molecule of the present invention is bound to a porous substrate, e.g., a membrane, typically comprising nitrocellulose, nylon, or positively-charged derivatized nylon. The nucleic acid molecule of the present invention can be used to detect a hybridizing nucleic acid molecule that is present within a labeled nucleic acid sample, e.g., a sample of transcript-derived nucleic acids. In another embodiment, the nucleic acid molecule is bound to a solid substrate, including, without limitation, glass, amorphous silicon, crystalline silicon or plastics. Examples of plastics include, without limitation, polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof. The solid substrate may be any shape, including rectangular, disk-like and spherical. In a preferred embodiment, the solid substrate is a microscope slide or slide-shaped substrate.

The nucleic acid molecule of the present invention can be attached covalently to a surface of the support substrate or applied to a derivatized surface in a chaotropic agent that facilitates denaturation and adherence by presumed noncovalent interactions, or some combination thereof. The nucleic acid molecule of the present invention can be bound to a substrate to which a plurality of other nucleic acids are concurrently bound, hybridization to each of the plurality of bound nucleic acids being separately detectable. At low density, e.g. on a porous membrane, these substrate-bound collections are typically denominated macroarrays; at higher density, typically on a solid support, such as glass, these substrate bound collections of plural nucleic acids are colloquially termed microarrays. As used herein, the term microarray includes arrays of all densities. It is, therefore, another aspect of the invention to provide microarrays that include the nucleic acids of the present invention.

Expression Vectors, Host Cells and Recombinant Methods of producing Polypeptides Another aspect of the present invention relates to vectors that comprise one or more of the isolated nucleic acid molecules of the present invention, and host cells in which such vectors have been introduced.

The vectors can be used, inter alia, for propagating the nucleic acids of the present invention in host cells (cloning vectors), for shuttling the nucleic acids of the present invention between host cells derived from disparate organisms (shuttle vectors), for inserting the nucleic acids of the present invention into host cell chromosomes (insertion vectors), for expressing sense or antisense RNA transcripts of the nucleic acids of the present invention in vitro or within a host cell, and for expressing polypeptides encoded by the nucleic acids of the present invention, alone or as fusions to heterologous polypeptides (expression vectors). Vectors of the present invention will often be suitable for several such uses.

Vectors are by now well-known in the art, and are described, inter alia, in Jones et al. (eds.), *Vectors: Cloning Applications: Essential Techniques* (Essential Techniques Series), John Wiley & Son Ltd. (1998); Jones et al. (eds.), *Vectors: Expression Systems: Essential Techniques* (Essential Techniques Series), John Wiley & Son Ltd. (1998); Gacesa et al., *Vectors: Essential Data*, John Wiley & Sons Ltd. (1995); Cid-Arregui (eds.), *Viral Vectors: Basic Science and Gene Therapy*, Eaton Publishing Co. (2000); Sambrook (2001), supra; Ausubel (1999), supra; the disclosures of which are incorporated herein by reference in their entireties. Furthermore, an enormous variety of vectors are available commercially. Use of existing vectors and modifications thereof being well within the skill in the art, only basic features need be described here.

Nucleic acid sequences may be expressed by operatively linking them to an expression control sequence in an appropriate expression vector and employing that expression vector to transform an appropriate unicellular host. Expression control sequences are sequences which control the transcription, post-transcriptional events and translation of nucleic acid sequences. Such operative linking of a nucleic sequence of this invention to an expression control sequence, of course, includes, if not already part of the nucleic acid sequence, the provision of a translation initiation codon, ATG or GTG, in the correct reading frame upstream of the nucleic acid sequence.

A wide variety of host/expression vector combinations may be employed in expressing the nucleic acid sequences of this invention. Useful expression vectors, for example, may consist of segments of chromosomal, non-chromosomal and synthetic nucleic acid sequences.

In one embodiment, prokaryotic cells may be used with an appropriate vector. Prokaryotic host cells are often used for cloning and expression. In a preferred embodiment, prokaryotic host cells include *E. coli, Pseudomonas, Bacillus* and *Streptomyces*. In a preferred embodiment, bacterial host cells are used to express the nucleic acid molecules of the instant invention. Useful expression vectors for bacterial hosts include bacterial plasmids, such as those from *E. coli, Bacillus* or *Streptomyces*, including pBluescript, pGEX-2T, pUC vectors, col E1, pCR1, pBR322, pMB9 and their derivatives, wider host range plasmids, such as RP4, phage DNAs, e.g., the numerous derivatives of phage lambda, e.g., NM989, λGT10 and λGT11, and other phages, e.g., M13 and filamentous single-stranded phage DNA. Where *E. coli* is used as host, selectable markers are, analogously, chosen for selectivity in gram negative bacteria: e.g., typical markers confer resistance to antibiotics, such as ampicillin, tetracycline, chloramphenicol, kanamycin, streptomycin and zeocin; auxotrophic markers can also be used.

In other embodiments, eukaryotic host cells, such as yeast, insect, mammalian or plant cells, may be used. Yeast cells, typically *S. cerevisiae*, are useful for eukaryotic genetic studies, due to the ease of targeting genetic changes by homologous recombination and the ability to easily complement genetic defects using recombinantly expressed proteins. Yeast cells are useful for identifying interacting protein components, e.g. through use of a two-hybrid system. In a preferred embodiment, yeast cells are useful for protein expression. Vectors of the present invention for use in yeast will typically, but not invariably, contain an origin of replication suitable for use in yeast and a selectable marker that is functional in yeast. Yeast vectors include Yeast Integrating plasmids (e.g., YIp5) and Yeast Replicating plasmids (the YRp and YEp series plasmids), Yeast Centromere plasmids (the YCp series plasmids), Yeast Artificial Chromosomes (YACs) which are based on yeast linear plasmids, denoted YLp, pGPD-2, 2μ plasmids and derivatives thereof, and improved shuttle vectors such as those described in Gietz et al., *Gene*, 74: 527–34 (1988) (YIplac, YEplac and YCplac). Selectable markers in yeast vectors include a variety of auxotrophic markers, the most common of which are (in *Saccharomyces cerevisiae*) URA3, HIS3, LEU2, TRP1 and LYS2, which complement specific auxotrophic mutations, such as ura3-52, his3-D1, leu2-D 1, trp1-D1 and lys2-201.

Insect cells are often chosen for high efficiency protein expression. Where the host cells are from *Spodoptera frugiperda*, e.g., Sf9 and Sf21 cell lines, and expresSF™ cells (Protein Sciences Corp., Meriden, Conn., USA)), the vector replicative strategy is typically based upon the baculovirus life cycle. Typically, baculovirus transfer vectors are used to replace the wild-type AcMNPV polyhedrin gene with a heterologous gene of interest. Sequences that flank the polyhedrin gene in the wild-type genome are positioned 5' and 3' of the expression cassette on the transfer vectors. Following co-transfection with AcMNPV DNA, a homologous recombination event occurs between these sequences resulting in a recombinant virus carrying the gene of interest and the polyhedrin or p10 promoter. Selection can be based upon visual screening for 1acZ fusion activity.

In another embodiment, the host cells may be mammalian cells, which are particularly useful for expression of proteins intended as pharmaceutical agents, and for screening of potential agonists and antagonists of a protein or a physiological pathway. Mammalian vectors intended for autonomous extrachromosomal replication will typically include a viral origin, such as the SV40 origin (for replication in cell lines expressing the large T-antigen, such as COS1 and COS7 cells), the papillomavirus origin, or the EBV origin for long term episomal replication (for use, e.g., in 293-EBNA cells, which constitutively express the EBV EBNA-1 gene product and adenovirus E1A). Vectors intended for integration, and thus replication as part of the mammalian chromosome, can, but need not, include an origin of replication functional in mammalian cells, such as the SV40 origin. Vectors based upon viruses, such as adenovirus, adeno-associated virus, vaccinia virus, and various mammalian retroviruses, will typically replicate according to the viral replicative strategy. Selectable markers for use in mammalian cells include resistance to neomycin (G418), blasticidin, hygromycin and to zeocin, and selection based upon the purine salvage pathway using HAT medium.

Expression in mammalian cells can be achieved using a variety of plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL 941.

Plant cells can also be used for expression, with the vector replicon typically derived from a plant virus (e.g., cauliflower mosaic virus, CaMV; tobacco mosaic virus, TMV) and selectable markers chosen for suitability in plants.

It is known that codon usage of different host cells may be different. For example, a plant cell and a human cell may exhibit a difference in codon preference for encoding a particular amino acid. As a result, human mRNA may not be efficiently translated in a plant, bacteria or insect host cell. Therefore, another embodiment of this invention is directed to codon optimization. The codons of the nucleic acid molecules of the invention may be modified to resemble, as much as possible, genes naturally contained within the host cell without altering the amino acid sequence encoded by the nucleic acid molecule.

Any of a wide variety of expression control sequences may be used in these vectors to express the DNA sequences of this invention. Such useful expression control sequences include the expression control sequences associated with structural genes of the foregoing expression vectors. Expression control sequences that control transcription include, e.g., promoters, enhancers and transcription termination sites. Expression control sequences in eukaryotic cells that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct targeted expression of the polypeptide to or within particular cellular compartments, and sequences in the 5' and 3' untranslated regions that modify the rate or efficiency of translation.

Examples of useful expression control sequences for a prokaryote, e.g., *E. coli*, will include a promoter, often a phage promoter, such as phage lambda pL promoter, the trc promoter, a hybrid derived from the trp and lac promoters, the bacteriophage T7 promoter (in *E. coli* cells engineered to express the T7 polymerase), the *TAC* or *TRC* system, the major operator and promoter regions of phage lambda, the control regions of fd coat protein, or the araBAD operon. Prokaryotic expression vectors may further include transcription terminators, such as the aspA terminator, and elements that facilitate translation, such as a consensus ribosome binding site and translation termination codon, Schomer et al., *Proc. Natl. Acad. Sci. USA* 83: 8506–8510 (1986).

Expression control sequences for yeast cells, typically *S. cereviaiae*, will include a yeast promoter, such as the CYC1 promoter, the GAL1 promoter, the GAL10 promoter, ADH1 promoter, the promoters of the yeast α-mating system, or the GPD promoter, and will typically have elements that facilitate transcription termination, such as the transcription termination signals from the CYC1 or ADH1 gene.

Expression vectors useful for expressing proteins in mammalian cells will include a promoter active in mammalian cells. These promoters include those derived from mammalian viruses, such as the enhancer-promoter sequences from the immediate early gene of the human cytomegalovirus (CMV), the enhancer-promoter sequences from the Rous sarcoma virus long terminal repeat (RSV LTR), the enhancer-promoter from SV40 or the early and late promoters of adenovirus. Other expression control sequences include the promoter for 3-phosphoglycerate kinase or other glycolytic enzymes, the promoters of acid phosphatase. Other expression control sequences include those from the gene comprising the LSNA of interest. Often, expression is enhanced by incorporation of polyadenylation sites, such as the late SV40 polyadenylation site and the polyadenylation signal and transcription termination sequences from the bovine growth hormone (BGH) gene, and ribosome binding sites. Furthermore, vectors can include introns, such as intron II of rabbit β-globin gene and the SV40 splice elements.

Preferred nucleic acid vectors also include a selectable or amplifiable marker gene and means for amplifying the copy number of the gene of interest. Such marker genes are well-known in the art. Nucleic acid vectors may also comprise stabilizing sequences (e.g., ori- or ARS-like sequences and telomere-like sequences), or may alternatively be designed to favor directed or non-directed integration into the host cell genome. In a preferred embodiment, nucleic acid sequences of this invention are inserted in frame into an expression vector that allows high level expression of an RNA which encodes a protein comprising the encoded nucleic acid sequence of interest. Nucleic acid cloning and sequencing methods are well-known to those of skill in the art and are described in an assortment of laboratory manuals, including Sambrook (1989), supra, Sambrook (2000), supra; and Ausubel (1992), supra, Ausubel (1999), supra. Product information from manufacturers of biological, chemical and immunological reagents also provide useful information.

Expression vectors may be either constitutive or inducible. Inducible vectors include either naturally inducible promoters, such as the trc promoter, which is regulated by the lac operon, and the pL promoter, which is regulated by tryptophan, the MMTV-LTR promoter, which is inducible by dexamethasone, or can contain synthetic promoters and/or additional elements that confer inducible control on adjacent promoters. Examples of inducible synthetic promoters are the hybrid Plac/ara-1 promoter and the PLtetO-1 promoter. The PltetO-1 promoter takes advantage of the high expression levels from the PL promoter of phage lambda, but replaces the lambda repressor sites with two copies of operator 2 of the Tn10 tetracycline resistance operon, causing this promoter to be tightly repressed by the Tet repressor protein and induced in response to tetracycline (Tc) and Tc derivatives such as anhydrotetracycline. Vectors may also be inducible because they contain hormone response elements, such as the glucocorticoid response element (GRE) and the estrogen response element (ERE), which can confer hormone inducibility where vectors are used for expression in cells having the respective hormone receptors. To reduce background levels of expression, elements responsive to ecdysone, an insect hormone, can be used instead, with coexpression of the ecdysone receptor.

In one aspect of the invention, expression vectors can be designed to fuse the expressed polypeptide to small protein tags that facilitate purification and/or visualization. Tags that facilitate purification include a polyhistidine tag that facilitates purification of the fusion protein by immobilized metal affinity chromatography, for example using NiNTA resin (Qiagen Inc., Valencia, Calif., USA) or TALON™ resin (cobalt immobilized affinity chromatography medium, Clontech Labs, Palo Alto, Calif., USA). The fusion protein can include a chitin-binding tag and self-excising intein, permitting chitin-based purification with self-removal of the fused tag (IMPACT™ system, New England Biolabs, Inc., Beverley, Mass., USA). Alternatively, the fusion protein can include a calmodulin-binding peptide tag, permitting purification by calmodulin affinity resin (Stratagene, La Jolla, Calif., USA), or a specifically excisable fragment of the biotin carboxylase carrier protein, permitting purification of in vivo biotinylated protein using an avidin resin and subsequent tag removal (Promega, Madison, Wis., USA). As another useful alternative, the proteins of the present invention can be expressed as a fusion protein with glutathione-S-transferase, the affinity and specificity of binding to glutathione permitting purification using glutathione affinity resins, such as Glutathione-Superflow Resin (Clontech Laboratories, Palo Alto, Calif., USA), with subsequent elution with free glutathione. Other tags include, for example, the Xpress epitope, detectable by anti-Xpress antibody (Invitrogen, Carlsbad, Calif., USA), a myc tag, detectable by anti-myc tag antibody, the V5 epitope, detectable by anti-V5 antibody (Invitrogen, Carlsbad, Calif., USA), FLAG® epitope, detectable by anti-FLAG® antibody (Stratagene, La Jolla, Calif., USA), and the HA epitope.

For secretion of expressed proteins, vectors can include appropriate sequences that encode secretion signals, such as leader peptides. For example, the pSecTag2 vectors (Invitrogen, Carlsbad, Calif., USA) are 5.2 kb mammalian expression vectors that carry the secretion signal from the V-J2-C region of the mouse Ig kappa-chain for efficient secretion of recombinant proteins from a variety of mammalian cell lines.

Expression vectors can also be designed to fuse proteins encoded by the heterologous nucleic acid insert to polypeptides that are larger than purification and/or identification tags. Useful fusion proteins include those that permit display of the encoded protein on the surface of a phage or cell, fusion to intrinsically fluorescent proteins, such as those that have a green fluorescent protein (GFP)-like chromophore, fusions to the IgG Fc region, and fusion proteins for use in two hybrid systems.

Vectors for phage display fuse the encoded polypeptide to, e.g., the gene III protein (pIII) or gene VIII protein (pVIII) for display on the surface of filamentous phage, such as M13. See Barbas et al., *Phage Display: A Laboratory Manual*, Cold Spring Harbor Laboratory Press (2001); Kay et al. (eds.), *Phage Display of Peptides and Proteins: A Laboratory Manual*, Academic Press, Inc., (1996); Abelson et al (eds.), *Combinatorial Chemistry* (Methods in Enzymology, Vol. 267) Academic Press (1996). Vectors for yeast display, e.g. the pYD1 yeast display vector (Invitrogen, Carlsbad, Calif., USA), use the -agglutinin yeast adhesion receptor to display recombinant protein on the surface of *S. cerevisiae*. Vectors for mammalian display, e.g., the pDisplay™ vector (Invitrogen, Carlsbad, Calif., USA), target recombinant proteins using an N-terminal cell surface targeting signal and a C-terminal transmembrane anchoring domain of platelet derived growth factor receptor.

A wide variety of vectors now exist that fuse proteins encoded by heterologous nucleic acids to the chromophore of the substrate-independent, intrinsically fluorescent green fluorescent protein from *Aequorea Victoria* ("GFP") and its variants. The GFP-like chromophore can be selected from GFP-like chromophores found in naturally occurring proteins, such as *A. Victoria* GFP (GenBank accession number AAA27721), *Renilla reniformis* GFP, FP583 (GenBank accession no. AF168419) (DsRed), FP593 (AF272711), FP483 (AF168420), FP484 (AF168424), FP595 (AF246709), FP486 (AF168421), FP538 (AF168423), and FP506 (AF168422), and need include only so much of the native protein as is needed to retain the chromophore's intrinsic fluorescence. Methods for determining the minimal domain required for fluorescence are known in the art. See Li et al., *J. Biol. Chem.* 272: 28545–28549 (1997). Alternatively, the GFP-like chromophore can be selected from GFP-like chromophores modified from those found in nature. The methods for engineering such modified GFP-like chromophores and testing them for fluorescence activity, both alone and as part of protein fusions, are well-known in the art. See Heim et al., *Curr. Biol.* 6: 178–182 (1996) and Palm et al., *Methods Enzymol.* 302: 378–394 (1999), incorporated herein by reference in its entirety. A variety of such modified chromophores are now commercially available and can readily be used in the fusion proteins of the present invention. These include EGFP ("enhanced GFP"), EBFP ("enhanced blue fluorescent protein"), BFP2, EYFP ("enhanced yellow fluorescent protein"), ECFP ("enhanced cyan fluorescent protein") or Citrine. EGFP (see, e.g, Cormack et al, *Gene* 173: 33–38 (1996); U.S. Pat. Nos. 6,090,919 and 5,804,387) is found on a variety of vectors, both plasmid and viral, which are available commercially (Clontech Labs, Palo Alto, Calif., USA); EBFP is optimized for expression in mammalian cells whereas BFP2, which retains the original jellyfish codons, can be expressed in bacteria (see, e.g. Heim et al., *Curr. Biol.* 6: 178–182 (1996) and Cormack et al., *Gene* 173: 33–38 (1996)). Vectors containing these blue-shifted variants are available from Clontech Labs (Palo Alto, Calif., USA). Vectors containing EYFP, ECFP (see, e.g., Heim et al., *Curr. Biol.* 6: 178–182 (1996); Miyawaki et al., *Nature* 388: 882–887 (1997)) and Citrine (see, e.g., Heikal et al., *Proc. Natl. Acad. Sci. USA* 97: 11996–12001 (2000)) are also available from Clontech Labs. The GFP-like chromophore can also be drawn from other modified GFPs, including those described in U.S. Pat. Nos. 6,124,128; 6,096,865; 6,090,919; 6,066,476; 6,054,321; 6,027,881; 5,968,750; 5,874,304; 5,804,387; 5,777,079; 5,741,668; and 5,625,048, the disclosures of which are incorporated herein by reference in their entireties. See also Conn (ed.), *Green Fluorescent Protein* (Methods in Enzymology, Vol. 302), Academic Press, Inc. (1999). The GFP-like chromophore of each of these GFP variants can usefully be included in the fusion proteins of the present invention.

Fusions to the IgG Fc region increase serum half life of protein pharmaceutical products through interaction with the FcRn receptor (also denominated the FcRp receptor and the Brambell receptor, FcRb), further described in International Patent Application Nos. WO 97/43316, WO 97/34631, WO 96/32478, WO 96/18412.

For long-term, high-yield recombinant production of the proteins, protein fusions, and protein fragments of the present invention, stable expression is preferred. Stable expression is readily achieved by integration into the host cell genome of vectors having selectable markers, followed by selection of these integrants. Vectors such as pUB6/V5-His A, B, and C (Invitrogen, Carlsbad, Calif., USA) are designed for high-level stable expression of heterologous proteins in a wide range of mammalian tissue types and cell lines. pUB6/ V5-His uses the promoter/enhancer sequence from the human ubiquitin C gene to drive expression of recombinant proteins: expression levels in 293, CHO, and NIH3T3 cells are comparable to levels from the CMV and human EF-1a promoters. The bsd gene permits rapid selection of stably transfected mammalian cells with the potent antibiotic blasticidin.

Replication incompetent retroviral vectors, typically derived from Moloney murine leukemia virus, also are useful for creating stable transfectants having integrated provirus. The highly efficient transduction machinery of retroviruses, coupled with the availability of a variety of packaging cell lines such as RetroPack™ PT 67, EcoPack2™-293, AmphoPack-293, and GP2-293 cell lines (all available from Clontech Laboratories, Palo Alto, Calif., USA), allow a wide host range to be infected with high efficiency; varying the multiplicity of infection readily adjusts the copy number of the integrated provirus.

Of course, not all vectors and expression control sequences will function equally well to express the nucleic acid sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must be replicated in it. The vector's copy number, the ability to control that copy number, the ability to control integration, if any, and the expression of any other proteins encoded by the vector, such as antibiotic or other selection markers, should also be considered. The present invention further includes host cells comprising the vectors of the present invention, either present episomally within the cell or integrated, in whole or in part, into the host cell chromosome. Among other considerations, some of which are described above, a host cell strain may be chosen for its ability to process the expressed protein in the desired fashion. Such post-translational modifications of the polypeptide include, but are not limited to, acetylation, carboxylation, glycosylation, phosphorylation, lipidation, and acylation, and it is an aspect of the present invention to provide LSPs with such post-translational modifications.

Polypeptides of the invention may be post-translationally modified. Post-translational modifications include phosphorylation of amino acid residues serine, threonine and/or tyrosine, N-linked and/or O-linked glycosylation, methylation, acetylation, prenylation, methylation, acetylation, arginylation, ubiquination and racemization. One may determine whether a polypeptide of the invention is likely to be post-translationally modified by analyzing the sequence of the polypeptide to determine if there are peptide motifs indicative of sites for post-translational modification. There are a number of computer programs that permit prediction of post-translational modifications. See, e.g., epasy.org of the world wide web (accessed Aug. 31, 2001), which includes PSORT, for prediction of protein sorting signals and localization sites, SignalP, for prediction of signal peptide cleavage sites, MITOPROT and Predotar, for prediction of mitochondrial targeting sequences, NetOGlyc, for prediction of type O-glycosylation sites in mammalian proteins, big-PI Predictor and DGPI, for prediction of prenylation-anchor and cleavage sites, and NetPhos, for prediction of Ser, Thr and Tyr phosphorylation sites in eukaryotic proteins. Other computer programs, such as those included in GcG, also may be used to determine post-translational modification peptide motifs.

General examplee of types of post-translational modifications may be found in web sites such as the Delta Mass database abrf.org/ABRF/Research Committees/deltamass/ deltamp.html of the world wide web (accessed Oct. 19, 2001); "GlycoSuiteDB: a new curated relational database of glycoprotein glycan structures and their biological sources" Cooper et al. Nucleic Acids Res. 29; 332–335 (2001) and glycosuite.com/ of the world wide web (accessed Oct. 19, 2001); "O-GLYCEASE version 4.0; a revised database of O-glycosylated proteins" Gupta at al. Nucleic Acids Research, 27; 370–372 (1999) and cbs.dtu.dk/databases/ OGLYCBASE/ of the world wide web (accessed Oct. 19, 2001); "Phosphobase, a database of phosphorylation sites: release 2.0.", Kreegipuu et al. Nucleic Acids Res 27(1):237–239 (1999) and cbs.dtu.dk/databases/PhosnhoBase/ of the world wide web (accessed Oct. 19, 2001); or pir.georgetown.edu/pirwww/search/textresid.html of the world wide web (accessed Oct. 19, 2001).

Tumorigenesis is often accompanied by alterations in the post-translational modifications of proteins. Thus, in another embodiment, the invention provides polypeptides from cancerous cells or tissues that have altered post-translational modifications compared to the post-translational modifications of polypeptides from normal cells or tissues. A number of altered post-translational modifications are known. One common alteration is a change in phosphorylation state, wherein the polypeptide from the cancerous cell or tissue is hyperphosphorylated or hypophosphorylated compared to the polypeptide from a normal tissue, or wherein the polypeptide is phosphorylated on different residues than the polypeptide from a normal cell. Another common alteration is a change in glycosylation state, wherein the polypeptide from the cancerous cell or tissue has more or less glycosylation than the polypeptide from a normal tissue, and/or wherein the polypeptide from the cancerous cell or tissue has a different type of glycosylation than the polypeptide from a noncancerous cell or tissue. Changes in glycosylation may be critical because carbohydrate-protein and carbohydrate-carbohydrate interactions are important in cancer cell progression, dissemination and invasion. See, e.g., Barchi, *Curr. Pharm. Des.* 6: 485–501 (2000), Verma, *Cancer Biochem. Biophys.* 14: 151–162 (1994) and Dennis et al., *Bioessays* 5: 412–421 (1999).

Another post-translational modification that may be altered in cancer cells is prenylation. Prenylation is the covalent attachment of a hydrophobic prenyl group (either famesyl or geranylgeranyl) to a polypeptide. Prenylation is required for localizing a protein to a cell membrane and is often required for polypeptide function. For instance, the Ras superfamily of GTPase signaling proteins must be prenylated for function in a cell. See, e.g., Prendergast et al., *Semin. Cancer Biol.* 10: 443–452 (2000) and Khwaja et al., *Lancet* 355: 741–744 (2000).

Other post-translation modifications that may be altered in cancer cells include, without limitation, polypeptide methylation, acetylation, arginylation or racemization of amino acid residues. In these cases, the polypeptide from the cancerous cell may exhibit either increased or decreased amounts of the post-translational modification compared to the corresponding polypeptides from noncancerous cells.

Other polypeptide alterations in cancer cells include abnormal polypeptide cleavage of proteins and aberrant protein-protein interactions. Abnormal polypeptide cleavage may be cleavage of a polypeptide in a cancerous cell that does not usually occur in a normal cell, or a lack of cleavage in a cancerous cell, wherein the polypeptide is cleaved in a normal cell. Aberrant protein-protein interactions may be either covalent cross-linking or non-covalent binding between proteins that do not normally bind to each other. Alternatively, in a cancerous cell, a protein may fail to bind to another protein to which it is bound in a noncancerous cell. Alterations in cleavage or in protein-protein interactions may be due to over- or underproduction of a polypeptide in a cancerous cell compared to that in a normal cell, or may be due to alterations in post-translational modifications (see above) of one or more proteins in the cancerous cell. See, e.g., Henschen-Edman, *Ann. N.Y. Acad. Sci.* 936: 580–593 (2001).

Alterations in polypeptide post-translational modifications, as well as changes in polypeptide cleavage and protein-protein interactions, may be determined by any method known in the art. For instance, alterations in phosphorylation may be determined by using anti-phosphoserine, anti-phosphothreonine or anti-phosphotyrosine antibodies or by amino acid analysis. Glycosylation alterations may be determined using antibodies specific for different sugar residues, by carbohydrate sequencing, or by alterations in the size of the glycoprotein, which can be determined by, e.g., SDS polyacrylamide gel electrophoresis (PAGE). Other alterations of post-translational modifications, such as prenylation, racemization, methylation, acetylation and arginylation, may be determined by chemical analysis, protein sequencing, amino acid analysis, or by using antibodies specific for the particular post-translational modifications. Changes in protein-protein interactions and in polypeptide cleavage may be analyzed by any method known in the art including, without limitation, non-denaturing PAGE (for non-covalent protein-protein interactions), SDS PAGE (for covalent protein-protein interactions and protein cleavage), chemical cleavage, protein sequencing or immunoassays.

In another embodiment, the invention provides polypeptidee that have been post-translationally modifisd. In one embodiment, polypeptides may be modified enzymatically or chemically, by addition or removal of a post-translational modification. For example, a polypeptide may be glyeosylated or deglycosylated enzymatically. Similarly, polypeptides may be phosphorylated using a purified kinase, such as a MAP kinase (e.g, p38, ERK, or JNK) or a tyrosine kinase (e.g., Src or erbB2). A polypeptide may also be modified through synthetic chemistry. Alternatively, one may isolate the polypeptide of interest from a cell or tissue that expresses the polypeptide with the desired post-translational modification. In another embodiment, a nucleic acid molecule encoding the polypeptide of interest is introduced into a host cell that is capable of post-translationally modifying the encoded polypeptide in the desired fashion. If the polypeptide does not contain a motif for a desired post-translational modification, one may alter the post-translational modification by mutating the nucleic acid sequence of a nucleic acid molecule encoding the polypeptide so that it contains a site for the desired post-translational modification. Amino acid sequences that may be post-translationally modified are known in the art. See, e.g., the programs described above on the website expasy.org of the world wide web. The nucleic acid molecule is then be introduced into a host cell that is capable of poet-translationally modifying the encoded polypeptide. Similarly, one may delete sites that are post-translationally modified by either mutating the nucleic acid sequence so that the encoded polypeptide does not contain the post-translational modification motif, or by introducing the native nucleic acid molecule into a host cell that is not capable of post-translationally modifying the encoded polypeptide.

In selecting an expression control sequence, a variety of factors should also be considered. These include, for example, the relative strength of the sequence, its controllability, and its compatibility with the nucleic acid sequence of this invention, particularly with regard to potential secondary structures. Unicellular hosts should be selected by consideration of their compatibility with the chosen vector, the toxicity of the product coded for by the nucleic acid sequences of this invention, their secretion characteristics, their ability to fold the polypeptide correctly, their fermentation or culture requirements, and the ease of purification from them of the products coded for by the nucleic acid sequences of this invention.

The recombinant nucleic acid molecules and more particularly, the expression vectors of this invention may be used to express the polypeptides of this invention as recombinant polypeptides in a heterologous host cell. The polypeptides of this invention may be full-length or less than full-length polypeptide fragments recombinantly expressed from the nucleic acid sequences according to this invention. Such polypeptides include analogs, derivatives and muteins that may or may not have biological activity.

Vectors of the present invention will also often include elements that permit in vitro transcription of RNA from the inserted heterologous nucleic acid. Such vectors typically include a phage promoter, such as that from T7, T3, or SP6, flanking the nucleic acid insert. Often two different such promoters flank the inserted nucleic acid, permitting separate in vitro production of both sense and antisense strands.

Transformation and other methods of introducing nucleic acids into a host cell (e.g., conjugation, protoplast transformation or fusion, transfection, electroporation, liposome delivery, membrane fusion techniques, high velocity DNA-coated pellets, viral infection and protoplast fusion) can be accomplished by a variety of methods which are well-known in the art (See, for instance, Ausubel, supra, and Sambrook et al., supra). Bacterial, yeast, plant or mammalian cells are transformed or transfected with an expression vector, such as a plasmid, a cosmid, or the like, wherein the expression vector comprises the nucleic acid of interest. Alternatively, the cells may be infected by a viral expression vector comprising the nucleic acid of interest. Depending upon the host cell, vector, and method of transformation used, transient or stable expression of the polypeptide will be constitutive or inducible. One having ordinary skill in the art will be able to decide whether to express a polypeptide transiently or stably, and whether to express the protein constitutively or inducibly.

A wide variety of unicellular host cells are useful in expressing the DNA sequences of this invention. These hosts may include well-known eukaryotic and prokaryotic hosts, such as strains of, fungi, yeast, insect cells such as *Spodoptera frugiperda* (SF9), animal cells such as CHO, as well as plant cells in tissue culture. Representative examples of appropriate host cells include, but are not limited to, bacterial cells, such as *E. coli, Caulobacter crescentus, Streptomyces* species, and *Salmonella typhimurium*; yeast cells, such as *Saccharomyces cerevisiae, Schizosaccharomyces pombe, Pichia pastoris, Pichia methanolica*; insect cell lines, such as those from *Spodoptera frugiperda*, e.g., Sf9 and Sf21 cell lines, and expresSF™ cells (Protein Sciences Corp., Meriden, Conn., USA), Drosophila S2 cells, and *Trichoplusia ni* High Five® Cells (Invitrogen, Carlsbad, Calif., USA); and mammalian cells. Typical mammalian cells include BHK cells, BSC 1 cells, BSC 40 cells, BMT 10 cells, VERO cells, COS1 cells, COS7 cells, Chinese hamster ovary (CHO) cells, 3T3 cells, NIH 3T3 cells, 293 cells, HEPG2 cells, HeLa cells, L cells, MDCK cells, HEK293 cells, WI38 cells, murine ES cell lines (e.g., from strains 129/SV, C57/BL6, DBA-1, 129/SVJ), K562 cells, Jurkat cells, and BW5147 cells. Other mammalian cell lines are well-known and readily available from the American Type Culture Collection (ATCC) (Manassas, Va., USA) and the National Institute of General Medical Sciences (NIGMS) Human Genetic Cell Repository at the Coriell Cell Repositories (Camden, N.J., USA). Cells or cell lines derived from lung are particularly preferred because they may provide a more native post-translational processing. Particularly preferred are human lung cells.

Particular details of the transfection, expression and purification of recombinant proteins are well documented and are understood by those of skill in the art. Further details on the various technical aspects of each of the steps used in recombinant production of foreign genes in bacterial cell expression systems can be found in a number of texts and laboratory manuals in the art. See, e.g., Ausubel (1992), supra, Ausubel (1999), supra, Sambrook (1989), supra, and Sambrook (2001), supra, herein incorporated by reference.

Methods for introducing the vectors and nucleic acids of the present invention into the host cells are well-known in the art; the choice of technique will depend primarily upon the specific vector to be introduced and the host cell chosen.

Nucleic acid molecules and vectors may be introduced into prokaryotes, such as E. coli, in a number of ways. For instance, phage lambda vectors will typically be packaged using a packaging extract (e.g., Gigapack® packaging extract, Stratagene, La Jolla, Calif., USA), and the packaged virus used to infect E. coli.

Plasmid vectors will typically be introduced into chemically competent or electrocompetent bacterial cells. E. coil cells can be rendered chemically competent by treatment, e.g., with $CaCl_2$, or a solution of $Mg^{2-}$, $Mn^{2+}$, $Ca^{2+}$, $Rb^+$ or $K^+$, dimethyl sulfoxide, dithiothreitol, and hexamine cobalt (III), Hanahan, J. Mol. Biol. 166 (4):557–80 (1983), and vectors introduced by heat shock. A wide variety of chemically competent strains are also available commercially (e.g., *Epicurian Coli@* XL10-Gold@ Ultracompetent Cells (Stratagene, La Jolla, Calif., USA); DH5α competent cells (Clontech Laboratories, Palo Alto, Calif., USA); and TOP10 Chemically Competent *E. coli* Kit (Invitrogen, Carlsbad, Calif., USA)). Bacterial cells can be rendered electrocompetent, that is, competent to take up exogenous DNA by electroporation, by various pre-pulse treatments; vectors are introduced by electroporation followed by subsequent outgrowth in selected media. An extensive series of protocols is provided online in Electroprotocols (BioRad, Richmond, Calif., USA) biorad.com/Lifescience/pdf/New_Gene_Pulser.pdf of the world wide web).

Vectors can be introduced into yeast cells by spheroplasting, treatment with lithium salts, electroporation, or protoplast fusion. Spheroplasts are prepared by the action of hydrolytic enzymes such as snail-gut extract, usually denoted Glusulase, or Zymolyase, an enzyme from *Arthrobacter luteus*, to remove portions of the cell wall in the presence of osmotic stabilizers, typically 1 M sorbitol. DNA is added to the spheroplasts, and the mixture is co-precipitated with a solution of polyethylene glycol (PEG) and $Ca^{2+}$. Subsequently, the cells are resuspended in a solution of sorbitol, mixed with molten agar and then layered on the surface of a selective plate containing sorbitol.

For lithium-mediated transformation, yeast cells are treated with lithium acetate, which apparently permeabilizes the cell wall, DNA is added and the cells are co-precipitated with PEG. The cells are exposed to a brief heat shock, washed free of PEG and lithium acetate, and subsequently spread on plates containing ordinary selective medium. Increased frequencies of transformation are obtained by using specially-prepared single-stranded carrier DNA and certain organic solvents. Schiestl et al., *Curr. Genet.* 16(5–6): 339–46 (1989).

For electroporation, freshly-grown yeast cultures are typically washed, suspended in an osmotic protectant, such as sorbitol, mixed with DNA, and the cell suspension pulsed in an electroporation device. Subsequently, the cells are spread on the surface of plates containing selective media. Becker et al., *Methods Enzymol.* 194: 182–187 (1991). The efficiency of transformation by electroporation can be increased over 100-fold by using PEG, single-stranded carrier DNA and cells that are in late log-phase of growth. Larger constructs, such as YACs, can be introduced by protoplast fusion.

Mammalian and insect cells can be directly infected by packaged viral vectors, or transfected by chemical or electrical means. For chemical transfection, DNA can be coprecipitated with $CaPO_4$ or introduced using liposomal and nonliposomal lipid-based agents. Commercial kits are available for $CaPO_4$ transfection (CalPhos™ Mammalian Transfection kit, Clontech Laboratories, Palo Alto, Calif., USA), and lipid-mediated transfection can be practiced using commercial reagents, such as LIPOFECTAMINE™ 2000, LIPOFECTAMINE™ Reagent, CELLFECTIN™ Reagent, and LIPOFECTIN™ Reagent (Invitrogen, Carlsbad, Calif. USA), DOTAP Liposomal Transfection Reagent, FuGENE 6, X-tremeGENE Q2, DOSPER, (Roche Molecular Biochemicals, Indianapolis, Ind. USA) Effectene™, PolyFect™, Superfect™ (Qiagen, Inc., Valencia, Calif., USA). Protocols for electroporating mammalian cells can be found online in Electroprotocols (Bio-Rad, Richmond, Calif, USA) bio-rad.com/Lifescience/pdf/New_Gene_Pulser.pdf of the world wide web); Norton et al. (eds.), Gene Transfer Methods: Introducing DNA into Living Cells and Organisms, BioTechniques Books, Eaton Publishing Co. (2000); incorporated herein by reference in its entirety. Other transfection techniques include transfection by particle bombardment and microinjection. See, e.g., Cheng et al., Proc. Natl. Acad. Sci. USA 90(10): 4455–9 (1993); Yang et al., Proc. Natl. Acad. Sci. USA 87 (24): 9568–72 (1990).

Production of the recombinantly produced proteins of the present invention can optionally be followed by purification.

Purification of recombinantly expressed proteins is now well by those skilled in the art. See, e.g., Thorner et al. (eds.), *Applications of Chimeric Genes and Hybrid Proteins, Part A: Gene Expression and Protein Purification* (Methods in Enzymology, Vol. 326), Academic Press (2000); Harbin (ed.), *Cloning, Gene Expression and Protein Purification: Experimental Procedures and Process Rationale*, Oxford Univ. Press (2001); Marshak et al, *Strategies for Protein Purification and Characterization: A Laboratory Course Manual*, Cold Spring Harbor Laboratory Press (1996); and Roe (ed.), *Protein Purification Applications*, Oxford University Press (2001); the disclosures of which are incorporated herein by reference in their entireties, and thus need not be detailed here.

Briefly, however, if purification tags have been fused through use of an expression vector that appends such tags, purification can be effected, at least in part, by means appropriate to the tag, such as use of immobilized metal affinity chromatography for polyhistidine tags. Other techniques common in the art include ammonium sulfate fractionation, immunoprecipitation, fast protein liquid chromatography (FPLC), high performance liquid chromatography (HPLC), and preparative gel electrophoresis.

Polypeptides

Another object of the invention is to provide polypeptides encoded by the nucleic acid molecules of the instant invention. In a preferred embodiment, the polypeptide is a lung specific polypeptide (LSP). In an even more preferred embodiment, the polypeptide is derived from a polypeptide comprising the amino acid sequence of SEQ ID NO: 143 through 277. A polypeptide as defined herein may be produced recombinantly, as discussed supra, may be isolated from a cell that naturally expresses the protein, or may be chemically synthesized following the teachings of the specification and using methods well-known to those having ordinary skill in the art.

In another aspect, the polypeptide may comprise a fragment of a polypeptide, wherein the fragment is as defined herein. In a preferred embodiment, the polypeptide fragment is a fragment of an LSP. In a more preferred embodiment, the fragment is derived from a polypeptide comprising the amino acid sequence of SEQ ID NO: 143 through 277. A polypeptide that comprises only a fragment of an entire LSP may or may not be a polypeptide that is also an LSP. For instance, a full-length polypeptide may be lung-specific, while a fragment thereof may be found in other tissues as well as in lung. A polypeptide that is not an LSP, whether it is a fragment, analog, mutein, homologous protein or derivative, is nevertheless useful, especially for immunizing animals to prepare anti-LSP antibodies. However, in a preferred embodiment, the part or fragment is an LSP. Methods of determining whether a polypeptide is an LSP are described infra.

Fragments of at least 6 contiguous amino acids are useful in mapping B cell and T cell epitopes of the reference protein. See, e.g., Geysen et al., *Proc. Natl. Acad. Sci. USA* 81: 3998–4002 (1984) and U.S. Pat. Nos. 4,708,871 and 5,595,915, the disclosures of which are incorporated herein by reference in their entireties. Because the fragment need not itself be immunogenic, part of an immunodominant epitope, nor even recognized by native antibody, to be useful in such epitope mapping, all fragments of at least 6 amino acids of the proteins of the present invention have utility in such a study.

Fragments of at least 8 contiguous amino acids, often at least 15 contiguous amino acids, are useful as immunogens for raising antibodies that recognize the proteins of the present invention. See, e.g., Lemer, Nature 299: 592–596 (1982); Shinnick et al., *Annu. Rev. Microbiol.* 37: 425–46 (1983); Sutcliffe et al, *Science* 219: 660–6 (1983), the disclosures of which are incorporated herein by reference in their entireties. As further described in the above-cited references, virtually all 8-mers, conjugated to a carrier, such as a protein, prove immunogenic, meaning that they are capable of eliciting antibody for the conjugated peptide; accordingly, all fragments of at least 8 amino acids of the proteins of the present invention have utility as immunogens.

Fragments of at least 8, 9, 10 or 12 contiguous amino acids are also useful as competitive inhibitors of binding of the entire protein, or a portion thereof, to antibodies (as in epitope mapping), and to natural binding partners, such as subunits in a multimeric complex or to receptors or ligands of the subject protein; this competitive inhibition permits identification and separation of molecules that bind specifically to the protein of interest, U.S. Pat. Nos. 5,539,084 and 5,783,674, incorporated herein by reference in their entireties.

The protein, or protein fragment, of the present invention is thus at least 6 amino acids in length, typically at least 8, 9, 10 or 12 amino acids in length, and often at least 15 amino acids in length. Often, the protein of the present invention, or fragment thereof, is at least 20 amino acids in length, even 25 amino acids, 30 amino acids, 35 amino acids, or 50 amino acids or more in length. Of course, larger fragments having at least 75 amino acids, 100 amino acids, or even 150 amino acids are also useful, and at times preferred.

One having ordinary skill in the art can produce fragments of a polypeptide by truncating the nucleic acid molecule, e.g., an LSNA, encoding the polypeptide and then expressing it recombinantly. Alternatively, one can produce a fragment by chemically synthesizing a portion of the full-length polypeptide. One may also produce a fragment by enzymatically cleaving either a recombinant polypeptide or an isolated naturally-occurring polypeptide. Methods of producing polypeptide fragments are well-known in the art. See, e.g., Sambrook (1989), supra; Sambrook (2001), supra; Ausubel (1992), supra; and Ausubel (1999), supra. In one embodiment, a polypeptide comprising only a fragment of polypeptide of the invention, preferably an LSP, may be produced by chemical or enzymatic cleavage of a polypeptide. In a preferred embodiment, a polypeptide fragment is produced by expressing a nucleic acid molecule encoding a fragment of the polypeptide, preferably an LSP, in a host cell.

By "polypeptides" as used herein it is also meant to be inclusive of mutants, fusion proteins, homologous proteins and allelic variants of the polypeptides specifically exemplified.

A mutant protein, or mutein, may have the same or different properties compared to a naturally-occurring polypeptide and comprises at least one amino acid insertion, duplication, deletion, rearrangement or substitution compared to the amino acid sequence of a native protein. Small deletions and insertions can often be found that do not alter the function of the protein. In one embodiment, the mutein may or may not be lung-specific. In a preferred embodiment, the mutein is lung-specific. In a preferred embodiment, the mutein is a polypeptide that comprises at least one amino acid insertion, duplication, deletion, rearrangement or substitution compared to the amino acid sequence of SEQ ID NO: 143 through 277. In a more preferred embodiment, the mutein is one that exhibits at least 50% sequence identity, more preferably at least 60% sequence identity, even more preferably at least 70%, yet more preferably at least 80% sequence identity to an LSP comprising an amino acid sequence of SEQ ID NO: 143 through 277. In yet a more preferred embodiment, the mutein exhibits at least 85%, more preferably 90%, even more preferably 95% or 96%, and yet more preferably at least 97%, 98%, 99% or 99.5% sequence identity to an LSP comprising an amino acid sequence of SEQ ID NO: 143 through 277.

A mutein may be produced by isolation from a naturally-occurring mutant cell, tissue or organism. A mutein may be produced by isolation from a cell, tissue or organism that has been experimentally mutagenized. Alternatively, a mutein may be produced by chemical manipulation of a polypeptide, such as by altering the amino acid residue to another amino acid residue using synthetic or semi-synthetic chemical techniques. In a preferred embodiment, a mutein may be produced from a host cell comprising an altered nucleic acid molecule compared to the naturally-occurring nucleic acid molecule. For instance, one may produce a mutein of a polypeptide by introducing one or more mutations into a nucleic acid sequence of the invention and then expressing it recombinantly. These mutations may be targeted, in which particular encoded amino acids are altered, or may be untargeted, in which random encoded amino acids within the polypeptide are altered. Muteins with random amino acid alterations can be screened for a particular biological activity or property, particularly whether the polypeptide is lung-specific, as described below. Multiple random mutations can be introduced into the gene by methods well-known to the art, e.g., by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis and site-specific mutagenesis. Methods of producing muteins with targeted or random amino acid alterations are well-known in the art. See, e.g., Sambrook (1989), supra; Sambrook (2001), supra; Ausubel (1992), supra; and Ausubel (1999), U.S. Pat. No. 5,223,408, and the references discussed supra, each herein incorporated by reference.

By "polypeptide" as used herein it is also meant to be inclusive of polypeptides homologous to those polypeptides exemplified herein. In a preferred embodiment, the polypeptide is homologous to an LSP. In an even more preferred embodiment, the polypeptide is homologous to an LSP selected from the group having an amino acid sequence of SEQ ID NO: 143 through 277. In a preferred embodiment, the homologous polypeptide is one that exhibits significant sequence identity to an LSP. In a more preferred embodiment, the polypeptide is one that exhibits significant sequence identity to an comprising an amino acid sequence of SEQ ID NO: 143 through 277. In an even more preferred embodiment, the homologous polypeptide is one that exhibits at least 50% sequence identity, more preferably at least 60% sequence identity, even more preferably at least 70%, yet more preferably at least 80% sequence identity to an LSP comprising an amino acid sequence of SEQ ID NO: 143 through 277. In a yet more preferred embodiment, the homologous polypeptide is one that exhibits at least 85%, more preferably 90%, even more preferably 95% or 96%, and yet more preferably at least 97% or 98% sequence identity to an LSP comprising an amino acid sequence of SEQ ID NO: 143 through 277. In another preferred embodiment, the homologous polypeptide is one that exhibits at least 99%, more preferably 99.5%, even more preferably 99.6%, 99.7%, 99.8% or 99.9% sequence identity to an LSP comprising an amino acid sequence of SEQ ID NO: 143 through 277. In a preferred embodiment, the amino acid substitutions are conservative amino acid substitutions as discussed above.

In another embodiment, the homologous polypeptide is one that is encoded by a nucleic acid molecule that selectively hybridizes to an LSNA. In a preferred embodiment, the homologous polypeptide is encoded by a nucleic acid molecule that hybridizes to an LSNA under low stringency, moderate stringency or high stringency conditions, as defined herein. In a more preferred embodiment, the LSNA is selected from the group consisting of SEQ ID NO: 1 through 142. In another preferred embodiment, the homologous polypeptide is encoded by a nucleic acid molecule that hybridizes to a nucleic acid molecule that encodes an LSP under low stringency, moderate stringency or high stringency conditions, as defined herein. In a more preferred embodiment, the LSP is selected from the group consisting of SEQ ID NO: 143 through 277.

The homologous polypeptide may be a naturally-occurring one that is derived from another species, especially one derived from another primate, such as chimpanzee, gorilla, rhesus macaque, baboon or gorilla, wherein the homologous polypeptide comprises an amino acid sequence that exhibits significant sequence identity to that of SEQ ID NO: 143 through 277. The homologous polypeptide may also be a naturally-occuring polypeptide from a human, when the LSP is a member of a family of polypeptides. The homologous polypeptide may also be a naturally-occurring polypeptide derived from a non-primate, mammalian species, including without limitation, domesticated species, e.g., dog, cat, mouse, rat, rabbit, guinea pig, hamster, cow, horse, goat or pig. The homologous polypeptide may also be a naturally-occurring polypeptide derived from a non-mammalian species, such as birds or reptiles. The naturally-occurring homologous protein may be isolated directly from humans or other species. Alternatively, the nucleic acid molecule encoding the naturally-occurring homologous polypeptide may be isolated and used to express the homologous polypeptide recombinantly. In another embodiment, the homologous polypeptide may be one that is experimentally produced by random mutation of a nucleic acid molecule and subsequent expression of the nucleic acid molecule. In another embodiment, the homologous polypeptide may be one that is experimentally produced by directed mutation of one or more codons to alter the encoded amino acid of an LSP. Further, the homologous protein may or may not encode polypeptide that is an LSP. However, in a preferred embodiment, the homologous polypeptide encodes a polypeptide that is an LSP.

Relatedness of proteins can also be characterized using a second functional test, the ability of a first protein competitively to inhibit the binding of a second protein to an antibody. It is, therefore, another aspect of the present invention to provide isolated proteins not only identical in sequence to those described with particularity herein, but also to provide isolated proteins ("cross-reactive proteins") that competitively inhibit the binding of antibodies to all or to a portion of various of the isolated polypeptides of the present invention. Such competitive inhibition can readily be determined using immunoassays well-known in the art.

As discussed above, single nucleotide polymorphisms (SNPs) occur frequently in eukaryotic genomes, and the sequence determined from one individual of a species may differ from other allelic forms present within the population. Thus, by "polypeptide" as used herein it is also meant to be inclusive of polypeptides encoded by an allelic variant of a nucleic acid molecule encoding an LSP. In a preferred embodiment, the polypeptide is encoded by an allelic variant of a gene that encodes a polypeptide having the amino acid sequence selected from the group consisting of SEQ ID NO: 143 through 277. In a yet more preferred embodiment, the polypeptide is encoded by an allelic variant of a gene that has the nucleic acid sequence selected from the group consisting of SEQ ID NO: 1 through 142.

In another embodiment, the invention provides polypeptides which comprise derivatives of a polypeptide encoded by a nucleic acid molecule according to the instant invention. In a preferred embodiment, the polypeptide is an LSP. In a preferred embodiment, the polypeptide has an amino acid sequence selected from the group consisting of SEQ ID NO: 143 through 277, or is a mutein, allelic variant, homologous protein or fragment thereof. In a preferred embodiment, the derivative has been acetylated, carboxylated, phosphorylated, glycosylated or ubiquitinated. In another preferred embodiment, the derivative has been labeled with, e.g., radioactive isotopes such as $^{125}$I, $^{32}$P, $^{35}$S, and $^3$H. In another preferred embodiment, the derivative has been labeled with fluorophores, chemiluminescent agents, enzymes, and antiligands that can serve as specific binding pair members for a labeled ligand.

Polypeptide modifications are well-known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance Creighton, *Protein Structure and Molecular Properties*, 2nd ed., W. H. Freeman and Company (1993). Many detailed reviews are available on this subject, such as, for example, those provided by Wold, in Johnson (ed.), *Posttranslational Covalent Modification of Proteins*, pgs. 1–12, Academic Press (1983); Seifter et al., *Meth. Enzymol.* 182: 626–646 (1990) and Rattan et al., *Ann. N.Y. Acad. Sci.* 663: 48–62 (1992).

It will be appreciated, as is well-known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to proteolytic processing, almost invariably will be N-formylmethionine.

Useful post-synthetic (and post-translational) modifications include conjugation to detectable labels, such as fluorophores. A wide variety of amine-reactive and thiol-reactive fluorophore derivatives have been synthesized that react under nondenaturing conditions with N-terminal amino groups and epsilon amino groups of lysine residues, on the one hand, and with free thiol groups of cysteine residues, on the other.

Kits are available commercially that permit conjugation of proteins to a variety of amine-reactive or thiol-reactive fluorophores: Molecular Probes, Inc. (Eugene, Oreg., USA), e.g., offers kits for conjugating proteins to Alexa Fluor 350, Alexa Fluor 430, Fluorescein-EX, Alexa Fluor 488, Oregon Green 488, Alexa Fluor 532, Alexa Fluor 546, Alexa Fluor 546, Alexa Fluor 568, Alexa Fluor 594, and Texas Red-X.

A wide variety of other amine-reactive and thiol-reactive fluorophores are available commercially (Molecular Probes, Inc., Eugene, Oreg., USA), including Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA).

The polypeptides of the present invention can also be conjugated to fluorophores, other proteins, and other macromolecules, using bifunctional linking reagents. Common homobifunctional reagents include, e.g., APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS (all available from Pierce, Rockford, Ill., USA); common heterobifunctional cross-linkers include ABH, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, M2C2H, MPBH, MSA, NHS-ASA, PDPH, PMPI, SADP, SAED, SAND, SANPAH, SASD, SATP, SBAP, SFAD, SIA, SIAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS, Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS (all available Pierce, Rockford, Ill., USA).

The polypeptides, fragments, and fusion proteins of the present invention can be conjugated, using such cross-linking reagents, to fluorophores that are not amine- or thiol-reactive. Other labels that usefully can be conjugated to the polypeptides, fragments, and fusion proteins of the present invention include radioactive labels, echosonographic contrast reagents, and MRI contrast agents.

The polypeptides, fragments, and fusion proteins of the present invention can also usefully be conjugated using cross-linking agents to carrier proteins, such as KLH, bovine thyroglobulin, and even bovine serum albumin (BSA), to increase immunogenicity for raising anti-LSP antibodies.

The polypeptides, fragments, and fusion proteins of the present invention can also usefully be conjugated to polyethylene glycol (PEG); PEGylation increases the serum half-life of proteins administered intravenously for replacement therapy. Delgado et al., *Crit. Rev. Ther. Drug Carrier Syst.* 9(3–4): 249–304 (1992); Scott et al., *Curr. Pharm. Des.* 4(6): 423–38 (1998); DeSantis et al., *Curr. Opin. Biotechnol.* 10(4): 324–30 (1999) incorporated herein by reference in their entireties. PEG monomers can be attached to the protein directly or through a linker, with PEGylation using PEG monomers activated with tresyl chloride (2,2,2-trifluoroethanesulphonyl chloride) permitting direct attachment under mild conditions.

In yet another embodiment, the invention provides analogs of a polypeptide encoded by a nucleic acid molecule according to the instant invention. In a preferred embodiment, the polypeptide is an LSP. In a more preferred embodiment, the analog is derived from a polypeptide having part or all of the amino acid sequence of SEQ ID NO: 143 through 277. In a preferred embodiment, the analog is one that comprises one or more substitutions of non-natural amino acids or non-native inter-residue bonds compared to the naturally-occurring polypeptide. In general, the non-peptide analog is structurally similar to an LSP, but one or more peptide linkages is replaced by a linkage selected from the group consisting of —$CH_2NH$—, —$CH_2S$—, —$CH_2$—$CH_2$—, —CH=CH-(cis and trans), —$COCH_2$—, —CH(OH)$CH_2$— and —$CH_2SO$—. In another embodiment, the non-peptide analog comprises substitution of one or more amino acids of an LSP with a D-amino acid of the same type or other non-natural amino acid in order to generate more stable peptides. D-amino acids can readily be incorporated during chemical peptide synthesis: peptides assembled from D-amino acids are more resistant to aproteolytic attack; incorporation of D-amino acids can also be used to confer specific three-dimensional conformations on the peptide. Other amino acid analogues commonly added during chemical synthesis include ornithine, norleucine, phosphorylated amino acids (typically phosphoserine, phosphothreonine, phosphotyrosine), L-malonyltyrosine, a non-hydrolyzable analog of phosphotyrosine (see, e.g., Kole et al., *Biochem. Biophys. Res. Com.* 209: 817–821 (1995)), and various halogenated phenylalanine derivatives.

Non-natural amino acids can be incorporated during solid phase chemical synthesis or by recombinant techniques, although the former is typically more common. Solid phase chemical synthesis of peptides is well established in the art. Procedures are described, inter alia, in Chan et al. (eds.), *Fmoc Solid Phase Peptide Synthesis: A Practical Approach* (Practical Approach Series), Oxford Univ. Press (March 2000); Jones, *Amino Acid and Peptide Synthesis* (Oxford Chemistry Primers, No 7), Oxford Univ. Press (1992); and Bodanszky, *Principles of Peptide Synthesis* (Springer Laboratory), Springer Verlag (1993); the disclosures of which are incorporated herein by reference in their entireties.

Amino acid analogues having detectable labels are also usefully incorporated during synthesis to provide derivatives and analogs. Biotin, for example can be added using biotinoyl-(9-fluorenylmethoxycarbonyl)-L-lysine (FMOC biocytin) (Molecular Probes, Eugene, Oreg., USA). Biotin can also be added enzymatically by incorporation into a fusion protein of a *E. coli* BirA substrate peptide. The FMOC and tBOC derivatives of dabcyl-L-lysine (Molecular Probes, Inc., Eugene, Oreg., USA) can be used to incorporate the dabcyl chromophore at selected sites in the peptide sequence during synthesis. The aminonaphthalene derivative EDANS, the most common fluorophore for pairing with the dabcyl quencher in fluorescence resonance energy transfer (FRET) systems, can be introduced during automated synthesis of peptides by using EDANS-FMOC-L-glutamic acid or the corresponding tBOC derivative (both from Molecular Probes, Inc., Eugene, Oreg., USA). Tetramethyl-rhodamine fluorophores can be incorporated during automated FMOC synthesis of peptides using (FMOC)-TMR-L-lysine (Molecular Probes, Inc. Eugene, Oreg., USA).

Other useful amino acid analogues that can be incorporated during chemical synthesis include aspartic acid, glutamic acid, lysine, and tyrosine analogues having allyl side-chain protection (Applied Biosystems, Inc., Foster City, Calif., USA); the allyl side chain permits synthesis of cyclic, branched-chain, sulfonated, glycosylated, and phosphorylated peptides.

A large number of other FMOC-protected non-natural amino acid analogues capable of incorporation during chemical synthesis are available commercially, including, e.g., Fmoc-2-aminobicyclo[2.2.1]heptane-2-carboxylic acid, Fmoc-3-endo-aminobicyclo[2.2.1]heptane-2-endo-carboxylic acid, Fmoc-3-exo-aminobicyclo[2.2.1]heptane-2-exo-carboxylic acid, Fmoc-3-endo-amino-bicyclo[2.2.1]hept-5-ene-2-endo-carboxylic acid, Fmoc-3-exo-amino-bicyclo[2.2.1]hept-5-ene-2-exo-carboxylic acid, Fmoc-cis-2-amino-1-cyclohexanecarboxylic acid, Fmoc-trans-2-amino-1-cyclohexanecarboxylic acid, Fmoc-1-amino-1-cyclopentanecarboxylic acid, Fmoc-cis-2-amino-1-cyclopentanecarboxylic acid, Fmoc-1-amino-1-cyclopropanecarboxylic acid, Fmoc-D-2-amino-4-(ethylthio)butyric acid, Fmoc-L-2-amino-4-(ethylthio) butyric acid, Fmoc-L-buthionine, Fmoc-S-methyl-L-Cysteine, Fmoc-2-aminobenzoic acid (anthranillic acid), Fmoc-3-aminobenzoic acid, Fmoc-4-aminobenzoic acid, Fmoc-2-aminobenzophenone-2'-carboxylic acid, Fmoc-N-(4-aminobenzoyl)-β-alanine, Fmoc-2-amino-4,5-dimethoxybenzoic acid, Fmoc-4-aminohippuric acid, Fmoc-2-amino-3-hydroxybenzoic acid, Fmoc-2-amino-5-hydroxybenzoic acid, Fmoc-3-amino-4-hydroxybenzoic acid, Fmoc-4-amino-3-hydroxybenzoic acid, Fmoc-4-amino-2-hydroxybenzoic acid, Fmoc-5-amino-2-hydroxybenzoic acid, Fmoc-2-amino-3-methoxybenzoic acid, Fmoc-4-amino-3-methoxybenzoic acid, Fmoc-2-amino-3-methylbenzoic acid, Fmoc-2-amino-5-methoxybenzoic acid, Fmoc-2-amino-6-methylbenzoic acid, Fmoc-3-amino-2-methoxybenzoic acid, Fmoc-3-amino-4-methylbenzoic acid, Fmoc-4-amino-3-methoxybenzoic acid, Fmoc-3-amino-2-naphtoic acid, Fmoc-D,L-3-amino-3-phenylpropionic acid, Fmoc-L-Methyldopa, Fmoc-2-amino-4,6-dimethyl-3-pyridinecarboxylic acid, Fmoc-D,L-amino-2-thiophenacetic acid, Fmoc-4-(carboxymethyl)piperazine, Fmoc-4-carboxypiperazine, Fmoc-4-(carboxymethyl) homopiperazine, Fmoc-4-phenyl-4-piperidinecarboxylic acid, Fmoc-Loc-1,2,3,4-tetrahydronorharman-3-carboxylic acid, Fmoc-L-thiazolidine-4-carboxylic acid, all available from The Peptide Laboratory (Richmond, Calif., USA).

Non-natural residues can also be added biosynthetically by engineering a suppressor tRNA, typically one that recognizes the UAG stop codon, by chemical aminoacylation with the desired unnatural amino acid. Conventional site-directed mutagenesis is used to introduce the chosen stop codon UAG at the site of interest in the protein gene. When the acylated suppressor tRNA and the mutant gene are combined in an in vitro transcription/translation system, the unnatural amino acid is incorporated in response to the UAG codon to give a protein containing that amino acid at the specified position. Liu et al., *Proc. Natl Acad. Sci. USA* 96(9): 4780–5 (1999); Wang et al., *Science* 292(5516): 498–500 (2001).

Fusion Proteins

The present invention further provides fusions of each of the polypeptides and fragments of the present invention to heterologous polypeptides. In a preferred embodiment, the polypeptide is an LSP. In a more preferred embodiment, the polypeptide that is fused to the heterologous polypeptide comprises part or all of the amino acid sequence of SEQ ID NO: 143 through 277, or is a mutein, homologous polypeptide, analog or derivative thereof. In an even more preferred embodiment, the nucleic acid molecule encoding the fusion protein comprises all or part of the nucleic acid sequence of SEQ ID NO: 1 through 142, or comprises all or part of a nucleic acid sequence that selectively hybridizes or is homologous to a nucleic acid molecule comprising a nucleic acid sequence of SEQ ID NO: 1 through 142.

The fusion proteins of the present invention will include at least one fragment of the protein of the present invention, which fragment is at least 6, typically at least 8, often at least 15, and usefully at least 16, 17, 18, 19, or 20 amino acids long. The fragment of the protein of the present to be included in the fusion can usefully be at least 25 amino acids long, at least 50 amino acids long, and can be at least 75, 100, or even 150 amino acids long. Fusions that include the entirety of the proteins of the present invention have particular utility.

The heterologous polypeptide included within the fusion protein of the present invention is at least 6 amino acids in length, often at least 8 amino acids in length, and usefully at least 15, 20, and 25 amino acids in length. Fusions that include larger polypeptides, such as the IgG Fc region, and even entire proteins (such as GFP chromophore-containing proteins) are particular useful.

As described above in the description of vectors and expression vectors of the present invention, which discussion is incorporated here by reference in its entirety, heterologous polypeptides to be included in the fusion proteins of the present invention can usefully include those designed to facilitate purification and/or visualization of recombinantly-expressed proteins. See, e.g., Ausubel, Chapter 16, (1992), supra. Although purification tags can also be incorporated into fusions that are chemically synthesized, chemical synthesis typically provides sufficient purity that further purification by HPLC suffices; however, visualization tags as above described retain their utility even when the protein is produced by chemical synthesis, and when so included render the fusion proteins of the present invention useful as directly detectable markers of the presence of a polypeptide of the invention.

As also discussed above, heterologous polypeptides to be included in the fusion proteins of the present invention can usefully include those that facilitate secretion of recombinantly expressed proteins—into the periplasmic space or extracellular milieu for prokaryotic hosts, into the culture medium for eukaryotic cells—through incorporation of secretion signals and/or leader sequences. For example, a His$^6$ tagged protein can be purified on a Ni affinity column and a GST fusion protein can be purified on a glutathione affinity column. Similarly, a fusion protein comprising the Fc domain of IgG can be purified on a Protein A or Protein G column and a fusion protein comprising an epitope tag such as myc can be purified using an immunoaffinity column containing an anti-c-myc antibody. It is preferable that the epitope tag be separated from the protein encoded by the essential gene by an enzymatic cleavage site that can be cleaved after purification. See also the discussion of nucleic acid molecules encoding fusion proteins that may be expressed on the surface of a cell.

Other useful protein fusions of the present invention include those that permit use of the protein of the present invention as bait in a yeast two-hybrid system. See Bartel et al. (eds.), *The Yeast Two-Hybrid System*, Oxford University Press (1997); Zhu et al., *Yeast Hybrid Technologies*, Eaton Publishing (2000); Fields et al., *Trends Genet.* 10(8): 286–92 (1994); Mendelsohn et al., *Curr. Opin. Biotechnol.* 5(5): 482–6 (1994); Luban et al., *Curr. Opin. Biotechnol.* 6(1): 59–64 (1995); Allen et al, *Trends Biochem. Sci.* 20(12): 511–6 (1995); Drees, *Curr. Opin. Chem. Biol.* 3(1): 64–70 (1999); Topcu et al., *Pharm. Res.* 17(9): 1049–55 (2000); Fashena et al., *Gene* 250(1–2): 1–14(2000);; Colas et al., (1996) Genitic selection of peptide aptamers that recognize and inhibit cyclin-dependent kinase 2. *Nature* 380, 548–550; Noorman, T. et al., (1999) Genitic selection of peptide inhibitors of biological pathways. *Science* 285, 591–595, Fabbrizio et al, (1999) Inhibition of mammalian cell proliferation by genetically selected peptide aptamers that functionally antagonize E2F activity. *Oncogene* 18, 4357–4363; Xu et al., (1997) Cells that register logical relationships among proteins. *Proc Natl Acad Sci USA*. 94, 12473–12478; Yang, et al., (1995) Protein-peptide interactions analyzed with the yeast two-hybrid system. *Nuc. Acids Res.* 23, 1152–1156; Kolonin et al., (1998) Targeting cyclin-dependent kinases in Drosophila with peptide aptamers. *Proc Natl Acad Sci USA* 95, 14266–14271; Cohen et al., (1998) An artificial cell-cycle inhibitor isolated from a combinatorial library. *Proc Natl Acad Sci USA* 95, 14272–14277; Uetz, P.; Giot, L.; al, e.; Fields, S.; Rothberg, J. M. (2000) A comprehensive analysis of protein-protein interactions in Saccharomyces cerevisiae. *Nature* 403, 623–627; Ito, et al., (2001) A comprehensive two-hybrid analysis to explore the yeast protein interactome. *Proc Natl Acad Sci USA* 98, 4569–4574, the disclosures of which are incorporated herein by reference in their entireties. Typically, such fusion is to either *E. coli* LexA or yeast GAL4 DNA binding domains. Related bait plasmids are available that express the bait fused to a nuclear localization signal.

Other useful fusion proteins include those that permit display of the encoded protein on the surface of a phage or cell, fusions to intrinsically fluorescent proteins, such as green fluorescent protein (GFP), and fusions to the IgG Fc region, as described above, which discussion is incorporated here by reference in its entirety.

The polypeptides and fragments of the present invention can also usefully be fused to protein toxins, such as *Pseudomonas* exotoxin A, *diphtheria* toxin, *shiga* toxin A, *anthrax* toxin lethal factor, ricin, in order to effect ablation of cells that bind or take up the proteins of the present invention.

Fusion partners include, inter alia, myc, hemagglutinin (HA), GST, immunoglobulins, β-galactosidase, biotin trpE, protein A, β-lactamase, -amylase, maltose binding protein, alcohol dehydrogenase, polyhistidine (for example, six histidine at the amino and/or carboxyl terminus of the polypeptide), lacZ, green fluorescent protein (GFP), yeast mating factor, GAL4 transcription activation or DNA binding domain, luciferase, and serum proteins such as ovalbumin, albumin and the constant domain of IgG. See, e.g., Ausubel (1992), supra and Ausubel (1999), supra. Fusion proteins may also contain sites for specific enzymatic cleavage, such as a site that is recognized by enzymes such as Factor XIII, trypsin, pepsin, or any other enzyme known in the art. Fusion proteins will typically be made by either recombinant nucleic acid methods, as described above, chemically synthesized using techniques well-known in the art (e.g., a Merrifield synthesis), or produced by chemical cross-linking.

Another advantage of fusion proteins is that the epitope tag can be used to bind the fusion protein to a plate or column through an affinity linkage for screening binding proteins or other molecules that bind to the LSP.

As further described below, the isolated polypeptides, muteins, fusion proteins, homologous proteins or allelic variants of the present invention can readily be used as specific immunogens to raise antibodies that specifically recognize LSPs, their allelic variants and homologues. The antibodies, in turn, can be used, inter alia, specifically to assay for the polypeptides of the present invention, particularly LSPs, e.g. by ELISA for detection of protein fluid samples, such as serum, by immunohistochemistry or laser scanning cytometry, for detection of protein in tissue samples, or by flow cytometry, for detection of intracellular protein in cell suspensions, for specific antibody-mediated isolation and/or purification of LSPs, as for example by immunoprecipitation, and for use as specific agonists or antagonists of LSPs.

One may determine whether polypeptides including muteins, fusion proteins, homologous proteins or allelic variants are functional by methods known in the art. For instance, residues that are tolerant of change while retaining function can be identified by altering the protein at known residues using methods known in the art, such as alanine scanning mutagenesis, Cunningham et al., *Science* 244 (4908): 1081–5 (1989); transposon linker scanning mutagenesis, Chen et al., *Gene* 263(1–2): 39–48 (2001); combinations of homolog- and alanine-scanning mutagenesis, Jin et al., *J. Mol. Biol.* 226(3): 851–65 (1992); combinatorial alanine scanning, Weiss et al., *Proc. Natl. Acad. Sci USA* 97(16): 8950–4 (2000), followed by functional assay. Transposon linker scanning kits are available commercially (New England Biolabs, Beverly, Mass., USA, catalog. no. E7–102S; EZ::TN™ In-Frame Linker Insertion Kit, catalogue no. EZI04KN, Epicentre Technologies Corporation, Madison, Wis., USA).

Purification of the polypeptides including fragments, homologous polypeptides, muteins, analogs, derivatives and fusion proteins is well-known and within the skill of one having ordinary skill in the art. See, e.g., Scopes, *Protein Purification*, 2d ed. (1987). Purification of recombinantly expressed polypeptides is described above. Purification of chemically-synthesized peptides can readily be effected, e.g., by HPLC.

Accordingly, it is an aspect of the present invention to provide the isolated proteins of the present invention in pure or substantially pure form in the presence of absence of a stabilizing agent. Stabilizing agents include both proteinaceous or non-proteinaceous material and are well-known in the art. Stabilizing agents, such as albumin and polyethylene glycol (PEG) are known and are commercially available.

Although high levels of purity are preferred when the isolated proteins of the present invention are used as therapeutic agents, such as in vaccines and as replacement therapy, the isolated proteins of the present invention are also useful at lower purity. For example, partially purified proteins of the present invention can be used as immunogens to raise antibodies in laboratory animals.

In preferred embodiments, the purified and substantially purified proteins of the present invention are in compositions that lack detectable ampholytes, acrylamide monomers, bis-acrylamide monomers, and polyacrylamide.

The polypeptides, fragments, analogs, derivatives and fusions of the present invention can usefully be attached to a substrate. The substrate can be porous or solid, planar or non-planar; the bond can be covalent or noncovalent.

For example, the polypeptides, fragments, analogs, derivatives and fusions of the present invention can usefully be bound to a porous substrate, commonly a membrane, typically comprising nitrocellulose, polyvinylidene fluoride (PVDF), or cationically derivatized, hydrophilic PVDF; so bound, the proteins, fragments, and fusions of the present invention can be used to detect and quantify antibodies, e.g. in serum, that bind specifically to the immobilized protein of the present invention.

As another example, the polypeptides, fragments, analogs, derivatives and fusions of the present invention can usefully be bound to a substantially nonporous substrate, such as plastic, to detect and quantify antibodies, e.g. in serum, that bind specifically to the immobilized protein of the present invention. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof; when the assay is performed in a standard microtiter dish, the plastic is typically polystyrene.

The polypeptides, fragments, analogs, derivatives and fusions of the present invention can also be attached to a substrate suitable for use as a surface enhanced laser desorption ionization source; so attached, the protein, fragment, or fusion of the present invention is useful for binding and then detecting secondary proteins that bind with sufficient affinity or avidity to the surface-bound protein to indicate biologic interaction there between. The proteins, fragments, and fusions of the present invention can also be attached to a substrate suitable for use in surface plasmon resonance detection; so attached, the protein, fragment, or fusion of the present invention is useful for binding and then detecting secondary proteins that bind with sufficient affinity or avidity to the surface-bound protein to indicate biological interaction there between.

Antibodies

In another aspect, the invention provides antibodies, including fragments and derivatives thereof, that bind specifically to polypeptides encoded by the nucleic acid molecules of the invention, as well as antibodies that bind to fragments, muteins, derivatives and analogs of the polypeptides. In a preferred embodiment, the antibodies are specific for a polypeptide that is an LSP, or a fragment, mutein, derivative, analog or fusion protein thereof. In a more preferred embodiment, the antibodies are specific for a polypeptide that comprises SEQ ID NO: 143 through 277, or a fragment, mutein, derivative, analog or fusion protein thereof.

The antibodies of the present invention can be specific for linear epitopes, discontinuous epitopes, or conformational epitopes of such proteins or protein fragments, either as present on the protein in its native conformation or, in some cases, as present on the proteins as denatured, as, e.g., by solubilization in SDS. New epitopes may be also due to a difference in post translational modifications (PTMs) in disease versus normal tissue. For example, a particular site on a LSP may be glycosylated in cancerous cells, but not glycosylated in normal cells or visa versa. In addition, alternative splice forms of a LSP may be indicative of cancer. Differential degradation of the C or N-terminus of a LSP may also be a marker or target for anticancer therapy. For example, a LSP may be N-terminal degraded in cancer cells exposing new epitopes to which antibodies may selectively bind for diagnostic or therapeutic uses.

As is well-known in the art, the degree to which an antibody can discriminate as among molecular species in a mixture will depend, in part, upon the conformational relatedness of the species in the mixture; typically, the antibodies of the present invention will discriminate over adventitious binding to non-LSP polypeptides by at least 2-fold, more typically by at least 5-fold, typically by more than 10-fold, 25-fold, 50-fold, 75-fold, and often by more than 100-fold, and on occasion by more than 500-fold or 1000-fold. When used to detect the proteins or protein fragments of the present invention, the antibody of the present invention is sufficiently specific when it can be used to determine the presence of the protein of the present invention in samples derived from human lung.

Typically, the affinity or avidity of an antibody (or antibody multimer, as in the case of an IgM pentamer) of the present invention for a protein or protein fragment of the present invention will be at least about $1 \times 10^{-6}$ molar (M), typically at least about $5 \times 10^{-7}$ M, $1 \times 10^{-7}$ M, with affinities and avidities of at least $1 \times 10^{-8}$ M, $5 \times 10^{-9}$ M, $1 \times 10^{-10}$ M and up to $1 \times 10^{-13}$ M proving especially useful.

The antibodies of the present invention can be naturally-occurring forms, such as IgG, IgM, IgD, IgE, IgY, and IgA, from any avian, reptilian, or mammalian species.

Human antibodies can, but will infrequently, be drawn directly from human donors or human cells. In this case, antibodies to the proteins of the present invention will typically have resulted from fortuitous immunization, such as autoimmune immunization, with the protein or protein fragments of the present invention. Such antibodies will typically, but will not invariably, be polyclonal. In addition, individual polyclonal antibodies may be isolated and cloned to generate monoclonals.

Human antibodies are more frequently obtained using transgenic animals that express human immunoglobulin genes, which transgenic animals can be affirmatively immunized with the protein immunogen of the present invention. Human Ig-transgenic mice capable of producing human antibodies and methods of producing human antibodies therefrom upon specific immunization are described, inter alia, in U.S. Pat. Nos. 6,162,963; 6,150,584; 6,114,598; 6,075,181; 5,939,598; 5,877,397; 5,874,299; 5,814,318; 5,789,650; 5,770,429; 5,661,016; 5,633,425; 5,625,126; 5,569,825; 5,545,807; 5,545,806, and 5,591,669, the disclosures of which are incorporated herein by reference in their entireties. Such antibodies are typically monoclonal, and are typically produced using techniques developed for production of murine antibodies.

Human antibodies are particularly useful, and often preferred, when the antibodies of the present invention are to be administered to human beings as in vivo diagnostic or therapeutic agents, since recipient immune response to the administered antibody will often be substantially less than that occasioned by administration of an antibody derived from another species, such as mouse.

IgG, IgM, IgD, IgE, IgY, and IgA antibodies of the present invention can also be obtained from other species, including mammals such as rodents (typically mouse, but also rat, guinea pig, and hamster) lagomorphs, typically rabbits, and also larger mammals, such as sheep, goats, cows, and horses, and other egg laying birds or reptiles such as chickens or alligators. For example, avian antibodies may be generated using techniques described in WO 00/29444, published 25 May 2000, the contents of which are hereby incorporated in their entirety. In such cases, as with the transgenic human-antibody-producing non-human mammals, fortuitous immunization is not required, and the non-human mammal is typically affirmatively immunized, according to standard immunization protocols, with the protein or protein fragment of the present invention.

As discussed above, virtually all fragments of 8 or more contiguous amino acids of the proteins of the present invention can be used effectively as immunogens when conjugated to a carrier, typically a protein such as bovine thyroglobulin, keyhole limpet hemocyanin, or bovine serum albumin, conveniently using a bifunctional linker such as those described elsewhere above, which discussion is incorporated by reference here.

Immunogenicity can also be conferred by fusion of the polypeptide and fragments of the present invention to other moieties. For example, peptides of the present invention can be produced by solid phase synthesis on a branched polylysine core matrix; these multiple antigenic peptides (MAPs) provide high purity, increased avidity, accurate chemical definition and improved safety in vaccine development. Tam et al, *Proc. Natl. Acad. Sci. USA* 85: 5409–5413 (1988); Posnett et al., *J. Biol. Chem.* 263: 1719–1725 (1988).

Protocols for immunizing non-human mammals or avian species are well-established in the art. See Harlow et al (eds.), *Using Antibodies: A Laboratory Manual*, Cold Spring Harbor Laboratory (1998); Coligan et al. (eds.), *Current Protocols in Immunology*, John Wiley & Sons, Inc. (2001); Zola, *Monoclonal Antibodies: Preparation and Use of Monoclonal Antibodies and Engineered Antibody Derivatives (Basics: From Background to Bench)*, Springer Verlag (2000); Gross M, Speck *J. Dtsch. Tierarztl. Wochenschr.* 103: 417–422 (1996), the disclosures of which are incorporated herein by reference. Immunization protocols often include multiple immunizations, either with or without adjuvants such as Freund's complete adjuvant and Freund's incomplete adjuvant, and may include naked DNA immunization (Moss, *Semin. Immunol.* 2: 317–327 (1990).

Antibodies from non-human mammals and avian species can be polyclonal or monoclonal, with polyclonal antibodies having certain advantages in immunohistochemical detection of the proteins of the present invention and monoclonal antibodies having advantages in identifying and distinguishing particular epitopes of the proteins of the present invention. Antibodies from avian species may have particular advantage in detection of the proteins of the present invention, in human serum or tissues (Vikinge et al., *Biosens. Bioelectron.* 13: 1257–1262 (1998).

Following immunization, the antibodies of the present invention can be produced using any art-accepted technique. Such techniques are well-known in the art, Coligan, supra; Zola, supra; Howard et al. (eds.), *Basic Methods in Antibody Production and Characterization*, CRC Press (2000); Harlow, supra; Davis (ed.), *Monoclonal Antibody Protocols*, Vol. 45, Humana Press (1995); Delves (ed.), *Antibody Production: Essential Techniques*, John Wiley & Son Ltd (1997); Kenney, *Antibody Solution: An Antibody Methods Manual*, Chapman & Hall (1997), incorporated herein by reference in their entireties, and thus need not be detailed here.

Briefly, however, such techniques include, inter alia, production of monoclonal antibodies by hybridomas and expression of antibodies or fragments or derivatives thereof from host cells engineered to express immunoglobulin genes or fragments thereof. These two methods of production are not mutually exclusive: genes encoding antibodies specific for the proteins or protein fragments of the present invention can be cloned from hybridomas and thereafter expressed in other host cells. Nor need the two necessarily be performed together: e.g., genes encoding antibodies specific for the proteins and protein fragments of the present invention can be cloned directly from B cells known to be specific for the desired protein, as further described in U.S. Pat. No. 5,627,052, the disclosure of which is incorporated herein by reference in its entirety, or from antibody-displaying phage.

Recombinant expression in host cells is particularly useful when fragments or derivatives of the antibodies of the present invention are desired.

Host cells for recombinant production of either whole antibodies, antibody fragments, or antibody derivatives can be prokaryotic or eukaryotic.

Prokaryotic hosts are particularly useful for producing phage displayed antibodies of the present invention.

The technology of phage-displayed antibodies, in which antibody variable region fragments are fused, for example, to the gene III protein (pIII) or gene VIII protein (pVIII) for display on the surface of filamentous phage, such as M13, is by now well-established. See, e.g., Sidhu, *Curr. Opin. Biotechnol.* 11(6): 610–6 (2000); Griffiths et al, *Curr. Opin. Biotechnol.* 9(1): 102–8 (1998); Hoogenboom et al, *Immunotechnology*, 4(1): 1–20 (1998); Rader et al., *Current Opinion in Biotechnology* 8: 503–508 (1997); Aujame et al., *Human Antibodies* 8: 155–168 (1997); Hoogenboom, *Trends in Biotechnol.* 15: 62–70 (1997); de Kruif et al., 17: 453–455 (1996); Barbas et al., *Trends in Biotechnol.* 14: 230–234 (1996); Winter et al., *Ann. Rev. Immunol.* 433–455 (1994). Techniques and protocols required to generate, propagate, screen (pan), and use the antibody fragments from such libraries have recently been compiled. See, e.g., Barbas (2001), supra; Kay, supra; Abelson, supra, the disclosures of which are incorporated herein by reference in their entireties.

Typically, phage-displayed antibody fragments are scFv fragments or Fab fragments; when desired, full length antibodies can be produced by cloning the variable regions from the displaying phage into a complete antibody and expressing the full length antibody in a further prokaryotic or a eukaryotic host cell.

Eukaryotic cells are also useful for expression of the antibodies, antibody fragments, and antibody derivatives of the present invention.

For example, antibody fragments of the present invention can be produced in *Pichia pastoris* and in *Saccharomyces cerevisiae*. See, e.g., Takahashi et al., *Biosci. Biotechnol Biochem.* 64(10): 2138–44 (2000); Freyre et al., J. Biotechnol. 76(2–3):1 57–63 (2000); Fischer et al., *Biotechnol. Appl. Biochem.* 30 (Pt 2): 117–20 (1999); Pennell et al., *Res. Immunol.* 149(6): 599–603 (1998); Eldin et al., *J. Immunol. Methods.* 201(1): 67–75 (1997);, Frenken et al., *Res. Immunol.* 149(6): 589–99 (1998); Shusta et al., *Nature Biotechnol.* 16(8): 773–7 (1998), the disclosures of which are incorporated herein by reference in their entireties.

Antibodies, including antibody fragments and derivatives, of the present invention can also be produced in insect cells. See, e.g., Li et al, *Protein Expr. Purif.* 21(1): 121–8 (2001); Ailor et al., *Biotechnol Bioeng.* 58(2–3): 196–203 (1998); Hsu et al., *Biotechnol. Prog.* 13(1): 96–104 (1997); Edelman et al., *Immunology* 91(1): 13–9 (1997); and Nesbit et al., *J. Immunol. Methods* 151(1–2): 201–8 (1992), the disclosures of with are incorporated herein by reference in their entireties.

Antibodies and fragments and derivatives thereof of the present invention can also be produced in plant cells, particularly maize or tobacco, Giddings et al., *Nature Biotechnol.* 18(11): 1151–5 (2000); Gavilondo et al., *Biotechniques* 29(1): 128–38 (2000); Fischer et al., *J. Biol. Regul Homeost. Agents* 14(2): 83–92 (2000); Fischer et al., *Biotechnol. Appl. Biochem.* 30 (Pt 2): 113–6 (1999); Fischer et al., *Biol. Chem.* 380(7–8): 825–39 (1999); Russell, *Curr. Top. Microbiol. Immunol.* 240: 119–38 (1999); and Ma et al., *Plant Physiol.* 109(2): 341–6 (1995), the disclosures of which are incorporated herein by reference in their entireties.

Antibodies, including antibody fragments and derivatives, of the present invention can also be produced in transgenic, non-human, mammalian milk. See, e.g. Pollock et al., *J. Immunol Methods.* 231: 147–57 (1999); Young et al., *Res. Immunol.* 149: 609–10 (1998); Limonta et al., *Immunotechnology* 1: 107–13 (1995), the disclosures of which are incorporated herein by reference in their entireties.

Mammalian cells useful for recombinant expression of antibodies, antibody fragments, and antibody derivatives of the present invention include CHO cells, COS cells, 293 cells, and myeloma cells.

Verma et al, *J. Immunol. Methods* 216(1–2):165–81 (1998), herein incorporated by reference, review and compare bacterial, yeast, insect and mammalian expression systems for expression of antibodies.

Antibodies of the present invention can also be prepared by cell free translation, as further described in Merk et al., *J. Biochem. (Tokyo)* 125(2): 328–33 (1999) and Ryabova et al., *Nature Biotechnol.* 15(1): 79–84 (1997), and in the milk of transgenic animals, as further described in Pollock et al., *J Immunol Methods* 231(1–2): 147–57 (1999), the disclosures of which are incorporated herein by reference in their entireties.

The invention further provides antibody fragments that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Among such useful fragments are Fab, Fab', Fv, F(ab)'$_2$, and single chain Fv (scFv) fragments. Other useful fragments are described in Hudson, *Curr. Opin. Biotechnol.* 9(4): 395–402 (1998).

It is also an aspect of the present invention to provide antibody derivatives that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Among such useful derivatives are chimeric, primatized, and humanized antibodies; such derivatives are less immunogenic in human beings, and thus more suitable for in vivo administration, than are unmodified antibodies from non-human mammalian species. Another useful derivative is PEGylation to increase the serum half life of the antibodies.

Chimeric antibodies typically include heavy and/or light chain variable regions (including both CDR and framework residues) of immunoglobulins of one species, typically mouse, fused to constant regions of another species, typically human. See, e.g., U.S. Pat. No. 5,807,715; Morrison et al., *Proc. Natl. Acad. Sci USA*. 81(21): 6851–5 (1984); Sharon et al, *Nature* 309(5966): 364–7 (1984); Takeda et al., *Nature* 314(6010): 452–4 (1985), the disclosures of which are incorporated herein by reference in their entireties. Primatized and humanized antibodies typically include heavy and/or light chain CDRs from a murine antibody grafted into a non-human primate or human antibody V region framework, usually further comprising a human constant region, Riechmann et al., *Nature* 332(6162): 323–7 (1988); Co et al., *Nature* 351(6326): 501–2 (1991); U.S. Pat. Nos. 6,054,297; 5,821,337; 5,770,196; 5,766,886; 5,821,123; 5,869,619; 6,180,377; 6,013,256; 5,693,761; and 6,180,370, the disclosures of which are incorporated herein by reference in their entireties.

Other useful antibody derivatives of the invention include heteromeric antibody complexes and antibody fusions, such as diabodies (bispecific antibodies), single-chain diabodies, and intrabodies.

It is contemplated that the nucleic acids encoding the antibodies of the present invention can be operably joined to other nucleic acids forming a recombinant vector for cloning or for expression of the antibodies of the invention. The present invention includes any recombinant vector containing the coding sequences, or part thereof, whether for eukaryotic transduction, transfection or gene therapy. Such vectors may be prepared using conventional molecular biology techniques, known to those with skill in the art, and would comprise DNA encoding sequences for the immunoglobulin V-regions including framework and CDRs or parts thereof, and a suitable promoter either with or without a signal sequence for intracellular transport. Such vectors may be transduced or transfected into eukaryotic cells or used for gene therapy (Marasco et al., *Proc. Natl. Acad. Sci.* (*USA*) 90: 7889–7893 (1993); Duan et al., *Proc. Natl. Acad. Sci.* (*USA*) 91: 5075–5079 (1994), by conventional techniques, known to those with skill in the art.

The antibodies of the present invention, including fragments and derivatives thereof, can usefully be labeled. It is, therefore, another aspect of the present invention to provide labeled antibodies that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

The choice of label depends, in part, upon the desired use.

For example, when the antibodies of the present invention are used for immunohistochemical staining of tissue samples, the label is preferably an enzyme that catalyzes production and local deposition of a detectable product.

Enzymes typically conjugated to antibodies to permit their immunohistochemical visualization are well-known, and include alkaline phosphatase, β-galactosidase, glucose oxidase, horseradish peroxidase (HRP), and urease. Typical substrates for production and deposition of visually detectable products include o-nitrophenyl-beta-D-galatopyranoside (ONPG); o-phenylenediamine dihydrochloride (OPD); p-nitrophenyl phosphate (PNPP); p-nitrophenyl-beta-D-galactopryanoside (PNPG); 3',3'- diaminobenzidine (DAB); 3-amino-9-ethylcarbazole (AEC); 4-chloro-1-naphthol (CN); 5-bromo-4-chloro-3-indolyl-phosphate (BCIP); ABTS®; BluoGal; iodonitrotetrazolium (INT); nitroblue tetrazolium chloride (NBT); phenazine methosulfate (PMS); phenolphthalein monophosphate (PMP); tetramethyl benzidine (TMB); tetranitroblue tetrazolium (TNBT); X-Gal; X-Gluc; and X-Glucoside.

Other substrates can be used to produce products for local deposition that are luminescent. For example, in the presence of hydrogen peroxide ($H_2O_2$), horseradish peroxidase (HRP) can catalyze the oxidation of cyclic diacylhydrazides, such as luminol. Immediately following the oxidation, the luminol is in an excited state (intermediate reaction product), which decays to the ground state by emitting light. Strong enhancement of the light emission is produced by enhancers, such as phenolic compounds. Advantages include high sensitivity, high resolution, and rapid detection without radioactivity and requiring only small amounts of antibody. See, e.g., Thorpe et al., *Methods Enzymol.* 133: 331–53 (1986); Kricka et al., *J. Immunoassay* 17(1): 67–83 (1996); and Lundqvist et al., *J. Biolumin. Chemilumin.* 10(6): 353–9 (1995), the disclosures of which are incorporated herein by reference in their entireties. Kits for such enhanced chemiluminescent detection (ECL) are available commercially.

The antibodies can also be labeled using colloidal gold.

As another example, when the antibodies of the present invention are used, e.g., for flow cytometric detection, for scanning laser cytometric detection, or for fluorescent immunoassay, they can usefully be labeled with fluorophores.

There are a wide variety of fluorophore labels that can usefully be attached to the antibodies of the present invention.

For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCP-Cy5.5, PE-Cy5, PE-Cy5.5, PE-Cy7, PE-Texas Red, and APC-Cy7.

Other fluorophores include, inter alia, Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7, all of which are also useful for fluorescently labeling the antibodies of the present invention.

For secondary detection using labeled avidin, streptavidin, captavidin or neutravidin, the antibodies of the present invention can usefully be labeled with biotin.

When the antibodies of the present invention are used, e.g., for Western blotting applications, they can usefully be labeled with radioisotopes, such as $^{33}P$, $^{32}P$, $^{35}S$, $^{3}H$, and 125I.

As another example, when the antibodies of the present invention are used for radioimmunotherapy, the label can usefully be $^{228}Th$, $^{227}Ac$, $^{225}Ac$, $^{223}Ra$, $^{213}Bi$, $^{212}Pb$, $^{212}Bi$, $^{211}At$, $^{203}Pb$, $^{194}Os$, $^{188}Re$, $^{186}Re$, $^{153}Sm$, $^{149}Tb$, $^{131}I$, $^{125}I$, $^{111}In$, $^{105}Rh$, $^{99m}Tc$, $^{97}Ru$, $^{90}Y$, $^{90}Sr$, $^{88}y$, $^{72}Se$, $^{67}Cu$, or $^{47}Sc$.

As another example, when the antibodies of the present invention are to be used for in vivo diagnostic use, they can be rendered detectable by conjugation to MRI contrast agents, such as gadolinium diethylenetriaminepentaacetic acid (DTPA), Lauffer et al., *Radiology* 207(2): 529–38 (1998), or by radioisotopic labeling.

As would be understood, use of the labels described above is not restricted to the application for which they are mentioned.

The antibodies of the present invention, including fragments and derivatives thereof, can also be conjugated to toxins, in order to target the toxin's ablative action to cells that display and/or express the proteins of the present invention. Commonly, the antibody in such immunotoxins is conjugated to Pseudomonas exotoxin A, diphtheria toxin, shiga toxin A, anthrax toxin lethal factor, or ricin. See Hall (ed.), *Immunotoxin Methods and Protocols* (Methods in Molecular Biology, vol. 166), Humana Press (2000); and Frankel et al. (eds.), *Clinical Applications of Immunotoxins*, Springer-Verlag (1998), the disclosures of which are incorporated herein by reference in their entireties.

The antibodies of the present invention can usefully be attached to a substrate, and it is, therefore, another aspect of the invention to provide antibodies that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention, attached to a substrate.

Substrates can be porous or nonporous, planar or nonplanar.

For example, the antibodies of the present invention can usefully be conjugated to filtration media, such as NHS-activated Sepharose or CNBr-activated Sepharose for purposes of immunoaffinity chromatography.

For example, the antibodies of the present invention can usefully be attached to paramagnetic microspheres, typically by biotin-streptavidin interaction, which microspheres can then be used for isolation of cells that express or display the proteins of the present invention. As another example, the antibodies of the present invention can usefully be attached to the surface of a microtiter plate for ELISA.

As noted above, the antibodies of the present invention can be produced in prokaryotic and eukaryotic cells. It is, therefore, another aspect of the present invention to provide cells that express the antibodies of the present invention, including hybridoma cells, B cells, plasma cells, and host cells recombinantly modified to express the antibodies of the present invention.

In yet a further aspect, the present invention provides aptamers evolved to bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

Transgenic Animals and Cells

In another aspect, the invention provides transgenic cells and non-human organisms comprising nucleic acid molecules of the invention. In a preferred embodiment, the transgenic cells and non-human organisms comprise a nucleic acid molecule encoding an LSP. In a preferred embodiment, the LSP comprises an amino acid sequence selected from SEQ ID NO: 143 through 277, or a fragment, mutein, homologous protein or allelic variant thereof. In another preferred embodiment, the transgenic cells and non-human organism comprise an LSNA of the invention, preferably an LSNA comprising a nucleotide sequence selected from the group consisting of SEQ ID NO: 1 through 142, or a part, substantially similar nucleic acid molecule, allelic variant or hybridizing nucleic acid molecule thereof.

In another embodiment, the transgenic cells and non-human organisms have a targeted disruption or replacement of the endogenous orthologue of the human LSG. The transgenic cells can be embryonic stem cells or somatic cells. The transgenic non-human organisms can be chimeric, nonchimeric heterozygotes, and nonchimeric homozygotes. Methods of producing transgenic animals are well-known in the art. See, e.g., Hogan et al., *Manipulating the Mouse Embryo: A Laboratory Manual*, 2d ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999).

Any technique known in the art may be used to introduce a nucleic acid molecule of the invention into an animal to produce the founder lines of transgenic animals. Such techniques include, but are not limited to, pronuclear microinjection. (see, e.g., Paterson et al., *Appl. Microbiol Biotechnol.* 40: 691–698 (1994); Carver et al., *Biotechnology* 11: 1263–1270 (1993); Wright et al., *Biotechnology* 9: 830–834 (1991); and U.S. Pat. No. 4,873,191 (1989 retrovirus-mediated gene transfer into germ lines, blastocysts or embryos (see, e.g., Van der Putten et al., *Proc. Natl. Acad. Sci., USA* 82: 6148–6152 (1985)); gene targeting in embryonic stem cells (see, e.g., Thompson et al., *Cell* 56: 313–321 (1989)); electroporation of cells or embryos (see, e.g., Lo, 1983, *Mol. Cell. Biol.* 3: 1803–1814 (1983)); introduction using a gene gun (see, e.g., Ulmer et al., *Science* 259: 1745–49 (1993); introducing nucleic acid constructs into embryonic pleuripotent stem cells and transferring the stem cells back into the blastocyst; and sperm-mediated gene transfer (see, e.g., Lavitrano et al., *Cell* 57: 717–723 (1989)).

Other techniques include, for example, nuclear transfer into enucleated oocytes of nuclei from cultured embryonic, fetal, or adult cells induced to quiescence (see, e.g., Campell et al., *Nature* 380: 64–66 (1996); Wilmut et al, *Nature* 385: 810–813 (1997)). The present invention provides for transgenic animals that carry the transgene (i.e., a nucleic acid molecule of the invention) in all their cells, as well as animals which carry the transgene in some, but not all their cells, i. e., mosaic animals or chimeric animals.

The transgene may be integrated as a single transgene or as multiple copies, such as in concatamers, e. g., head-to-head tandems or head-to-tail tandems. The transgene may also be selectively introduced into and activated in a particular cell type by following, e.g., the teaching of Lasko et al. et al., *Proc. Natl. Acad. Sci. USA* 89: 6232–6236 (1992). The regulatory sequences required for such a cell-type specific activation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Methods for creating a transgenic animal with a disruption of a targeted gene are also well-known in the art. In general, a vector is designed to comprise some nucleotide sequences homologous to the endogenous targeted gene. The vector is introduced into a cell so that it may integrate, via homologous recombination with chromosomal sequences, into the endogenous gene, thereby disrupting the function of the endogenous gene. The transgene may also be selectively introduced into a particular cell type, thus inactivating the endogenous gene in only that cell type. See, e.g., Gu et al., *Science* 265: 103–106 (1994). The regulatory sequences required for such a cell-type specific inactivation will depend upon the particular cell type of interest, and will be apparent to those of skill in the art. See, e.g., Smithies et al., *Nature* 317: 230–234 (1985); Thomas et al., *Cell* 51: 503–512 (1987); Thompson et al., *Cell* 5: 313–321 (1989).

In one embodiment, a mutant, non-functional nucleic acid molecule of the invention (or a completely unrelated DNA sequence) flanked by DNA homologous to the endogenous nucleic acid sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene. See, e.g., Thomas, supra and Thompson, supra. However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from an animal or patient or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc.

The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. See, e.g., U.S. Pat. Nos. 5,399,349 and 5,460,959, each of which is incorporated by reference herein in its entirety.

When the cells to be administered are non-autologous or non-MHC compatible cells, they can be administered using well-known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Computer Readable Means

A further aspect of the invention relates to a computer readable means for storing the nucleic acid and amino acid sequences of the instant invention. In a preferred embodiment, the invention provides a computer readable means for storing SEQ ID NO: 1 through 142 and SEQ ID NO: 143 through 277 as described herein, as the complete set of sequences or in any combination. The records of the computer readable means can be accessed for reading and display and for interface with a computer system for the application of programs allowing for the location of data upon a query for data meeting certain criteria, the comparison of sequences, the alignment or ordering of sequences meeting a set of criteria, and the like.

The nucleic acid and amino acid sequences of the invention are particularly useful as components in databases useful for search analyses as well as in sequence analysis algorithms. As used herein, the terms "nucleic acid sequences of the invention" and "amino acid sequences of the invention" mean any detectable chemical or physical characteristic of a polynucleotide or polypeptide of the invention that is or may be reduced to or stored in a computer readable form. These include, without limitation, chromatographic scan data or peak data, photographic data or scan data therefrom, and mass spectrographic data.

This invention provides computer readable media having stored thereon sequences of the invention. A computer readable medium may comprise one or more of the following: a nucleic acid sequence comprising a sequence of a nucleic acid sequence of the invention; an amino acid sequence comprising an amino acid sequence of the invention; a set of nucleic acid sequences wherein at least one of said sequences comprises the sequence of a nucleic acid sequence of the invention; a set of amino acid sequences wherein at least one of said sequences comprises the sequence of an amino acid sequence of the invention; a data set representing a nucleic acid sequence comprising the sequence of one or more nucleic acid sequences of the invention; a data set representing a nucleic acid sequence encoding an amino acid sequence comprising the sequence of an amino acid sequence of the invention; a set of nucleic acid sequences wherein at least one of said sequences comprises the sequence of a nucleic acid sequence of the invention; a set of amino acid sequences wherein at least one of said sequences comprises the sequence of an amino acid sequence of the invention; a data set representing a nucleic acid sequence comprising the sequence of a nucleic acid sequence of the invention; a data set representing a nucleic acid sequence encoding an amino acid sequence comprising the sequence of an amino acid sequence of the invention. The computer readable medium can be any composition of matter used to store information or data, including, for example, commercially available floppy disks, tapes, hard drives, compact disks, and video disks.

Also provided by the invention are methods for the analysis of character sequences, particularly genetic sequences. Preferred methods of sequence analysis include, for example, methods of sequence homology analysis, such as identity and similarity analysis, RNA structure analysis, sequence assembly, cladistic analysis, sequence motif analysis, open reading frame determination, nucleic acid base calling, and sequencing chromatogram peak analysis.

A computer-based method is provided for performing nucleic acid sequence identity or similarity identification. This method comprises the steps of providing a nucleic acid sequence comprising the sequence of a nucleic acid of the invention in a computer readable medium; and comparing said nucleic acid sequence to at least one nucleic acid or amino acid sequence to identify sequence identity or similarity.

A computer-based method is also provided for performing amino acid homology identification, said method comprising the steps of: providing an amino acid sequence comprising the sequence of an amino acid of the invention in a computer readable medium; and comparing said an amino acid sequence to at least one nucleic acid or an amino acid sequence to identify homology.

A computer-based method is still further provided for assembly of overlapping nucleic acid sequences into a single nucleic acid sequence, said method comprising the steps of: providing a first nucleic acid sequence comprising the sequence of a nucleic acid of the invention in a computer readable medium; and screening for at least one overlapping region between said first nucleic acid sequence and a second nucleic acid sequence.

Diagnostic Methods for Lung Cancer

The present invention also relates to quantitative and qualitative diagnostic assays and methods for detecting, diagnosing, monitoring, staging and predicting cancers by comparing expression of an LSNA or an LSP in a human patient that has or may have lung cancer, or who is at risk of developing lung cancer, with the expression of an LSNA or an LSP in a normal human control. For purposes of the present invention, "expression of an LSNA" or "LSNA expression" means the quantity of LSG mRNA that can be measured by any method known in the art or the level of transcription that can be measured by any method known in the art in a cell, tissue, organ or whole patient. Similarly, the term "expression of an LSP" or "LSP expression" means the amount of LSP that can be measured by any method known in the art or the level of translation of an LSG LSNA that can be measured by any method known in the art.

The present invention provides methods for diagnosing lung cancer in a patient, in particular squamous cell carcinoma, by analyzing for changes in levels of LSNA or LSP in cells, tissues, organs or bodily fluids compared with levels of LSNA or LSP in cells, tissues, organs or bodily fluids of preferably the same type from a normal human control, wherein an increase, or decrease in certain cases, in levels of an LSNA or LSP in the patient versus the normal human control is associated with the presence of lung cancer or with a predilection to the disease. In another preferred embodiment, the present invention provides methods for diagnosing lung cancer in a patient by analyzing changes in the structure of the mRNA of an LSG compared to the mRNA from a normal control. These changes include, without limitation, aberrant splicing, alterations in polyadenylation and/or alterations in 5' nucleotide capping. In yet another preferred embodiment, the present invention provides methods for diagnosing lung cancer in a patient by analyzing changes in an LSP compared to an LSP from a normal control. These changes include, e.g., alterations in glycosylation and/or phosphorylation of the LSP or subcellular LSP localization.

In a preferred embodiment, the expression of an LSNA is measured by determining the amount of an mRNA that encodes an amino acid sequence selected from SEQ ID NO: 143 through 277, a homolog, an allelic variant, or a fragment thereof. In a more preferred embodiment, the LSNA expression that is measured is the level of expression of an LSNA mRNA selected from SEQ ID NO: 1 through 142, or a hybridizing nucleic acid, homologous nucleic acid or allelic variant thereof, or a part of any of these nucleic acids. LSNA expression may be measured by any method known in the art, such as those described supra, including measuring mRNA expression by Northern blot, quantitative or qualitative reverse transcriptase PCR (RT-PCR), microarray, dot or slot blots or in situ hybridization. See, e.g., Ausubel (1992), supra; Ausubel (1999), supra; Sambrook (1989), supra; and Sambrook (2001), supra. LSNA transcription may be measured by any method known in the art including using a reporter gene hooked up to the promoter of an LSG of interest or doing nuclear run-off assays. Alterations in mRNA structure, e.g., aberrant splicing variants, may be determined by any method known in the art, including, RT-PCR followed by sequencing or restriction analysis. As necessary, LSNA expression may be compared to a known control, such as normal lung nucleic acid, to detect a change in expression.

In another preferred embodiment, the expression of an LSP is measured by determining the level of an LSP having an amino acid sequence selected from the group consisting of SEQ ID NO: 143 through 277, a homolog, an allelic variant, or a fragment thereof. Such levels are preferably determined in at least one of cells, tissues, organs and/or bodily fluids, including determination of normal and abnormal levels. Thus, for instance, a diagnostic assay in accordance with the invention for diagnosing over- or underexpression of LSNA or LSP compared to normal control bodily fluids, cells, or -tissue samples may be used to diagnose the presence of lung cancer. The expression level of an LSP may be determined by any method known in the art, such as those described supra. In a preferred embodiment, the LSP expression level may be determined by radioimmunoassays, competitive-binding assays, ELISA, Western blot, FACS, immunohistochemistry, immunoprecipitation, proteomic approaches: two-dimensional gel electrophoresis (2D electrophoresis) and non-gel-based approaches such as mass spectrometry or protein interaction profiling. See, e.g, Harlow (1999), supra; Ausubel (1992), supra; and Ausubel (1999), supra. Alterations in the LSP structure may be determined by any method known in the art, including, e.g., using antibodies that specifically recognize phosphoserine, phosphothreonine or phosphotyrosine residues, two-dimensional polyacrylamide gel electrophoresis (2D PAGE) and/or chemical analysis of amino acid residues of the protein. Id.

In a preferred embodiment, a radioimmunoassay (RIA) or an ELISA is used. An antibody specific to an LSP is prepared if one is not already available. In a preferred embodiment, the antibody is a monoclonal antibody. The anti-LSP antibody is bound to a solid support and any free protein binding sites on the solid support are blocked with a protein such as bovine serum albumin. A sample of interest is incubated with the antibody on the solid support under conditions in which the LSP will bind to the anti-LSP antibody. The sample is removed, the solid support is washed to remove unbound material, and an anti-LSP antibody that is linked to a detectable reagent (a radioactive substance for RIA and an enzyme for ELISA) is added to the solid support and incubated under conditions in which binding of the LSP to the labeled antibody will occur. After binding, the unbound labeled antibody is removed by washing. For an ELISA, one or more substrates are added to produce a colored reaction product that is based upon the amount of an LSP in the sample. For an RIA, the solid support is counted for radioactive decay signals by any method known in the art. Quantitative results for both RIA and ELISA typically are obtained by reference to a standard curve.

Other methods to measure LSP levels are known in the art. For instance, a competition assay may be employed wherein an anti-LSP antibody is attached to a solid support and an allocated amount of a labeled LSP and a sample of interest are incubated with the solid support. The amount of labeled LSP detected which is attached to the solid support can be correlated to the quantity of an LSP in the sample.

Of the proteomic approaches, 2D PAGE is a well-known technique. Isolation of individual proteins from a sample such as serum is accomplished using sequential separation of proteins by isoelectric point and molecular weight. Typically, polypeptides are first separated by isoelectric point (the first dimension) and then separated by size using an electric current (the second dimension). In general, the second dimension is perpendicular to the first dimension. Because no two proteins with different sequences are identical on the basis of both size and charge, the result of 2D PAGE is a roughly square gel in which each protein occupies a unique spot. Analysis of the spots with chemical or antibody probes, or subsequent protein microsequencing can reveal the relative abundance of a given protein and the identity of the proteins in the sample.

Expression levels of an LSNA can be determined by any method known in the art, including PCR and other nucleic acid methods, such as ligase chain reaction (LCR) and nucleic acid sequence based amplification (NASBA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction.

Hybridization to specific DNA molecules (e.g., oligonucleotides) arrayed on a solid support can be used to both detect the expression of and quantitate the level of expression of one or more LSNAs of interest. In this approach, all or a portion of one or more LSNAs is fixed to a substrate. A sample of interest, which may comprise RNA, e.g., total RNA or polyA-selected mRNA, or a complementary DNA (cDNA) copy of the RNA is incubated with the solid support under conditions in which hybridization will occur between the DNA on the solid support and the nucleic acid molecules in the sample of interest. Hybridization between the substrate-bound DNA and the nucleic acid molecules in the sample can be detected and quantitated by several means, including, without limitation, radioactive labeling or fluorescent labeling of the nucleic acid molecule or a secondary molecule designed to detect the hybrid.

The above tests can be carried out on samples derived from a variety of cells, bodily fluids and/or tissue extracts such as homogenates or solubilized tissue obtained from a patient. Tissue extracts are obtained routinely from tissue biopsy and autopsy material. Bodily fluids useful in the present invention include blood, urine, saliva or any other bodily secretion or derivative thereof. By blood it is meant to include whole blood, plasma, serum or any derivative of blood. In a preferred embodiment, the specimen tested for expression of LSNA or LSP includes, without limitation, lung tissue, fluid obtained by bronchial alveolar lavage (BAL), sputum, lung cells grown in cell culture, blood, serum, lymph node tissue and lymphatic fluid. In another preferred embodiment, especially when metastasis of a primary lung cancer is known or suspected, specimens include, without limitation, tissues from brain, bone, bone marrow, liver, adrenal glands and colon. In general, the tissues may be sampled by biopsy, including, without limitation, needle biopsy, e.g., transthoracic needle aspiration, cervical mediatinoscopy, endoscopic lymph node biopsy, video-assisted thoracoscopy, exploratory thoracotomy, bone marrow biopsy and bone marrow aspiration. See Scott, supra and Franklin, pp. 529–570, in Kane, supra. For early and inexpensive detection, assaying for changes in LSNAs or LSPs in cells in sputum samples may be particularly useful. Methods of obtaining and analyzing sputum samples is disclosed in Franklin, supra.

All the methods of the present invention may optionally include determining the expression levels of one or more other cancer markers in addition to determining the expression level of an LSNA or LSP. In many cases, the use of another cancer marker will decrease the likelihood of false positives or false negatives. In one embodiment, the one or more other cancer markers include other LSNA or LSPs as disclosed herein. Other cancer markers useful in the present invention will depend on the cancer being tested and are known to those of skill in the art. In a preferred embodiment, at least one other cancer marker in addition to a particular LSNA or LSP is measured. In a more preferred embodiment, at least two other additional cancer markers are used. In an even more preferred embodiment, at least three, more preferably at least five, even more preferably at least ten additional cancer markers are used.

Diagnosing

In one aspect, the invention provides a method for determining the expression levels and/or structural alterations of one or more LSNAs and/or LSPs in a sample from a patient suspected of having lung cancer. In general, the method comprises the steps of obtaining the sample from the patient, determining the expression level or structural alterations of an LSNA and/or LSP and then ascertaining whether the patient has lung cancer from the expression level of the LSNA or LSP. In general, if high expression relative to a control of an LSNA or LSP is indicative of lung cancer, a diagnostic assay is considered positive if the level of expression of the LSNA or LSP is at least two times higher, and more preferably are at least five times higher, even more preferably at least ten times higher, than in preferably the same cells, tissues or bodily fluid of a normal human control. In contrast, if low expression relative to a control of an LSNA or LSP is indicative of lung cancer, a diagnostic assay is considered positive if the level of expression of the LSNA or LSP is at least two times lower, more preferably are at least five times lower, even more preferably at least ten times lower than in preferably the same cells, tissues or bodily fluid of a normal human control. The normal human control may be from a different patient or from uninvolved tissue of the same patient.

The present invention also provides a method of determining whether lung cancer has metastasized in a patient. One may identify whether the lung cancer has metastasized by measuring the expression levels and/or structural alterations of one or more LSNAs and/or LSPs in a variety of tissues. The presence of an LSNA or LSP in a certain tissue at levels higher than that of corresponding noncancerous tissue (e.g., the same tissue from another individual) is indicative of metastasis if high level expression of an LSNA or LSP is associated with lung cancer. Similarly, the presence of an LSNA or LSP in a tissue at levels lower than that of corresponding noncancerous tissue is indicative of metastasis if low level expression of an LSNA or LSP is associated with lung cancer. Further, the presence of a structurally altered LSNA or LSP that is associated with lung cancer is also indicative of metastasis.

In general, if high expression relative to a control of an LSNA or LSP is indicative of metastasis, an assay for metastasis is considered positive if the level of expression of the LSNA or LSP is at least two times higher, and more preferably are at least five times higher, even more preferably at least ten times higher, than in preferably the same cells, tissues or bodily fluid of a normal human control. In contrast, if low expression relative to a control of an LSNA or LSP is indicative of metastasis, an assay for metastasis is considered positive if the level of expression of the LSNA or LSP is at least two times lower, more preferably are at least five times lower, even more preferably at least ten times lower than in preferably the same cells, tissues or bodily fluid of a normal human control.

The LSNA or LSP of this invention may be used as element in an array or a multi-analyte test to recognize expression patterns associated with lung cancers or other lung related disorders. In addition, the sequences of either the nucleic acids or proteins may be used as elements in a computer program for pattern recognition of lung disorders.

Staging

The invention also provides a method of staging lung cancer in a human patient. The method comprises identifying a human patient having lung cancer and analyzing cells, tissues or bodily fluids from such human patient for expression levels and/or structural alterations of one or more LSNAs or LSPs. First, one or more tumors from a variety of patients are staged according to procedures well-known in the art, and the expression level of one or more LSNAs or LSPs is determined for each stage to obtain a standard expression level for each LSNA and LSP. Then, the LSNA or LSP expression levels are determined in a biological sample from a patient whose stage of cancer is not known. The LSNA or LSP expression levels from the patient are then compared to the standard expression level. By comparing the expression level of the LSNAs and LSPs from the patient to the standard expression levels, one may determine the stage of the tumor. The same procedure may be followed using structural alterations of an LSNA or LSP to determine the stage of a lung cancer.

Monitoring

Further provided is a method of monitoring lung cancer in a human patient. One may monitor a human patient to determine whether there has been metastasis and, if there has been, when metastasis began to occur. One may also monitor a human patient to determine whether a preneoplastic lesion has become cancerous. One may also monitor a human patient to determine whether a therapy, e.g., chemotherapy, radiotherapy or surgery, has decreased or eliminated the lung cancer. The method comprises identifying a human patient that one wants to monitor for lung cancer, periodically analyzing cells, tissues or bodily fluids from such human patient for expression levels of one or more LSNAs or LSPs, and comparing the LSNA or LSP levels over time to those LSNA or LSP expression levels obtained previously. Patients may also be monitored by measuring one or more structural alterations in an LSNA or LSP that are associated with lung cancer.

If increased expression of an LSNA or LSP is associated with metastasis, treatment failure, or conversion of a preneoplastic lesion to a cancerous lesion, then detecting an increase in the expression level of an LSNA or LSP indicates that the tumor is metastasizing, that treatment has failed or that the lesion is cancerous, respectively. One having ordinary skill in the art would recognize that if this were the case, then a decreased expression level would be indicative of no metastasis, effective therapy or failure to progress to a neoplastic lesion. If decreased expression of an LSNA or LSP is associated with metastasis, treatment failure, or conversion of a preneoplastic lesion to a cancerous lesion, then detecting an decrease in the expression level of an LSNA or LSP indicates that the tumor is metastasizing, that treatment has failed or that the lesion is cancerous, respectively. In a preferred embodiment, the levels of LSNAs or LSPs are determined from the same cell type, tissue or bodily fluid as prior patient samples. Monitoring a patient for onset of lung cancer metastasis is periodic and preferably is done on a quarterly basis, but may be done more or less frequently.

The methods described herein can further be utilized as prognostic assays to identify subjects having or at risk of developing a disease or disorder associated with increased or decreased expression levels of an LSNA and/or LSP. The present invention provides a method in which a test sample is obtained from a human patient and one or more LSNAs and/or LSPs are detected. The presence of higher (or lower) LSNA or LSP levels as compared to normal human controls is diagnostic for the human patient being at risk for developing cancer, particularly lung cancer. The effectiveness of therapeutic agents to decrease (or increase) expression or activity of one or more LSNAs and/or LSPs of the invention can also be monitored by analyzing levels of expression of the LSNAs and/or LSPs in a human patient in clinical trials or in in vitro screening assays such as in human cells. In this way, the gene expression pattern can serve as a marker, indicative of the physiological response of the human patient or cells, as the case may be, to the agent being tested.

Detection of Genetic Lesions or Mutations

The methods of the present invention can also be used to detect genetic lesions or mutations in an LSG, thereby determining if a human with the genetic lesion is susceptible to developing lung cancer or to determine what genetic lesions are responsible, or are partly responsible, for a person's existing lung cancer. Genetic lesions can be detected, for example, by ascertaining the existence of a deletion, insertion and/or substitution of one or more nucleotides from the LSGs of this invention, a chromosomal rearrangement of LSG, an aberrant modification of LSG (such as of the methylation pattern of the genomic DNA), or allelic loss of an LSG. Methods to detect such lesions in the LSG of this invention are known to those having ordinary skill in the art following the teachings of the specification.

Methods of Detecting Noncancerous Lung Diseases

The invention also provides a method for determining the expression levels and/or structural alterations of one or more LSNAs and/or LSPs in a sample from a patient suspected of having or known to have a noncancerous lung disease. In general, the method comprises the steps of obtaining a sample from the patient, determining the expression level or structural alterations of an LSNA and/or LSP, comparing the expression level or structural alteration of the LSNA or LSP to a normal lung control, and then ascertaining whether the patient has a noncancerous lung disease. In general, if high expression relative to a control of an LSNA or LSP is indicative of a particular noncancerous lung disease, a diagnostic assay is considered positive if the level of expression of the LSNA or LSP is at least two times higher, and more preferably are at least five times higher, even more preferably at least ten times higher, than in preferably the same cells, tissues or bodily fluid of a normal human control. In contrast, if low expression relative to a control of an LSNA or LSP is indicative of a noncancerous lung disease, a diagnostic assay is considered positive if the level of expression of the LSNA or LSP is at least two times lower, more preferably are at least five times lower, even more preferably at least ten times lower than in preferably the same cells, tissues or bodily fluid of a normal human control. The normal human control may be from a different patient or from uninvolved tissue of the same patient.

One having ordinary skill in the art may determine whether an LSNA and/or LSP is associated with a particular noncancerous lung disease by obtaining lung tissue from a patient having a noncancerous lung disease of interest and determining which LSNAs and/or LSPs are expressed in the tissue at either a higher or a lower level than in normal lung tissue. In another embodiment, one may determine whether an LSNA or LSP exhibits structural alterations in a particular noncancerous lung disease state by obtaining lung tissue from a patient having a noncancerous lung disease of interest and determining the structural alterations in one or more LSNAs and/or LSPs relative to normal lung tissue.

Methods for Identifying Lung Tissue

In another aspect, the invention provides methods for identifying lung tissue.

These methods are particularly useful in, e.g., forensic science, lung cell differentiation and development, and in tissue engineering.

In one embodiment, the invention provides a method for determining whether a sample is lung tissue or has lung tissue-like characteristics. The method comprises the steps of providing a sample suspected of comprising lung tissue or having lung tissue-like characteristics, determining whether the sample expresses one or more LSNAs and/or LSPs, and, if the sample expresses one or more LSNAs and/or LSPs, concluding that the sample comprises lung tissue. In a preferred embodiment, the LSNA encodes a polypeptide having an amino acid sequence selected from SEQ ID NO: 143 through 277, or a homolog, allelic variant or fragment thereof. In a more preferred embodiment, the LSNA has a nucleotide sequence selected from SEQ ID NO: 1 through 142, or a hybridizing nucleic acid, an allelic variant or a part thereof. Determining whether a sample expresses an LSNA can be accomplished by any method known in the art. Preferred methods include hybridization to microarrays, Northern blot hybridization, and quantitative or qualitative RT-PCR. In another preferred embodiment, the method can be practiced by determining whether an LSP is expressed. Determining whether a sample expresses an LSP can be accomplished by any method known in the art. Preferred methods include Western blot, ELISA, RIA and 2D PAGE. In one embodiment, the LSP has an amino acid sequence selected from SEQ ID NO: 143 through 277, or a homolog, allelic variant or fragment thereof. In another preferred embodiment, the expression of at least two LSNAs and/or LSPs is determined. In a more preferred embodiment, the expression of at least three, more preferably four and even more preferably five LSNAs and/or LSPs are determined.

In one embodiment, the method can be used to determine whether an unknown tissue is lung tissue. This is particularly useful in forensic science, in which small, damaged pieces of tissues that are not identifiable by microscopic or other means are recovered from a crime or accident scene. In another embodiment, the method can be used to determine whether a tissue is differentiating or developing into lung tissue. This is important in monitoring the effects of the addition of various agents to cell or tissue culture, e.g., in producing new lung tissue by tissue engineering. These agents include, e.g., growth and differentiation factors, extracellular matrix proteins and culture medium. Other factors that may be measured for effects on tissue development and differentiation include gene transfer into the cells or tissues, alterations in pH, aqueous:air interface and various other culture conditions.

Methods for Producing and Modifying Lung Tissue

In another aspect, the invention provides methods for producing engineered lung tissue or cells. In one embodiment, the method comprises the steps of providing cells, introducing an LSNA or an LSG into the cells, and growing the cells under conditions in which they exhibit one or more properties of lung tissue cells. In a preferred embodiment, the cells are pluripotent. As is well-known in the art, normal lung tissue comprises a large number of different cell types. Thus, in one embodiment, the engineered lung tissue or cells comprises one of these cell types. In another embodiment, the engineered lung tissue or cells comprises more than one lung cell type. Further, the culture conditions of the cells or tissue may require manipulation in order to achieve full differentiation and development of the lung cell tissue. Methods for manipulating culture conditions are well-known in the art.

Nucleic acid molecules encoding one or more LSPs are introduced into cells, preferably pluripotent cells. In a preferred embodiment, the nucleic acid molecules encode LSPs having amino acid sequences selected from SEQ ID NO: 143 through 277, or homologous proteins, analogs, allelic variants or fragments thereof. In a more preferred embodiment, the nucleic acid molecules have a nucleotide sequence selected from SEQ ID NO: 1 through 142, or hybridizing nucleic acids, allelic variants or parts thereof. In another highly preferred embodiment, an LSG is introduced into the cells. Expression vectors and methods of introducing nucleic acid molecules into cells are well-known in the art and are described in detail, supra.

Artificial lung tissue may be used to treat patients who have lost some or all of their lung function.

Pharmaceutical Compositions

In another aspect, the invention provides pharmaceutical compositions comprising the nucleic acid molecules, polypeptides, antibodies, antibody derivatives, antibody fragments, agonists, antagonists, and inhibitors of the present invention. In a preferred embodiment, the pharmaceutical composition comprises an LSNA or part thereof. In a more preferred embodiment, the LSNA has a nucleotide sequence selected from the group consisting of SEQ ID NO: 1 through 142, a nucleic acid that hybridizes thereto, an allelic variant thereof, or a nucleic acid that has substantial sequence identity thereto. In another preferred embodiment, the pharmaceutical composition comprises an LSP or fragment thereof. In a more preferred embodiment, the LSP having an amino acid sequence that is selected from the group consisting of SEQ ID NO: 143 through 277, a polypeptide that is homologous thereto, a fusion protein comprising all or a portion of the polypeptide, or an analog or derivative thereof. In another preferred embodiment, the pharmaceutical composition comprises an anti-LSP antibody, preferably an antibody that specifically binds to an LSP having an amino acid that is selected from the group consisting of SEQ ID NO: 143 through 277, or an antibody that binds to a polypeptide that is homologous thereto, a fusion protein comprising all or a portion of the polypeptide, or an analog or derivative thereof.

Such a composition typically contains from about 0.1 to 90% by weight of a therapeutic agent of the invention formulated in and/or with a pharmaceutically acceptable carrier or excipient.

Pharmaceutical formulation is a well-established art, and is further described in Gennaro (ed.), *Remington: The Science and Practice of Pharmacy*, 20$^{th}$ ed., Lippincott, Williams & Wilkins (2000); Ansel et al., *Pharmaceutical Dosage Forms and Drug Delivery Systems*, 7$^{th}$ ed., Lippincott Williams & Wilkins (1999); and Kibbe (ed.), *Handbook of Pharmaceutical Excipients* American Pharmaceutical Association, 3$^{rd}$ ed. (2000), the disclosures of which are incorporated herein by reference in their entireties, and thus need not be described in detail herein.

Briefly, formulation of the pharmaceutical compositions of the present invention will depend upon the route chosen for administration. The pharmaceutical compositions utilized in this invention can be administered by various routes including both enteral and parenteral routes, including oral, intravenous, intramuscular, subcutaneous, inhalation, topical, sublingual, rectal, intra-arterial, intramedullary, intrathecal, intraventricular, transmucosal, transdermal, intranasal, intraperitoneal, intrapulmonary, and intrauterine.

Oral dosage forms can be formulated as tablets, pills, dragees, capsules, liquids, gels, syrups, slurries, suspensions, and the like, for ingestion by the patient.

Solid formulations of the compositions for oral administration can contain suitable carriers or excipients, such as carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, sodium carboxymethylcellulose, or microcrystalline cellulose; gums including arabic and tragacanth; proteins such as gelatin and collagen; inorganics, such as kaolin, calcium carbonate, dicalcium phosphate, sodium chloride; and other agents such as acacia and alginic acid.

Agents that facilitate disintegration and/or solubilization can be added, such as the cross-linked polyvinyl pyrrolidone, agar, alginic acid, or a salt thereof, such as sodium alginate, microcrystalline cellulose, corn starch, sodium starch glycolate, and alginic acid.

Tablet binders that can be used include acacia, methylcellulose, sodium carboxymethylcellulose, polyvinylpyrrolidone (Povidone™), hydroxypropyl methylcellulose, sucrose, starch and ethylcellulose.

Lubricants that can be used include magnesium stearates, stearic acid, silicone fluid, talc, waxes, oils, and colloidal silica.

Fillers, agents that facilitate disintegration and/or solubilization, tablet binders and lubricants, including the aforementioned, can be used singly or in combination.

Solid oral dosage forms need not be uniform throughout. For example, dragee cores can be used in conjunction with suitable coatings, such as concentrated sugar solutions, which can also contain gum arabic, talc, polyvinylpyrrolidone, carbopol gel, polyethylene glycol, and/or titanium dioxide, lacquer solutions, and suitable organic solvents or solvent mixtures.

Oral dosage forms of the present invention include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Additionally, dyestuffs or pigments can be added to the tablets or dragee coatings for product identification or to characterize the quantity of active compound, i.e., dosage.

Liquid formulations of the pharmaceutical compositions for oral (enteral) administration are prepared in water or other aqueous vehicles and can contain various suspending agents such as methylcellulose, alginates, tragacanth, pectin, kelgin, carrageenan, acacia, polyvinylpyrrolidone, and polyvinyl alcohol. The liquid formulations can also include solutions, emulsions, syrups and elixirs containing, together with the active compound(s), wetting agents, sweeteners, and coloring and flavoring agents.

The pharmaceutical compositions of the present invention can also be formulated for parenteral administration. Formulations for parenteral administration can be in the form of aqueous or non-aqueous isotonic sterile injection solutions or suspensions.

For intravenous injection, water soluble versions of the compounds of the present invention are formulated in, or if provided as a lyophilate, mixed with, a physiologically acceptable fluid vehicle, such as 5% dextrose ("D5"), physiologically buffered saline, 0.9% saline, Hanks' solution, or Ringer's solution. Intravenous formulations may include carriers, excipients or stabilizers including, without limitation, calcium, human serum albumin, citrate, acetate, calcium chloride, carbonate, and other salts.

Intramuscular preparations, e.g. a sterile formulation of a suitable soluble salt form of the compounds of the present invention, can be dissolved and administered in a pharmaceutical excipient such as Water-for-Injection, 0.9% saline, or 5% glucose solution. Alternatively, a suitable insoluble form of the compound can be prepared and administered as a suspension in an aqueous base or a pharmaceutically acceptable oil base, such as an ester of a long chain fatty acid (e.g., ethyl oleate), fatty oils such as sesame oil, triglycerides, or liposomes.

Parenteral formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like).

Aqueous injection suspensions can also contain substances that increase the viscosity of the suspension, such as sodium carboxymethyl cellulose, sorbitol, or dextran. Non-lipid polycationic amino polymers can also be used for delivery. Optionally, the suspension can also contain suitable stabilizers or agents that increase the solubility of the compounds to allow for the preparation of highly concentrated solutions.

Pharmaceutical compositions of the present invention can also be formulated to permit injectable, long-term, deposition. Injectable depot forms may be made by forming microencapsulated matrices of the compound in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in microemulsions that are compatible with body tissues.

The pharmaceutical compositions of the present invention can be administered topically.

For topical use the compounds of the present invention can also be prepared in suitable forms to be applied to the skin, or mucus membranes of the nose and throat, and can take the form of lotions, creams, ointments, liquid sprays or inhalants, drops, tinctures, lozenges, or throat paints. Such topical formulations further can include chemical compounds such as dimethylsulfoxide (DMSO) to facilitate surface penetration of the active ingredient. In other transdermal formulations, typically in patch-delivered formulations, the pharmaceutically active compound is formulated with one or more skin penetrants, such as 2-N-methyl-pyrrolidone (NMP) or Azone. A topical semi-solid ointment formulation typically contains a concentration of the active ingredient from about 1 to 20%, e.g., 5 to 10%, in a carrier such as a pharmaceutical cream base.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Inhalation formulations can also readily be formulated. For inhalation, various powder and liquid formulations can be prepared. For aerosol preparations, a sterile formulation of the compound or salt form of the compound may be used in inhalers, such as metered dose inhalers, and nebulizers. Aerosolized forms may be especially useful for treating respiratory disorders.

Alternatively, the compounds of the present invention can be in powder form for reconstitution in the appropriate pharmaceutically acceptable carrier at the time of delivery.

The pharmaceutically active compound in the pharmaceutical compositions of the present invention can be provided as the salt of a variety of acids, including but not limited to hydrochloric, sulfuric, acetic, lactic, tartaric, malic, and succinic acid. Salts tend to be more soluble in aqueous or other protonic solvents than are the corresponding free base forms.

After pharmaceutical compositions have been prepared, they are packaged in an appropriate container and labeled for treatment of an indicated condition.

The active compound will be present in an amount effective to achieve the intended purpose. The determination of an effective dose is well within the capability of those skilled in the art.

A "therapeutically effective dose" refers to that amount of active ingredient, for example LSP polypeptide, fusion protein, or fragments thereof, antibodies specific for LSP, agonists, antagonists or inhibitors of LSP, which ameliorates the signs or symptoms of the disease or prevents progression thereof; as would be understood in the medical arts, cure, although desired, is not required.

The therapeutically effective dose of the pharmaceutical agents of the present invention can be estimated initially by in vitro tests, such as cell culture assays, followed by assay in model animals, usually mice, rats, rabbits, dogs, or pigs. The animal model can also be used to determine an initial preferred concentration range and route of administration.

For example, the ED50 (the dose therapeutically effective in 50% of the population) and LD50 (the dose lethal to 50% of the population) can be determined in one or more cell culture of animal model systems. The dose ratio of toxic to therapeutic effects is the therapeutic index, which can be expressed as LD50/ED50. Pharmaceutical compositions that exhibit large therapeutic indices are preferred.

The data obtained from cell culture assays and animal studies are used in formulating an initial dosage range for human use, and preferably provide a range of circulating concentrations that includes the ED50 with little or no toxicity. After administration, or between successive administrations, the circulating concentration of active agent varies within this range depending upon pharmacokinetic factors well-known in the art, such as the dosage form employed, sensitivity of the patient, and the route of administration.

The exact dosage will be determined by the practitioner, in light of factors specific to the subject requiring treatment. Factors that can be taken into account by the practitioner include the severity of the disease state, general health of the subject, age, weight, gender of the subject, diet, time and frequency of administration, drug combination(s), reaction sensitivities, and tolerance/response to therapy. Long-acting pharmaceutical compositions can be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Where the therapeutic agent is a protein or antibody of the present invention, the therapeutic protein or antibody agent typically is administered at a daily dosage of 0.01 mg to 30 mg/kg of body weight of the patient (e.g., 1 mg/kg to 5 mg/kg). The pharmaceutical formulation can be administered in multiple doses per day, if desired, to achieve the total desired daily dose.

Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Conventional methods, known to those of ordinary skill in the art of medicine, can be used to administer the pharmaceutical formulation(s) of the present invention to the patient. The pharmaceutical compositions of the present invention can be administered alone, or in combination with other therapeutic agents or interventions.

Therapeutic Methods

The present invention further provides methods of treating subjects having defects in a gene of the invention, e.g., in expression, activity, distribution, localization, and/or solubility, which can manifest as a disorder of lung function. As used herein, "treating" includes all medically-acceptable types of therapeutic intervention, including palliation and prophylaxis (prevention) of disease. The term "treating" encompasses any improvement of a disease, including minor improvements. These methods are discussed below.

Gene Therapy and Vaccines

The isolated nucleic acids of the present invention can also be used to drive in vivo expression of the polypeptides of the present invention. In vivo expression can be driven from a vector, typically a viral vector, often a vector based upon a replication incompetent retrovirus, an adenovirus, or an adeno-associated virus (AAV), for purpose of gene therapy. In vivo expression can also be driven from signals endogenous to the nucleic acid or from a vector, often a plasmid vector, such as pVAX1 (Invitrogen, Carlsbad, Calif., USA), for purpose of "naked" nucleic acid vaccination, as further described in U.S. Pat. Nos. 5,589, 466; 5,679,647; 5,804,566; 5,830,877; 5,843,913; 5,880, 104; 5,958,891; 5,985,847; 6,017,897; 6,110,898; and 6,204, 250, the disclosures of which are incorporated herein by reference in their entireties. For cancer therapy, it is preferred that the vector also be tumor-selective. See, e.g., Doronin et al., J. Virol. 75: 3314–24 (2001).

In another embodiment of the therapeutic methods of the present invention, a therapeutically effective amount of a pharmaceutical composition comprising a nucleic acid of the present invention is administered. The nucleic acid can be delivered in a vector that drives expression of an LSP, fusion protein, or fragment thereof, or without such vector. Nucleic acid compositions that can drive expression of an LSP are administered, for example, to complement a deficiency in the native LSP, or as DNA vaccines. Expression vectors derived from virus, replication deficient retroviruses, adenovirus, adeno-associated (AAV) virus, herpes virus, or vaccinia virus can be used as can plasmids. See, e.g., Cid-Arregui, supra. In a preferred embodiment, the nucleic acid molecule encodes an LSP having the amino acid sequence of SEQ ID NO: 143 through 277, or a fragment, fusion protein, allelic variant or homolog thereof.

In still other therapeutic methods of the present invention, pharmaceutical compositions comprising host cells that express an LSP, fusions, or fragments thereof can be administered. In such cases, the cells are typically autologous, so as to circumvent xenogeneic or allotypic rejection, and are administered to complement defects in LSP production or activity. In a preferred embodiment, the nucleic acid molecules in the cells encode an LSP having the amino acid sequence of SEQ ID NO: 143 through 277, or a fragment, fusion protein, allelic variant or homolog thereof.

Antisense Administration

Antisense nucleic acid compositions, or vectors that drive expression of an LSG antisense nucleic acid, are administered to downregulate transcription and/or translation of an LSG in circumstances in which excessive production, or production of aberrant protein, is the pathophysiologic basis of disease.

Antisense compositions useful in therapy can have a sequence that is complementary to coding or to noncoding regions of an LSG. For example, oligonucleotides derived from the transcription initiation site, e.g., between positions −10 and +10 from the start site, are preferred.

Catalytic antisense compositions, such as ribozymes, that are capable of sequence-specific hybridization to LSG transcripts, are also useful in therapy. See, e.g., Phylactou, *Adv. Drug Deliv. Rev.* 44(2–3): 97–108 (2000); Phylactou et al., *Hum. Mol. Genet.* 7(10): 1649–53 (1998); Rossi, *Ciba Found. Symp.* 209: 195–204 (1997); and Sigurdsson et al., *Trends Biotechnol.* 13(8): 286–9 (1995), the disclosures of which are incorporated herein by reference in their entireties.

Other nucleic acids useful in the therapeutic methods of the present invention are those that are capable of triplex helix formation in or near the LSG genomic locus. Such triplexing oligonucleotides are able to inhibit transcription. See, e.g., Intody et al., *Nucleic Acids Res.* 28(21): 4283–90 (2000); McGuffie et al., *Cancer Res.* 60(14): 3790–9 (2000), the disclosures of which are incorporated herein by reference. Pharmaceutical compositions comprising such triplex forming oligos (TFOs) are administered in circumstances in which excessive production, or production of aberrant protein, is a pathophysiologic basis of disease.

In a preferred embodiment, the antisense molecule is derived from a nucleic acid molecule encoding an LSP, preferably an LSP comprising an amino acid sequence of SEQ ID NO: 143 through 277, or a fragment, allelic variant or homolog thereof. In a more preferred embodiment, the antisense molecule is derived from a nucleic acid molecule having a nucleotide sequence of SEQ ID NO: 1 through 142, or a part, allelic variant, substantially similar or hybridizing nucleic acid thereof.

Polypeptide Administration

In one embodiment of the therapeutic methods of the present invention, a therapeutically effective amount of a pharmaceutical composition comprising an LSP, a fusion protein, fragment, analog or derivative thereof is administered to a subject with a clinically-significant LSP defect.

Protein compositions are administered, for example, to complement a deficiency in native LSP. In other embodiments, protein compositions are administered as a vaccine to elicit a humoral and/or cellular immune response to LSP. The immune response can be used to modulate activity of LSP or, depending on the immunogen, to immunize against aberrant or aberrantly expressed forms, such as mutant or inappropriately expressed isoforms. In yet other embodiments, protein fusions having a toxic moiety are administered to ablate cells that aberrantly accumulate LSP.

In a preferred embodiment, the polypeptide is an LSP comprising an amino acid sequence of SEQ ID NO: 143 through 277, or a fusion protein, allelic variant, homolog, analog or derivative thereof. In a more preferred embodiment, the polypeptide is encoded by a nucleic acid molecule having a nucleotide sequence of SEQ ID NO: 1 through 142, or a part, allelic variant, substantially similar or hybridizing nucleic acid thereof.

Antibody, Agonist and Antagonist Administration

In another embodiment of the therapeutic methods of the present invention, a therapeutically effective amount of a pharmaceutical composition comprising an antibody (including fragment or derivative thereof) of the present invention is administered. As is well-known, antibody compositions are administered, for example, to antagonize activity of LSP, or to target therapeutic agents to sites of LSP presence and/or accumulation. In a preferred embodiment, the antibody specifically binds to an LSP comprising an amino acid sequence of SEQ ID NO: 143 through 277, or a fusion protein, allelic variant, homolog, analog or derivative thereof. In a more preferred embodiment, the antibody specifically binds to an LSP encoded by a nucleic acid molecule having a nucleotide sequence of SEQ ID NO: 1 through 142, or a part, allelic variant, substantially similar or hybridizing nucleic acid thereof.

The present invention also provides methods for identifying modulators which bind to an LSP or have a modulatory effect on the expression or activity of an LSP. Modulators which decrease the expression or activity of LSP (antagonists) are believed to be useful in treating lung cancer. Such screening assays are known to those of skill in the art and include, without limitation, cell-based assays and cell-free assays. Small molecules predicted via computer imaging to specifically bind to regions of an LSP can also be designed, synthesized and tested for use in the imaging and treatment of lung cancer. Further, libraries of molecules can be screened for potential anticancer agents by assessing the ability of the molecule to bind to the LSPs identified herein. Molecules identified in the library as being capable of binding to an LSP are key candidates for further evaluation for use in the treatment of lung cancer. In a preferred embodiment, these molecules will downregulate expression and/or activity of an LSP in cells.

In another embodiment of the therapeutic methods of the present invention, a pharmaceutical composition comprising a non-antibody antagonist of LSP is administered. Antagonists of LSP can be produced using methods generally known in the art. In particular, purified LSP can be used to screen libraries of pharmaceutical agents, often combinatorial libraries of small molecules, to identify those that specifically bind and antagonize at least one activity of an LSP.

In other embodiments a pharmaceutical composition comprising an agonist of an LSP is administered. Agonists can be identified using methods analogous to those used to identify antagonists.

In a preferred embodiment, the antagonist or agonist specifically binds to and antagonizes or agonizes, respectively, an LSP comprising an amino acid sequence of SEQ ID NO: 143 through 277, or a fusion protein, allelic variant, homolog, analog or derivative thereof. In a more preferred embodiment, the antagonist or agonist specifically binds to and antagonizes or agonizes, respectively, an LSP encoded by a nucleic acid molecule having a nucleotide sequence of SEQ ID NO: 1 through 142, or a part, allelic variant, substantially similar or hybridizing nucleic acid thereof.

Targeting Lung Tissue

The invention also provides a method in which a polypeptide of the invention, or an antibody thereto, is linked to a therapeutic agent such that it can be delivered to the lung or to specific cells in the lung. In a preferred embodiment, an anti-LSP antibody is linked to a therapeutic agent and is administered to a patient in need of such therapeutic agent. The therapeutic agent may be a toxin, if lung tissue needs to be selectively destroyed. This would be useful for targeting and killing lung cancer cells. In another embodiment, the therapeutic agent may be a growth or differentiation factor, which would be useful for promoting lung cell function.

In another embodiment, an anti-LSP antibody may be linked to an imaging agent that can be detected using, e.g., magnetic resonance imaging, CT or PET. This would be useful for determining and monitoring lung function, identifying lung cancer tumors, and identifying noncancerous lung diseases.

EXAMPLES

Example 1

Gene Expression Analysis

LSGs were identified by a systematic analysis of gene expression data in the LIFESEQ® Gold database available from Incyte Genomics Inc (Palo Alto, Calif.) using the data mining software package CLASP™ (Candidate Lead Automatic Search Program). CLASP™ is a set of algorithms that interrogate Incyte's database to identify genes that are both specific to particular tissue types as well as differentially expressed in tissues from patients with cancer. LifeSeq® Gold contains information about which genes are expressed in various tissues in the body and about the dynamics of expression in both normal and diseased states. CLASP™ first sorts the LifeSeq® Gold database into defined tissue types, such as breast, ovary and prostate. Whereas over half of the diseased samples in the LifeSeq® Gold database are cancer-related, there is considerable variability in the number of patient samples across different cancers. CLASP™ categorizes each tissue sample by disease state. Disease states include "healthy," "cancer," "associated with cancer," "other disease" and "other." Categorizing the disease states filters out data that might otherwise impair our ability to identify tissue and cancer-specific molecular targets. CLASP™ then performs a simultaneous parallel search for genes that are expressed both (1) selectively in the defined tissue type compared to other tissue types and (2) differentially in the "cancer" disease state compared to the other disease states affecting the same, or different, tissues. This sorting is accomplished by using mathematical and statistical filters that specify the minimum change in expression levels and the minimum frequency that the differential expression pattern must be observed across the tissue samples for the gene to be considered statistically significant. The CLASP™ algorithm quantifies the relative abundance of a particular gene in each tissue type and in each disease state.

To find the LSGs of this invention, the following specific CLASP™ profiles were utilized: detectable expression only in cancer tissue (CLASP 2), differential expression in cancer tissue (CLASP 5), and tissue-specific expression (CLASP 1). cDNA libraries were divided into 60 unique tissue types (early versions of LifeSeq® had 48 tissue types). Genes were grouped into "gene bins," where each bin is a cluster of sequences grouped together where they share a common contig. The expression level for each gene bin was calculated for each tissue type. Differential expression significance was calculated with rigorous statistical significant testing taking into account variations in sample size and relative gene abundance in different libraries and within each library (for the equations used to determine statistically significant expression see Audic and Claverie "The significance of digital gene expression profiles," Genome Res 7(10): 986–995 (1997), including Equation 1 on page 987 and Equation 2 on page 988, the contents of which are incorporated by reference). Differently expressed tissue-specific genes were selected based on the percentage abundance level in the targeted tissue versus all the other tissues (tissue-specificity). The expression levels for each gene in normal tissue libraries was compared with the expression level in tissue libraries associated with tumor or disease (cancer-specificity). The results were analyzed for statistical significance.

The selection of the target genes meeting the rigorous CLASP™ profile criteria were as follows:

(a) CLASP 2: detectable expression only in cancer tissue: To qualify as a CLASP 2H (High) candidate, a gene must exhibit detectable expression in tumor tissues and undetectable expression in libraries from normal individuals and libraries from normal tissue obtained from diseased patients. In addition, such a gene must also exhibit further specificity for lung tumor tissues.

(b) CLASP 5: differential expression in cancer tissue: To qualify as a CLASP 5H (High) candidate, a gene must be differentially expressed in tumor libraries in the target tissue compared to normal libraries for all tissues. Only if the gene exhibits cancer-specific differential expression with a 90% of confidence level is it selected as a CLASP 5H lead.

(c) CLASP 1: tissue-specific expression: To qualify as a CLASP 1H (High) candidate, a gene must exhibit statistically significant tissue-specific expression. At first, the percentage abundance level in each gene in each tissue was calculated to identify the tissue with the highest expression percentage level. If the gene shows expression in more than four tissue types, the candidate is considered CLASP 1H candidate only if it exhibits a five-fold absolute abundance in the target tissue compared with the secondary tissue and a 1.5-fold relative abundance in the target tissue compared with secondary tissue. If the candidate gene shows expression in less than 4 tissues, three situations are considered for prioritization of the candidate.

a. If there are less than 3 tumor libraries for the target tissue, the candidate is considered a high priority (1H) candidate only if it exhibits expression in at least one tumor library, otherwise, it is only a medium priority (M) candidate and not considered further.

b. If there are 3 or 4 tumor libraries for the target tissue and the candidate shows expression in at least one tumor library, the candidate is considered a high priority (1H) candidate only if it exhibits a higher percentage expression in the tumor tissues compared to the normal tissues. Otherwise, it is only a medium (M) priority candidate and not considered further.

c. If there are more than 4 tumor libraries of the tissue of interest, the candidate exhibits expression in less than 40% of tumor libraries and the percentage abundance in tumor is 3 fold greater than in normal, the candidate is considered a 1H candidate. If the candidate exhibits expression percentage less than 0.00001, it is considered a low (L) priority candidate. Otherwise, it is considered a medium (M) priority candidate.

The CLASP scores for SEQ ID NO: 1 through 142 are listed below:

| ID | Name | Score |
|---|---|---|
| DEX0241_1 | CLASP | 5 H |
| DEX0241_2 | CLASP | 5 H |
| DEX0241_4 | CLASP | 2 H |
| DEX0241_5 | CLASP | 2 H |
| DEX0241_6 | CLASP | 2 H |
| DEX0241_7 | CLASP | 5 H 1 H |
| DEX0241_8 | CLASP | 5 H 1 H |
| DEX0241_9 | CLASP | 2 H |
| DEX0241_10 | CLASP | 2 H |
| DEX0241_11 | CLASP | 2 H |
| DEX0241_12 | CLASP | 2 H |
| DEX0241_13 | CLASP | 2 H |
| DEX0241_14 | CLASP | 2 H |
| DEX0241_15 | CLASP | 2 H 1 H |
| DEX0241_16 | CLASP | 2 H |
| DEX0241_17 | CLASP | 2 H |
| DEX0241_18 | CLASP | 2 H 1 H |
| DEX0241_19 | CLASP | 2 H 1 H |
| DEX0241_20 | CLASP | 5 H |
| DEX0241_21 | CLASP | 5 H |
| DEX0241_22 | CLASP | 2 H |
| DEX0241_23 | CLASP | 2 H |
| DEX0241_24 | CLASP | 5 H |
| DEX0241_25 | CLASP | 5 H |
| DEX0241_26 | CLASP | 2 H |
| DEX0241_27 | CLASP | 2 H 1 H |
| DEX0241_28 | CLASP | 2 H |
| DEX0241_29 | CLASP | 2 H |
| DEX0241_30 | CLASP | 2 H 1 H |
| DEX0241_31 | CLASP | 2 H 1 H |
| DEX0241_32 | CLASP | 2 H |
| DEX0241_33 | CLASP | 2 H |
| DEX0241_34 | CLASP | 5 H |
| DEX0241_35 | CLASP | 5 H |
| DEX0241_36 | CLASP | 2 H 1 H |
| DEX0241_37 | CLASP | 2 H |
| DEX0241_38 | CLASP | 2 H |
| DEX0241_39 | CLASP | 2 H |
| DEX0241_40 | CLASP | 5 H |
| DEX0241_41 | CLASP | 5 H |
| DEX0241_42 | CLASP | 5 H 1 H |
| DEX0241_43 | CLASP | 2 H |
| DEX0241_44 | CLASP | 2 H |
| DEX0241_45 | CLASP | 2 H |
| DEX0241_47 | CLASP | 2 H |
| DEX0241_48 | CLASP | 2 H |
| DEX0241_49 | CLASP | 5 H 1 H |
| DEX0241_50 | CLASP | 2 H |
| DEX0241_53 | CLASP | 2 H |
| DEX0241_54 | CLASP | 2 H |
| DEX0241_56 | CLASP | 2 H |
| DEX0241_57 | CLASP | 2 H |
| DEX0241_58 | CLASP | 2 H |
| DEX0241_61 | CLASP | 2 H |
| DEX0241_62 | CLASP | 2 H |
| DEX024L_63 | CLASP | 2 H |
| DEX0241_64 | CLASP | 2 H |
| DEX0241_65 | CLASP | 2 H |
| DEX0241_66 | CLASP | 2 H |
| DEX0241_67 | CLASP | 2 H |
| DEX0241_68 | CLASP | 2 H |
| DEX0241_69 | CLASP | 2 H |
| DEX0241_70 | CLASP | 2 H |
| DEX0241_71 | CLASP | 2 H |
| DEX0241_72 | CLASP | 2 H |
| DEX0241_73 | CLASP | 2 H |
| DEX0241_74 | CLASP | 2 H |
| DEX0241_75 | CLASP | 2 H |
| DEX0241_76 | CLASP | 2 H |
| DEX0241_77 | CLASP | 2 H |
| DEX0241_80 | CLASP | 2 H |
| DEX0241_81 | CLASP | 2 H |
| DEX0241_82 | CLASP | 2 H |
| DEX0241_83 | CLASP | 1 H |
| DEX0241_84 | CLASP | 2 H |
| DEX0241_85 | CLASP | 2 H |
| DEX0241_86 | CLASP | 5 H 1 H |
| DEX0241_87 | CLASP | 5 H 1 H |
| DEX0241_88 | CLASP | 2 H |
| DEX0241_89 | CLASP | 2 H |
| DEX0241_90 | CLASP | 2 H |
| DEX0241_91 | CLASP | 2 H |
| DEX0241_92 | CLASP | 2 H |
| DEX0241_93 | CLASP | 2 H |
| DEX0241_94 | CLASP | 2 H |
| DEX0241_95 | CLASP | 2 H |
| DEX0241_96 | CLASP | 2 H |
| DEX0241_97 | CLASP | 2 H |
| DEX0241_98 | CLASP | 2 H |
| DEX0241_99 | CLASP | 2 H |
| DEX0241_101 | CLASP | 5 H 1 H |
| DEX0241_102 | CLASP | 1 H |
| DEX0241_103 | CLASP | 1 H |
| DEX0241_104 | CLASP | 5 H 1 H |
| DEX0241_105 | CLASP | 2 H |
| DEX0241_108 | CLASP | 2 H |
| DEX0241_109 | CLASP | 2 H |
| DEX0241_110 | CLASP | 5 H |
| DEX0241_113 | CLASP | 5 H |
| DEX0241_114 | CLASP | 5 H |
| DEX0241_115 | CLASP | 2 H |
| DEX0241_116 | CLASP | 2 H |
| DEX0241_117 | CLASP | 2 H |
| DEX0241_118 | CLASP | 2 H |
| DEX0241_121 | CLASP | 2 H |
| DEX0241_122 | CLASP | 2 H |
| DEX0241_124 | CLASP | 2 H |
| DEX0241_125 | CLASP | 5 H |
| DEX0241_126 | CLASP | 5 H |
| DEX0241_127 | CLASP | 2 H |
| DEX0241_128 | CLASP | 2 H |
| DEX0241_129 | CLASP | 5 H 1 H |
| DEX0241_130 | CLASP | 5 H 1 H |
| DEX0241_131 | CLASP | 2 H |
| DEX0241_132 | CLASP | 2 H |
| DEX0241_133 | CLASP | 2 H |
| DEX0241_135 | CLASP | 2 H |
| DEX0241_137 | CLASP | 2 H 1 H |
| DEX0241_138 | CLASP | 2 H 1 H |
| DEX0241_139 | CLASP | 1 H |
| DEX0241_142 | CLASP | 2 H |

Example 2

Relative Quantitation of Gene Expression

Real-Time quantitative PCR with fluorescent Taqman probes is a quantitation detection system utilizing the 5'–3' nuclease activity of Taq DNA polymerase. The method uses an internal fluorescent oligonucleotide probe (Taqman) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA). Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH), ATPase, or 18S ribosomal RNA (rRNA) is used as this endogenous control. To calculate relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System).

The tissue distribution and the level of the target gene are evaluated for every sample in normal and cancer tissues. Total RNA is extracted from normal tissues, cancer tissues, and from cancers and the corresponding matched adjacent tissues. Subsequently, first strand cDNA is prepared with reverse transcriptase and the polymerase chain reaction is done using primers and Taqman probes specific to each target gene. The results are analyzed using the ABI PRISM 7700 Sequence Detector. The absolute numbers are relative levels of expression of the target gene in a particular tissue compared to the calibrator tissue.

One of ordinary skill can design appropriate primers. The relative levels of expression of the LSNA versus normal tissues and other cancer tissues can then be determined. All the values are compared to normal thymus (calibrator). These RNA samples are commercially available pools, originated by pooling samples of a particular tissue from different individuals.

The relative levels of expression of the LSNA in pairs of matching samples and 1 cancer and 1 normal/normal adjacent of tissue may also be determined. All the values are compared to normal thymus (calibrator). A matching pair is formed by mRNA from the cancer sample for a particular tissue and mRNA from the normal adjacent sample for that same tissue from the same individual.

In the analysis of matching samples, the LSNAs that show a high degree of tissue specificity for the tissue of interest. These results confirm the tissue specificity results obtained with normal pooled samples.

Further, the level of mRNA expression in cancer samples and the isogenic normal adjacent tissue from the same individual are compared. This comparison provides an indication of specificity for the cancer stage (e.g. higher levels of mRNA expression in the cancer sample compared to the normal adjacent).

Altogether, the high level of tissue specificity, plus the mRNA overexpression in matching samples tested are indicative of SEQ ID NO: 1 through 142 being a diagnostic marker for cancer.

| Sequences | Gene ID | ddx QPCR lung code | SEQ ID NO: |
|---|---|---|---|
| DEX0241_84 | 206814 | Lng179 | 84 |

Table 1. The absolute numbers are relative levels of expression of Lng179 in 24 normal different tissues. All the values are compared to normal brain (calibrator). These RNA samples are commercially pools, originated by pooling samples of a particular tissue from different individuals.

| Tissue | NORMAL |
|---|---|
| Adrenal Gland | 0.00 |
| Bladder | 0.12 |
| Brain | 1.00 |
| Cervix | 0.00 |
| Colon | 0.00 |
| Endometrium | 0.14 |
| Esophagus | 0.00 |
| Heart | 0.00 |
| Kidney | 0.03 |
| Liver | 0.00 |
| Lung | 0.72 |
| Mammary Gland | 0.04 |
| Muscle | 0.00 |
| Ovary | 0.09 |
| Pancreas | 0.41 |
| Prostate | 0.00 |
| Rectum | 0.00 |

-continued

| Tissue | NORMAL |
|---|---|
| Small Intestine | 0.03 |
| Spleen | 0.17 |
| Stomach | 0.00 |
| Testis | 0.64 |
| Thymus | 0.12 |
| Trachea | 0.11 |
| Uterus | 0.11 |

0 = negative

The relative levels of expression in Table 1 show that Lng179 mRNA expression is relatively higher in lung compared with most other normal tissues analyzed.

The absolute numbers in Table 1 were obtained analyzing pools of samples of a particular tissue from different individuals. They can not be compared to the absolute numbers originated from RNA obtained from tissue samples of a single individual in Table 2.

Table 2. The absolute numbers are relative levels of expression of Lng179 in 20 pairs of matching samples. All the values are compared to normal brain (calibrator). A matching pair is formed by mRNA from the cancer sample for a particular tissue and mRNA from the normal adjacent sample for that same tissue from the same individual.

| Sample ID | Cancer Type | Tissue | CANCER | MATCHING NORMAL ADJACENT |
|---|---|---|---|---|
| Lng 60L | Adenocarcinoma | Lung 1 | 0.01 | 0.00 |
| Lng AC66 | Adenocarcinoma | Lung 2 | 0.13 | 0.06 |
| Lng AC69 | Adenocarcinoma | Lung 3 | 0.11 | 0.00 |
| Lng AC94 | Adenocarcinoma | Lung 4 | 0.00 | 0.00 |
| Lng AC11 | Adenocarcinoma | Lung 5 | 0.18 | 0.00 |
| Lng AC32 | Adenocarcinoma | Lung 6 | 0.00 | 0.04 |
| Lng 223L | Adenocarcinoma | Lung 7 | 0.11 | 0.00 |
| Lng SQ45 | Squamous cell carcinoma | Lung 8 | 0.15 | 1.35 |
| Lng SQ16 | Squamous cell carcinoma | Lung 9 | 0.04 | 0.00 |
| Lng SQ79 | Squamous cell carcinoma | Lung 10 | 0.62 | 0.16 |
| Bld46XK | | Bladder 1 | 0.00 | 0.00 |
| BldTR14 | | Bladder 2 | 0.22 | 0.09 |
| ClnAS43 | | Colon 1 | 0.00 | 0.00 |
| ClnAS45 | | Colon 2 | 0.00 | 0.01 |
| ClnAS46 | | Colon 3 | 0.03 | 0.02 |
| ClnAS67 | | Colon 4 | 0.00 | 0.05 |
| ClnAS89 | | Colon 5 | 0.01 | 0.31 |
| Liv94Xa | | Liver 1 | 0.00 | 0.00 |
| Tst647T | | Testis 1 | 0.38 | 0.18 |
| Utr135XO | | Uterus 1 | 0.15 | 0.11 |

0 = Negative

In the analysis of matching samples, higher expression of Ing179 is detected in lung samples showing a high degree of tissue specificity for lung tissue. These results confirm the tissue specificity results obtained with normal pooled samples (Table 1).

Furthermore, we compared the level of mRNA expression in cancer samples and the isogenic normal adjacent tissue from the same individual. This comparison provides an indication of specificity for the cancer stage (e.g. higher levels of mRNA expression in the cancer sample compared to the normal adjacent). Table 2 shows overexpression of Lng179 in 10 lung cancer tissues compared with their respective normal adjacent (lung samples #1, 2, 3, 5, 7, 9, and 10). There is overexpression in the cancer tissue for 70% of the lung matching samples tested (7 out of total of 10 lung matching samples).

Altogether, the high level of tissue specificity, plus the mRNA differential expression in the lung matching samples tested are believed to make Lng179 a good marker for diagnosing, monitoring, staging, imaging and treating lung cancer.

Primers Used for QPCR Expression Analysis

| Primer Probe Oligo | Start From | End To | QueryLength | SbjctDescript |
|---|---|---|---|---|
| Lng179For | 69 | 93 | 25 | DEX0241_84 (SEQ ID NO:84) |
| Lng179Rev | 218 | 193 | 26 | DEX0241_84 (SEQ ID NO:84) |
| Lng179Probe | 94 | 128 | 35 | DEX0241_84 (SEQ ID NO:84) |

Example 2B

Custom Microarray Experiment

Custom oligonucleotide microarrays were provided by Agilent Technologies, Inc. (Palo Alto, Calif.). The microarrays were fabricated by Agilent using their technology for the in-situ synthesis of 60mer oligonucleotides (Hughes, et al. 2001, Nature Biotechnology 19:342–347). The 60mer microarray probes were designed by Agilent, from gene sequences provided by diaDexus, using Agilent proprietary algorithms. Whenever possible two different 60mers were designed for each gene of interest.

All microarray experiments were two-color experiments and were preformed using Agilent-recommended protocols and reagents. Briefly, each microarray was hybridized with cRNAs synthesized from polyA+RNA, isolated from cancer and normal tissues, labeled with fluorescent dyes Cyanine3 and Cyanine5 (NEN Life Science Products, Inc., Boston, Mass.) using a linear amplification method (Agilent). In each experiment the experimental sample was polyA+RNA isolated from cancer tissue from a single individual and the reference sample was a pool of polyA+RNA isolated from normal tissues of the same organ as the cancerous tissue (i.e. normal lung tissue in experiments with lung cancer samples). Hybridizations were carried out at 60° C., overnight using Agilent in-situ hybridization buffer. Following washing, arrays were scanned with a GenePix 4000B Microarray Scanner (Axon Instruments, Inc., Union City, Calif.). The resulting images were analyzed with GenePix Pro 3.0 Microarray Acquisition and Analysis Software (Axon). A total of 29 experiments comparing the expression patterns of lung cancer derived polyA+RNA (15 squamous cell carcinomas, 14 adenocarcinomas) to polyA+RNA isolated from a pool of 12 normal lung tissues were analyzed.

Data normalization and expression profiling were done with Expressionist software from GeneData Inc. (Daly City, Calif.,/Basel, Switzerland). Gene expression analysis was performed using only experiments that meet certain quality criteria. The quality criteria that experiments must meet are a combination of evaluations performed by the Expressionist software and evaluations performed manually using raw and normalized data. To evaluate raw data quality, detection limits (the mean signal for a replicated negative control+2 Standard Deviations (SD)) for each channel were calculated. The detection limit is a measure of non-specific hybridization. Arrays with poor detection limits were not analyzed and the experiments were repeated. To evaluate normalized data quality, positive control elements included in the array were utilized. These array features should have a mean ratio of 1 (no differential expression). If these features have a mean ratio of greater than 1.5-fold up or down, the experiments were not analyzed further and were repeated. In addition to traditional scatter plots demonstrating the distribution of signal in each experiment, the Expressionist software also has minimum thresholding criteria that employ user defined parameters to identify quality data. Only those features that meet the threshold criteria were included in the filtering and analyses carried out by Expressionist. The thresholding settings employed require a minimum area percentage of 60% [(% pixels>background+2SD)–(% pixels saturated)], and a minimum signal to noise ratio of 2.0 in both channels. By these criteria, very low expressors and saturated features were not included in analysis.

Relative expression data was collected from Expressionist based on filtering and clustering analyses. Up- and down-regulated genes were identified using criteria for percentage of valid values obtained, and the percentage of experiments in which the gene is up- or down-regulated. These criteria were set independently for each data set, depending on the size and the nature of the data set. The results for the statistically significant upregulated and downregulated genes are shown in Table 1. The first three columns of the table contain information about the sequence itself (Oligo ID, Parent ID, and Patent#), the next 3 columns show the results obtained. '% valid' indicates the percentage of 29 unique experiments total in which a valid expression value was obtained, '% up' indicates the percentage of 29 experiments in which up-regulation of at least 2.5-fold was observed, and '% down' indicates the percentage of the 29 experiments in which down-regulation of at least 2.5-fold was observed. The last column in Table 1 describes the location of the microarray probe (oligo) relative to the parent sequence. Additional sequences were examined but the data was inconclusive.

TABLE 1

Sensitivity data for DEX0241 series microarray features.

| Oligo ID | Parent ID | Patent # | Sensitivity of up and down regulation | | | Oligo Seq location |
|---|---|---|---|---|---|---|
| | | | % valid | % up | % down | |
| 4176 | 2881 | DEX0241_49 (SEQ ID NO: 49) | 62% | 0% | 48% | 564–623 |
| 4177 | 2881 | DEX0241_49 (SEQ ID NO: 49) | 45% | 0% | 31% | 554–613 |
| 7140 | 1950 | DEX0241_100 (SEQ ID NO: 100) | 86% | 0% | 79% | 1342–1401 |
| 7141 | 1950 | DEX0241_100 (SEQ ID NO: 100) | 93% | 0% | 86% | 1246–1305 |

Example 3

Protein Expression

The LSNA is amplified by polymerase chain reaction (PCR) and the amplified DNA fragment encoding the LSNA is subcloned in pET-21d for expression in E. coli. In addition to the LSNA coding sequence, codons for two amino acids, Met-Ala, flanking the $NH_2$-terminus of the coding sequence of LSNA, and six histidines, flanking the COOH-terminus of the coding sequence of LSNA, are incorporated to serve as initiating Met/restriction site and purification tag, respectively.

An over-expressed protein band of the appropriate molecular weight may be observed on a Coomassie blue stained polyacrylamide gel. This protein band is confirmed by Western blot analysis using monoclonal antibody against 6×Histidine tag.

Large-scale purification of LSP was achieved using cell paste generated from 6-liter bacterial cultures, and purified using immobilized metal affinity chromatography (IMAC). Soluble fractions that had been separated from total cell lysate were incubated with a nickle chelating resin. The column was packed and washed with five column volumes of wash buffer. LSP was eluted stepwise with various concentration imidazole buffers.

Example 4
Protein Fusions

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 2, is ligated into this BamHI site. Note that the polynucleotide is cloned without a stop codon, otherwise a fusion protein will not be produced. If the naturally occurring signal sequence is used to produce the secreted protein, pC4 does not need a second signal peptide. Alternatively, if the naturally occurring signal sequence is not used, the vector can be modified to include a heterologous signal sequence. See, e. g., WO 96/34891.

Example 5
Production of an Antibody from a Polypeptide

In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100, µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al., *Gastroenterology* 80: 225–232 (1981).

The hybridoma cells obtained through such a selection are then assayed to identify clones which secrete antibodies capable of binding the polypeptide. Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein specific antibody and can be used to immunize an animal to induce formation of further protein-specific antibodies. Using the Jameson-Wolf methods the following epitopes were predicted. (Jameson and Wolf CABIOS, 4(1), 181–186, 1988, the contents of which are incorporated by reference).

Examples of post-translational modifications (PTMs) of the LSP of this invention are listed below. In addition, antibodies that specifically bind such post-translational modifications may be useful as a diagnostic or as therapeutic. Using the ProSite database (Bairoch et al., Nucleic Acids Res. 25(1):217–221 (1997), the contents of which are incorporated by reference), the following PTMs were predicted for the LSPs of the invention (http://npsa-pbil.ibcp.fr/cgi-bin/npsa automat.pl?page=npsa prosite.html most recently accessed Oct. 23, 2001).

| | |
|---|---|
| DEX0241_143 | Ck2_Phospho_Site 16–19; 38–41; Myristyl 50–55; |
| DEX0241_144 | Ck2_Phospho_Site 16–19; 38–41; Myristyl 50–55; |
| DEX0241_145 | Myristyl 5–10; |
| DEX0241_146 | Pkc_Phospho_Site 2–4; |
| DEX0241_147 | Myristyl 26–31; Pkc_Phospho_Site 75–77; |
| DEX0241_149 | Amidation 3–6; Camp_Phospho_Site 8–11; Ck2_Phospho_Site 12–15; 17–20; 51–54; 93–96; 155–158; Myristyl 156–161; Pkc_Phospho_Site 12–14; 34–36; 101–103; 117–119; |
| DEX0241_150 | Asn_Glycosylation 23–26; 141–144; 187–190; Camp_Phospho_Site 246–249; Ck2_Phospho_Site 5–8; 15–18; 27–30; 32–35; 43–46; 53–56; 95–98; 217–220; Myristyl 139–144; 288–293; Pkc_Phospho_Site 103–105; 119–121; 174–176; 222–224; 245–247; 249–251; 308–310; |
| DEX0241_152 | Myristyl 4–9; |
| DEX0241_153 | Ck2_Phospho_Site 8–11; Myb_1 7–15; |
| DEX0241_154 | Leucine_Zipper 69–90; Myristyl 77–82; |
| DEX0241_155 | Asn_Glycosylation 23–26; Ck2_Phospho_Site 11–14; Myristyl 48–53; Pkc_Phospho_Site 18–20; 25–27; |
| DEX0241_156 | Amidation 33–36; Ck2_Phospho_Site 4–7; 20–23; Myristyl 40–45; 54–59; 69–74; 70–75; 78–83; |
| DEX0241_157 | Ck2_Phospho_Site 28–31; Myristyl 51–56; 58–63; |
| DEX0241_158 | Ck2_Phospho_Site 42–45; Pkc_Phospho_Site 7–9; 23–25; |
| DEX0241_159 | Amidation 43–46; Asn_Glycosylation 6–9; Pkc_Phospho_Site 95–97; Tyr_Phospho_Site 70–77; |
| DEX0241_160 | Myristyl 65–70; Pkc_Phospho_Site 75–77; |
| DEX0241_161 | Ck2_Phospho_Site 31–34; |
| DEX0241_162 | Ck2_Phospho_Site 34–37; |
| DEX0241_163 | Pkc_Phospho_Site 7–9; 14–16; |

-continued

| | |
|---|---|
| DEX0241_164 | Asn_Glycosylation 18–21; 31–34; |
| DEX0241_166 | Camp_Phospho_Site 10–13; Ck2_Phospho_Site 9–12; Myristyl 33–38; Pkc_Phospho_Site 9–11; 37–39; Tyr_Phospho_Site 10–17; 11–17; |
| DEX0241_167 | Pkc_Phospho_Site 26–28; |
| DEX0241_168 | Ck2_Phospho_Site 66–69; Myristyl 23–28; 72–77; Pkc_Phospho_Site 11–13; 36–38; 73–75; 76–78; |
| DEX0241_169 | Camp_Phospho_Site 17–20; Ck2_Phospho_Site 3–6; |
| DEX0241_170 | Amidation 89–92; Ck2_Phospho_Site 84–87; Myristyl 81–86; 101–106; Pkc_Phospho_Site 7–9; Prokar_Lipoprotein 38–48; 50–60; 52–62; |
| DEX0241_171 | Camp_Phospho_Site 13–16; Ck2_Phospho_Site 21–24; 56–59; Myristyl 27–32; 31–36; 41–46; 47–52; |
| DEX0241_172 | Ck2_Phospho_Site 63–66; Myristyl 12–17; 64–69; Pkc_Phospho_Site 76–78; Prokar_Lipoprotein 17–27; |
| DEX0241_173 | Ck2_Phospho_Site 63–66; Myristyl 12–17; 64–69; Pkc_Phospho_Site 76–78; Prokar_Lipoprotein 17–27; |
| DEX0241_174 | Asn_Glycosylation 56–59; Myristyl 7–12; Tyr_Phospho_Site 32–40; |
| DEX0241_175 | Asn_Glycosylation 56–59; Myristyl 7–12; Tyr_Phospho_Site 32–40; |
| DEX0241_176 | Ck2_Phospho_Site 30–33; Glycosaminoglycan 26–29; Myristyl 49–54; 50–55; |
| DEX0241_177 | Asn_Glycosylation 20–23; Ck2_Phospho_Site 52–55; Glycosaminoglycan 48–51; Myristyl 71–76; 72–77; |
| DEX0241_179 | Myristyl 34–39; |
| DEX0241_180 | Asn_Glycosylation 10–13; |
| DEX0241_181 | Myristyl 17–22; 32–37; 44–49; |
| DEX0241_182 | Ck2_Phospho_Site 5–8; |
| DEX0241_183 | Ck2_Phospho_Site 23–26; 52–55; 54–57; Pkc_Phospho_Site 48–50; 83–85; |
| DEX0241_184 | Asn_Glycosylation 32–35; Pkc_Phospho_Site 7–9; |
| DEX0241_186 | Amidation 24–27; Ck2_Phospho_Site 54–57; Myristyl 70–75; Pkc_Phospho_Site 4–6; 24–26; |
| DEX0241_188 | Tyr_Phospho_Site 21–28; |
| DEX0241_189 | Ck2_Phospho_Site 18–21; |
| DEX0241_190 | Asn_Glycosylation 21–24; Pkc_Phospho_Site 31–33; |
| DEX0241_191 | Pkc_Phospho_Site 7–9; 51–53; |
| DEX0241_192 | Pkc_Phospho_Site 21–23; |
| DEX0241_193 | Asn_Glycosylation 30–33; |
| DEX0241_194 | Asn_Glycosylation 30–33; |
| DEX0241_195 | Myristyl 23–28; Pkc_Phospho_Site 62–64; |
| DEX0241_196 | Asn_Glycosylation 70–73; Myristyl 25–30; Pkc_Phospho_Site 45–47; |
| DEX0241_197 | Ck2_Phospho_Site 2–5; 19–22; 26–29; Pkc_Phospho_Site 19–21; 34–36; |
| DEX0241_198 | Ck2_Phospho_Site 2–5; 19–22; 26–29; Pkc_Phospho_Site 19–21; 34–36; |
| DEX0241_199 | Myristyl 14–19; 37–42; Pkc_Phospho_Site 69–71; |
| DEX0241_200 | Asn_Glycosylation 58–61; Ck2_Phospho_Site 38–41; Myristyl 50–55; 54–59; Pkc_Phospho_Site 60–62; |
| DEX0241_201 | Asn_Glycosylation 299–302; 345–348; 435–438; Camp_Phospho_Site 398–401; Ck2_Phospho_Site 42–45; 64–67; 130–133; 165–168; 178–181; 187–190; 195–198; 240–243; 286–289; 301–304; 315–318; 365–368; 419–422; 430–433; 454–457; 477–480; Myristyl 184–189; 402–407; Pkc_Phospho_Site 130–132; 138–140; 465–467; |
| DEX0241_202 | Myristyl 41–46; Pkc_Phospho_Site 27–29; |
| DEX0241_203 | Myristyl 41–46; Pkc_Phospho_Site 27–29; |
| DEX0241_204 | Camp_Phospho_Site 35–38; Ck2_Phospho_Site 4–7; 23–26; Pkc_Phospho_Site 33–35; 47–49; |
| DEX0241_205 | Ck2_Phospho_Site 7–10; |
| DEX0241_206 | Pkc_Phospho_Site 7–9; 57–59; |
| DEX0241_207 | Pkc_Phospho_Site 7–9; 57–59; |
| DEX0241_210 | Myristyl 44–49; Pkc_Phospho_Site 9–11; 23–25; Prokar_Lipoprotein 54–64; |
| DEX0241_211 | Asn_Glycosylation 15–18; 43–46; |
| DEX0241_212 | Asn_Glycosylation 17–20; |
| DEX0241_213 | Ck2_Phospho_Site 17–20; 36–39; 59–62; Myristyl 43–48; Pkc_Phospho_Site 17–19; 26–28; |
| DEX0241_215 | Asn_Glycosylation 4–7; Ck2_Phospho_Site 37–40; |
| DEX0241_216 | Pkc_Phospho_Site 13–15; |
| DEX0241_218 | Ck2_Phospho_Site 14–17; Pkc_Phospho_Site 10–12; 14–16; |
| DEX0241_219 | Pkc_Phospho_Site 80–82; |
| DEX0241_220 | Myristyl 18–23; |
| DEX0241_221 | Asn_Glycosylation 304–307; 617–620; 623–626; 643–646; 686–689; Cadherin 93–103; 198–208; 309–319; Camp_Phospho_Site 527–530; Ck2_Phospho_Site 109–112; 128–131; 130–133; 233–236; 235–238; 248–251; 457–460; 530–533; 593–596; 654–657; 668–671; 727– |

-continued

|  |  |
|---|---|
|  | 730; 758–761; Egf_1 506–517; Glycosaminoglycan 438–441; 452–455; 658–661; Myristyl 117–122; 121–126; 138–143; 296–301; 370–375; 434–439; 435–440; 436–441; 437–442; 439–444; 440–445; 453–458; 454–459; 511–516; 512–517; 513–518; 514–519; 555–560; 601–606; 618–623; 742–747; 767–772; Pkc_Phospho_Site 5–7; 26–28; 55–57; 109–111; 130–132; 155–157; 192–194; 235–237; 387–389; 576–578; 654–656; 673–675; 697–699; Tyr_Phospho_Site 339–345; |
| DEX0241_222 | Camp_Phospho_Site 3–6; Ck2_Phospho_Site 14–17; Pkc_Phospho_Site 6–8; 30–32; Tyr_Phospho_Site 41–48; |
| DEX0241_223 | Ck2_Phospho_Site 42–45; Myristyl 10–15; Pkc_Phospho_Site 35–37; Prokar_Lipoprotein 12–22; |
| DEX0241_224 | Pkc_Phospho_Site 32–34; |
| DEX0241_225 | Asn_Glycosylation 13–16; Pkc_Phospho_Site 59–61; |
| DEX0241_226 | Asn_Glycosylation 18–21; |
| DEX0241_227 | Amidation 14–17; Asn_Glycosylation 10–13; Ck2_Phospho_Site 25–28; Pkc_Phospho_Site 9–11; |
| DEX0241_228 | Camp_Phospho_Site 11–14; 25–28; Ck2_Phospho_Site 14–17; Myristyl 52–57; Pkc_Phospho_Site 14–16; |
| DEX0241_229 | Amidation 34–37; |
| DEX0241_230 | Ck2_Phospho_Site 11–14; |
| DEX0241_232 | Ck2_Phospho Site_21–24; Myristyl 19–24; |
| DEX0241_235 | Asn_Glycosylation 32–35; Pkc_Phospho_Site 34–36; |
| DEX0241_236 | Asn_Glycosylation 86–89; Camp_Phospho_Site 42–45; Ck2_Phospho_Site 82–85; 105–108; Myristyl 49–54; 51–56; 63–68; Pkc_Phospho_Site 128–130; |
| DEX0241_237 | Camp_Phospho_Site 28–31; 69–72; 316–319; Ck2_Phospho_Site 5–8; 46–49; 191–194; 208–211; 270–273; 304–307; 361–364; 381–384; Myristyl 78–83; 90–95; 97–102; 168–173; 174–179; 197–202; 278–283; 297–302; 299–304; 310–315; 318–323; 321–326; 368–373; 376–381; Pkc_Phospho_Site 210–212; 214–216; 311–313; |
| DEX0241_238 | Myristyl 45–50; Pkc_Phospho_Site 51–53; |
| DEX0241_239 | Myristyl 45–50; Pkc_Phospho_Site 51–53; |
| DEX0241_240 | Asn_Glycosylation 27–30; 63–66; Ck2_Phospho_Site 39–42; Pkc_Phospho_Site 46–48; |
| DEX0241_241 | Asn_Glycosylation 27–30; 63–66; Ck2_Phospho_Site 39–42; Pkc_Phospho_Site 46–48; |
| DEX0241_242 | Asn_Glycosylation 25–28; Myristyl 30–35; Pkc_Phospho_Site 27–29; |
| DEX0241_243 | Pkc_Phospho_Site 67–69; Tyr_Phospho_Site 31–39; |
| DEX0241_244 | Myristyl 14–19; 18–23; 78–83; |
| DEX0241_245 | Pkc_Phospho_Site 7–9; |
| DEX0241_246 | Myristyl 4–9; 5–10; |
| DEX0241_247 | Myristyl 31–36; |
| DEX0241_248 | Myristyl 20–25; 96–101; Pkc_Phospho_Site 13–15; |
| DEX0241_250 | Myristyl 44–49; |
| DEX0241_251 | Myristyl 28–33; |
| DEX0241_256 | Myristyl 54–59; 85–90; Pkc_Phospho_Site 74–76; |
| DEX0241_257 | Amidation 84–87; Myristyl 54–59; 103–108; Pkc_Phospho_Site 74–76; 84–86; |
| DEX0241_258 | Ck2_Phospho_Site 13–16; Myristyl 5–10; |
| DEX0241_259 | Myristyl 42–47; |
| DEX0241_260 | Pkc_Phospho_Site 29–31; |
| DEX0241_261 | Asn_Glycosylation 21–24; |
| DEX0241_262 | Ck2_Phospho_Site 2–5; 3–6; 17–20; Myristyl 9–14; |
| DEX0241_263 | Ck2_Phospho Site_12–15; Myristyl 17–22; Pkc_Phospho_Site 64–66; |
| DEX0241_264 | Asn_Glycosylation 62–65; Myristyl 60–65; Pkc_Phospho_Site 28–30; |
| DEX0241_265 | Amidation 12–15; Pkc_Phospho_Site 3–5; |
| DEX0241_266 | Asn_Glycosylation 42–45; Ck2_Phospho_Site 17–20; Pkc_Phospho_Site 50–52; 55–57; |
| DEX0241_267 | Ck2_Phospho_Site 51–54; Pkc_Phospho_Site 15–17; |
| DEX0241_268 | Ck2_Phospho_Site 35–38; Pkc_Phospho_Site 24–26; |
| DEX0241_269 | Myristyl 12–17; Pkc_Phospho_Site 48–50; |
| DEX0241_270 | Camp_Phospho_Site 11–14; Pkc_Phospho_Site 16–18; |
| DEX0241_271 | Asn_Glycosylation 70–73; Ck2_Phospho_Site 72–75; Pkc_Phospho_Site 15–17; 51–53; 56–58; 72–74; |
| DEX0241_272 | Myristyl 33–38; |
| DEX0241_273 | Asn_Glycosylation 8–11; 15–18; 35–38; |
| DEX0241_274 | Asn_Glycosylation 16–19; |
| DEX0241_276 | Ck2_Phospho_Site 67–70; 210–213; Glycosaminoglycan 121–124; Myristyl 197–202; Pkc_Phospho_Site 28–30; 111–113; 165–167; 204–206; 229–231; 241–243; Rgd 206–208; Tyr_Phospho_Site 155–163; |
| DEX0241_277 | Ck2_Phospho_Site 13–16; |

Example 6
Method of Determining Alterations in a Gene Corresponding to a Polynucleotide RNA is isolated from individual patients or from a family of individuals that have a phenotype of interest. cDNA is then generated from these RNA samples using protocols known in the art. See, Sambrook (2001), supra. The cDNA is then used as a template for PCR, employing primers surrounding regions of interest in SEQ ID NO: 1 through 142. Suggested PCR conditions consist of 35 cycles at 95° C. for 30 seconds; 60–120 seconds at 52–58° C.; and 60–120 seconds at 70° C., using buffer solutions described in Sidransky et al., *Science* 252(5006): 706–9 (1991). See also Sidransky et al., *Science* 278(5340): 1054–9 (1997).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations are then cloned and sequenced to validate the results of the direct sequencing. PCR products is cloned into T-tailed vectors as described in Holton et al., *Nucleic Acids Res.*, 19: 1156 (1991) and sequenced with T7 polymerase (United States Biochemical). Affected individuals are identified by mutations not present in unaffected individuals.

Genomic rearrangements may also be determined. Genomic clones are nick-translated with digoxigenin deoxyuridine 5' triphosphate (Boehringer Manheim), and FISH is performed as described in Johnson et al., *Methods Cell Biol.* 35: 73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C-and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. Id. Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 7
Method of Detecting Abnormal Levels of a Polypeptide in a Biological Sample Antibody-sandwich ELISAs are used to detect polypeptides in a sample, preferably a biological sample. Wells of a microtiter plate are coated with specific antibodies, at a final concentration of 0.2 to 10 µg/ml. The antibodies are either monoclonal or polyclonal and are produced by the method described above. The wells are blocked so that non-specific binding of the polypeptide to the well is reduced. The coated wells are then incubated for>2 hours at RT with a sample containing the polypeptide. Preferably, serial dilutions of the sample should be used to validate results. The plates are then washed three times with deionized or distilled water to remove unbound polypeptide. Next, 50 µl of specific antibody-alkaline phosphatase conjugate, at a concentration of 25–400 ng, is added and incubated for 2 hours at room temperature. The plates are again washed three times with deionized or distilled water to remove unbound conjugate. 75 µl of 4-methylumbelliferyl phosphate (MUP) or p-nitrophenyl phosphate (NPP) substrate solution are added to each well and incubated 1 hour at room temperature.

The reaction is measured by a microtiter plate reader. A standard curve is prepared, using serial dilutions of a control sample, and polypeptide concentrations are plotted on the X-axis (log scale) and fluorescence or absorbance on the Y-axis (linear scale). The concentration of the polypeptide in the sample is calculated using the standard curve.

Example 8
Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1, µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 µg/kg/hour to about 50 mg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semipermeable polymer matrices in the form of shaped articles, e. g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22: 547–556 (1983)), poly (2-hydroxyethyl methacrylate) (R. Langer et al., J. Biomed. Mater. Res. 15: 167–277 (1981), and R. Langer, Chem. Tech. 12: 98–105 (1982)), ethylene vinyl acetate (R. Langer et al.) or poly-D-(−)-3-hydroxybutyric acid (EP 133,988). Sustained-release compositions also include liposomally entrapped polypeptides. Liposomes containing the secreted polypeptide are prepared by methods known per se: DE Epstein et al., Proc. Natl. Acad. Sci. USA 82: 3688–3692 (1985); Hwang et al., Proc. Natl. Acad. Sci. USA 77: 4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, I. e., one that is non-toxic to recipients at the dosages and concentrations employed and is compatible with other ingredients of the formulation.

For example, the formulation preferably does not include oxidizing agents and other compounds that are known to be deleterious to polypeptides. Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e. g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e. g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multidose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container (s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 9
Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 $\mu$g/kg of the polypeptide for six consecutive days. Preferably, the polypeptide is in the secreted form. The exact details of the dosing scheme, based on administration and formulation, are provided above.

Example 10
Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided above.

Example 11
Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e. g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al., DNA, 7: 219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5'primer contains an EcoRI site and the 3'primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB 101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media.

If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 12
Method of Treatment Using Gene Therapy-In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide.

The polynucleotide of the present invention may be operatively linked to a promoter or any other genetic elements necessary for the expression of the polypeptide by the target tissue. Such gene therapy and delivery techniques and methods are known in the art, see, for example, WO 90/11092, WO 98/11779; U.S. Pat. Nos. 5,693,622; 5,705,151; 5,580,859; Tabata H. et al. (1997) Cardiovasc. Res. 35 (3): 470–479, Chao J et al. (1997) Pharmacol. Res. 35 (6): 517–522, Wolff J. A. (1997) Neuromuscul. Disord. 7 (5): 314–318, Schwartz B. et al. (1996) Gene Ther. 3 (5): 405–411, Tsurumi Y. et al. (1996) Circulation 94 (12): 3281–3290 (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772: 126–139 and Abdallah B. et al. (1995) Biol. Cell 85 (1): 1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 $\mu$g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e. g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice.

The results of the above experimentation in mice can be use to extrapolate proper dosages and other treatment parameters in humans and other animals using naked DNA.

Example 13

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e. g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i. e., polynucleotides of the invention) into animals to produce the founder lines of transgenic animals. Such techniques include, but are not limited to, pronuclear microinjection (Paterson et al., Appl. Microbiol. Biotechnol. 40: 691–698 (1994); Carver et al., Biotechnology (NY) 11: 1263–1270 (1993); Wright et al., Biotechnology (NY) 9: 830–834 (1991); and Hoppe et al., U.S. Pat No. 4,873,191 (1989)); retrovirus mediated gene transfer into germ lines (Van der Putten et al., Proc. Natl. Acad. Sci., USA 82: 6148–6152 (1985)), blastocysts or embryos; gene targeting in embryonic stem cells (Thompson et al., Cell 56: 313–321 (1989)); electroporation of cells or embryos (Lo, 1983, Mol Cell. Biol. 3: 1803–1814 (1983)); introduction of the polynucleotides of the invention using a gene gun (see, e. g., Ulmer et al., Science 259: 1745 (1993); introducing nucleic acid constructs into embryonic pleuripotent stem cells and transferring the stem cells back into the blastocyst; and sperm mediated gene transfer (Lavitrano et al., Cell 57: 717–723 (1989); etc. For a review of such techniques, see Gordon, "Transgenic Animals," Intl. Rev. Cytol. 115: 171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380: 64–66 (1996); Wilmut et al., Nature 385: 810813 (1997)).

The present invention provides for transgenic animals that carry the transgene in all their cells, as well as animals which carry the transgene in some, but not all their cells, I. e., mosaic animals or chimeric. The transgene may be integrated as a single transgene or as multiple copies such as in concatamers, e. g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89: 6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265: 103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 14

Knock-Out Animals

Endogenous gene expression can also be reduced by inactivating or "knocking out" the gene and/or its promoter using targeted homologous recombination. (E. g., see Smithies et al., Nature 317: 230–234 (1985); Thomas & Capecchi, Cell 51: 503512 (1987); Thompson et al., Cell 5: 313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e. g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e. g., knockouts) are administered to a patient in vivo. Such cells may be obtained from the patient (I. e., animal, including human) or an MHC compatible donor and can include, but are not limited to fibroblasts, bone marrow cells, blood cells (e. g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e. g., by transduction (using viral vectors, and preferably vectors that integrate the transgene into the cell genome) or transfection procedures, including, but not limited to, the use of plasmids, cosmids, YACs, naked DNA, electroporation, liposomes, etc.

The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e. g., in the circulation, or intraperitoneally.

Alternatively, the cells can be incorporated into a matrix and implanted in the body, e. g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

---

What is claimed is:

1. An isolated nucleic acid molecule comprising
   (a) a nucleic acid molecule comprising a nucleic acid sequence that encodes an amino acid sequence of SEQ ID NO:221;
   (b) a nucleic acid molecule comprising a nucleic acid sequence of SEQ ID NO: 81; or
   a nucleic acid molecule which is an allelic variant of a nucleic acid of SEQ ID NO:81 encoding an amino acid sequence of SEQ ID NO:221;
   wherein said nucleic acid molecule is detectably expressed in lung tumor tissues.

2. The nucleic acid molecule according to claim 1, wherein the nucleic acid molecule is a cDNA.

3. The nucleic acid molecule according to claim 1, wherein the nucleic acid molecule is a mammalian nucleic acid molecule.

4. The nucleic acid molecule according to claim 3, wherein the nucleic acid molecule is a human nucleic acid molecule.

5. A vector comprising the nucleic acid molecule of claim 1.

6. A host cell comprising the vector according to claim 5.

7. A method for producing a polypeptide encoded by the nucleic acid molecule according to claim 1, comprising the steps of (a) providing a host cell comprising the nucleic acid molecule operably linked to one or more expression control sequences, and (b) incubating the host cell under conditions in which the polypeptide is produced.

8. The nucleic acid molecule of claim 1 comprising a nucleic acid molecule that encodes an amino acid sequence comprising amino acids residues 1 through 782 or 62 through 782 of SEQ ID NO:221.

* * * * *